(12) United States Patent
Sasaki et al.

(10) Patent No.: US 9,975,903 B2
(45) Date of Patent: May 22, 2018

(54) CONDENSED HETEROCYCLIC COMPOUND

(71) Applicant: Takeda Pharmaceutical Company Limited, Chuo-ku, Osaka-shi, Osaka (JP)

(72) Inventors: Minoru Sasaki, Kanagawa (JP); Fumiaki Kikuchi, Kanagawa (JP); Zenichi Ikeda, Kanagawa (JP); Keiko Kakegawa, Kanagawa (JP); Yoichi Nishikawa, Hyogo (JP); Shigekazu Sasaki, Kanagawa (JP); Koichiro Fukuda, Kanagawa (JP); Kazuaki Takami, Kanagawa (JP); Yoshihiro Banno, Kanagawa (JP); Masahiro Kamaura, Kanagawa (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days. days.

(21) Appl. No.: 15/539,607

(22) PCT Filed: Dec. 24, 2015

(86) PCT No.: PCT/JP2015/086070
§ 371 (c)(1),
(2) Date: Jun. 23, 2017

(87) PCT Pub. No.: WO2016/104630
PCT Pub. Date: Jun. 30, 2016

(65) Prior Publication Data
US 2017/0349605 A1 Dec. 7, 2017

(30) Foreign Application Priority Data

Dec. 26, 2014 (JP) .................. 2014-266064

(51) Int. Cl.
*C07D 493/04* (2006.01)
*C07D 495/04* (2006.01)
*C07D 321/00* (2006.01)
*C07D 405/06* (2006.01)
*C07D 321/12* (2006.01)
*C07D 413/06* (2006.01)
*C07D 323/00* (2006.01)
*C07D 491/044* (2006.01)
*C07D 313/00* (2006.01)
*C07D 313/20* (2006.01)

(52) U.S. Cl.
CPC ......... *C07D 495/04* (2013.01); *C07D 313/00* (2013.01); *C07D 313/20* (2013.01); *C07D 321/00* (2013.01); *C07D 321/12* (2013.01); *C07D 323/00* (2013.01); *C07D 405/06* (2013.01); *C07D 413/06* (2013.01); *C07D 491/044* (2013.01); *C07D 493/04* (2013.01)

(58) Field of Classification Search
CPC .. C07D 493/04; C07D 495/04; C07D 313/00; C07D 313/20; C07D 321/00; C07D 321/12; C07D 323/00; C07D 405/06; C07D 413/06; C07D 491/044
See application file for complete search history.

(56) References Cited

U.S. PATENT DOCUMENTS

| 5,089,634 | A | * | 2/1992 | Powers | C07D 311/76 514/822 |
| 5,324,648 | A | * | 6/1994 | Powers | C07D 311/76 435/184 |
| 5,652,237 | A | * | 7/1997 | Augelli-Szafran | C07D 265/24 514/224.2 |
| 6,297,233 | B1 | | 11/2001 | Stein et al. | |
| 6,552,042 | B2 | * | 4/2003 | Han | C07D 209/34 514/322 |
| 6,599,918 | B2 | * | 7/2003 | Burns | C07D 307/81 514/314 |

(Continued)

FOREIGN PATENT DOCUMENTS

| JP | 02-536411 A | 10/2002 |
| WO | WO 2009/071601 A1 | 6/2009 |

(Continued)

OTHER PUBLICATIONS

C-M Kam et al., 27 Biochemistry, 2547-2557 A1 (1988).*
J.C. Powers et al., 39 Journal of Cellular Biochemistry, 33-46 (1989).*
International Search Report dated Mar. 22, 2016, in PCT/JP2015/086070.

(Continued)

*Primary Examiner* — Alexander R Pagano
(74) *Attorney, Agent, or Firm* — Foley & Lardner LLP

(57) ABSTRACT

The present invention relates to a condensed heterocyclic compound that has an enteropeptidase inhibitory effect and is useful in the treatment or prevention of obesity, diabetes mellitus, or the like, and a medicament containing the same. Specifically, the present invention relates to a compound represented by the following formula (I) or a salt thereof, and a medicament containing the same [in the formula, each symbol is as defined in the specification].

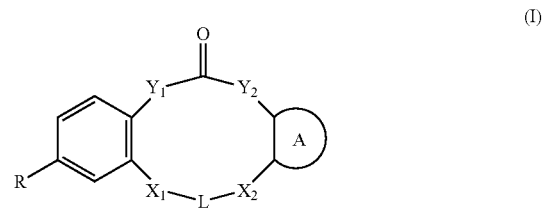

11 Claims, No Drawings

(56) References Cited

U.S. PATENT DOCUMENTS

| | | | |
|---|---|---|---|
| 7,790,726 B2 * | 9/2010 | Zhang | C07D 231/56 514/254.02 |
| 9,388,126 B2 * | 7/2016 | Kim | A61K 45/06 |
| 2006/0100225 A1 * | 5/2006 | Chen | C07C 279/18 514/269 |
| 2012/0283222 A1 * | 11/2012 | Konishi | C07D 277/20 514/95 |
| 2013/0023563 A1 * | 1/2013 | Matsumoto | C07D 207/08 514/316 |
| 2014/0094489 A1 * | 4/2014 | Suzuki | C07D 333/38 514/301 |
| 2014/0378459 A1 | 12/2014 | Fujiyasu et al. | |

FOREIGN PATENT DOCUMENTS

| | | |
|---|---|---|
| WO | WO 2011/071048 A1 | 6/2011 |
| WO | WO 2012/169579 A1 | 12/2012 |
| WO | WO 2013/039187 A1 | 3/2013 |
| WO | WO 2013/187533 A1 | 12/2013 |

OTHER PUBLICATIONS

Siddiqui, Bina S. et al., "Two new compounds from the aerial parts of Bergenia himalaica Boriss and their anti-hyperglycemic effect in streptozotocin-nicotinamide induced diabetic rats," Journal of Ethnopharmacology, Feb. 15, 2014, vol. 152, p. 561-567.

* cited by examiner

CONDENSED HETEROCYCLIC COMPOUND

RELATED APPLICATIONS

The present application is a National Stage application of PCT/JP2015/086070, filed Dec. 24, 2015, which claims priority from Japanese Patent Application No. 2014-266064, filed Dec. 26, 2014, the contents of which are incorporated herein by reference.

TECHNICAL FIELD

The present invention relates to a condensed heterocyclic compound that has an enteropeptidase inhibitory effect and is useful in the treatment or prevention of obesity, diabetes mellitus, or the like, and a medicament containing the same.

BACKGROUND OF INVENTION

Enteropeptidase is a serine protease that converts trypsinogen secreted from the pancreas after meal to trypsin. Trypsin in a state activated by enteropeptidase then activates protease precursors such as chymotrypsinogen, procarboxypeptidase, and proelastase. These activated proteases decompose dietary proteins into amino acid units. The resulting amino acids are absorbed into the small intestine. Thus, enteropeptidase inhibitors are capable of suppressing the degradation or absorption of proteins and is useful as a drug for treating obesity.

Examples of heterocyclic compounds include the following:

(1) A compound which has a trypsin inhibitory effect and is useful in the treatment or prevention of a renal disease or a disease involving trypsin, the compound being represented by the following formula:

[Formula 1]

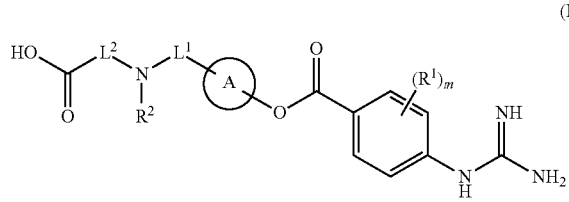

(I)

wherein
ring A represents

[Formula 2]

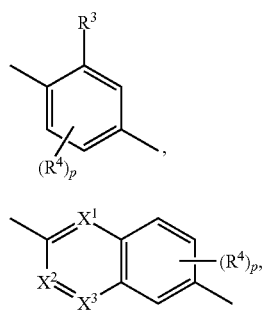

(a)

(b)

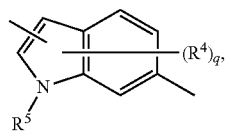

(c)

$R^1$ represents halogen, lower alkyl, or OH;
$R^2$ represents H, optionally substituted cycloalkyl, optionally substituted aryl, an optionally substituted aromatic heterocyclic ring, an optionally substituted nonaromatic heterocyclic ring, —C(O)-lower alkylene-optionally substituted aryl, or lower alkyl optionally substituted by halogen or the like;
$L^1$ represents —$Y^1$-lower alkylene-$Y^2$—, or —C(O)—N($R^6$)—;
$Y^1$ represents a bond or —C(O)—;
$Y^2$ represents a bond, —N($R^6$)—, or —C(O)—N($R^6$)—;
$L^2$ represents -(lower alkylene optionally substituted by $CO_2H$ or the like)-, —$Y^3$-cyclohexanediyl-$Y^4$—, or —$Y^3$-phenylene-$Y^4$—, and $L^2$ optionally forms optionally substituted cyclic amino together with $R^2$;
$Y^3$ represents a bond or lower alkylene;
$Y^4$ represents a bond, lower alkylene, or —C(O)—;
$R^3$ represents H, lower alkyl optionally substituted by halogen, halogen, OH, —O-lower alkyl, cycloalkyl, aryl, or the like;
$R^4$ represents lower alkyl optionally substituted by halogen, halogen, OH, —O-lower alkyl, cycloalkyl, aryl, or the like;
$R^5$ and $R^6$ each represent H or lower alkyl;
$X^1$, $X^2$, and $X^3$ each represent CH or N (except that at least one of $X^1$, $X^2$, and $X^3$ is N);
m represents an integer of 0 to 4;
p represents an integer of 0 to 3; and
q represents an integer of 0 to 4
(Patent Literature 1).

(2) A compound which has a serine protease inhibitory effect and is useful in the treatment or prevention of obesity, hyperlipidemia, diabetes mellitus, diabetic complications, or metabolic syndrome, the compound being represented by the following formula:

[Formula 3]

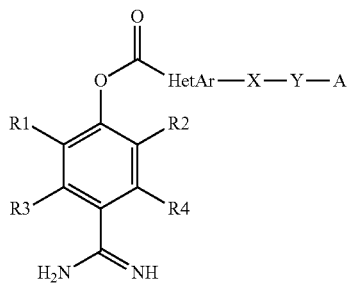

wherein
R1, R2, R3, and R4 each represent H or the like;
HetAr represents an optionally substituted heteroaromatic ring;
X represents optionally substituted lower alkylene or the like;
Y represents carbonyl or the like;

A represents

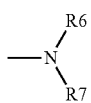

or the like; and

R6 and R7 each represent H, optionally substituted lower alkyl, or the like (Patent Literature 2).

(3) A compound which has a serine protease inhibitory effect and is useful in the treatment or prevention of obesity, hyperlipidemia, diabetes mellitus, diabetic complications, or metabolic syndrome, the compound being represented by the following formula:

[Formula 5]

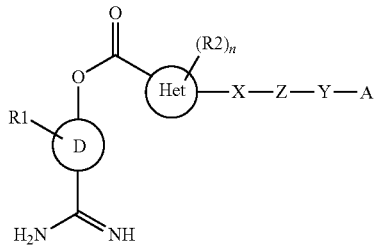

wherein

D represents a benzene ring, a naphthalene ring, or a pyridine ring;

Het represents a heterocyclic ring;

R1 represents H or the like;

R2 represents nitro, lower alkyl, or the like;

X represents optionally substituted lower alkylene;

Z represents —N(R3)-(wherein R3 represents H, optionally substituted lower alkyl, optionally substituted lower cycloalkyl, or the like);

Y represents a single bond or —(CH$_2$)p-C(R4a) (R4b)-(CH$_2$)q- (wherein R4a and R4b each represent H, lower alkyl, or aralkyl, and p and q each represents an integer of 0 to 5); and A represents —CO$_2$R6 (wherein R6 represents H or lower alkyl) or

[Formula 6]

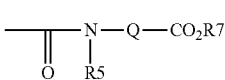

wherein Q represents optionally substituted lower alkylene, and R7 represents H or lower alkyl (Patent Literature 3).

(4) A compound which has an enteropeptidase inhibitory effect and is useful in the treatment or prevention of a disease related to obesity or abnormal fat metabolism, the compound being represented by the following formula:

[Formula 7]

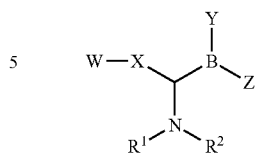

wherein

B represents boron;

W represents a nitrogen-containing functional group (

[Formula 8]

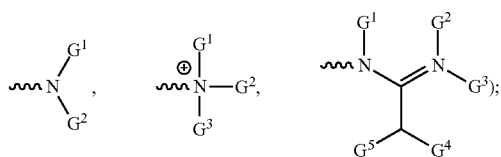

X represents a linker (CX$^1$X$^2$)p;

Y and Z each represent OH, OR (R represents alkyl), a homocyclic ring, a heterocyclic ring, or the like;

R$^2$ represents aminoacyl, acyl, or the like; and

R$^2$ represents H, alkyl, or OR (R represents H or alkyl)

(Patent Literature 4).

(5) A compound which has a serine protease inhibitory effect and is useful in the treatment or prevention of obesity, diabetes mellitus, or the like, the compound being represented by the following formula:

[Formula 9]

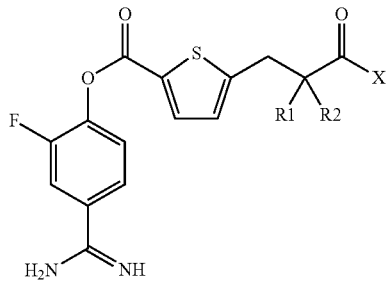

wherein

R$^1$ and R$^2$ each represent alkyl or the like; and

X represents —OR$^3$, —NR$^4$R$^5$, or the like (Patent Literature 5).

CITATION LIST

Patent Literature

Patent Literature 1: WO2013/039187
Patent Literature 2: WO2011/071048
Patent Literature 3: WO2012/169579
Patent Literature 4: WO2009/071601
Patent Literature 5: WO2013/187533

SUMMARY OF INVENTION

Technical Problem

An object of the present invention is to provide a condensed heterocyclic compound that has an excellent enteropeptidase inhibitory effect and is useful in the treatment or prevention of obesity, diabetes mellitus, or the like, and a medicament containing the same.

Solution to Problem

The present inventors have conducted diligent studies to attain the object and consequently completed the present invention by finding that a compound represented by the formula (I) given below has an excellent enteropeptidase inhibitory effect.

Specifically, the present invention is as follows:

[1] A compound represented by the formula (I) or a salt thereof:

[Formula 10]

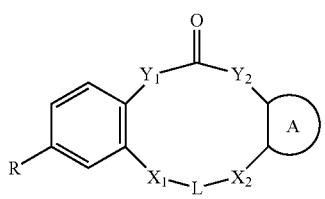

wherein
ring A represents an optionally substituted 5- or 6-membered aromatic ring, and the substituent of ring A optionally forms an optionally substituted ring together with constituent atoms of ring A;
L represents a bond or a $C_{1-6}$ alkylene group;
$X_1$ and $X_2$ are the same or different and each represent —O— or a bond;
R represents a guanidino group or an amidino group;
one of $Y_1$ and $Y_2$ is —O—, and the other moiety is a bond, provided that
when R is a guanidino group, $Y_1$ represents a bond and $Y_2$ represents —O—, and
when R is an amidino group, $Y_1$ represents —O— and $Y_2$ represents a bond
(hereinafter, the compound or the salt is also referred to as compound (I)).

[2]
The compound according to the above [1] or a salt thereof, wherein
ring A is
(1) a benzene ring optionally substituted by 1 to 3 substituents selected from
1) a halogen atom,
2) a carboxy group,
3) a cyano group,
4) a carbamoyl group optionally substituted by a $C_{6-14}$ aryl group optionally substituted by 1 to 3 substituents selected from a sulfo group; and a $C_{1-6}$ alkyl group optionally substituted by a mono- or di-$C_{1-6}$ alkylphosphono group,
5) 3- to 14-membered nonaromatic heterocyclylcarbonyl optionally substituted by 1 to 3 substituents selected from a carboxy group; and a mono- or di-$C_{1-6}$ alkyl-carbamoyl group substituted by 1 or 2 carboxy groups,
6) a 3- to 14-membered nonaromatic heterocyclic group optionally substituted by 1 to 3 substituents selected from a $C_{1-6}$ alkyl group substituted by 1 or 2 carboxy groups; and a carboxy group,
7) a $C_{1-6}$ alkyl group optionally substituted by 1 to 3 substituents selected from a mono- or di-$C_{1-6}$ alkyl-carbamoyl group substituted by 1 to 3 substituents selected from a carboxy group, a hydroxy-phenyl group, and a carbamoyl group; a $C_{1-6}$ alkoxy-carbonyl group; and a carboxy group,
8) a $C_{1-6}$ alkoxy group optionally substituted by a mono- or di-$C_{1-6}$ alkyl-carbamoyl group substituted by 1 or 2 carboxy groups,
9) a mono- or di-$C_{1-6}$ alkyl-carbamoyl group optionally substituted by 1 to 3 substituents selected from
(a) a carboxy group;
(b) a sulfo group;
(c) a hydroxy group;
(d) a $C_{1-6}$ alkoxy group optionally substituted by a phenyl group;
(e) a $C_{1-6}$ alkoxy-carbonyl group;
(f) a guanidino group;
(g) a $C_{6-14}$ aryl group optionally substituted by 1 to 3 substituents selected from
  (g-1) a hydroxy group,
  (g-2) a carboxy group,
  (g-3) a $C_{1-6}$ alkoxy group,
  (g-4) a $C_{1-6}$ alkyl group substituted by a carboxy group,
  (g-5) a $C_{1-6}$ alkyl group substituted by a mono- or di-$C_{1-6}$ alkyl-amino group substituted by 1 or 2 carboxy groups, and
  (g-6) a mono- or di-$C_{1-6}$ alkyl-amino-$C_{1-6}$ alkoxy group substituted by 1 or 2 substituents selected from a carboxy group and a phenyl group;
(h) a thienyl group optionally substituted by 1 or 2 carboxy groups;
(i) a pyridinyl group optionally substituted by a mono- or di-$C_{1-6}$ alkyl-amino-$C_{1-6}$ alkyl group substituted by 1 or 2 carboxy groups;
(j) a $C_{1-6}$ alkyl-amino group substituted by 1 or 2 carboxy groups;
(k) a carbamoyl group optionally substituted by 1 or 2 $C_{1-6}$ alkyl groups substituted by 1 or 2 substituents selected from a carboxy group and a carboxy-phenyl group; and
(l) a phosphono group; and
10) a $C_{3-10}$ cycloalkyl group,
(2) 2,3-dihydrobenzofuran optionally substituted by 1 to 3 substituents selected from
1) a mono- or di-$C_{1-6}$ alkyl-carbamoyl group optionally substituted by 1 to 3 substituents selected from a carboxy group and a sulfo group, and
2) a $C_{1-6}$ alkyl group optionally substituted by a mono- or di-$C_{1-6}$ alkyl-carbamoyl group substituted by 1 to 3 substituents selected from a carboxy group and a sulfo group,
(3) pyridine optionally substituted by $C_{1-6}$ alkyl optionally substituted by a mono- or di-$C_{1-6}$ alkyl-carbamoyl group substituted by 1 or 2 carboxy groups, or
(4) thiophene optionally substituted by a mono- or di-$C_{1-6}$ alkyl-carbamoyl group optionally substituted by 1 or 2 carboxy groups.

[3]
The compound according to the above [1] or [2] or a salt thereof, wherein L is propylene.
[4]
The compound according to the above [1], [2] or [3] or a salt thereof, wherein $X_1$ is a bond, and $X_2$ is —O—.
[5]
The compound according to the above [1], [2], [3] or [4] or a salt thereof, wherein R is a guanidino group.
[6]
The compound according to the above [1], [2], [3], [4] or [5] or a salt thereof, wherein $Y_1$ is a bond, and $Y_2$ is —O—.

[7]

The compound according to the above [1] or a salt thereof, wherein
ring A is
(1) a benzene ring optionally substituted by 1 to 3 substituents selected from
1) a halogen atom,
2) a carboxy group,
3) a cyano group,
4) a carbamoyl group optionally substituted by a $C_{6-14}$ aryl group optionally substituted by 1 to 3 substituents selected from a sulfo group; and a $C_{1-6}$ alkyl group optionally substituted by a mono- or di-$C_{1-6}$ alkylphosphono group,
5) 3- to 14-membered nonaromatic heterocyclylcarbonyl optionally substituted by 1 to 3 substituents selected from a carboxy group; and a mono- or di-$C_{1-6}$ alkyl-carbamoyl group substituted by 1 or 2 carboxy groups,
6) a 3- to 14-membered nonaromatic heterocyclic group optionally substituted by 1 to 3 substituents selected from a $C_{1-6}$ alkyl group substituted by 1 or 2 carboxy groups; and a carboxy group,
7) a $C_{1-6}$ alkyl group optionally substituted by 1 to 3 substituents selected from a mono- or di-$C_{1-6}$ alkyl-carbamoyl group substituted by 1 to 3 substituents selected from a carboxy group, a hydroxy-phenyl group, and a carbamoyl group; a $C_{1-6}$ alkoxy-carbonyl group; and a carboxy group,
8) a $C_{1-6}$ alkoxy group optionally substituted by a mono- or di-$C_{1-6}$ alkyl-carbamoyl group substituted by 1 or 2 carboxy groups,
9) a mono- or di-$C_{1-6}$ alkyl-carbamoyl group optionally substituted by 1 to 3 substituents selected from
(a) a carboxy group;
(b) a sulfo group;
(c) a hydroxy group;
(d) a $C_{1-6}$ alkoxy group optionally substituted by a phenyl group;
(e) a $C_{1-6}$ alkoxy-carbonyl group;
(f) a guanidino group;
(g) a $C_{6-14}$ aryl group optionally substituted by 1 to 3 substituents selected from
  (g-1) a hydroxy group,
  (g-2) a carboxy group,
  (g-3) a $C_{1-6}$ alkoxy group,
  (g-4) a $C_{1-6}$ alkyl group substituted by a carboxy group,
  (g-5) a $C_{1-6}$ alkyl group substituted by a mono- or di-$C_{1-6}$ alkyl-amino group substituted by 1 or 2 carboxy groups, and
  (g-6) a mono- or di-$C_{1-6}$ alkyl-amino-$C_{1-6}$ alkoxy group substituted by 1 or 2 substituents selected from a carboxy group and a phenyl group;
(h) a thienyl group optionally substituted by 1 or 2 carboxy groups;
(i) a pyridinyl group optionally substituted by a mono- or di-$C_{1-6}$ alkyl-amino-$C_{1-6}$ alkyl group substituted by 1 or 2 carboxy groups;
(j) a $C_{1-6}$ alkyl-amino group substituted by 1 or 2 carboxy groups;
(k) a carbamoyl group optionally substituted by 1 or 2 $C_{1-6}$ alkyl groups substituted by 1 or 2 substituents selected from a carboxy group and a carboxy-phenyl group; and
(l) a phosphono group; and
10) a $C_{3-10}$ cycloalkyl group,
(2) 2,3-dihydrobenzofuran optionally substituted by 1 to 3 substituents selected from
1) a mono- or di-$C_{1-6}$ alkyl-carbamoyl group optionally substituted by 1 to 3 substituents selected from a carboxy group and a sulfo group, and
2) a $C_{1-6}$ alkyl group optionally substituted by a mono- or di-$C_{1-6}$ alkyl-carbamoyl group substituted by 1 to 3 substituents selected from a carboxy group and a sulfo group,
(3) pyridine optionally substituted by $C_{1-6}$ alkyl optionally substituted by a mono- or di-$C_{1-6}$ alkyl-carbamoyl group substituted by 1 or 2 carboxy groups, or
(4) thiophene optionally substituted by a mono- or di-$C_{1-6}$ alkyl-carbamoyl group optionally substituted by 1 or 2 carboxy groups;
L is propylene;
$X_1$ is a bond, and $X_2$ is —O—;
R is a guanidino group; and
$Y_1$ is a bond, and $Y_2$ is —O—.

[8]

N-((10-Carbamimidamido-13-oxo-6,7,8,13-tetrahydrodibenzo[b,f][1,4]dioxecin-4-yl)carbonyl)-N-(carboxymethyl)-O-methyl-L-tyrosine or a salt thereof.

[9]

N-(2-(Bis(carboxymethyl)amino)ethyl)-N-((10-carbamimidamido-13-oxo-6,7,8,13-tetrahydrodibenzo[b,f][1,4]dioxecin-4-yl)carbonyl)glycine or a salt thereof.

[10]

N-((10-Carbamimidamido-13-oxo-6,7,8,13-tetrahydrodibenzo[b,f][1,4]dioxecin-4-yl)carbonyl)-N-(3-carboxybenzyl)-L-aspartic acid or a salt thereof.

[11]

A medicament comprising a compound according to the above [1], [2], [3], [4], [5], [6], [7], [8], [9] or [10] or a salt thereof.

[12]

The medicament according to the above [11], wherein the medicament is an enteropeptidase inhibitor.

[13]

The medicament according to the above [11] or [12], wherein the medicament is an agent for preventing or treating obesity or diabetes mellitus.

[14]

A method for preventing or treating obesity or diabetes mellitus in a mammal, comprising administering an effective amount of a compound according to the above [1], [2], [3], [4], [5], [6], [7], [8], [9] or [10] or a salt thereof to the mammal.

[15]

A method for inhibiting enteropeptidase in a mammal, comprising administering an effective amount of a compound according to the above [1], [2], [3], [4], [5], [6], [7], [8], [9] or [10] or a salt thereof to the mammal.

[16]

Use of a compound according to the above [1], [2], [3], [4], [5], [6], [7], [8], [9] or [10] or a salt thereof for producing an agent for preventing or treating obesity or diabetes mellitus.

[17]

The compound according to the above [1], [2], [3], [4], [5], [6], [7], [8], [9] or [10] or a salt thereof for use in the prevention or treatment of obesity or diabetes mellitus.

Advantageous Effects of Invention

Compound (I) has an excellent enteropeptidase inhibitory effect and is useful in the treatment or prevention of obesity, diabetes mellitus, or the like.

DETAILED DESCRIPTION OF THE INVENTION

Hereinafter, the present invention will be described in detail.

The definition of each substituent used in the present specification is described in detail in the following. Unless otherwise specified, each substituent has the following definition.

In the present specification, examples of the "halogen atom" include fluorine, chlorine, bromine and iodine.

In the present specification, examples of the "$C_{1-6}$ alkyl group" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl and 2-ethylbutyl.

In the present specification, examples of the "optionally halogenated $C_{1-6}$ alkyl group" include a $C_{1-6}$ alkyl group optionally having 1 to 7, preferably 1 to 5, halogen atoms. Specific examples thereof include methyl, chloromethyl, difluoromethyl, trichloromethyl, trifluoromethyl, ethyl, 2-bromoethyl, 2,2,2-trifluoroethyl, tetrafluoroethyl, pentafluoroethyl, propyl, 2,2-difluoropropyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl and 6,6,6-trifluorohexyl.

In the present specification, examples of the "$C_{2-6}$ alkenyl group" include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl and 5-hexenyl.

In the present specification, examples of the "$C_{2-6}$ alkynyl group" include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and 4-methyl-2-pentynyl.

In the present specification, examples of the "$C_{3-10}$ cycloalkyl group" include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl and adamantyl.

In the present specification, examples of the "optionally halogenated $C_{3-10}$ cycloalkyl group" include a $C_{3-10}$ cycloalkyl group optionally having 1 to 7, preferably 1 to 5, halogen atoms. Specific examples thereof include cyclopropyl, 2,2-difluorocyclopropyl, 2,3-difluorocyclopropyl, cyclobutyl, difluorocyclobutyl, cyclopentyl, cyclohexyl, cycloheptyl and cyclooctyl.

In the present specification, examples of the "$C_{3-10}$ cycloalkenyl group" include cyclopropenyl, cyclobutenyl, cyclopentenyl, cyclohexenyl, cycloheptenyl and cyclooctenyl.

In the present specification, examples of the "$C_{6-14}$ aryl group" include phenyl, 1-naphthyl, 2-naphthyl, 1-anthryl, 2-anthryl and 9-anthryl.

In the present specification, examples of the "$C_{7-16}$ aralkyl group" include benzyl, phenethyl, naphthylmethyl and phenylpropyl.

In the present specification, examples of the "$C_{1-6}$ alkoxy group" include methoxy, ethoxy, propoxy, isopropoxy, butoxy, isobutoxy, sec-butoxy, tert-butoxy, pentyloxy and hexyloxy.

In the present specification, examples of the "optionally halogenated $C_{1-6}$ alkoxy group" include a $C_{1-6}$ alkoxy group optionally having 1 to 7, preferably 1 to 5, halogen atoms. Specific examples thereof include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy and hexyloxy.

In the present specification, examples of the "$C_{3-10}$ cycloalkyloxy group" include cyclopropyloxy, cyclobutyloxy, cyclopentyloxy, cyclohexyloxy, cycloheptyloxy and cyclooctyloxy.

In the present specification, examples of the "$C_{1-6}$ alkylthio group" include methylthio, ethylthio, propylthio, isopropylthio, butylthio, sec-butylthio, tert-butylthio, pentylthio and hexylthio.

In the present specification, examples of the "optionally halogenated $C_{1-6}$ alkylthio group" include a $C_{1-6}$ alkylthio group optionally having 1 to 7, preferably 1 to 5, halogen atoms. Specific examples thereof include methylthio, difluoromethylthio, trifluoromethylthio, ethylthio, propylthio, isopropylthio, butylthio, 4,4,4-trifluorobutylthio, pentylthio and hexylthio.

In the present specification, examples of the "$C_{1-6}$ alkyl-carbonyl group" include acetyl, propanoyl, butanoyl, 2-methylpropanoyl, pentanoyl, 3-methylbutanoyl, 2-methylbutanoyl, 2,2-dimethylpropanoyl, hexanoyl and heptanoyl.

In the present specification, examples of the "optionally halogenated $C_{1-6}$ alkyl-carbonyl group" include a $C_{1-6}$ alkyl-carbonyl group optionally having 1 to 7, preferably 1 to 5, halogen atoms. Specific examples thereof include acetyl, chloroacetyl, trifluoroacetyl, trichloroacetyl, propanoyl, butanoyl, pentanoyl and hexanoyl.

In the present specification, examples of the "$C_{1-6}$ alkoxy-carbonyl group" include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl and hexyloxycarbonyl.

In the present specification, examples of the "$C_{6-14}$ aryl-carbonyl group" include benzoyl, 1-naphthoyl and 2-naphthoyl.

In the present specification, examples of the "$C_{7-16}$ aralkyl-carbonyl group" include phenylacetyl and phenylpropionyl.

In the present specification, examples of the "5- to 14-membered aromatic heterocyclylcarbonyl group" include nicotinoyl, isonicotinoyl, thenoyl and furoyl.

In the present specification, examples of the "3- to 14-membered non-aromatic heterocyclylcarbonyl group" include morpholinylcarbonyl, piperidinylcarbonyl and pyrrolidinylcarbonyl.

In the present specification, examples of the "mono- or di-$C_{1-6}$ alkyl-carbamoyl group" include methylcarbamoyl, ethylcarbamoyl, dimethylcarbamoyl, diethylcarbamoyl and N-ethyl-N-methylcarbamoyl.

In the present specification, examples of the "mono- or di-$C_{7-16}$ aralkyl-carbamoyl group" include benzylcarbamoyl and phenethylcarbamoyl.

In the present specification, examples of the "$C_{1-6}$ alkylsulfonyl group" include methylsulfonyl, ethylsulfonyl, propylsulfonyl, isopropylsulfonyl, butylsulfonyl, sec-butylsulfonyl and tert-butylsulfonyl.

In the present specification, examples of the "optionally halogenated $C_{1-6}$ alkylsulfonyl group" include a $C_{1-6}$ alkylsulfonyl group optionally having 1 to 7, preferably 1 to 5, halogen atoms. Specific examples thereof include methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, pentylsulfonyl and hexylsulfonyl.

In the present specification, examples of the "C$_{6-14}$ arylsulfonyl group" include phenylsulfonyl, 1-naphthylsulfonyl and 2-naphthylsulfonyl.

In the present specification, examples of the "substituent" include a halogen atom, a cyano group, a nitro group, an optionally substituted hydrocarbon group, an optionally substituted heterocyclic group, an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl (SH) group and an optionally substituted silyl group.

In the present specification, examples of the "hydrocarbon group" (including "hydrocarbon group" of "optionally substituted hydrocarbon group") include a C$_{1-6}$ alkyl group, a C$_{2-6}$ alkenyl group, a C$_{2-6}$ alkynyl group, a C$_{3-10}$ cycloalkyl group, a C$_{3-10}$ cycloalkenyl group, a C$_{6-14}$ aryl group and a C$_{7-16}$ aralkyl group.

In the present specification, examples of the "optionally substituted hydrocarbon group" include a hydrocarbon group optionally having substituent(s) selected from the following substituent group A.

[Substituent Group A]
(1) a halogen atom,
(2) a nitro group,
(3) a cyano group,
(4) an oxo group,
(5) a hydroxy group,
(6) an optionally halogenated C$_{1-6}$ alkoxy group,
(7) a C$_{6-14}$ aryloxy group (e.g., phenoxy, naphthoxy),
(8) a C$_{7-16}$ aralkyloxy group (e.g., benzyloxy),
(9) a 5- to 14-membered aromatic heterocyclyloxy group (e.g., pyridyloxy),
(10) a 3- to 14-membered non-aromatic heterocyclyloxy group (e.g., morpholinyloxy, piperidinyloxy),
(11) a C$_{1-6}$ alkyl-carbonyloxy group (e.g., acetoxy, propanoyloxy),
(12) a C$_{6-14}$ aryl-carbonyloxy group (e.g., benzoyloxy, 1-naphthoyloxy, 2-naphthoyloxy),
(13) a C$_{1-6}$ alkoxy-carbonyloxy group (e.g., methoxycarbonyloxy, ethoxycarbonyloxy, propoxycarbonyloxy, butoxycarbonyloxy),
(14) a mono- or di-C$_{1-6}$ alkyl-carbamoyloxy group (e.g., methylcarbamoyloxy, ethylcarbamoyloxy, dimethylcarbamoyloxy, diethylcarbamoyloxy),
(15) a C$_{6-14}$ aryl-carbamoyloxy group (e.g., phenylcarbamoyloxy, naphthylcarbamoyloxy),
(16) a 5- to 14-membered aromatic heterocyclylcarbonyloxy group (e.g., nicotinoyloxy),
(17) a 3- to 14-membered non-aromatic heterocyclylcarbonyloxy group (e.g., morpholinylcarbonyloxy, piperidinylcarbonyloxy),
(18) an optionally halogenated C$_{1-6}$ alkylsulfonyloxy group (e.g., methylsulfonyloxy, trifluoromethylsulfonyloxy),
(19) a C$_{6-14}$ arylsulfonyloxy group optionally substituted by a C$_{1-6}$ alkyl group (e.g., phenylsulfonyloxy, toluenesulfonyloxy),
(20) an optionally halogenated C$_{1-6}$ alkylthio group,
(21) a 5- to 14-membered aromatic heterocyclic group,
(22) a 3- to 14-membered non-aromatic heterocyclic group,
(23) a formyl group,
(24) a carboxy group,
(25) an optionally halogenated C$_{1-6}$ alkyl-carbonyl group,
(26) a C$_{6-14}$ aryl-carbonyl group,
(27) a 5- to 14-membered aromatic heterocyclylcarbonyl group,
(28) a 3- to 14-membered non-aromatic heterocyclylcarbonyl group,
(29) a C$_{1-6}$ alkoxy-carbonyl group,
(30) a C$_{6-14}$ aryloxy-carbonyl group (e.g., phenyloxycarbonyl, 1-naphthyloxycarbonyl, 2-naphthyloxycarbonyl),
(31) a C$_{7-16}$ aralkyloxy-carbonyl group (e.g., benzyloxycarbonyl, phenethyloxycarbonyl),
(32) a carbamoyl group,
(33) a thiocarbamoyl group,
(34) a mono- or di-C$_{1-6}$ alkyl-carbamoyl group,
(35) a C$_{6-14}$ aryl-carbamoyl group (e.g., phenylcarbamoyl),
(36) a 5- to 14-membered aromatic heterocyclylcarbamoyl group (e.g., pyridylcarbamoyl, thienylcarbamoyl),
(37) a 3- to 14-membered non-aromatic heterocyclylcarbamoyl group (e.g., morpholinylcarbamoyl, piperidinylcarbamoyl),
(38) an optionally halogenated C$_{1-6}$ alkylsulfonyl group,
(39) a C$_{6-14}$ arylsulfonyl group,
(40) a 5- to 14-membered aromatic heterocyclylsulfonyl group (e.g., pyridylsulfonyl, thienylsulfonyl),
(41) an optionally halogenated C$_{1-6}$ alkylsulfinyl group,
(42) a C$_{6-14}$ arylsulfinyl group (e.g., phenylsulfinyl, 1-naphthylsulfinyl, 2-naphthylsulfinyl),
(43) a 5- to 14-membered aromatic heterocyclylsulfinyl group (e.g., pyridylsulfinyl, thienylsulfinyl),
(44) an amino group,
(45) a mono- or di-C$_{1-6}$ alkylamino group (e.g., methylamino, ethylamino, propylamino, isopropylamino, butylamino, dimethylamino, diethylamino, dipropylamino, dibutylamino, N-ethyl-N-methylamino),
(46) a mono- or di-C$_{6-14}$ arylamino group (e.g., phenylamino),
(47) a 5- to 14-membered aromatic heterocyclylamino group (e.g., pyridylamino),
(48) a C$_{7-16}$ aralkylamino group (e.g., benzylamino),
(49) a formylamino group,
(50) a C$_{1-6}$ alkyl-carbonylamino group (e.g., acetylamino, propanoylamino, butanoylamino),
(51) a (C$_{1-6}$ alkyl) (C$_{1-6}$ alkyl-carbonyl)amino group (e.g., N-acetyl-N-methylamino),
(52) a C$_{6-14}$ aryl-carbonylamino group (e.g., phenylcarbonylamino, naphthylcarbonylamino),
(53) a C$_{1-6}$ alkoxy-carbonylamino group (e.g., methoxycarbonylamino, ethoxycarbonylamino, propoxycarbonylamino, butoxycarbonylamino, tert-butoxycarbonylamino),
(54) a C$_{7-16}$ aralkyloxy-carbonylamino group (e.g., benzyloxycarbonylamino),
(55) a C$_{1-6}$ alkylsulfonylamino group (e.g., methylsulfonylamino, ethylsulfonylamino),
(56) a C$_{6-14}$ arylsulfonylamino group optionally substituted by a C$_{1-6}$ alkyl group (e.g., phenylsulfonylamino, toluenesulfonylamino),
(57) an optionally halogenated C$_{1-6}$ alkyl group,
(58) a C$_{2-6}$ alkenyl group,
(59) a C$_{2-6}$ alkynyl group,
(60) a C$_{3-10}$ cycloalkyl group,
(61) a C$_{3-10}$ cycloalkenyl group and
(62) a C$_{6-14}$ aryl group.

The number of the above-mentioned substituents in the "optionally substituted hydrocarbon group" is, for example, 1 to 5, preferably 1 to 3. When the number of the substituents is two or more, the respective substituents may be the same or different.

In the present specification, examples of the "heterocyclic group" (including "heterocyclic group" of "optionally substituted heterocyclic group") include (i) an aromatic heterocyclic group, (ii) a non-aromatic heterocyclic group and (iii) a 7- to 10-membered bridged heterocyclic group, each containing, as a ring-constituting atom besides carbon atom, 1 to 4 hetero atoms selected from a nitrogen atom, a sulfur atom and an oxygen atom.

In the present specification, examples of the "aromatic heterocyclic group" (including "5- to 14-membered aromatic heterocyclic group") include a 5- to 14-membered (preferably 5- to 10-membered) aromatic heterocyclic group containing, as a ring-constituting atom besides carbon atom, 1 to 4 hetero atoms selected from a nitrogen atom, a sulfur atom and an oxygen atom.

Preferable examples of the "aromatic heterocyclic group" include 5- or 6-membered monocyclic aromatic heterocyclic groups such as thienyl, furyl, pyrrolyl, imidazolyl, pyrazolyl, triazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, triazinyl and the like; and
8- to 14-membered fused polycyclic (preferably bi or tricyclic) aromatic heterocyclic groups such as benzothiophenyl, benzofuranyl, benzimidazolyl, benzoxazolyl, benzisoxazolyl, benzothiazolyl, benzisothiazolyl, benzotriazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, naphtho[2,3-b]thienyl, phenoxathiinyl, indolyl, isoindolyl, 1H-indazolyl, purinyl, isoquinolyl, quinolyl, phthalazinyl, naphthyridinyl, quinoxalinyl, quinazolinyl, cinnolinyl, carbazolyl, β-carbolinyl, phenanthridinyl, acridinyl, phenazinyl, phenothiazinyl, phenoxazinyl and the like.

In the present specification, examples of the "non-aromatic heterocyclic group" (including "3- to 14-membered non-aromatic heterocyclic group") include a 3- to 14-membered (preferably 4- to 10-membered) non-aromatic heterocyclic group containing, as a ring-constituting atom besides carbon atom, 1 to 4 hetero atoms selected from a nitrogen atom, a sulfur atom and an oxygen atom.

Preferable examples of the "non-aromatic heterocyclic group" include 3- to 8-membered monocyclic non-aromatic heterocyclic groups such as aziridinyl, oxiranyl, thiiranyl, azetidinyl, oxetanyl, thietanyl, tetrahydrothienyl, tetrahydrofuranyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydroisothiazolyl, tetrahydrooxazolyl, tetrahydroisooxazolyl, piperidinyl, piperazinyl, tetrahydropyridinyl, dihydropyridinyl, dihydrothiopyranyl, tetrahydropyrimidinyl, tetrahydropyridazinyl, dihydropyranyl, tetrahydropyranyl, tetrahydrothiopyranyl, morpholinyl, thiomorpholinyl, azepanyl, diazepanyl, azepinyl, oxepanyl, azocanyl, diazocanyl and the like; and
9- to 14-membered fused polycyclic (preferably bi or tricyclic) non-aromatic heterocyclic groups such as dihydrobenzofuranyl, dihydrobenzimidazolyl, dihydrobenzoxazolyl, dihydrobenzothiazolyl, dihydrobenzisothiazolyl, dihydronaphtho[2,3-b]thienyl, tetrahydroisoquinolyl, tetrahydroquinolyl, 4H-quinolizinyl, indolinyl, isoindolinyl, tetrahydrothieno[2,3-c]pyridinyl, tetrahydrobenzazepinyl, tetrahydroquinoxalinyl, tetrahydrophenanthridinyl, hexahydrophenothiazinyl, hexahydrophenoxazinyl, tetrahydrophthalazinyl, tetrahydronaphthyridinyl, tetrahydroquinazolinyl, tetrahydrocinnolinyl, tetrahydrocarbazolyl, tetrahydro-β-carbolinyl, tetrahydroacrydinyl, tetrahydrophenazinyl, tetrahydrothioxanthenyl, octahydroisoquinolyl and the like.

In the present specification, preferable examples of the "7- to 10-membered bridged heterocyclic group" include quinuclidinyl and 7-azabicyclo[2.2.1]heptanyl.

In the present specification, examples of the "nitrogen-containing heterocyclic group" include a "heterocyclic group" containing at least one nitrogen atom as a ring-constituting atom.

In the present specification, examples of the "optionally substituted heterocyclic group" include a heterocyclic group optionally having substituent(s) selected from the aforementioned substituent group A.

The number of the substituents in the "optionally substituted heterocyclic group" is, for example, 1 to 3. When the number of the substituents is two or more, the respective substituents may be the same or different.

In the present specification, examples of the "acyl group" include a formyl group, a carboxy group, a carbamoyl group, a thiocarbamoyl group, a sulfino group, a sulfo group, a sulfamoyl group and a phosphono group, each optionally having "1 or 2 substituents selected from a $C_{1-6}$ alkyl group, a $C_{2-6}$ alkenyl group, a $C_{3-10}$ cycloalkyl group, a $C_{3-10}$ cycloalkenyl group, a $C_{6-14}$ aryl group, a $C_{7-16}$ aralkyl group, a 5- to 14-membered aromatic heterocyclic group and a 3- to 14-membered non-aromatic heterocyclic group, each of which optionally has 1 to 3 substituents selected from a halogen atom, an optionally halogenated $C_{1-6}$ alkoxy group, a hydroxy group, a nitro group, a cyano group, an amino group and a carbamoyl group".

Examples of the "acyl group" also include a hydrocarbon-sulfonyl group, a heterocyclylsulfonyl group, a hydrocarbon-sulfinyl group and a heterocyclylsulfinyl group.

Here, the hydrocarbon-sulfonyl group means a hydrocarbon group-bonded sulfonyl group, the heterocyclylsulfonyl group means a heterocyclic group-bonded sulfonyl group, the hydrocarbon-sulfinyl group means a hydrocarbon group-bonded sulfinyl group and the heterocyclylsulfinyl group means a heterocyclic group-bonded sulfinyl group.

Preferable examples of the "acyl group" include a formyl group, a carboxy group, a $C_{1-6}$ alkyl-carbonyl group, a $C_{2-6}$ alkenyl-carbonyl group (e.g., crotonoyl), a $C_{3-10}$ cycloalkyl-carbonyl group (e.g., cyclobutanecarbonyl, cyclopentanecarbonyl, cyclohexanecarbonyl, cycloheptanecarbonyl), a $C_{3-10}$ cycloalkenyl-carbonyl group (e.g., 2-cyclohexenecarbonyl), a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a $C_{6-14}$ aryloxy-carbonyl group (e.g., phenyloxycarbonyl, naphthyloxycarbonyl), a $C_{7-16}$ aralkyloxy-carbonyl group (e.g., benzyloxycarbonyl, phenethyloxycarbonyl), a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl), a mono- or di-$C_{6-14}$ aryl-carbamoyl group (e.g., phenylcarbamoyl), a mono- or di-$C_{7-16}$ aralkyl-carbamoyl group, a 5- to 14-membered aromatic heterocyclylcarbamoyl group (e.g., pyridylcarbamoyl), a thiocarbamoyl group, a mono- or di-$C_{1-6}$ alkyl-thiocarbamoyl group (e.g., methylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a 5- to 14-membered aromatic heterocyclylthiocarbamoyl group (e.g., pyridylthiocarbamoyl), a sulfino group, a $C_{1-6}$ alkylsulfinyl group (e.g., methylsulfinyl, ethylsulfinyl), a sulfo group, a $C_{1-6}$ alkylsulfonyl group, a $C_{6-14}$ arylsulfonyl group, a phosphono group and a mono- or di-$C_{1-6}$ alkyl-phosphono group (e.g., dimethylphosphono, diethylphosphono, diisopropylphosphono, dibutylphosphono).

In the present specification, examples of the "optionally substituted amino group" include an amino group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from substituent group A".

Preferable examples of the optionally substituted amino group include an amino group, a mono- or di-(optionally halogenated $C_{1-6}$ alkyl)amino group (e.g., methylamino, trifluoromethylamino, dimethylamino, ethylamino, diethylamino, propylamino, dibutylamino), a mono- or di-$C_{2-6}$ alkenylamino group (e.g., diallylamino), a mono- or di-$C_{3-10}$ cycloalkylamino group (e.g., cyclopropylamino, cyclohexylamino), a mono- or di-$C_{6-14}$ arylamino group (e.g., phenylamino), a mono- or di-$C_{7-16}$ aralkylamino group (e.g., benzylamino, dibenzylamino), a mono- or di-(optionally halogenated $C_{1-6}$ alkyl)-carbonylamino group (e.g., acetylamino, propionylamino), a mono- or di-$C_{6-14}$ aryl-carbonylamino group (e.g., benzoylamino), a mono- or di-$C_{7-16}$ aralkyl-carbonylamino group (e.g., benzylcarbonylamino), a mono- or di-5- to 14-membered aromatic heterocyclylcarbonylamino group (e.g., nicotinoylamino, isonicotinoylamino), a mono- or di-3- to 14-membered non-aromatic heterocyclylcarbonylamino group (e.g., piperidinylcarbonylamino), a mono- or di-$C_{1-6}$ alkoxy-carbonylamino group (e.g., tert-butoxycarbonylamino), a 5- to 14-membered aromatic heterocyclylamino group (e.g., pyridylamino), a carbamoylamino group, a (mono- or di-$C_{1-6}$ alkyl-carbamoyl) amino group (e.g., methylcarbamoylamino), a (mono- or di-$C_{7-16}$ aralkyl-carbamoyl)amino group (e.g., benzylcarbamoylamino), a $C_{1-6}$ alkylsulfonylamino group (e.g., methylsulfonylamino, ethylsulfonylamino), a $C_{6-14}$ arylsulfonylamino group (e.g., phenylsulfonylamino), a ($C_{1-6}$ alkyl) ($C_{1-6}$ alkyl-carbonyl)amino group (e.g., N-acetyl-N-methylamino) and a ($C_{1-6}$ alkyl) ($C_{6-14}$ aryl-carbonyl)amino group (e.g., N-benzoyl-N-methylamino).

In the present specification, examples of the "optionally substituted carbamoyl group" include a carbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted carbamoyl group include a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl, cyclohexylcarbamoyl), a mono- or di-$C_{6-14}$ aryl-carbamoyl group (e.g., phenylcarbamoyl), a mono- or di-$C_{7-16}$ aralkyl-carbamoyl group, a mono- or di-$C_{1-6}$ alkyl-carbonyl-carbamoyl group (e.g., acetylcarbamoyl, propionylcarbamoyl), a mono- or di-$C_{6-14}$ aryl-carbonyl-carbamoyl group (e.g., benzoylcarbamoyl) and a 5- to 14-membered aromatic heterocyclylcarbamoyl group (e.g., pyridylcarbamoyl).

In the present specification, examples of the "optionally substituted thiocarbamoyl group" include a thiocarbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{716}$ aralkyl-carbamoyl group, each of which optionally has 1 to 3 substituents selected from substituent group A".

Preferable examples of the optionally substituted thiocarbamoyl group include a thiocarbamoyl group, a mono- or di-$C_{1-6}$ alkyl-thiocarbamoyl group (e.g., methylthiocarbamoyl, ethylthiocarbamoyl, dimethylthiocarbamoyl, diethylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{716}$ aralkyl-thiocarbamoyl group (e.g., benzylthiocarbamoyl, phenethylthiocarbamoyl), a mono- or di-$C_{1-6}$ alkyl-carbonyl-thiocarbamoyl group (e.g., acetylthiocarbamoyl, propionylthiocarbamoyl), a mono- or di-$C_{6-14}$ aryl-carbonyl-thiocarbamoyl group (e.g., benzoylthiocarbamoyl) and a 5- to 14-membered aromatic heterocyclylthiocarbamoyl group (e.g., pyridylthiocarbamoyl).

In the present specification, examples of the "optionally substituted sulfamoyl group" include a sulfamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted sulfamoyl group include a sulfamoyl group, a mono- or di-$C_{1-6}$ alkyl-sulfamoyl group (e.g., methylsulfamoyl, ethylsulfamoyl, dimethylsulfamoyl, diethylsulfamoyl, N-ethyl-N-methylsulfamoyl), a mono- or di-$C_{2-6}$ alkenyl-sulfamoyl group (e.g., diallylsulfamoyl), a mono- or di-$C_{3-10}$ cycloalkyl-sulfamoyl group (e.g., cyclopropylsulfamoyl, cyclohexylsulfamoyl), a mono- or di-$C_{6-14}$ aryl-sulfamoyl group (e.g., phenylsulfamoyl), a mono- or di-$C_{7-16}$ aralkyl-sulfamoyl group (e.g., benzylsulfamoyl, phenethylsulfamoyl), a mono- or di-$C_{1-6}$ alkyl-carbonyl-sulfamoyl group (e.g., acetylsulfamoyl, propionylsulfamoyl), a mono- or di-$C_{6-14}$ aryl-carbonyl-sulfamoyl group (e.g., benzoylsulfamoyl) and a 5- to 14-membered aromatic heterocyclylsulfamoyl group (e.g., pyridylsulfamoyl).

In the present specification, examples of the "optionally substituted hydroxy group" include a hydroxyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from substituent group A".

Preferable examples of the optionally substituted hydroxy group include a hydroxy group, a $C_{1-6}$ alkoxy group, a $C_{2-6}$ alkenyloxy group (e.g., allyloxy, 2-butenyloxy, 2-pentenyloxy, 3-hexenyloxy), a $C_{3-10}$ cycloalkyloxy group (e.g., cyclohexyloxy), a $C_{6-14}$ aryloxy group (e.g., phenoxy, naphthyloxy), a $C_{7-16}$ aralkyloxy group (e.g., benzyloxy, phenethyloxy), a $C_{1-6}$ alkyl-carbonyloxy group (e.g., acetyloxy, propionyloxy, butyryloxy, isobutyryloxy, pivaloyloxy), a $C_{6-14}$ aryl-carbonyloxy group (e.g., benzoyloxy), a $C_{7-16}$ aralkyl-carbonyloxy group (e.g., benzylcarbonyloxy), a 5- to 14-membered aromatic heterocyclylcarbonyloxy group (e.g., nicotinoyloxy), a 3- to 14-membered non-aromatic heterocyclylcarbonyloxy group (e.g., piperidinylcarbonyloxy), a $C_{1-6}$ alkoxy-carbonyloxy group (e.g., tert-butoxycarbonyloxy), a 5- to 14-membered aromatic heterocyclyloxy group (e.g., pyridyloxy), a carbamoyloxy group, a $C_{1-6}$ alkyl-carbamoyloxy group (e.g., methylcarbamoyloxy), a $C_{7-16}$ aralkyl-carbamoyloxy group (e.g., benzylcarbamoyloxy), a $C_{1-6}$ alkylsulfonyloxy group (e.g., methylsulfonyloxy, ethylsulfonyloxy) and a $C_{6-14}$ arylsulfonyloxy group (e.g., phenylsulfonyloxy).

In the present specification, examples of the "optionally substituted sulfanyl group" include a sulfanyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group and a 5- to 14-membered aromatic heterocyclic group, each of which optionally has 1 to 3 substituents selected from substituent group A" and a halogenated sulfanyl group.

Preferable examples of the optionally substituted sulfanyl group include a sulfanyl (—SH) group, a $C_{1-6}$ alkylthio group, a $C_{2-6}$ alkenylthio group (e.g., allylthio, 2-butenylthio, 2-pentenylthio, 3-hexenylthio), a $C_{3-10}$ cycloalkylthio group (e.g., cyclohexylthio), a $C_{6-14}$ arylthio group (e.g., phenylthio, naphthylthio), a $C_{7-16}$ aralkylthio group (e.g., benzylthio, phenethylthio), a $C_{1-6}$ alkyl-carbonylthio group (e.g., acetylthio, propionylthio, butyrylthio, isobutyrylthio, pivaloylthio), a $C_{6-14}$ aryl-carbonylthio group (e.g., benzoylthio), a 5- to 14-membered aromatic heterocyclylthio group (e.g., pyridylthio) and a halogenated thio group (e.g., pentafluorothio).

In the present specification, examples of the "optionally substituted silyl group" include a silyl group optionally having "1 to 3 substituents selected from a $C_{1-6}$ alkyl group, a $C_{2-6}$ alkenyl group, a $C_{3-10}$ cycloalkyl group, a $C_{6-14}$ aryl group and a $C_{7-16}$ aralkyl group, each of which optionally has 1 to 3 substituents selected from substituent group A".

Preferable examples of the optionally substituted silyl group include a tri-$C_{1-6}$ alkylsilyl group (e.g., trimethylsilyl, tert-butyl(dimethyl)silyl).

In the present specification, examples of the "$C_{1-6}$ alkylene group" include —$CH_2$—, —$(CH_2)_2$—, —$(CH_2)_3$—, —$(CH_2)_4$—, —$(CH_2)_5$—, —$(CH_2)_6$—, —$CH(CH_3)$—, —$C(CH_3)_2$—, —$CH(C_2H_5)$—, —$CH(C_3H_7)$—, —$CH(CH(CH_3)_2)$—, —$(CH(CH_3))_2$—, —$CH_2$—$CH(CH_3)$—, —$CH(CH_3)$—$CH_2$—, —$CH_2$—$CH_2$—$C(CH_3)_2$—, —$C(CH_3)_2$—$CH_2$—$CH_2$—, —$CH_2$—$CH_2$—$CH_2$—$C(CH_3)_2$— and —$C(CH_3)_2$—$CH_2$—$CH_2$—$CH_2$—.

In the present specification, examples of the "hydrocarbon ring" include a $C_{6-14}$ aromatic hydrocarbon ring, $C_{3-10}$ cycloalkane and $C_{3-10}$ cycloalkene.

In the present specification, examples of the "$C_{6-14}$ aromatic hydrocarbon ring" include benzene and naphthalene.

In the present specification, examples of the "$C_{3-10}$ cycloalkane" include cyclopropane, cyclobutane, cyclopentane, cyclohexane, cycloheptane and cyclooctane.

In the present specification, examples of the "$C_{3-10}$ cycloalkene" include cyclopropene, cyclobutene, cyclopentene, cyclohexene, cycloheptene and cyclooctene.

In the present specification, examples of the "heterocycle" include an aromatic heterocycle and a non-aromatic heterocycle, each containing, as a ring-constituting atom besides carbon atom, 1 to 4 hetero atoms selected from a nitrogen atom, a sulfur atom and an oxygen atom.

In the present specification, examples of the "aromatic heterocycle" include a 5- to 14-membered (preferably 5- to 10-membered) aromatic heterocycle containing, as a ring-constituting atom besides carbon atom, 1 to 4 hetero atoms selected from a nitrogen atom, a sulfur atom and an oxygen atom. Preferable examples of the "aromatic heterocycle" include 5- or 6-membered monocyclic aromatic heterocycles such as thiophene, furan, pyrrole, imidazole, pyrazole, thiazole, isothiazole, oxazole, isoxazole, pyridine, pyrazine, pyrimidine, pyridazine, 1,2,4-oxadiazole, 1,3,4-oxadiazole, 1,2,4-thiadiazole, 1,3,4-thiadiazole, triazole, tetrazole, triazine and the like; and 8- to 14-membered fused polycyclic (preferably bi or tricyclic) aromatic heterocycles such as benzothiophene, benzofuran, benzimidazole, benzoxazole, benzisoxazole, benzothiazole, benzisothiazole, benzotriazole, imidazopyridine, thienopyridine, furopyridine, pyrrolopyridine, pyrazolopyridine, oxazolopyridine, thiazolopyridine, imidazopyrazine, imidazopyrimidine, thienopyrimidine, furopyrimidine, pyrrolopyrimidine, pyrazolopyrimidine, oxazolopyrimidine, thiazolopyrimidine, pyrazolopyrimidine, pyrazolotriazine, naphtho[2,3-b]thiophene, phenoxathiin, indole, isoindole, 1H-indazole, purine, isoquinoline, quinoline, phthalazine, naphthyridine, quinoxaline, quinazoline, cinnoline, carbazole, β-carboline, phenanthridine, acridine, phenazine, phenothiazine, phenoxazine and the like.

In the present specification, examples of the "non-aromatic heterocycle" include a 3- to 14-membered (preferably 4- to 10-membered) non-aromatic heterocycle containing, as a ring-constituting atom besides carbon atom, 1 to 4 hetero atoms selected from a nitrogen atom, a sulfur atom and an oxygen atom. Preferable examples of the "non-aromatic heterocycle" include 3- to 8-membered monocyclic non-aromatic heterocycles such as aziridine, oxirane, thiirane, azetidine, oxetane, thietane, tetrahydrothiophene, tetrahydrofuran, pyrroline, pyrrolidine, imidazoline, imidazolidine, oxazoline, oxazolidine, pyrazoline, pyrazolidine, thiazoline, thiazolidine, tetrahydroisothiazole, tetrahydrooxazole, tetrahydroisoxazole, piperidine, piperazine, tetrahydropyridine, dihydropyridine, dihydrothiopyran, tetrahydropyrimidine, tetrahydropyridazine, dihydropyran, tetrahydropyran, tetrahydrothiopyran, morpholine, thiomorpholine, azepanine, diazepane, azepine, azocane, diazocane, oxepane and the like; and 9- to 14-membered fused polycyclic (preferably bi or tricyclic) non-aromatic heterocycles such as dihydrobenzofuran, dihydrobenzimidazole, dihydrobenzoxazole, dihydrobenzothiazole, dihydrobenzisothiazole, dihydronaphtho[2,3-b]thiophene, tetrahydroisoquinoline, tetrahydroquinoline, 4H-quinolizine, indoline, isoindoline, tetrahydrothieno[2,3-c]pyridine, tetrahydrobenzazepine, tetrahydroquinoxaline, tetrahydrophenanthridine, hexahydrophenothiazine, hexahydrophenoxazine, tetrahydrophthalazine, tetrahydronaphthyridine, tetrahydroquinazoline, tetrahydrocinnoline, tetrahydrocarbazole, tetrahydro-β-carboline, tetrahydroacridine, tetrahydrophenazine, tetrahydrothioxanthene, octahydroisoquinoline and the like.

In the present specification, examples of the "nitrogen-containing heterocycle" include a "heterocycle" containing at least one nitrogen atom as a ring-constituting atom.

Hereinafter, each symbol of the formula (I) will be described.

Ring A represents an optionally substituted 5- or 6-membered aromatic ring, and the substituent of ring A optionally forms an optionally substituted ring together with constituent atoms of ring A.

Specifically, ring A may be an optionally substituted condensed ring formed by a 5- or 6-membered aromatic ring and its substituent. In this context, examples of the condensed ring include 2,3-dihydrobenzofuran, benzofuran, 1,2,3,4-tetrahydronaphthalene, naphthalene, 2,3-dihydroindene, and benzothiophene. Among them, 2,3-dihydrobenzofuran is preferred.

Examples of the substituent on the condensed ring include 1 to 3 substituents selected from substituent group A. The substituent on the condensed ring may be present at any position on the condensed ring.

Examples of the "optionally substituted 5- or 6-membered aromatic ring" represented by ring A include a benzene ring and a 5- or 6-membered monocyclic aromatic heterocyclic ring (e.g., pyridine and thiophene) each optionally having a substituent selected from substituent group A. The number of substituents on the "optionally substituted 5- or 6-membered aromatic ring" is, for example, 1 to 5, preferably 1 to 3. When the number of substituents is 2 or more, these substituents may be the same or different.

Ring A is preferably an optionally substituted benzene ring, 2,3-dihydrobenzofuran, pyridine, or thiophene.

Ring A is more preferably
(1) a benzene ring optionally substituted by 1 to 3 substituents selected from
1) a halogen atom (e.g., fluorine and chlorine),
2) a carboxy group,
3) a cyano group,
4) a carbamoyl group optionally substituted by a $C_{6-14}$ aryl group (e.g., phenyl) optionally substituted by 1 to 3 substituents selected from a sulfo group; and a $C_{1-6}$ alkyl group (e.g., methyl) optionally substituted by a mono- or di-$C_{1-6}$ alkylphosphono group (e.g., a diethylphosphono group),
5) 3- to 14-membered nonaromatic heterocyclylcarbonyl (e.g., pyrrolidinylcarbonyl (particularly, 1-pyrrolidinylcarbonyl) and piperidinylcarbonyl (particularly, 1-piperidinylcarbonyl)) optionally substituted by 1 to 3 substituents selected from a carboxy group; and a mono- or di-$C_{1-6}$ alkyl-carbamoyl group substituted by 1 or 2 carboxy groups,
6) a 3- to 14-membered nonaromatic heterocyclic group (e.g., dihydrooxazolyl (particularly, 4,5-dihydro-1,2-oxazol-3-yl)) optionally substituted by 1 to 3 substituents selected from a $C_{1-6}$ alkyl group (e.g., methyl) substituted by 1 or 2 carboxy groups; and a carboxy group,
7) a $C_{1-6}$ alkyl group (e.g., methyl and ethyl) optionally substituted by 1 to 3 substituents selected from a mono- or di-$C_{1-6}$ alkyl-carbamoyl group substituted by 1 to 3 substituents selected from a carboxy group, a hydroxy-phenyl group, and a carbamoyl group; a $C_{1-6}$ alkoxy-carbonyl group; and a carboxy group,
8) a $C_{1-6}$ alkoxy group (e.g., methoxy) optionally substituted by a mono- or di-$C_{1-6}$ alkyl-carbamoyl group substituted by 1 or 2 carboxy groups,
9) a mono- or di-$C_{1-6}$ alkyl (e.g., methyl and ethyl)-carbamoyl group optionally substituted by 1 to 3 substituents selected from
  (a) a carboxy group;
  (b) a sulfo group;
  (c) a hydroxy group;
  (d) a $C_{1-6}$ alkoxy group (e.g., methoxy) optionally substituted by a phenyl group;
  (e) a $C_{1-6}$ alkoxy-carbonyl group (e.g., methoxycarbonyl);
  (f) a guanidino group;
  (g) a $C_{6-14}$ aryl group (e.g., phenyl) optionally substituted by 1 to 3 substituents selected from
    (g-1) a hydroxy group,
    (g-2) a carboxy group,
    (g-3) a $C_{1-6}$ alkoxy group (e.g., methoxy),
    (g-4) a $C_{1-6}$ alkyl group (e.g., methyl) substituted by a carboxy group,
    (g-5) a $C_{1-6}$ alkyl group (e.g., methyl) substituted by a mono- or di-$C_{1-6}$ alkyl-amino group (e.g., methyl) substituted by 1 or 2 carboxy groups, and
    (g-6) a mono- or di-$C_{1-6}$ alkyl-amino-$C_{1-6}$ alkoxy group (e.g., methoxy) substituted by 1 or 2 substituents selected from a carboxy group and a phenyl group;
  (h) a thienyl group optionally substituted by 1 or 2 carboxy group;
  (i) a pyridinyl group optionally substituted by a mono- or di-$C_{1-6}$ alkyl-amino-$C_{1-6}$ alkyl group (e.g., methyl) substituted by 1 or 2 carboxy groups;
  (j) a $C_{1-6}$ alkyl-amino group substituted by 1 or 2 carboxy groups;
  (k) a carbamoyl group optionally substituted by 1 or 2 $C_{1-6}$ alkyl groups (e.g., methyl) substituted by 1 or 2 substituents selected from a carboxy group and a carboxy-phenyl group; and
  (l) a phosphono group; and
10) a $C_{3-10}$ cycloalkyl group,
(2) 2,3-dihydrobenzofuran optionally substituted by 1 to 3 substituents selected from
1) a mono- or di-$C_{1-6}$ alkyl-carbamoyl group optionally substituted by 1 to 3 substituents selected from a carboxy group and a sulfo group, and
2) a $C_{1-6}$ alkyl group optionally substituted by a mono- or di-$C_{1-6}$ alkyl-carbamoyl group substituted by 1 to 3 substituents selected from a carboxy group and a sulfo group,
(3) pyridine optionally substituted by $C_{1-6}$ alkyl optionally substituted by a mono- or di-$C_{1-6}$ alkyl-carbamoyl group substituted by 1 or 2 carboxy groups, or
(4) thiophene optionally substituted by a mono- or di-$C_{1-6}$ alkyl-carbamoyl group optionally substituted by 1 or 2 carboxy groups.

Among (1) to (4) described above, (1) is preferred as ring A.

In another embodiment, ring A is preferably
(1) a benzene ring optionally substituted by 1 to 3 substituents selected from
1) a halogen atom (e.g., fluorine),
2) a carboxy group,
3) a carbamoyl group optionally substituted by a $C_{6-14}$ aryl group (e.g., phenyl) optionally substituted by 1 to 3 substituents selected from a sulfo group; and a $C_{1-6}$ alkyl group (e.g., methyl) optionally substituted by a mono- or di-$C_{1-6}$ alkylphosphono group (e.g., a diethylphosphono group),
4) 3- to 14-membered nonaromatic heterocyclylcarbonyl (e.g., pyrrolidinylcarbonyl) optionally substituted by a carboxy group,
5) a 3- to 14-membered nonaromatic heterocyclic group (e.g., 4,5-dihydro-1,2-oxazol-3-yl) optionally substituted by 1 to 3 substituents selected from a $C_{1-6}$ alkyl group (e.g., methyl) substituted by 1 or 2 carboxy groups; and a carboxy group,
6) a $C_{1-6}$ alkyl group (e.g., methyl and ethyl) optionally substituted by a mono- or di-$C_{1-6}$ alkyl-carbamoyl group substituted by 1 or 2 carboxy groups,
7) a $C_{1-6}$ alkoxy group (e.g., methoxy) optionally substituted by a mono- or di-$C_{1-6}$ alkyl-carbamoyl group substituted by 1 or 2 carboxy groups, and
8) a mono- or di-$C_{1-6}$ alkyl-carbamoyl group optionally substituted by 1 to 3 substituents selected from a carboxy group; a sulfo group; a $C_{1-6}$ alkoxy-carbonyl group (e.g., methoxycarbonyl); a guanidino group; a $C_{6-14}$ aryl group (e.g., phenyl) optionally substituted by a hydroxy group; a carbamoyl group; and a phosphono group,
(2) 2,3-dihydrobenzofuran optionally substituted by 1 to 3 substituents selected from
1) a mono- or di-$C_{1-6}$ alkyl-carbamoyl group optionally substituted by 1 to 3 substituents selected from a carboxy group and a sulfo group, and
2) a $C_{1-6}$ alkyl group optionally substituted by a mono- or di-$C_{1-6}$ alkyl-carbamoyl group substituted by 1 to 3 substituents selected from a carboxy group and a sulfo group,
(3) pyridine optionally substituted by $C_{1-6}$ alkyl optionally substituted by a mono- or di-$C_{1-6}$ alkyl-carbamoyl group substituted by 1 or 2 carboxy groups, or
(4) thiophene optionally substituted by a mono- or di-$C_{1-6}$ alkyl-carbamoyl group optionally substituted by 1 or 2 carboxy groups.

Ring A is more preferably a benzene ring optionally substituted by 1 to 3 substituents selected from
(1) a mono- or di-$C_{1-6}$ alkyl-carbamoyl group optionally substituted by 1 or 2 carboxy groups and further substituted by a sulfo group,
(2) a 3- to 14-membered nonaromatic heterocyclic group (e.g., 4,5-dihydro-1,2-oxazol-3-yl) optionally substituted by 1 to 3 substituents selected from a $C_{1-6}$ alkyl group (e.g., methyl) substituted by 1 or 2 carboxy groups, and a carboxy group, and
(3) a $C_{1-6}$ alkyl group (e.g., ethyl) optionally substituted by a mono- or di-$C_{1-6}$ alkyl-carbamoyl group substituted by 1 or 2 carboxy groups.

Ring A is particularly preferably a benzene ring substituted by a mono- or di-$C_{1-6}$ alkyl-carbamoyl group optionally substituted by 1 to 3 substituents selected from
(1) 1 or 2 carboxy groups,
(2) a phenyl group substituted by a $C_{1-6}$ alkoxy group (e.g., methoxy) or a carboxy group,
(3) a mono- or di-$C_{1-6}$ alkyl-carbamoyl group substituted by 1 or 2 carboxy groups, and
(4) mono- or di-$C_{1-6}$ alkyl-amino substituted by 1 or 2 carboxy groups.

In another embodiment, ring A is particularly preferably a benzene ring substituted by a mono- or di-$C_{1-6}$ alkyl-carbamoyl group substituted by 2 carboxy groups.

L represents a bond or a $C_{1-6}$ alkylene group (e.g., —CH$_2$—, —(CH$_2$)$_2$—, —(CH$_2$)$_3$—, —(CH$_2$)$_4$—, —CH(CH$_3$)—CH$_2$—CH$_2$—CH$_2$—, and —CH$_2$—CH(CH$_3$)—CH$_2$—CH$_2$—).

L is preferably a $C_{1-6}$ alkylene group (e.g., propylene and butylene), more preferably propylene.

$X_1$ and $X_2$ each represent —O— or a bond.

For $X_1$ and $X_2$, preferably, $X_1$ is a bond, and $X_2$ is —O—, or $X_1$ is a bond, and $X_2$ is a bond.

More preferably, $X_1$ is a bond, and $X_2$ is —O—.

R represents a guanidino group or an amidino group.

R is preferably a guanidino group.

One of $Y_1$ and $Y_2$ is —O—, and the other moiety is a bond.

When R is a guanidino group, $Y_1$ represents a bond and $Y_2$ represents —O—.

When R is an amidino group, $Y_1$ represents —O— and $Y_2$ represents a bond. Preferably, $Y_1$ is a bond, and $Y_2$ is —O—.

Preferred specific examples of compound (I) include the following:

[Compound A-0]

Compound (I) wherein
ring A is
(1) a benzene ring optionally substituted by 1 to 3 substituents selected from
1) a halogen atom (e.g., fluorine and chlorine),
2) a carboxy group,
3) a cyano group,
4) a carbamoyl group optionally substituted by a $C_{6-14}$ aryl group (e.g., phenyl) optionally substituted by 1 to 3 substituents selected from a sulfo group; and a $C_{1-6}$ alkyl group (e.g., methyl) optionally substituted by a mono- or di-$C_{1-6}$ alkylphosphono group (e.g., a diethylphosphono group),
5) 3- to 14-membered nonaromatic heterocyclylcarbonyl (e.g., pyrrolidinylcarbonyl (particularly, 1-pyrrolidinylcarbonyl) and piperidinylcarbonyl (particularly, 1-piperidinylcarbonyl)) optionally substituted by 1 to 3 substituents selected from a carboxy group; and a mono- or di-$C_{1-6}$ alkyl-carbamoyl group substituted by 1 or 2 carboxy groups,
6) a 3- to 14-membered nonaromatic heterocyclic group (e.g., dihydrooxazolyl (particularly, 4,5-dihydro-1,2-oxazol-3-yl)) optionally substituted by 1 to 3 substituents selected from a $C_{1-6}$ alkyl group (e.g., methyl) substituted by 1 or 2 carboxy groups; and a carboxy group,
7) a $C_{1-6}$ alkyl group (e.g., methyl and ethyl) optionally substituted by 1 to 3 substituents selected from a mono- or di-$C_{1-6}$ alkyl-carbamoyl group substituted by 1 to 3 substituents selected from a carboxy group, a hydroxy-phenyl group, and a carbamoyl group; a $C_{1-6}$ alkoxy-carbonyl group; and a carboxy group,
8) a $C_{1-6}$ alkoxy group (e.g., methoxy) optionally substituted by a mono- or di-$C_{1-6}$ alkyl-carbamoyl group substituted by 1 or 2 carboxy groups,
9) a mono- or di-$C_{1-6}$ alkyl (e.g., methyl and ethyl)-carbamoyl group optionally substituted by 1 to 3 substituents selected from
(a) a carboxy group;
(b) a sulfo group;
(c) a hydroxy group;
(d) a $C_{1-6}$ alkoxy group (e.g., methoxy) optionally substituted by a phenyl group;
(e) a $C_{1-6}$ alkoxy-carbonyl group (e.g., methoxycarbonyl);

(f) a guanidino group;
(g) a $C_{6-14}$ aryl group (e.g., phenyl) optionally substituted by 1 to 3 substituents selected from
  (g-1) a hydroxy group,
  (g-2) a carboxy group,
  (g-3) a $C_{1-6}$ alkoxy group (e.g., methoxy),
  (g-4) a $C_{1-6}$ alkyl group (e.g., methyl) substituted by a carboxy group,
  (g-5) a $C_{1-6}$ alkyl group (e.g., methyl) substituted by a mono- or di-$C_{1-6}$ alkyl-amino group substituted by 1 or 2 carboxy groups, and
  (g-6) a mono- or di-$C_{1-6}$ alkyl-amino-$C_{1-6}$ alkoxy group (e.g., methoxy) substituted by 1 or 2 substituents selected from a carboxy group and a phenyl group;
(h) a thienyl group optionally substituted by 1 or 2 carboxy group;
(i) a pyridinyl group optionally substituted by a mono- or di-$C_{1-6}$ alkyl-amino-$C_{1-6}$ alkyl group (e.g., methyl) substituted by 1 or 2 carboxy groups;
(j) a $C_{1-6}$ alkyl-amino group substituted by 1 or 2 carboxy groups;
(k) a carbamoyl group optionally substituted by 1 or 2 $C_{1-6}$ alkyl groups (e.g., methyl) substituted by 1 or 2 substituents selected from a carboxy group and a carboxy-phenyl group; and
(l) a phosphono group; and
10) a $C_{3-10}$ cycloalkyl group,
(2) 2,3-dihydrobenzofuran optionally substituted by 1 to 3 substituents selected from
1) a mono- or di-$C_{1-6}$ alkyl-carbamoyl group optionally substituted by 1 to 3 substituents selected from a carboxy group and a sulfo group, and
2) a $C_{1-6}$ alkyl group optionally substituted by a mono- or di-$C_{1-6}$ alkyl-carbamoyl group substituted by 1 to 3 substituents selected from a carboxy group and a sulfo group,
(3) pyridine optionally substituted by $C_{1-6}$ alkyl optionally substituted by a mono- or di-$C_{1-6}$ alkyl-carbamoyl group substituted by 1 or 2 carboxy groups, or
(4) thiophene optionally substituted by a mono- or di-$C_{1-6}$ alkyl-carbamoyl group optionally substituted by 1 or 2 carboxy group;
L is a $C_{1-6}$ alkylene group (e.g., —$CH_2$—, —$(CH_2)_2$—, —$(CH_2)_3$—, —$(CH_2)_4$—, —$CH(CH_3)$—$CH_2$—$CH_2$—$CH_2$—, and —$CH_2$—$CH(CH_3)$—$CH_2$—$CH_2$—) (preferably propylene);
$X_1$ is a bond, and $X_2$ is —O—;
R is a guanidino group; and
$Y_1$ is a bond, and $Y_2$ is —O—,
particularly, compound (I) wherein ring A is (1) among (1) to (4) described above.

[Compound A]
Compound (I) wherein
ring A is
(1) a benzene ring optionally substituted by 1 to 3 substituents selected from
1) a halogen atom (e.g., fluorine),
2) a carboxy group,
3) a carbamoyl group optionally substituted by a $C_{6-14}$ aryl group (e.g., phenyl) optionally substituted by 1 to 3 substituents selected from a sulfo group; and a $C_{1-6}$ alkyl group (e.g., methyl) optionally substituted by a mono- or di-$C_{1-6}$ alkylphosphono group (e.g., a diethylphosphono group),
4) 3- to 14-membered nonaromatic heterocyclylcarbonyl (e.g., pyrrolidinylcarbonyl) optionally substituted by a carboxy group,
5) a 3- to 14-membered nonaromatic heterocyclic group (e.g., 4,5-dihydro-1,2-oxazol-3-yl) optionally substituted by 1 to 3 substituents selected from a $C_{1-6}$ alkyl group (e.g., methyl) substituted by 1 or 2 carboxy groups; and a carboxy group,
6) a $C_{1-6}$ alkyl group (e.g., methyl and ethyl) optionally substituted by a mono- or di-$C_{1-6}$ alkyl-carbamoyl group substituted by 1 or 2 carboxy groups,
7) a $C_{1-6}$ alkoxy group (e.g., methoxy) optionally substituted by a mono- or di-$C_{1-6}$ alkyl-carbamoyl group substituted by 1 or 2 carboxy groups, and
8) a mono- or di-$C_{1-6}$ alkyl-carbamoyl group optionally substituted by 1 to 3 substituents selected from a carboxy group; a sulfo group; a $C_{1-6}$ alkoxy-carbonyl group (e.g., methoxycarbonyl); a guanidino group; a $C_{6-14}$ aryl group (e.g., phenyl) optionally substituted by a hydroxy group; a carbamoyl group; and a phosphono group,
(2) 2,3-dihydrobenzofuran optionally substituted by 1 to 3 substituents selected from
1) a mono- or di-$C_{1-6}$ alkyl-carbamoyl group optionally substituted by 1 to 3 substituents selected from a carboxy group and a sulfo group, and
2) a $C_{1-6}$ alkyl group optionally substituted by a mono- or di-$C_{1-6}$ alkyl-carbamoyl group substituted by 1 to 3 substituents selected from a carboxy group and a sulfo group,
(3) pyridine optionally substituted by $C_{1-6}$ alkyl optionally substituted by a mono- or di-$C_{1-6}$ alkyl-carbamoyl group substituted by 1 or 2 carboxy groups, or
(4) thiophene optionally substituted by a mono- or di-$C_{1-6}$ alkyl-carbamoyl group optionally substituted by 1 or 2 carboxy group; and
L is a $C_{1-6}$ alkylene group (e.g., —$CH_2$—, —$(CH_2)_2$—, —$(CH_2)_3$—, —$(CH_2)_4$—, —$CH(CH_3)$—$CH_2$—$CH_2$—$CH_2$—, and —$CH_2$—$CH(CH_3)$—$CH_2$—$CH_2$—).

[Compound A-1]
Compound (I) wherein
ring A is a benzene ring substituted by 1 or 2 substituents selected from
(1) $C_{1-6}$ alkyl-carbamoyl optionally substituted by 1 to 3 substituents selected from
1) a carboxy group,
2) a carbamoyl group,
3) a phenyl group optionally substituted by 1 to 3 substituents selected from
  a) a carboxy group,
  b) a $C_{1-6}$ alkoxy group,
  c) N-(carboxymethyl)-N-(carboxymethyl)amino-$C_{1-6}$ alkoxy,
  d) N-(carboxymethyl)-N-(carboxymethyl)amino-$C_{1-6}$ alkyl,
  e) (carboxymethyl)amino-$C_{1-6}$ alkoxy,
  f) N-(carboxymethyl)-N-(benzyl)amino-$C_{1-6}$ alkoxy, and
  g) a carboxymethyl group;
4) N-(carboxymethyl)-N-(carboxymethyl)amino,
5) N-(carboxymethyl)-N-(carboxymethyl)carbamoyl, and
6) N-(carboxymethyl)-N-(carboxyphenylmethyl)carbamoyl; and
(2) $C_{1-6}$ alkyl optionally substituted by a carboxy group;
L is propylene;
$X_1$ is a bond, and $X_2$ is —O—;
R is a guanidino group; and
$Y_1$ is a bond, and $Y_2$ is —O—.

[Compound B]
Compound (I) wherein
ring A is a benzene ring optionally substituted by 1 to 3 substituents selected from
(1) a mono- or di-$C_{1-6}$ alkyl-carbamoyl group optionally substituted by 1 or 2 carboxy groups and further substituted by a sulfo group, (2) a 5- to 14-membered nonaromatic heterocyclic group (e.g., 4,5-dihydro-1,2-oxazol-3-yl) optionally substituted by 1 to 3 substituents selected from a $C_{1-6}$ alkyl group (e.g., methyl) substituted by 1 or 2 carboxy groups, and a carboxy group, and (3) a $C_{1-6}$ alkyl group (e.g., ethyl) optionally substituted by a mono- or di-$C_{1-6}$ alkyl-carbamoyl group substituted by 1 or 2 carboxy groups;

L is propylene or butylene;
$X_1$ is a bond, and $X_2$ is —O—, or $X_1$ is a bond, and $X_2$ is a bond;
R is a guanidino group; and
$Y_1$ is a bond, and $Y_2$ is —O—.

[Compound B-1]
Compound (I) wherein
ring A is a benzene ring substituted by a mono- or di-$C_{1-6}$ alkyl-carbamoyl group optionally substituted by 1 to 3 substituents selected from
(1) 1 or 2 carboxy groups,
(2) a phenyl group substituted by a $C_{1-6}$ alkoxy group (e.g., methoxy) or a carboxy group,
(3) a $C_{1-6}$ alkyl-carbamoyl group substituted by 1 or 2 carboxy groups, and
(4) mono- or di-$C_{1-6}$ alkyl-amino substituted by 1 or 2 carboxy groups;
L is propylene or butylene;
$X_1$ is a bond, and $X_2$ is —O—;
R is a guanidino group; and
$Y_1$ is a bond, and $Y_2$ is —O—.

[Compound C]
Compound (I) wherein
ring A is a benzene ring substituted by a mono- or di-$C_{1-6}$ alkyl-carbamoyl group substituted by 2 carboxy groups;
L is propylene;
$X_1$ is a bond, and $X_2$ is —O—;
R is a guanidino group; and
$Y_1$ is a bond, and $Y_2$ is —O—.

[Compound D]
N-((10-Carbamimidamido-13-oxo-6,7,8,13-tetrahydrodibenzo[b,f][1,4]dioxecin-4-yl)carbonyl)-N-(carboxymethyl)-O-methyl-L-tyrosine or a salt thereof.
N-(2-(Bis(carboxymethyl)amino)ethyl)-N-((10-carbamimidamido-13-oxo-6,7,8,13-tetrahydrodibenzo[b,f][1,4]dioxecin-4-yl)carbonyl)glycine or a salt thereof.
N-((10-Carbamimidamido-13-oxo-6,7,8,13-tetrahydrodibenzo[b,f][1,4]dioxecin-4-yl)carbonyl)-N-(3-carboxybenzyl)-L-aspartic acid or a salt thereof.

Examples of the salt of the compound represented by the formula (I) include a metal salt, ammonium salt, a salt with an organic base, a salt with an inorganic acid, a salt with an organic acid, and a salt with a basic or acidic amino acid.

Preferred examples of the metal salt include: alkali metal salts such as sodium salt and potassium salt; alkaline earth metal salts such as calcium salt, magnesium salt, and barium salt; and aluminum salt.

Preferred examples of the salt with an organic base include a salt with trimethylamine, triethylamine, pyridine, picoline, 2,6-lutidine, ethanolamine, diethanolamine, triethanolamine, cyclohexylamine, dicyclohexylamine, or N,N-dibenzylethylenediamine.

Preferred examples of the salt with an inorganic acid include a salt with hydrochloric acid, hydrobromic acid, nitric acid, sulfuric acid, or phosphoric acid.

Preferred examples of the salt with an organic acid include a salt with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, or p-toluenesulfonic acid.

Preferred examples of the salt with a basic amino acid include a salt with arginine, lysine, or ornithine. Preferred examples of the salt with an acidic amino acid include a salt with aspartic acid or glutamic acid.

Among these salts, a pharmaceutically acceptable salt is preferred.

Compound (I) may be a prodrug.

The prodrug of compound (I) refers to a compound that is converted to the compound (I) through a reaction caused by an enzyme, gastric acid, or the like under physiological conditions in vivo, i.e., a compound that is converted to the compound (I) by enzymatic oxidation, reduction, hydrolysis, etc., or a compound that is converted to the compound (I) by hydrolysis, etc., caused by gastric acid or the like.

Examples of the prodrug of compound (I) include: a compound in which amino of the compound (I) is acylated, alkylated, or phosphorylated (e.g., a compound in which amino of the compound (I) is eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated, or tert-butylated); a compound in which hydroxy of the compound (I) is acylated, alkylated, phosphorylated, or borated (e.g., a compound in which hydroxy of the compound (I) is acetylated, palmitoylated, propanoylated, pivaloylated, succinylated, fumarylated, alanylated, or dimethylaminomethylcarbonylated); and a compound in which carboxy of the compound (I) is esterified or amidated (e.g., a compound in which carboxy of the compound (I) is $C_{1-6}$ alkyl-esterified, phenyl-esterified, carboxymethyl-esterified, dimethylaminomethyl-esterified, pivaloyloxymethyl-esterified, ethoxycarbonyloxyethyl-esterified, phthalidyl-esterified, (5-methyl-2-oxo-1,3-dioxolen-4-yl)methyl-esterified, cyclohexyloxycarbonylethyl-esterified, or methylamidated). Among them, a compound in which carboxy of the compound (I) is esterified with $C_{1-6}$ alkyl such as methyl, ethyl, or tert-butyl is preferably used. These compounds can be produced from the compound (I) by a method known per se in the art.

The prodrug of compound (I) may be converted to the compound (I) under physiological conditions as described in Iyakuhin No Kaihatsu (Development of Pharmaceuticals in English), Vol. 7, Molecular Design, p. 163-198, Hirokawa Shoten Ltd. (1990).

In the present specification, the prodrug may form a salt. Examples of such a salt include those listed above as the salt of the compound represented by the formula (I).

A method for producing the compound of the present invention will be described below.

A starting material or a reagent used in each step in the production method given below and the obtained compound may each form a salt. Examples of such a salt include the same as the aforementioned salt of the compound of the present invention.

When the compound obtained in each step is a free compound, this compound can be converted to a salt of interest by a method known per se in the art. On the contrary, when the compound obtained in each step is a salt, this salt can be converted to a free form or another type of salt of interest by a method known per se in the art.

The compound obtained in each step may be used in the next reaction in the form of its reaction solution or after being obtained as a crude product. Alternatively, the compound obtained in each step can be isolated and/or purified from the reaction mixture by a separation approach such as concentration, crystallization, recrystallization, distillation, solvent extraction, fractionation, or chromatography according to a routine method.

If a starting material or a reagent compound for each step is commercially available, the commercially available product can be used directly.

In the reaction of each step, the reaction time may differ depending on the reagent or the solvent used and is usually 1 minute to 48 hours, preferably 10 minutes to 8 hours, unless otherwise specified.

In the reaction of each step, the reaction temperature may differ depending on the reagent or the solvent used and is usually −78° C. to 300° C., preferably −78° C. to 150° C., unless otherwise specified.

In the reaction of each step, the pressure may differ depending on the reagent or the solvent used and is usually 1 atm to 20 atm, preferably 1 atm to 3 atm, unless otherwise specified.

In the reaction of each step, a microwave synthesis apparatus, for example, Initiator manufactured by Biotage Japan Ltd., may be used. The reaction temperature may differ depending on the reagent or the solvent used and is usually room temperature to 300° C., preferably 50° C. to 250° C., unless otherwise specified. The reaction time may differ depending on the reagent or the solvent used and is usually 1 minute to 48 hours, preferably 1 minute to 8 hours, unless otherwise specified.

In the reaction of each step, the reagent is used at 0.5 equivalents to 20 equivalents, preferably 0.8 equivalents to 5 equivalents, with respect to the substrate, unless otherwise specified. In the case of using the reagent as a catalyst, the reagent is used at 0.001 equivalents to 1 equivalent, preferably 0.01 equivalents to 0.2 equivalents, with respect to the substrate. When the reagent also serves as a reaction solvent, the reagent is used in the amount of the solvent.

In the reaction of each step, this reaction is carried out without a solvent or by dissolution or suspension in an appropriate solvent, unless otherwise specified. Specific examples of the solvent include solvents described in Examples and the following: alcohols: methanol, ethanol, tert-butyl alcohol, 2-methoxyethanol, and the like;
ethers: diethyl ether, diphenyl ether, tetrahydrofuran, 1,2-dimethoxyethane, and the like;
aromatic hydrocarbons: chlorobenzene, toluene, xylene, and the like;
saturated hydrocarbons: cyclohexane, hexane, and the like;
amides: N,N-dimethylformamide, N-methylpyrrolidone, and the like;
halogenated hydrocarbons: dichloromethane, carbon tetrachloride, and the like;
nitriles: acetonitrile and the like;
sulfoxides: dimethyl sulfoxide and the like;
aromatic organic bases: pyridine and the like;
acid anhydrides: acetic anhydride and the like;
organic acids: formic acid, acetic acid, trifluoroacetic acid, and the like;
inorganic acids: hydrochloric acid, sulfuric acid, and the like;
esters: ethyl acetate and the like;
ketones: acetone, methyl ethyl ketone, and the like; and water.

Two or more of these solvents may be used as a mixture at an appropriate ratio.

In the case of using a base in the reaction of each step, for example, the following base or a base described in Examples is used:

inorganic bases: sodium hydroxide, magnesium hydroxide, and the like;
basic salts: sodium carbonate, calcium carbonate, sodium bicarbonate, and the like;
organic bases: triethylamine, diethylamine, pyridine, 4-dimethylaminopyridine, N,N-dimethylaniline, 1,4-diazabicyclo[2.2.2]octane, 1,8-diazabicyclo[5.4.0]-7-undecene, imidazole, piperidine, and the like; metal alkoxides: sodium ethoxide, potassium tert-butoxide, and the like;
alkali metal hydrides: sodium hydride, and the like; metal amides: sodium amide, lithium diisopropylamide, lithium hexamethyldisilazide, and the like; and organic lithiums: n-butyllithium and the like.

In the case of using an acid or an acidic catalyst in the reaction of each step, for example, the following acid or acidic catalyst or an acid or an acidic catalyst described in Examples is used:

inorganic acids: hydrochloric acid, sulfuric acid, nitric acid, hydrobromic acid, phosphoric acid, and the like; organic acids: acetic acid, trifluoroacetic acid, citric acid, p-toluenesulfonic acid, 10-camphorsulfonic acid, and the like; and Lewis acids: boron trifluoride-diethyl ether complex, zinc iodide, anhydrous aluminum chloride, anhydrous zinc chloride, anhydrous iron chloride, and the like.

The reaction of each step is carried out according to a method known per se in the art, for example, a method described in The Fifth Series of Experimental Chemistry, Vol. 13 to Vol. 19 (edited by The Chemical Society of Japan); Shin Jikken Kagaku Koza (New Experimental Chemistry in English), Vol. 14 to Vol. 15 (edited by The Chemical Society of Japan); Syntheses in the Organic Chemistry Laboratory, Revised, 2nd Ed. (L. F. Tietze, Th. Eicher, Nankodo Co., Ltd.); Organic Name Reactions; The Reaction Mechanism and Essence, Revised (Hideo Tougo, Kodansha Ltd.); Organic Syntheses Collective Volume I to VII (John Wiley & Sons, Inc.); Modern Organic Synthesis in the Laboratory: A Collection of Standard Experimental Procedures (Jie Jack Li, Oxford University Press); Comprehensive Heterocyclic Chemistry III, Vol. 1 to Vol. 14 (Elsevier Japan KK); Strategic Applications of Named Reactions in Organic Synthesis (translated by Kiyoshi Tomioka, published by Kagaku-Dojin Publishing Company, Inc.); Comprehensive Organic Transformations (VCH Publishers, Inc.) (1989), etc., or a method described in Examples, unless otherwise specified.

In each step, the protection or deprotection reaction of a functional group is carried out according to a method known per se in the art, for example, a method described in "Protective Groups in Organic Synthesis, 4th Ed." (Theodora W. Greene, Peter G. M. Wuts), Wiley-Interscience (2007); "Protecting Groups, 3rd Ed." (P. J. Kocienski), Thieme Medical Publishers (2004), etc., or a method described in Examples.

Examples of a protective group for a hydroxy group or a phenolic hydroxy group in an alcohol or the like include: ether-type protective groups such as methoxy methyl ether, benzyl ether, t-butyl dimethyl silyl ether, and tetrahydropyranyl ether; carboxylic acid ester-type protective groups such as acetic acid ester; sulfonic acid ester-type protective groups such as methanesulfonic acid ester; and carbonic acid ester-type protective groups such as t-butyl carbonate.

Examples of a protective group for a carbonyl group in an aldehyde include: acetal-type protective groups such as dimethylacetal; and cyclic acetal-type protective groups such as cyclic 1,3-dioxane.

Examples of a protective group for a carbonyl group in a ketone include: ketal-type protective groups such as dimethylketal; cyclic ketal-type protective groups such as cyclic 1,3-dioxane; oxime-type protective groups such as O-methyloxime; and hydrazone-type protective groups such as N,N-dimethylhydrazone.

Examples of a protective group for a carboxyl group include: ester-type protective groups such as methyl ester; and amide-type protective groups such as N,N-dimethylamide.

Examples of a protective group for a thiol include: ether-type protective groups such as benzyl thioether; and ester-type protective groups such as thioacetic acid ester, thiocarbonate, and thiocarbamate.

Examples of a protective group for an amino group or an aromatic heterocyclic ring such as imidazole, pyrrole, or indole include: carbamate-type protective groups such as benzyl carbamate; amide-type protective groups such as acetamide; alkylamine-type protective groups such as N-triphenylmethylamine; and sulfonamide-type protective groups such as methanesulfonamide.

These protective groups can be removed by use of a method known per se in the art, for example, a method using an acid, a base, ultraviolet light, hydrazine, phenylhydrazine, sodium N-methyldithiocarbamate, tetrabutylammonium fluoride, palladium acetate, or trialkylsilyl halide (e.g., trimethylsilyl iodide and trimethylsilyl bromide), or a reduction method.

In the case of carrying out reduction reaction in each step, examples of the reducing agent used include: metal hydrides such as lithium aluminum hydride, sodium triacetoxyborohydride, sodium cyanoborohydride, diisobutyl aluminum hydride (DIBAL-H), sodium borohydride, and tetramethylammonium triacetoxyborohydride; boranes such as a borane-tetrahydrofuran complex; Raney nickel; Raney cobalt; hydrogen; and formic acid. In the case of reducing a carbon-carbon double bond or triple bond, a method using a catalyst such as palladium-carbon or a Lindlar's catalyst can be used.

In the case of carrying out oxidation reaction in each step, examples of the oxidizing agent used include: peracids such as m-chloroperbenzoic acid (MCPBA), hydrogen peroxide, and t-butyl hydroperoxide; perchlorates such as tetrabutylammonium perchlorate; chlorates such as sodium chlorate; chlorites such as sodium chlorite; periodates such as sodium periodate; high-valent iodine reagents such as iodosylbenzene; reagents having manganese, such as manganese dioxide and potassium permanganate; leads such as lead tetraacetate; reagents having chromium, such as pyridinium chlorochromate (PCC), pyridinium dichromate (PDC), and Jones reagents; halogen compounds such as N-bromosuccinimide (NBS); oxygen; ozone; a sulfur trioxide-pyridine complex; osmium tetroxide; selenium dioxide; and 2,3-dichloro-5,6-dicyano-1,4-benzoquinone (DDQ).

In the case of carrying out radical cyclization reaction in each step, examples of the radical initiator used include: azo compounds such as
azobisisobutyronitrile (AIBN); water-soluble radical initiators such as 4-4'-azobis-4-cyanopentanoic acid (ACPA); triethylboron in the presence of air or oxygen;
and benzoyl peroxide. Examples of the radical reaction agent used include tributylstannane, tristrimethylsilylsilane, 1,1,2,2-tetraphenyldisilane, diphenylsilane, and samarium iodide.

In the case of carrying out Wittig reaction in each step, examples of the Wittig reagent used include alkylidenephosphoranes. The alkylidenephosphoranes can be prepared by a method known per se in the art, for example, the reaction between a phosphonium salt and a strong base.

In the case of carrying out Horner-Emmons reaction in each step, examples of the reagent used include: phosphonoacetic acid esters such as methyl dimethylphosphonoacetate and ethyl diethylphosphonoacetate; and bases such as alkali metal hydrides and organic lithiums.

In the case of carrying out Friedel-Crafts reaction in each step, examples of the reagent used include a Lewis acid and an acid chloride or an alkylating agent (e.g., alkyl halides, alcohols, and olefins). Alternatively, an organic acid or an inorganic acid may be used instead of the Lewis acid, and an acid anhydride such as acetic anhydride may be used instead of the acid chloride.

In the case of carrying out aromatic nucleophilic substitution reaction in each step, a nucleophile (e.g., amines and imidazole) and a base (e.g., basic salts and organic bases) are used as reagents.

In the case of carrying out nucleophilic addition reaction using a carbanion, nucleophilic 1,4-addition reaction (Michael addition reaction) using a carbanion, or nucleophilic substitution reaction using a carbanion in each step, examples of the base used for generating the carbanion include organic lithiums, metal alkoxides, inorganic bases, and organic bases.

In the case of carrying out Grignard reaction in each step, examples of the Grignard reagent include: aryl magnesium halides such as phenyl magnesium bromide; and alkyl magnesium halides such as methyl magnesium bromide. The Grignard reagent can be prepared by a method known per se in the art, for example, the reaction between alkyl halide or aryl halide and metal magnesium with ether or tetrahydrofuran as a solvent.

In the case of carrying out Knoevenagel condensation reaction in each step, an active methylene compound flanked by two electron-attracting groups (e.g., malonic acid, diethyl malonate, and malononitrile) and a base (e.g., organic bases, metal alkoxides, and inorganic bases) are used as reagents.

In the case of carrying out Vilsmeier-Haack reaction in each step, phosphoryl chloride and an amide derivative (e.g., N,N-dimethylformamide) are used as reagents.

In the case of carrying out azidation reaction of alcohols, alkyl halides, or sulfonic acid esters in each step, examples of the azidating agent used include diphenylphosphorylazide (DPPA), trimethylsilylazide, and sodium azide. In the case of azidating, for example, alcohols, a method using diphenylphosphorylazide and 1,8-diazabicyclo[5.4.0]undec-7-ene (DBU), a method using trimethylsilylazide and a Lewis acid, or the like can be used.

In the case of carrying out reductive amination reaction in each step, examples of the reducing agent used include sodium triacetoxyborohydride, sodium cyanoborohydride, hydrogen, and formic acid. When the substrate is an amine compound, examples of the carbonyl compound used include p-formaldehyde as well as aldehydes such as acetaldehyde, and ketones such as cyclohexanone. When the substrate is a carbonyl compound, examples of the amines used include: primary amine such as ammonia and methylamine; and secondary amine such as dimethylamine.

In the case of carrying out Mitsunobu reaction in each step, azodicarboxylic acid esters (e.g., diethyl azodicarboxylate (DEAD) and diisopropyl azodicarboxylate (DIAD)) and triphenylphosphine are used as reagents.

In the case of carrying out esterification reaction, amidation reaction, or ureation reaction in each step, examples of the reagent used include: an acyl halide form of acid chloride, acid bromide, and the like; and activated carboxylic acids such as an acid anhydride, an active ester form, and a sulfuric acid ester form. Examples of the activator for carboxylic acid include: carbodiimide condensing agents such as 1-ethyl-3-(3-dimethylaminopropyl)carbodiimide hydrochloride (WSCD); triazine condensing agents such as 4-(4,6-dimethoxy-1,3,5-triazin-2-yl)-4-methylmorpholinium chloride-n-hydrate (DMT-MM); carbonic acid ester condensing agents such as 1,1-carbonyldiimidazole (CDI); diphenylphosphorylazide (DPPA); benzotriazol-1-yloxy-trisdimethylaminophosphonium salt (BOP reagent); 2-chloro-1-methyl-pyridinium iodide (Mukaiyama reagent); thionyl chloride; lower alkyl haloformate such as ethyl chloroformate; O-(7-azabenzotriazol-1-yl)-N,N,N',N'-tetramethyluronium hexafluorophosphate (HATU); sulfuric acid; and combinations thereof. In the case of using a carbodiimide condensing agent, an additive such as 1-hydroxybenzotriazole (HOBt), N-hydroxysuccinimide (HOSu), or dimethylaminopyridine (DMAP) may be further added for the reaction.

In the case of carrying out coupling reaction in each step, examples of the metal catalyst used include: palladium compounds such as palladium(II) acetate, tetrakis(triphenylphosphine)palladium(0), dichlorobis(triphenylphosphine) palladium(II), dichlorobis(triethylphosphine)palladium(II), tris(dibenzylideneacetone)dipalladium(0), and 1,1'-bis(diphenylphosphino)ferrocene palladium(II) chloride; nickel compounds such as tetrakis(triphenylphosphine)nickel(0); rhodium compounds such as tris(triphenylphosphine)rhodium(III) chloride; cobalt compounds; copper compounds such as copper oxide and copper(I) iodide; and platinum compounds. A base may be further added for the reaction. Examples of such a base include inorganic bases and basic salts.

In the case of carrying out thiocarbonylation reaction in each step, diphosphorus pentasulfide is typically used as a thiocarbonylating agent. A reagent having a 1,3,2,4-dithiadiphosphetane-2,4-disulfide structure such as 2,4-bis(4-methoxyphenyl-1,3,2,4-dithiadiphosphetane-2,4-disulfide (Lawesson's reagent) may be used instead of diphosphorus pentasulfide.

In the case of carrying out Wohl-Ziegler reaction in each step, examples of the halogenating agent used include N-iodosuccinimide, N-bromosuccinimide (NBS), N-chlorosuccinimide (NCS), bromine, and sulfuryl chloride. The reaction can be accelerated by the further addition of a radical initiator such as heat, light, benzoyl peroxide, or azobisisobutyronitrile for the reaction.

In the case of carrying out halogenation reaction of a hydroxy group in each step, examples of the halogenating agent used include a hydrohalic acid and an acid halide of an inorganic acid, specifically, hydrochloric acid, thionyl chloride, and phosphorus oxychloride for chlorination, and 48% hydrobromic acid for bromination. Also, a method for obtaining an alkyl halide form from an alcohol by the action of triphenylphosphine and carbon tetrachloride or carbon tetrabromide or the like may be used. Alternatively, a method for synthesizing an alkyl halide form through 2-stage reactions involving the conversion of an alcohol to sulfonic acid ester and the subsequent reaction with lithium bromide, lithium chloride, or sodium iodide may be used.

In the case of carrying out Arbuzov reaction in each step, examples of the reagent used include: alkyl halides such as ethyl bromoacetate; and phosphites such as triethyl phosphite and tri(isopropyl) phosphite.

In the case of carrying out sulfone-esterification reaction in each step, examples of the sulfonylating agent used include methanesulfonyl chloride, p-toluenesulfonyl chloride, methanesulfonic anhydride, and p-toluenesulfonic anhydride.

In the case of carrying out hydrolysis reaction in each step, an acid or a base is used as a reagent. In the case of carrying out acid hydrolysis reaction of t-butyl ester, formic acid, triethylsilane, or the like may be added in order to reductively trap a by-product t-butyl cation.

In the case of carrying out dehydration reaction in each step, examples of the dehydrating agent used include sulfuric acid, diphosphorus pentoxide, phosphorus oxychloride, N,N'-dicyclohexylcarbodiimide, alumina, and polyphosphoric acid.

Among the compounds (I), compound [1] can be produced by a method shown below from compound [1-1]. The compound [1] can be produced through guanidylation reaction of reacting compound [1-10] with cyanamide under acidic conditions. Also, some compounds [1] wherein ring A has a substituent can be produced by further carrying out various conversion reactions such as amidation reaction, protection, and deprotection for the substituent in their respective appropriate steps in the production method described below.

[Formula 11]

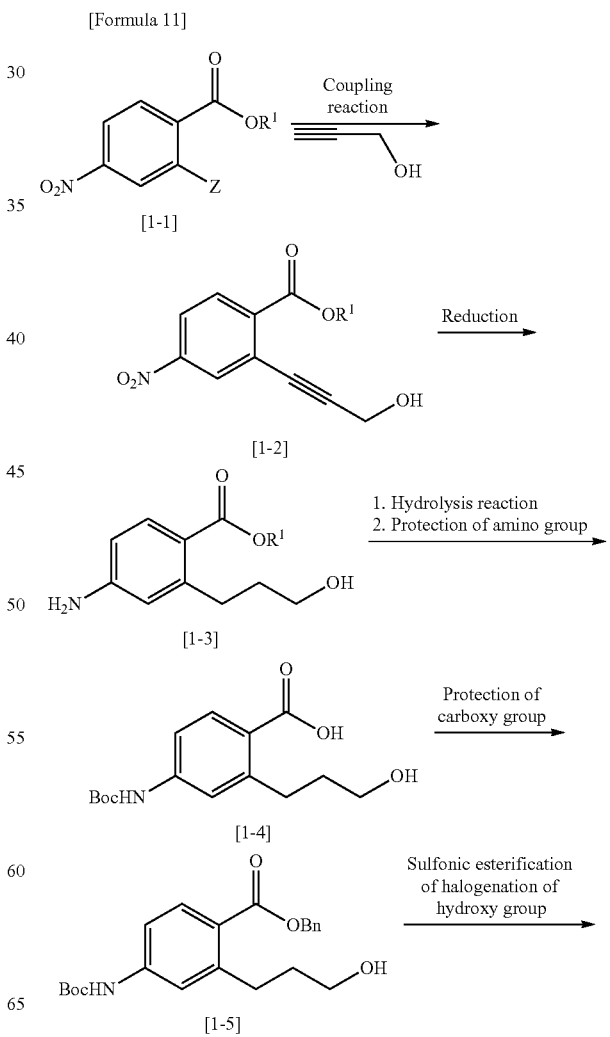

-continued

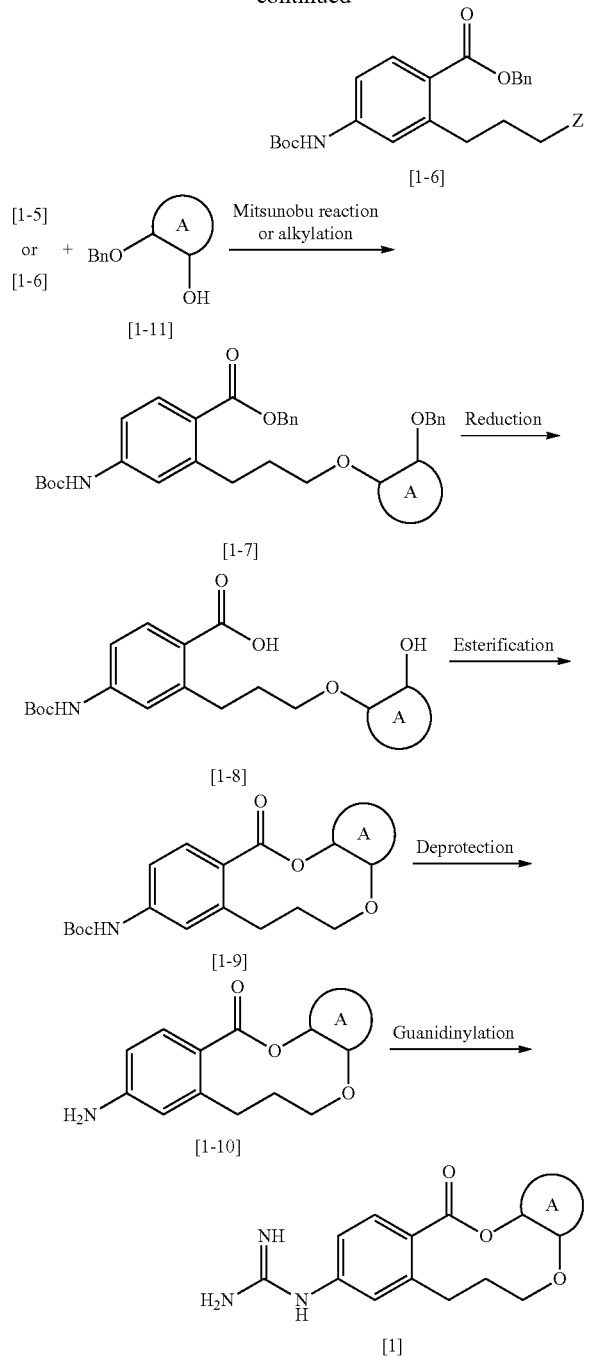

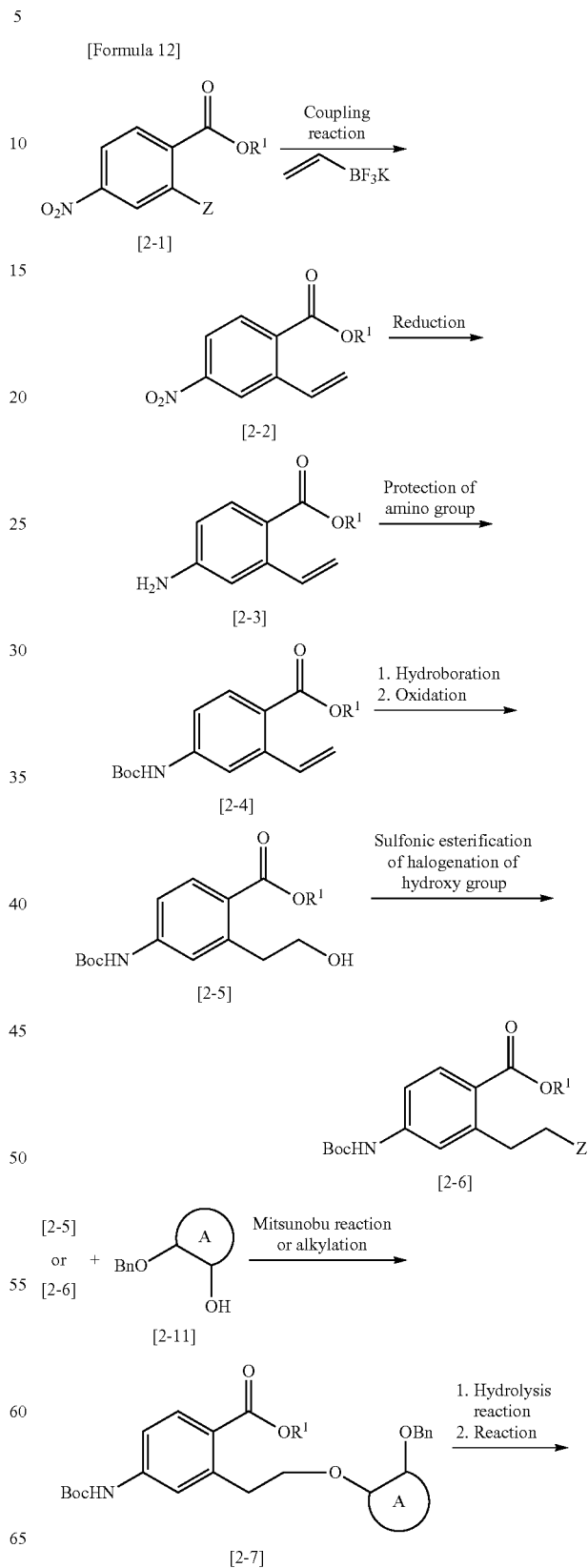

wherein $R^1$ represents a $C_{1-6}$ alkyl group, Z represents methanesulfonate, p-toluenesulfonate, trifluoromethanesulfonate, chloro, bromo, or iodine, and the other symbols are as defined above.

Among the compounds (I), compound [2] can be produced by a method shown below from compound [2-1]. The compound [2] can be produced by the Boc-protected guanidylation reaction of compound [2-10] followed by deprotection. Compound [2-5] can be produced by the hydroboration reaction of compound [2-4] followed by oxidation reaction. Also, some compounds [2] wherein ring A has a substituent can be produced by further carrying out various conversion reactions such as amidation reaction, protection, and deprotection for the substituent in their respective appropriate steps in the production method described below.

[Formula 12]

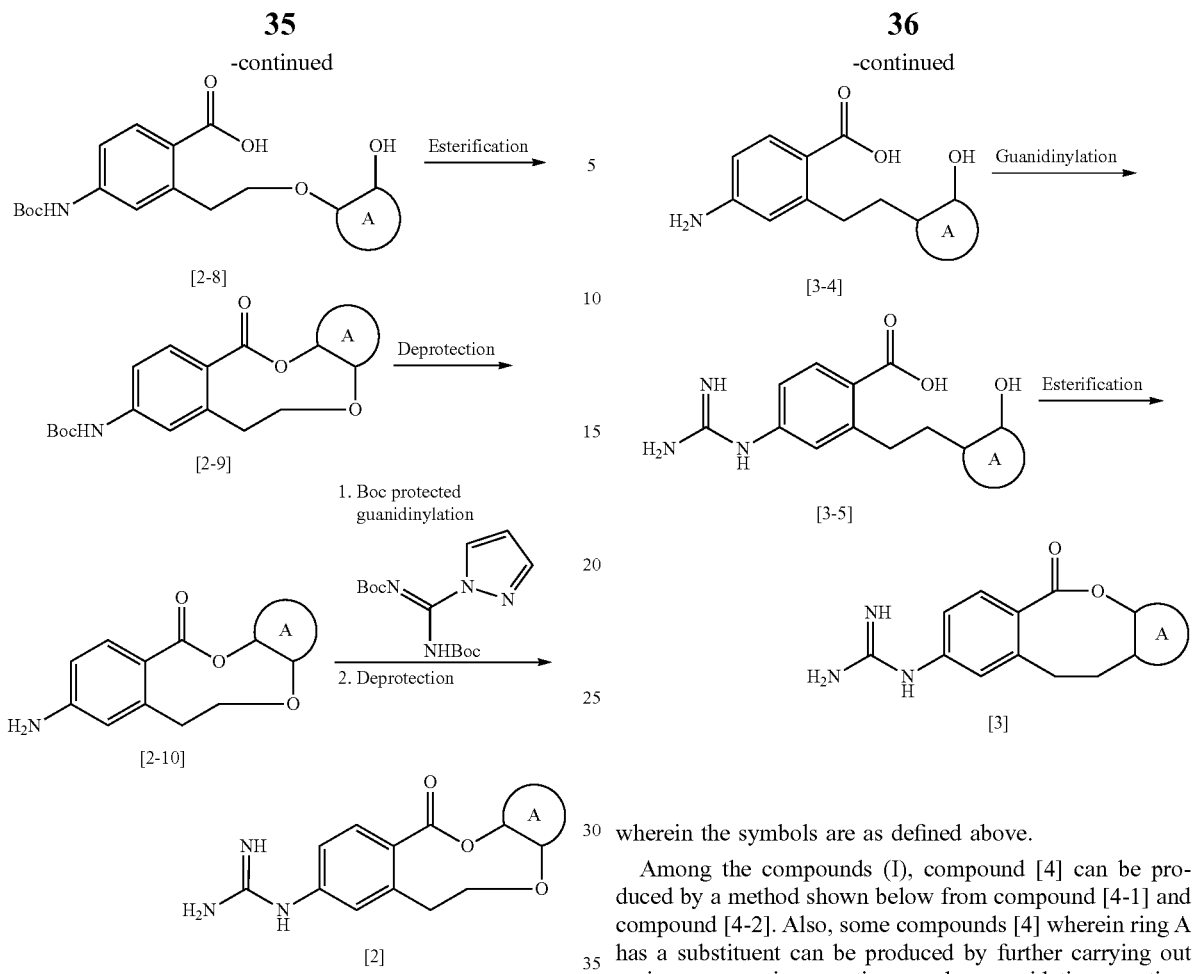

wherein the symbols are as defined above.

Among the compounds (I), compound [3] can be produced by a method shown below from compound [3-1] and compound [3-2]. Also, some compounds [3] wherein ring A has a substituent can be produced by further carrying out various conversion reactions such as amidation reaction, protection, and deprotection for the substituent in their respective appropriate steps in the production method described below.

[Formula 13]

wherein the symbols are as defined above.

Among the compounds (I), compound [4] can be produced by a method shown below from compound [4-1] and compound [4-2]. Also, some compounds [4] wherein ring A has a substituent can be produced by further carrying out various conversion reactions such as amidation reaction, protection, and deprotection for the substituent in their respective appropriate steps in the production method described below.

[Formula 14]

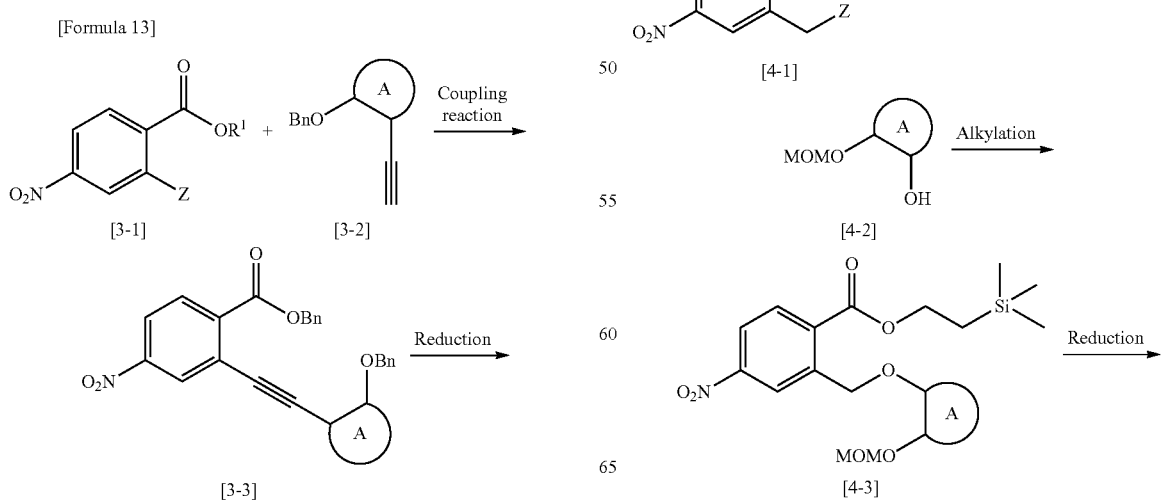

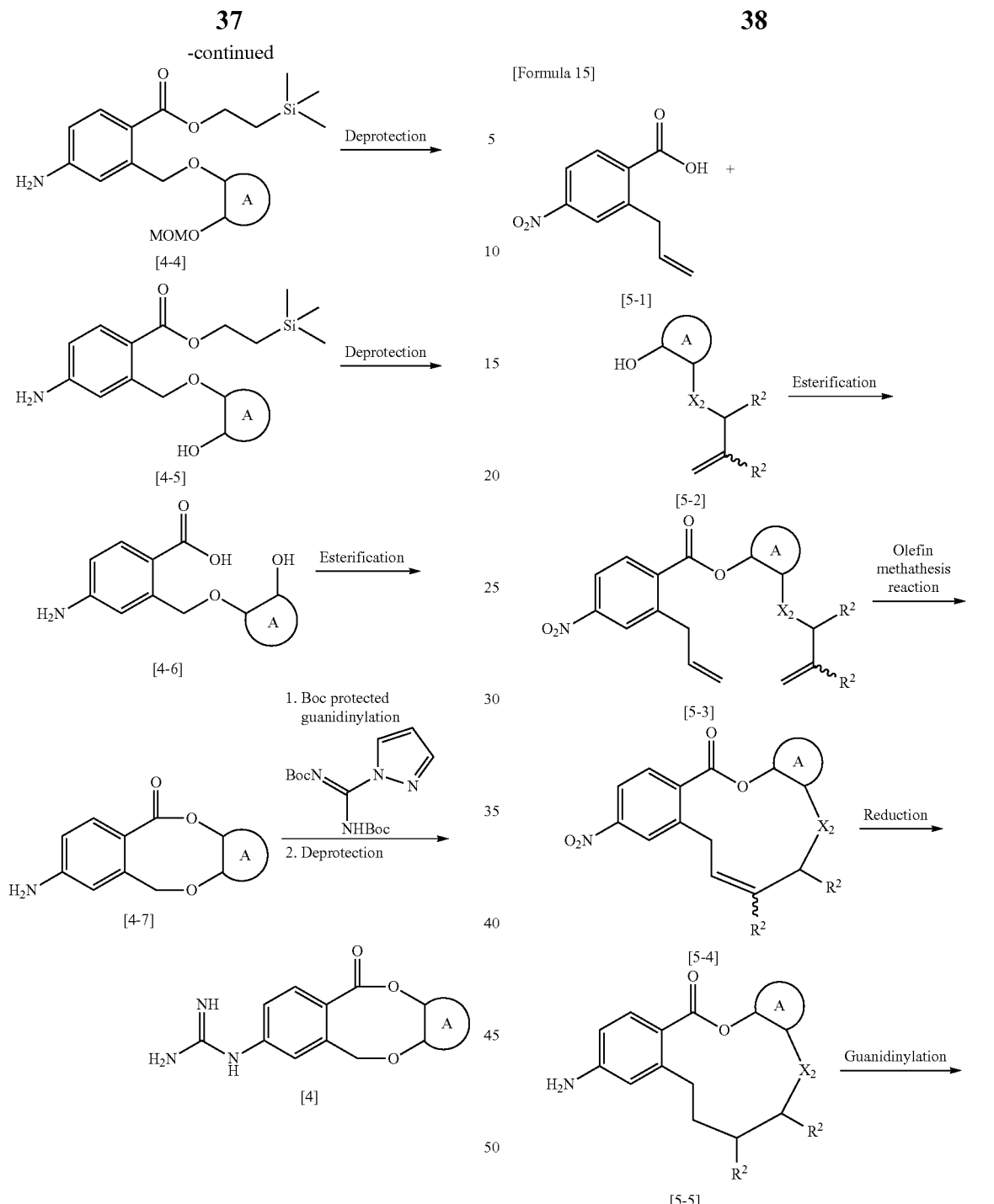

wherein the symbols are as defined above.

Among the compounds (I), compound [5] can be produced by a method shown below from compound [5-1] and compound [5-2]. Compound [5-4] can be produced through the olefin metathesis reaction of compound [5-3]. Examples of the reagent for the olefin metathesis reaction include first-generation Grubbs catalysts, second-generation Grubbs catalysts, and second-generation Hoveyda-Grubbs catalysts. Also, some compounds [5] wherein ring A has a substituent can be produced by further carrying out various conversion reactions such as amidation reaction, protection, and deprotection for the substituent in their respective appropriate steps in the production method described below.

wherein $R^2$ independently represents hydrogen or methyl, and the other symbols are as defined above.

Among the compounds (I), compound [6] can be produced by a method shown below from compound [6-1] and compound [6-2]. Also, some compounds [6] wherein ring A has a substituent can be produced by further carrying out various conversion reactions such as amidation reaction, protection, and deprotection for the substituent in their respective appropriate steps in the production method described below.

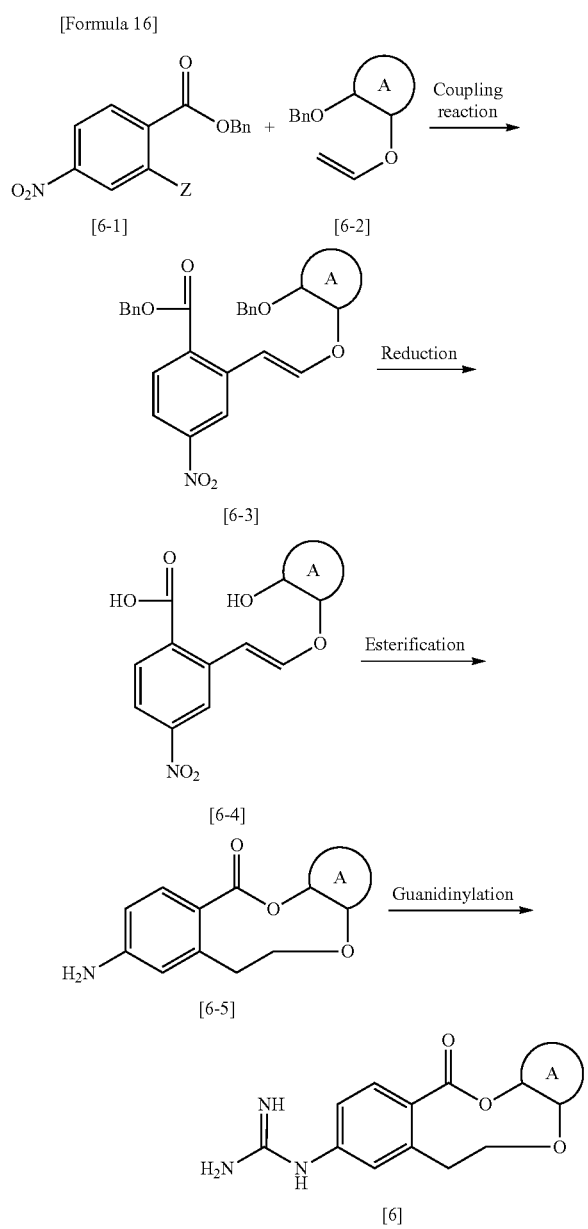

wherein the symbols are as defined above.

Among the compounds (I), compound [7] can be produced by a method shown below from compound [7-1]. Also, some compounds [7] wherein ring A has a substituent can be produced by further carrying out various conversion reactions such as amidation reaction, protection, and deprotection for the substituent in their respective appropriate steps in the production method described below.

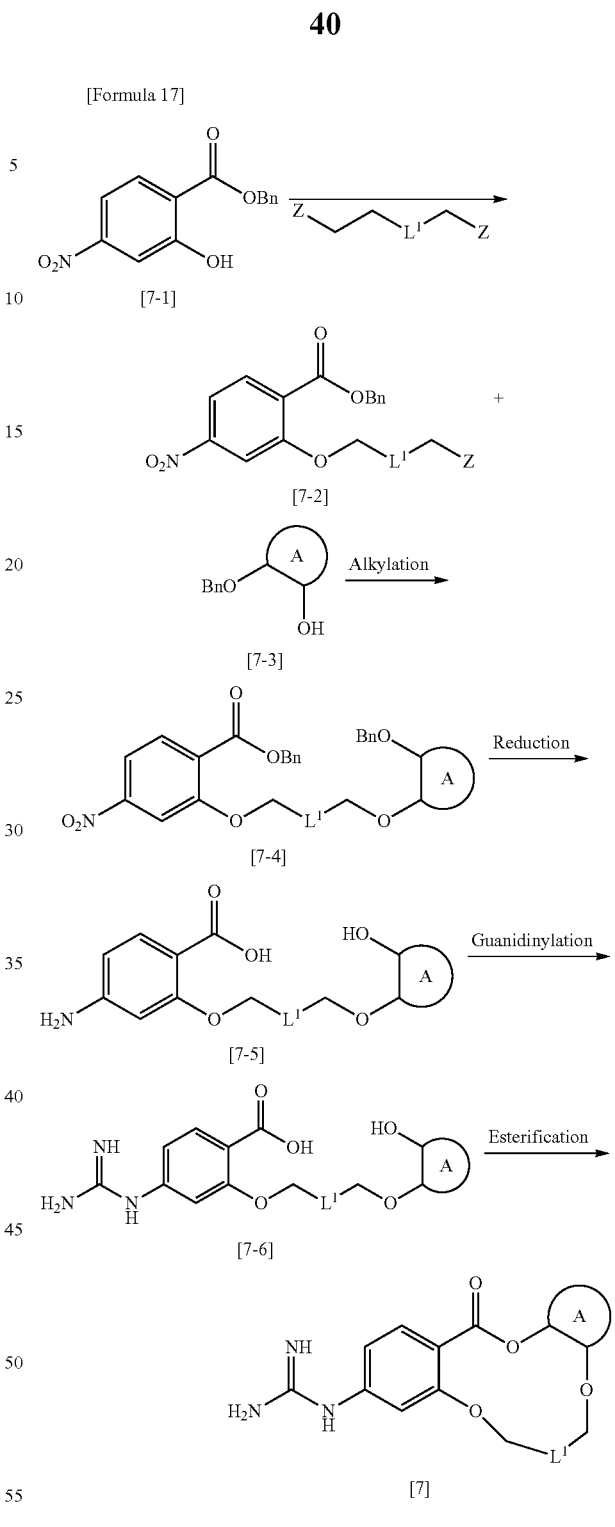

wherein $L^1$ represents methylene or ethylene, and the other symbols are as defined above.

Among the compounds (I), compound [8] can be produced by a method shown below from compound [8-1]. Also, some compounds [8] wherein ring A has a substituent can be produced by further carrying out various conversion reactions such as amidation reaction, protection, and deprotection for the substituent in their respective appropriate steps in the production method described below.

[Formula 18]

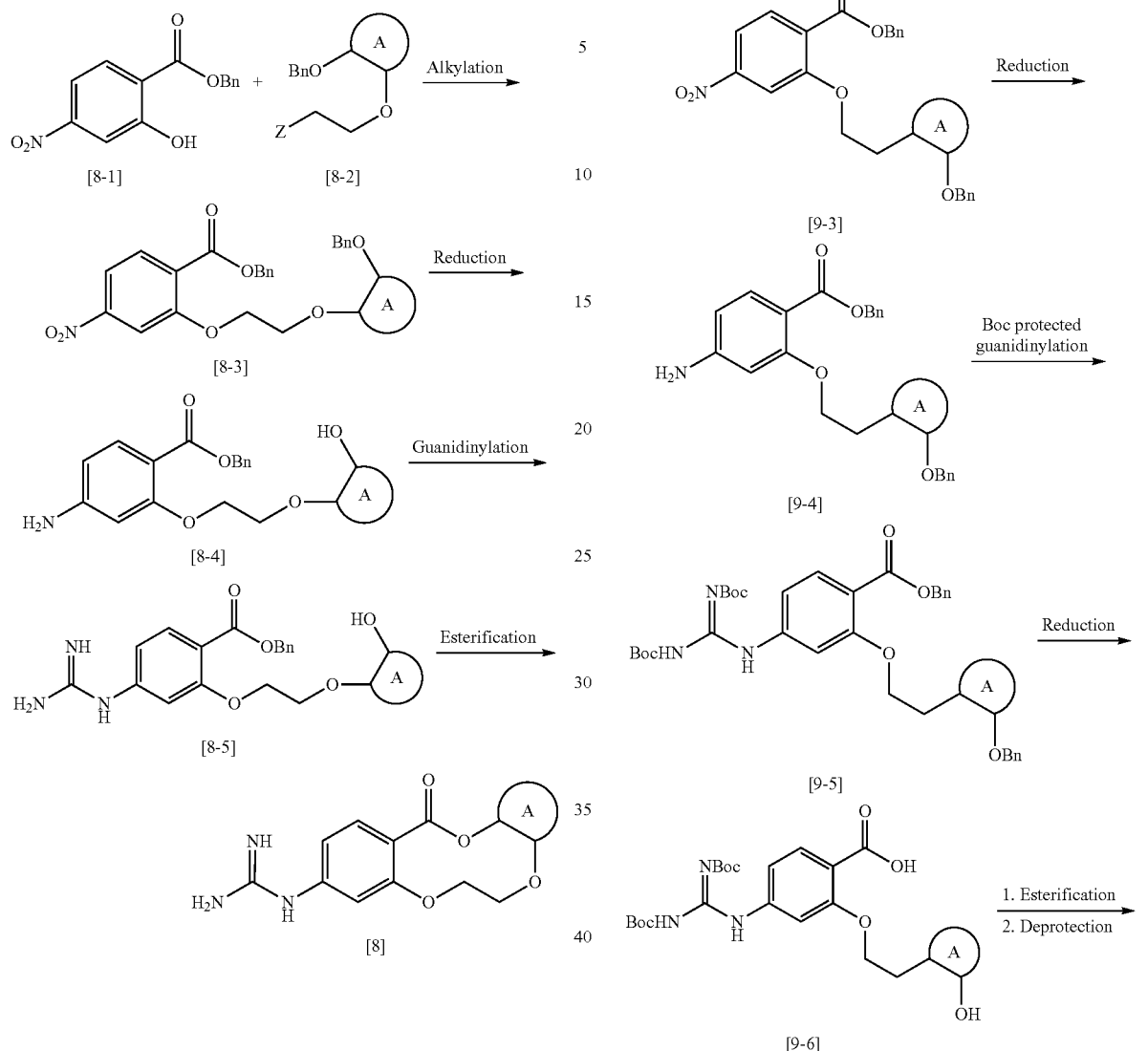

wherein the symbols are as defined above.

Among the compounds (I), compound [9] can be produced by a method shown below from compound [9-1]. Also, some compounds [9] wherein ring A has a substituent can be produced by further carrying out various conversion reactions such as amidation reaction, protection, and deprotection for the substituent in their respective appropriate steps in the production method described below.

[Formula 19]

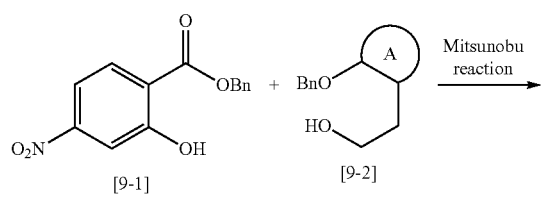

wherein the symbols are as defined above.

Among the compounds (I), compound [10] can be produced by a method shown below from compound [10-1]. Compound [10-4] can be produced through the amidination reaction of compound [10-3]. Also, some compounds [10] wherein ring A has a substituent can be produced by further carrying out various conversion reactions such as amidation reaction, protection, and deprotection for the substituent in their respective appropriate steps in the production method described below.

[Formula 20]

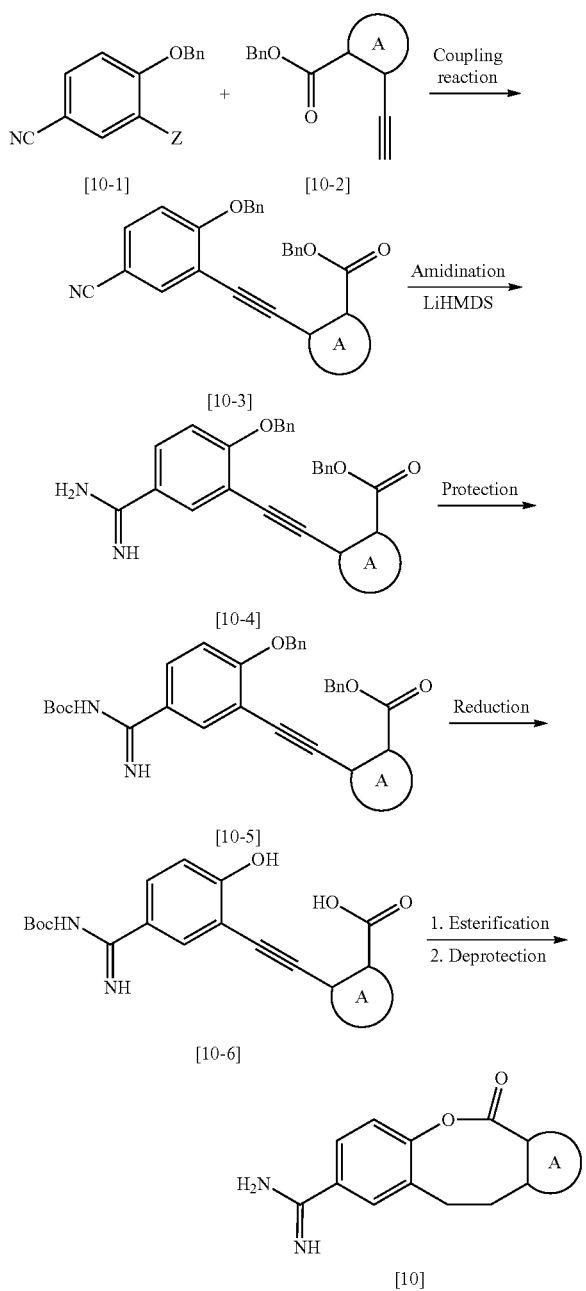

wherein the symbols are as defined above.

Compound (I) may have isomers such as optical isomers, stereoisomers, positional isomers, and rotational isomers. In such a case, one of the isomers and an isomeric mixture thereof are also included in compound (I). For example, when compound (I) has optical isomers, optical isomers resolved from a racemate are also included in compound (I). These isomers can each be obtained as a single compound by a synthesis approach, a separation approach (e.g., concentration, solvent extraction, column chromatography, and recrystallization), an optical resolution approach (e.g., fractional crystallization method, chiral column method, and diastereomer method,), and the like known per se in the art.

Compound (I) may be crystals. Single crystal forms and polymorphic mixtures are both included in compound (I).

The crystals can be produced by crystallizing compound (I) by the application of a crystallization method known per se in the art.

In addition, compound (I) may be a pharmaceutically acceptable cocrystal or cocrystal salt. In this context, the cocrystal or the cocrystal salt means a crystalline substance constituted by two or more unique substances that are solids at room temperature and differ in physical properties (e.g., structure, melting point, heat of melting, hygroscopicity, solubility, and stability). The cocrystal and the cocrystal salt can be produced according to a cocrystallization method known per se in the art.

In the present specification, a melting point means a melting point that is measured using, for example, a micro melting point apparatus (Yanaco model MP-500D or Buchi model B-545) or a DSC (differential scanning calorimetry) apparatus (SEIKO EXSTAR6000).

In general, melting points may vary depending on a measurement apparatus, measurement conditions, etc. In the present specification, the crystals may be crystals that exhibit a value different from the melting points described in the present specification as long as the value falls within a usual margin of error.

The crystals of the present invention are excellent in physicochemical properties (e.g., melting point, solubility, and stability) and biological properties (e.g., disposition (absorbability, distribution, metabolism, and excretion), and manifestation of efficacy) and are very useful as a medicament.

Compound (I) may be a solvate (e.g., a hydrate) or may be a non-solvate (e.g., a non-hydrate). All of them are included in compound (I).

A compound labeled with an isotope (e.g., $^{3}H$, $^{13}C$, $^{14}C$, $^{18}F$, $^{35}S$, and $^{125}I$) or the like is also included in compound (I).

A deuterium conversion form wherein $^{1}H$ is converted to $^{2}H(D)$ is also included in compound (I).

Compound (I) labeled or substituted with an isotope can be used as, for example, a tracer (PET tracer) for use in positron emission tomography (PET), and is useful in the fields of medical diagnosis and the like.

Compound (I) or a prodrug thereof (hereinafter, collectively referred to as the compound of the present invention) has an excellent enteropeptidase inhibitory effect, particularly, in vivo, and is useful as an enteropeptidase inhibitor.

Also, the compound of the present invention has an antifeeding effect and a body weight lowering effect.

The compound of the present invention has low toxicity (e.g., acute toxicity, chronic toxicity, genetic toxicity, reproductive toxicity, cardiac toxicity, and carcinogenicity). Thus, the compound of the present invention can be prepared into a pharmaceutical composition alone or as a mixture with a pharmacologically acceptable carrier or the like and thereby administered safely to a mammal (e.g., a mouse, a rat, a hamster, a rabbit, a cat, a dog, cattle, sheep, a monkey, and a human).

The compound of the present invention is useful as an agent for preventing or treating conditions or diseases caused by enteropeptidase.

Also, the compound of the present invention is low absorbable orally and is excellent in metabolic stability.

Specifically, the compound of the present invention can be used as an agent for preventing or treating obesity based on symptomatic obesity or simple obesity, conditions or diseases associated with obesity, eating disorder, diabetes mellitus (e.g., type 1 diabetes mellitus, type 2 diabetes mellitus, gestational diabetes mellitus, and obese diabetes mellitus), hyperlipidemia (e.g., hypertriglyceridemia, hypercholesterolemia, high LDL-cholesterolemia, low HDL-cholesterolemia, and postprandial hyperlipidemia), hypertension, cardiac failure, diabetic complications [e.g., neuropathy, nephropathy, retinopathy, diabetic cardiomyopathy, cataract, macroangiopathy, osteopenia, hyperosmolar diabetic coma, infectious disease (e.g., respiratory infection, urinary tract infection, gastrointestinal infection, dermal soft tissue infection, and inferior limb infection), diabetic gangrene, xerostomia, hypacusis, cerebrovascular disorder, and peripheral blood circulation disorder], metabolic syndrome (conditions having 3 or more selected from hypertriglycerid(TG)emia, low HDL cholesterol(HDL-C)emia, hypertension, abdominal obesity, and impaired glucose tolerance), sarcopenia, reflux esophagitis, and the like.

The compound of the present invention is particularly useful as an agent for preventing or treating obesity or an agent for preventing or treating diabetes mellitus on the basis of its enteropeptidase inhibitory effect.

Examples of the symptomatic obesity include endocrine obesity (e.g., Cushing syndrome, hypothyroidism, insulinoma, obese type II diabetes mellitus, pseudohypoparathyroidism, and hypogonadism), central obesity (e.g., hypothalamic obesity, frontal lobe syndrome, and Kleine-Levin syndrome), genetic obesity (e.g., Prader-Willi syndrome and Laurence-Moon-Biedl syndrome), and drug-induced obesity (e.g., obesity caused by steroids, phenothiazines, insulins, sulfonylurea (SU) agents, and (β-blockers).

Examples of the conditions or the diseases associated with obesity include impaired glucose tolerance, diabetes mellitus (particularly, type 2 diabetes mellitus and obese diabetes mellitus), abnormal lipid metabolism (which has the same meaning as that of the hyperlipidemia mentioned above), hypertension, cardiac failure, hyperuricemia or gout, fatty liver (including non-alcoholic steato-hepatitis), coronary diseases (myocardial infarction and angina pectoris), cerebral infarction (cerebral thrombosis and transient ischemic attack), bone or joint diseases (knee osteoarthritis, hip osteoarthritis, spondylosis deformans, and lumbago), sleep apnea syndrome or Pickwick syndrome, menstruation disorder (disorder of menstrual cycle, abnormality of the amount of blood lost at menstrual period and menstrual cycle, amenorrhea, and abnormality of menstruation-related symptoms), and metabolic syndrome.

The Japan Diabetes Society reported the diagnostic criteria of diabetes mellitus in 1999.

According to this report, diabetes mellitus refers to a state that meets any of a fasting blood glucose level (glucose concentration in venous plasma) of 126 mg/dl or more, a 2-hr value (glucose concentration in venous plasma) of 200 mg/dl or more in the 75 g oral glucose tolerance test (75 g OGTT), and a casual blood glucose level (glucose concentration in venous plasma) of 200 mg/dl or more. Also, a state that does not apply to the diabetes mellitus described above, and is not a state exhibiting "a fasting blood glucose level (glucose concentration in venous plasma) of less than 110 mg/dl or a 2-hr value (glucose concentration in venous plasma) of less than 140 mg/dl in the 75 g oral glucose tolerance test (75 g OGTT)" (normal type) is called "borderline type".

Also, the diagnostic criteria of diabetes mellitus were reported in 1997 by ADA (American Diabetes Association) and in 1998 by WHO (World Health Organization).

According to these reports, diabetes mellitus refers to a state that exhibits a fasting blood glucose level (glucose concentration in venous plasma) of 126 mg/dl or more and a 2-hr value (glucose concentration in venous plasma) of 200 mg/dl or more in the 75 g oral glucose tolerance test According to the reports of ADA and WHO, impaired glucose tolerance (IGT) refers to a state that exhibits a fasting blood glucose level (glucose concentration in venous plasma) of less than 126 mg/dl and a 2-hr value (glucose concentration in venous plasma) of 140 mg/dl or more and less than 200 mg/dl in the 75 g oral glucose tolerance test. According to the report of ADA, a state exhibiting a fasting blood glucose level (glucose concentration in venous plasma) of 110 mg/dl or more and less than 126 mg/dl is called IFG (impaired fasting glucose). On the other hand, according to the report of WHO, an IFG (impaired fasting glucose) state exhibiting a 2-hr value (glucose concentration in venous plasma) less than 140 mg/dl in the 75 g oral glucose tolerance test is called IFG (impaired fasting glycemia).

The compound of the present invention is also used as an agent for preventing or treating diabetes mellitus, borderline type, impaired glucose tolerance, IFG (impaired fasting glucose), and IFG (impaired fasting glycemia) determined according to the diagnostic criteria described above. In addition, the compound of the present invention can also prevent the progression of borderline type, impaired glucose tolerance, IFG (impaired fasting glucose), or IFG (impaired fasting glycemia) into diabetes mellitus.

The compound of the present invention has an effect of suppressing body weight gain and as such, can be used as an agent suppressing body weight gain in a mammal. The mammal to which the compound of the present invention is to be applied can be any mammal desired to avoid body weight gain and may be a mammal genetically having a risk of body weight gain or may be a mammal affected by a lifestyle-related disease such as diabetes mellitus, hypertension, and/or hyperlipidemia, etc. The body weight gain may be caused by excessive dietary intake or nutritionally unbalanced diet or may be derived from concomitant drugs (e.g., insulin sensitizers having a PPAR-gamma agonist-like effect, such as troglitazone, rosiglitazone, englitazone, ciglitazone, and pioglitazone). Also, the body weight gain may be body weight gain before reaching obesity or may be body weight gain in an obesity patient. In this context, the obesity is defined as having BMI (body mass index: Body weight (kg)/[Height (m)]$^2$) of 25 or more (according to the criteria of the Japan Society for the Study of Obesity (JASSO)) for Japanese or having BMI of 30 or more (according to the criteria of WHO) for Westerners.

The compound of the present invention is also useful as an agent for preventing or treating metabolic syndrome. The incidence of cardiovascular disease is significantly high in metabolic syndrome patients, compared with patients with a single lifestyle-related disease. Therefore, the prevention or treatment of metabolic syndrome is exceedingly important for preventing cardiovascular disease.

The diagnostic criteria of metabolic syndrome were announced by WHO in 1999 and by NCEP in 2001. According to the diagnostic criteria of WHO, an individual having hyperinsulinemia or abnormal glucose tolerance as a requirement and two or more of visceral obesity, dyslipidemia (high TG or low HDL), and hypertension is diagnosed as having metabolic syndrome (World Health Organization: Definition, Diagnosis and Classification of Diabetes Mellitus and Its Complications. Part I: Diagnosis and Classification of Diabetes Mellitus, World Health Organization, Geneva, 1999). According to the diagnostic criteria of the Adult Treatment Panel III of the National Cholesterol Education Program (guideline of ischemic heart disease) in USA, an individual having three or more of visceral obesity, hypertriglyceridemia, low HDL-cholesterolemia, hypertension, and abnormal glucose tolerance is diagnosed as having metabolic syndrome (National Cholesterol Education Program: Executive Summary of the Third Report of National Cholesterol Education Program (NCEP) Expert Panel on Detection, Evaluation, and Treatment of High Blood Cholesterol in Adults (Adults Treatment Panel III). The Journal of the American Medical Association, Vol. 285, 2486-2497, 2001).

The compound of the present invention can also be used as an agent for preventing or treating, for example, osteoporosis, cachexia (e.g., cancerous cachexia, tuberculous cachexia, diabetic cachexia, cachexia associated with blood disease, cachexia associated with endocrine disease, cachexia associated with infectious disease, or cachexia caused by acquired immunodeficiency syndrome), fatty liver, polycystic ovary syndrome, renal disease (e.g., diabetic nephropathy, glomerulonephritis, glomerulosclerosis, nephrotic syndrome, hypertensive nephrosclerosis, and end-stage renal disease), muscular dystrophy, myocardial infarction, angina pectoris, cerebrovascular disorder (e.g., cerebral infarction and stroke), Alzheimer's disease, Parkinson's disease, anxiety disorder, dementia, insulin resistant syndrome, syndrome X, hyperinsulinemia, paresthesia caused by hyperinsulinemia, acute or chronic diarrhea, inflammatory disease (e.g., chronic rheumatoid arthritis, spondylitis deformans, arthritis deformans, lumbago, gout, post-operational or post-traumatic inflammation, bloating, neuralgia, laryngopharyngitis, cystitis, hepatitis (including non-alcoholic steatohepatitis), pneumonia, pancreatitis, enteritis, inflammatory bowel disease (including inflammatory large bowel disease), colitis ulcerosa, and gastric mucosal injury (including gastric mucosal injury caused by aspirin)), small intestinal mucosal injury, malabsorption, testicular dysfunction, visceral obesity syndrome, and sarcopenia.

The compound of the present invention can also be used as an agent for preventing or treating various cancers (particularly, breast cancer (e.g., invasive ductal breast cancer, noninvasive ductal breast cancer, and inflammatory breast cancer), prostate cancer (e.g., hormone-dependent prostate cancer and hormone-independent prostate cancer), pancreatic cancer (e.g., ductal pancreatic cancer), gastric cancer (e.g., papillary adenocarcinoma, mucous adenocarcinoma, and adenosquamous carcinoma), lung cancer (e.g., non-small cell lung cancer, small-cell lung cancer, and malignant mesothelioma), colon cancer (e.g., gastrointestinal stromal tumor), rectal cancer (e.g., gastrointestinal stromal tumor), colorectal cancer (e.g., familial colorectal cancer, hereditary non-polyposis colorectal cancer, and gastrointestinal stromal tumor), small intestinal cancer (e.g., non-Hodgkin's lymphoma and gastrointestinal stromal tumor), esophageal cancer, duodenal cancer, tongue cancer, pharyngeal cancer (e.g., nasopharyngeal cancer, oropharynx cancer, and hypopharyngeal cancer), salivary gland cancer, brain tumor (e.g., pineal astrocytoma, pilocytic astrocytoma, diffuse astrocytoma, and anaplastic astrocytoma), neurilemmoma, liver cancer (e.g., primary liver cancer and extrahepatic bile duct cancer), renal cancer (e.g., renal cell cancer and transitional cell cancer of the renal pelvis and ureter), bile duct cancer, endometrial cancer, uterine cervical cancer, ovarian cancer (e.g., epithelial ovarian cancer, extragonadal germ cell tumor, ovarian germ cell tumor, and ovarian tumor of low malignant potential), bladder cancer, urethral cancer, skin cancer (e.g., intraocular (ocular) melanoma and Merkel cell carcinoma), hemangioma, malignant lymphoma, malignant melanoma, thyroid cancer (e.g., medullary thyroid cancer), parathyroid cancer, nasal cavity cancer, sinus cancer, bone tumor (e.g., osteosarcoma, Ewing tumor, uterine sarcoma, and soft tissue sarcoma), angiofibroma, sarcoma of the retina, penis cancer, testicular cancer, pediatric solid tumor (e.g., Wilms' tumor and childhood kidney tumor), Kaposi's sarcoma, Kaposi's sarcoma caused by AIDS, tumor of maxillary sinus, fibrous histiocytoma, leiomyosarcoma, rhabdomyosarcoma, leukemia (e.g., acute myeloid leukemia and acute lymphoblastic leukemia), etc.).

The compound of the present invention can also be used for the secondary prevention or suppression of progression of various diseases described above (e.g., cardiovascular events such as myocardial infarction).

A medicament comprising the compound of the present invention can be obtained using the compound of the present invention alone or as a mixture with a pharmacologically acceptable carrier according to a method known per se in the art (e.g., a method described in the Japanese Pharmacopoeia) as a method for producing pharmaceutical preparations, and safely administered orally or parenterally (e.g., administered intravenously, intramuscularly, subcutaneously, into an organ, into a nasal cavity, intracutaneously, through ocular instillation, intracerebrally, rectally, vaginally, intraperitoneally, to the inside of tumor, or to the proximity of tumor, and administered directly to a lesion) to a mammal as, for example, tablets (including sugar-coated tablets, film-coated tablets, sublingual tablets, orally disintegrating tablets, buccal tablets, and the like), pills, powders, granules, capsules (including soft capsules and microcapsules), troches, syrups, solutions, emulsions, suspensions, controlled release preparations (e.g., rapid release preparations, sustained-release preparations, and sustained-release microcapsules), aerosols, films, (e.g., orally disintegrating films, and patch films for application to the oral mucosa), injections (e.g., subcutaneous injections, intravenous injections, intramuscular injections, and intraperitoneal injections), transfusions, dermal preparations, ointments, lotions, patches, suppositories (e.g., rectal suppositories and vaginal suppositories), pellets, nasal preparations, pulmonary preparations (inhalants), or eye drops.

For the production of an oral preparation, the preparation may be coated, if necessary, for the purpose of taste masking, enteric properties, or durability.

Examples of the coating base for use in coating include sugar coating bases, aqueous film coating bases, enteric film coating bases, and sustained-release film coating bases.

Saccharose is used as the sugar coating base. Alternatively, one sugar coating base or two or more sugar coating bases in combination selected from talc, precipitated calcium carbonate, gelatin, gum arabic, pullulan, carnauba wax, and the like may be used.

Examples of the aqueous film coating base include: cellulose polymers such as hydroxypropylcellulose, hydroxypropylmethylcellulose, hydroxyethylcellulose, and methylhydroxyethylcellulose; synthetic polymers such as polyvinylacetal diethylaminoacetate, aminoalkyl methacrylate copolymer E [Eudragit E (trade name)], and polyvinylpyrrolidone; and polysaccharides such as pullulan.

Examples of the enteric film coating base include: cellulose polymers such as hydroxypropylmethylcellulose phthalate, hydroxypropylmethylcellulose acetate succinate, carboxymethylethylcellulose, and cellulose acetate phthalate; acrylic acid polymers such as methacrylic acid copolymer L [Eudragit L (trade name)], methacrylic acid copolymer LD [Eudragit L-30D55 (trade name)], and methacrylic acid copolymer S [Eudragit S (trade name)]; and naturally occurring substances such as shellac.

Examples of the sustained-release film coating base include: cellulose polymers such as ethyl cellulose; and acrylic acid polymers such as aminoalkyl methacrylate copolymer RS [Eudragit RS (trade name)] and an ethyl acrylate-methyl methacrylate copolymer suspension [Eudragit NE (trade name)].

The coating bases described above may be used as a mixture of two or more thereof at an appropriate ratio. For coating, for example, a light shielding agent such as titanium oxide or red ferric oxide may be used.

The content of the compound of the present invention in the pharmaceutical preparation is approximately 0.01 to approximately 100% by weight of the whole preparation. The dose differs depending on a recipient, an administration route, a disease, symptoms, etc. For example, when the compound of the present invention is orally administered to a diabetes mellitus patient (body weight: approximately 60 kg), the daily dose is approximately 0.01 to approximately 30 mg/kg body weight, preferably approximately 0.1 to approximately 20 mg/kg body weight, more preferably approximately 1 to approximately 20 mg/kg body weight, of the active ingredient [compound of the present invention]. This dose can be administered once a day or in several divided portions per day (e.g., in one to three portions per day).

Examples of the pharmacologically acceptable carrier described above include various organic or inorganic carrier materials routinely used as preparation materials. Examples thereof include: excipients, lubricants, binding agents, and disintegrants for solid preparations; and solvents, solubilizing agents, suspending agents, tonicity agents, buffering agents, and soothing agents for liquid preparations. If necessary, ordinary additives such as a preservative, an antioxidant, a colorant, a sweetening agent, an adsorbent, and a wetting agent can also be further used.

Examples of the excipient include lactose, saccharose, D-mannitol, starch, corn starch, crystalline cellulose, and light anhydrous silicic acid.

Examples of the lubricant include magnesium stearate, calcium stearate, talc, and colloidal silica.

Examples of the binding agent include crystalline cellulose, saccharose, D-mannitol, dextrin, hydroxypropylcellulose, hydroxypropylmethylcellulose, polyvinylpyrrolidone, starch, sucrose, gelatin, methylcellulose, and carboxymethylcellulose sodium.

Examples of the disintegrant include starch, carboxymethylcellulose, carboxymethylcellulose calcium, carboxymethyl starch sodium, and L-hydroxypropylcellulose.

Examples of the solvent include injectable water, alcohol, propylene glycol, Macrogol, sesame oil, corn oil, and olive oil.

Examples of the solubilizing agent include polyethylene glycol, propylene glycol, D-mannitol, benzyl benzoate, ethanol, trisaminomethane, cholesterol, triethanolamine, sodium carbonate, and sodium citrate.

Examples of the suspending agent include: surfactants such as stearyl triethanolamine, sodium lauryl sulfate, laurylaminopropionic acid, lecithin, benzalkonium chloride, benzethonium chloride, and glycerin monostearate; and hydrophilic polymers such as polyvinyl alcohol, polyvinylpyrrolidone, carboxymethylcellulose sodium, methylcellulose, hydroxymethylcellulose, hydroxyethylcellulose, and hydroxypropylcellulose.

Examples of the tonicity agent include glucose, D-sorbitol, sodium chloride, glycerin, and D-mannitol.

Examples of the buffering agent include buffer solutions of phosphate, acetate, carbonate, citrate, and the like.

Examples of the soothing agent include benzyl alcohol.

Examples of the preservative include p-hydroxybenzoic acid esters, chlorobutanol, benzyl alcohol, phenethyl alcohol, dehydroacetic acid, and sorbic acid.

Examples of the antioxidant include sulfites, ascorbic acid, and α-tocopherol.

Examples of the colorant include water-soluble food tar dyes (e.g., food dyes such as Food Red No. 2 and No. 3, Food Yellow No. 4 and No. 5, and Food Blue No. 1 and No. 2), water-insoluble lake dyes (e.g., aluminum salts of the water-soluble food tar dyes described above), and natural dyes (e.g., beta-carotene, chlorophyll, and ferric oxide red).

Examples of the sweetening agent include saccharin sodium, dipotassium glycyrrhizinate, aspartame, and *stevia*.

The compound of the present invention can be used in combination with a drug other than the compound of the present invention.

Examples of the drug (hereinafter, also referred to as a concomitant drug) that may be used in combination with the compound of the present invention include anti-obesity agents, agents for treating diabetes mellitus, agents for treating diabetic complications, agents for treating hyperlipidemia, antihypertensive agents, diuretics, chemotherapeutic agents, immunotherapeutic agents, anti-inflammatory drugs, antithrombotic agents, agents for treating osteoporosis, vitamins, antidementia drugs, drugs for the amelioration of erectile dysfunction, drugs for treating pollakiuria or urinary incontinence, and for treating difficulty of urination. Specific examples thereof include the following.

Examples of the anti-obesity agent include monoamine uptake inhibitors (e.g., phentermine, sibutramine, mazindol, fluoxetine, and tesofensine), serotonin 2C receptor agonists (e.g., lorcaserin), serotonin 6 receptor antagonists, histamine H3 receptor modulators, GABA modulators (e.g., topiramate), neuropeptide Y antagonists (e.g., velneperit), cannabinoid receptor antagonists (e.g., rimonabant and taranabant), ghrelin antagonists, ghrelin receptor antagonists, ghrelinacylation enzyme inhibitors, opioid receptor antagonists (e.g., GSK-1521498), orexin receptor antagonists, melanocortin 4 receptor agonists, 11β-hydroxysteroid dehydrogenase inhibitors (e.g., AZD-4017), pancreatic lipase inhibitors (e.g., orlistat and cetilistat), β3 agonists (e.g., N-5984), diacylglycerol acyltransferase 1 (DGAT1) inhibitors, acetyl-CoA carboxylase (ACC) inhibitors, stearoyl-CoA desaturated enzyme inhibitors, microsomal triglyceride transfer protein inhibitors (e.g., R-256918), Na-glucose cotransporter inhibitors (e.g., JNJ-28431754 and remogliflozin), NFκ inhibitors (e.g., HE-3286), PPAR agonists (e.g., GFT-505 and DRF-11605), phosphotyrosine phosphatase inhibitors (e.g., sodium vanadate and trodusquemine), GPR119 agonists (e.g., PSN821, MBX-2982, and APD597), glucokinase activators (e.g., AZD-1656), leptin, leptin derivatives (e.g., metreleptin), CNTF (ciliary neurotrophic factor), BDNF (brain-derived neurotrophic factor), cholecystokinin agonists, glucagon-like peptide-1 (GLP-1) preparations (e.g., animal GLP-1 preparations extracted from the bovine or swine pancreas; human GLP-1 preparations genetically synthesized by using *Escherichia. coli* or yeast; fragments or derivatives of GLP-1 (e.g., exenatide and liraglutide)), amylin preparations (e.g., pramlintide and AC-2307), neuropeptide Y agonists (e.g., PYY3-36, derivatives of PYY3-36, obineptide, TM-30339, and TM-30335), oxyntomodulin preparations: FGF21 preparations (e.g., animal FGF21 preparations extracted from the bovine or swine pancreas; human FGF21 preparations genetically synthesized using *Escherichia coli* or yeast; and fragments or derivatives of FGF21), and anorexigenic agents (e.g., P-57).

Examples of the agent for treating diabetes mellitus include insulin preparations (e.g., animal insulin preparations extracted from the bovine or swine pancreas; human insulin preparations genetically synthesized using *Escherichia coli* or yeast; zinc insulin; protamine zinc insulin; fragments or derivatives of insulin (e.g., INS-1), and oral insulin preparations), insulin sensitizers (e.g., pioglitazone or a salt thereof (preferably, hydrochloride), rosiglitazone or a salt thereof (preferably, maleate), metaglidasen, AMG-131, balaglitazone, MBX-2044, rivoglitazone, aleglitazar, chiglitazar, lobeglitazone, PLX-204, PN-2034, GFT-505, THR-0921, and compounds described in WO2007/013694, WO2007/018314, WO2008/093639, or WO2008/099794), α-glucosidase inhibitors (e.g., voglibose, acarbose, miglitol, and emiglitate), biguanides (e.g., metformin, buformin, and their salts (e.g., hydrochloride, fumarate, and succinate)), insulin secretagogues (e.g., sulfonylurea (e.g., tolbutamide, glibenclamide, gliclazide, chlorpropamide, tolazamide, acetohexamide, glyclopyramide, glimepiride, glipizide, and glybuzole), repaglinide, nateglinide, mitiglinide, or calcium salt hydrate thereof), dipeptidyl peptidase IV inhibitors (e.g., alogliptin or a salt thereof (preferably, benzoate), trelagliptin or a salt thereof (preferably, succinate), Vildagliptin, Sitagliptin, saxagliptin, BI1356, GRC8200, MP-513, PF-00734200, PHX1149, SK-0403, ALS2-0426, TA-6666, TS-021, KRP-104, β3 agonists (e.g., N-5984), GPR40 agonists (e.g., fasiglifam and compounds described in WO2004/041266, WO2004/106276, WO2005/063729, WO2005/063725, WO2005/087710, WO2005/095338, WO2007/013689, or WO2008/001931), GLP-1 receptor agonists (e.g., GLP-1, GLP-1 MR preparations, liraglutide, exenatide, AVE-0010, BIM-51077, Aib(8,35)hGLP-1(7,37)NH$_2$, CJC-1131, and albiglutide), amylin agonists (e.g., pramlintide), phosphotyrosine phosphatase inhibitors (e.g., sodium vanadate), gluconeogenesis inhibitors (e.g., glycogen phosphorylase inhibitors, glucose-6-phosphatase inhibitors, glucagon antagonists, and FBPase inhibitors), SGLT2 (sodium-glucose cotransporter 2) inhibitors (e.g., dapagliflozin, AVE2268, TS-033, YM543, TA-7284, remogliflozin, and ASP1941), SGLT1 inhibitors, 11β-hydroxysteroid dehydrogenase inhibitors (e.g., BVT-3498 and INCB-13739), adiponectin or agonists thereof, IKK inhibitors (e.g., AS-2868), leptin resistance improving drugs, somatostatin receptor agonists, glucokinase activators (e.g., piragliatin, AZD1656, AZD6370, TTP-355, and compounds described in WO2006/112549, WO2007/028135, WO2008/047821, WO2008/050821, WO2008/136428, or WO2008/156757), GIP (glucose-dependent insulinotropic peptide), GPR119 agonists (e.g. PSN821, MBX-2982, and APD597), FGF21, and FGF analogs.

Examples of the agent for treating diabetic complications include aldose reductase inhibitors (e.g., tolrestat, epalrestat, zopolrestat, fidarestat, CT-112, ranirestat (AS-3201), and lidorestat), neurotrophic factor and increasing agents thereof (e.g., NGF, NT-3, BDNF, neurotrophic production or secretion promoting agents described in WO01/14372 (e.g., 4-(4-chlorophenyl)-2-(2-methyl-1-imidazolyl)-5-[3-(2-methylphenoxy)propyl]oxazole), and compounds described in WO2004/039365), PKC inhibitors (e.g., ruboxistaurin mesylate), AGE inhibitors (e.g., ALT946, N-phenacylthiazolium bromide (ALT766), EXO-226, Pyridorin, and pyridoxamine), GABA receptor agonists (e.g., gabapentin and pregabalin), serotonin and noradrenalin reuptake inhibitors (e.g., duloxetine), sodium channel inhibitors (e.g., lacosamide), active oxygen scavengers (e.g., thioctic acid), cerebral vasodilators (e.g., tiapuride and mexiletine), somatostatin receptor agonists (e.g., BIM23190), and apoptosis signal regulating kinase-1 (ASK-1) inhibitors.

Examples of the agent for treating hyperlipidemia include HMG-CoA reductase inhibitors (e.g., pravastatin, simvastatin, lovastatin, atorvastatin, fluvastatin, rosuvastatin, pitavastatin, and their salts (e.g., sodium salt and calcium salt)), squalene synthase inhibitors (e.g., compounds described in WO97/10224, for example, N-[[(3R,5S)-1-(3-acetoxy-2,2-dimethylpropyl)-7-chloro-5-(2,3-dimethoxyphenyl)-2-oxo-1,2,3,5-tetrahydro-4,1-benzoxazepin-3-yl]acetyl]piperidin-4-acetic acid), fibrate compounds (e.g., bezafibrate, clofibrate, simfibrate, and clinofibrate), anion exchange resin (e.g., colestyramine), probucol, nicotinic acid drugs (e.g., nicomol, niceritrol, and Niaspan), ethyl icosapentate, phytosterol (e.g., soysterol and γ-oryzanol)), cholesterol absorption inhibitors (e.g., zechia), CETP inhibitors (e.g., dalcetrapib and anacetrapib), and ω-3 fatty acid preparations (e.g., ω-3-fatty acid ethyl esters 90).

Examples of the antihypertensive agent include angiotensin converting enzyme inhibitors (e.g., captopril, enalapril, and delapril), angiotensin II antagonists (e.g., candesartan cilexetil, candesartan, losartan, losartan potassium, eprosartan, valsartan, telmisartan, irbesartan, tasosartan, olmesartan, olmesartan medoxomil, azilsartan, and azilsartan medoxomil), calcium antagonists (e.g., manidipine, nifedipine, amlodipine, efonidipine, nicardipine, amlodipine, and cilnidipine), β blockers (e.g., metoprolol, atenolol, propranolol, carvedilol, and pindolol), and clonidine.

Examples of the diuretic include xanthine derivatives (e.g., theobromine sodium salicylate, and theobromine calcium salicylate), thiazide preparations (e.g., ethiazide, cyclopenthiazide, trichloromethiazide, hydrochlorothiazide, hydroflumethiazide, benzylhydrochlorothiazide, penfluthiazide, poly 5 thiazide, and methyclothiazide), antialdosterone preparations (e.g., spironolactone and triamterene), carbonic anhydrase inhibitors (e.g., acetazolamide), chlorobenzenesulfonamide agents (e.g., chlortalidone, mefruside, and indapamide), azosemide, isosorbide, ethacrynic acid, piretanide, bumetanide, and furosemide.

Examples of the chemotherapeutic agent include alkylating agents (e.g., cyclophosphamide and ifosfamide), antimetabolites (e.g., methotrexate and 5-fluorouracil), anticancer antibiotics (e.g., mitomycin and adriamycin), plant-derived anticancer agents (e.g., vincristine, vindesine, and Taxol), cisplatin, carboplatin, and etoposide. Among others, a 5-fluorouracil derivative furtulon or neofurtulon is preferred.

Examples of the immunotherapeutic agent include microbial or bacterial components (e.g., muramyl dipeptide derivatives and Picibanil), polysaccharides having immunoenhancing activity (e.g., lentinan, sizofiran, and Krestin), cytokines obtained by genetic engineering approaches (e.g., interferon and interleukin (IL)), and colony-stimulating factors (e.g., granulocyte colony-stimulating factor, and erythropoietin). Among others, interleukins such as IL-1, IL-2, and IL-12 are preferred.

Examples of the anti-inflammatory drug include non-steroidal anti-inflammatory drugs such as aspirin, acetaminophen, and indomethacin.

Examples of the antithrombotic agent include heparin (e.g., heparin sodium, heparin calcium, enoxaparin sodium, and dalteparin sodium), warfarin (e.g., warfarin potassium), anti-thrombin drugs (e.g., argatroban and dabigatran), FXa inhibitors (e.g., rivaroxaban, apixaban, edoxaban, YM150, and compounds described in WO02/06234, WO2004/048363, WO2005/030740, WO2005/058823, or WO2005/113504), thrombolytic agents (e.g., urokinase, tisokinase, alteplase, nateplase, monteplase, and pamiteplase), and platelet aggregation inhibitors (e.g., ticlopidine hydrochloride, clopidogrel, prasugrel, E5555, SHC530348, cilostazol, ethyl icosapentate, beraprost sodium, and sarpogrelate hydrochloride).

Examples of the agent for treating osteoporosis include alfacalcidol, calcitriol, elcatonin, calcitonin salmon, estriol, ipriflavone, pamidronate disodium, alendronate sodium hydrate, incadronate disodium, and risedronate disodium.

Examples of the vitamin include vitamin $B_1$ and vitamin $B_{12}$.

Examples of the antidementia drug include tacrine, donepezil, rivastigmine, and galanthamine.

Examples of the drug for the amelioration of erectile dysfunction include apomorphine and sildenafil citrate.

Examples of the drug for treating pollakiuria or urinary incontinence include flavoxate hydrochloride, oxybutynin hydrochloride, and propiverine hydrochloride.

Examples of the agent for treating difficulty of urination include acetylcholine esterase inhibitors (e.g., distigmine).

A drug confirmed to have a cachexia-ameliorating effect either in animal models or clinically, i.e., a cyclooxygenase inhibitor (e.g., indomethacin), a progesterone derivative (e.g., megestrol acetate), glucocorticoid (e.g., dexamethasone), a metoclopramide drug, a tetrahydrocannabinol drug, an agent improving fat metabolism (e.g., eicosapentaenoic acid), growth hormone, IGF-1, or an antibody against a cachexia-inducing factor TNF-α, LIF, IL-6 or oncostatin M, or the like can also be used in combination with the compound of the present invention.

Alternatively, a glycation inhibitor (e.g., ALT-711), a nerve regeneration-promoting drug (e.g., Y-128, VX853, and prosaptide), an antidepressant (e.g., desipramine, amitriptyline, and imipramine), an antiepileptic drug (e.g., lamotrigine, Trileptal, Keppra, Zonegran, Pregabalin, Harkoseride, and carbamazepine), an antiarrhythmic drug (e.g., mexiletine), an acetylcholine receptor ligand (e.g., ABT-594), an endothelin receptor antagonist (e.g., ABT-627), a monoamine uptake inhibitor (e.g., tramadol), a narcotic analgesic (e.g., morphine), a GABA receptor agonist (e.g., gabapentin and MR preparations of gabapentin), an α2 receptor agonist (e.g., clonidine), a local analgesic (e.g., capsaicin), an antianxiety drug (e.g., benzothiazepine), a phosphodiesterase inhibitor (e.g., sildenafil), a dopamine receptor agonist (e.g., apomorphine), midazolam, ketoconazole, or the like can also be used in combination with the compound of the present invention.

In the case of using the compound of the present invention and a concomitant drug in combination, the respective amounts of the drugs can be reduced within safe ranges in consideration of the adverse reactions of the drugs. In addition, the dosage of the concomitant drug can be reduced. As a result, adverse reactions that might be caused by the concomitant drug can be effectively prevented.

The compound of the present invention combined with a concomitant drug can produce excellent effects in such a way that:

(1) the dose of the compound of the present invention or a concomitant drug can be reduced as compared with single administration of the compound of the present invention or a concomitant drug;
(2) the period of treatment can be set longer by selecting a concomitant drug having a different mechanism of action from that of the compound of the present invention;
(3) sustained therapeutic effects can be achieved by selecting a concomitant drug having a different mechanism of action from that of the compound of the present invention; and
(4) synergistic effects can be obtained by a combined use of the compound of the present invention and a concomitant drug.

In the case of using the compound of the present invention and a concomitant drug in combination, the times of administration of the compound of the present invention and the concomitant drug are not limited, and the compound of the present invention and the concomitant drug may be administered simultaneously or in a staggered manner to a recipient. The dose of the concomitant drug can conform to doses clinically used and can be appropriately selected depending on a recipient, an administration route, a disease, a combination, etc.

Examples of the administration mode of the compound of the present invention and the concomitant drug include (1) administration of a single preparation obtained by simultaneously processing the compound of the present invention and the concomitant drug, (2) simultaneous administration of two preparations separately obtained from the compound of the present invention and the concomitant drug, through the same administration route, (3) administration of two preparations separately obtained from the compound of the present invention and the concomitant drug, through the same administration route in a staggered manner, (4) simultaneous administration of two preparations separately obtained from the compound of the present invention and the concomitant drug, through different administration routes, and (5) administration of two preparations separately obtained from the compound of the present invention and the concomitant drug, through different administration routes in a staggered manner (e.g., administration in the order of the compound of the present invention and the concomitant drug, or in the reverse order).

EXAMPLES

The present invention will be further described in detail by the following examples, test examples, and preparation examples, which are not intended to limit the present invention and may be modified within the scope of the present invention.

Throughout the following examples, the term "room temperature" generally refers to a temperature of about 10° C. to about 35° C.; the "ratio" shown in a solvent mixture is a volume ratio, unless otherwise specified; and the term "%" refers to % by weight, unless otherwise specified.

The term "NH" in silica gel column chromatography indicates that aminopropyl silane-bonded silica gel was used. The term "C18" in high-performance liquid chromatography (HPLC) indicates that octadecyl-bonded silica gel was used. The "ratio" of elution solvent is a volume ratio, unless otherwise specified.

In the following examples, the following abbreviations are used.

mp: melting point
MS: mass spectrum
$[M+H]^+$, $[M+Na]^+$, $[M-H]^-$, $[M+H-tBu]^+$: molecular ion peak
M: molar concentration
N: normal
$CDCl_3$: deuterated chloroform
DMSO-$d_6$: deuterated dimethyl sulfoxide
$^1$H NMR: proton nuclear magnetic resonance LC/MS: liquid chromatograph mass spectrometer
ESI: electrospray ionization
APCI: atmospheric pressure chemical ionization
THF: tetrahydrofuran
DME: 1,2-dimethoxyethane
DMF: N,N-dimethylformamide
DMA: N,N-dimethylacetamide
NMP: 1-methyl-2-pyrrolidone
HOBt: 1-hydroxybenzotriazole
WSC: 1-ethyl-3-(3-dimethylaminopropyl)carbodiimide
TFA: trifluoroacetic acid $^1$H NMR was measured by Fourier transform NMR. Analysis was performed with, for example, ACD/SpecManager (trade name). Very gentle peaks of protons of, for example, hydroxyl groups and amino groups, will not be described.

MS was measured by LC/MS. As an ionization method, an ESI method or an APCI method was used. Measured values (Found) are shown as the data. In general, a molecular ion peak is observed. However, in a compound including a tert-butoxycarbonyl group, the peak observed may be of a fragment ion where a tert-butoxycarbonyl group or a tert-butyl group is removed. In addition, in a compound including a hydroxyl group, the peak observed may be of a fragment ion where $H_2O$ is removed. In a salt, generally, the peak observed is of a free molecular ion or a fragment ion.

As elemental analysis value (Anal.), the calculated value (Calcd) and the measured value (Found) are shown.

Example 1

N-((10-Carbamimidamido-13-oxo-6,7,8,13-tetrahydrodibenzo[b,f][1,4]dioxecin-4-yl)carbonyl)-L-aspartic acid A) Methyl 2-(3-hydroxyprop-1-yn-1-yl)-4-nitrobenzoate Copper(I) iodide (0.381 g) and a 1,1'-bis(diphenylphosphino)ferrocene-palladium(II) dichloride-dichloromethane complex (1.633 g) were added to a mixture of methyl 2-bromo-4-nitrobenzoate (52.0 g), 2-propin-1-ol (29.1 mL), triethylamine (55.8 mL), and THF (200 mL) at room temperature, followed by stirring under a nitrogen atmosphere at 40° C. for 65 hours. The reaction mixture was diluted with ethyl acetate (200 mL), and Celite (trade name) (52 g) and NH-silica gel (52 g) were added thereto. The mixture was stirred at room temperature for 30 minutes, and insoluble matter was then removed by filtration, followed by washing with ethyl acetate (400 mL). The resulting filtrate was washed with 7% aqueous ammonia and a saturated saline solution and dried over anhydrous magnesium sulfate, and the solvent was then distilled under reduced pressure. The residue was purified by silica gel column chromatography (NH, ethyl acetate/hexane), and a mixture of the resulting solid and diisopropyl ether/hexane (1:2) was stirred at room temperature overnight. The precipitated solid was collected by filtration to obtain the title compound (35.5 g).

$^1$H NMR (400 MHz, DMSO-$d_6$) δ 3.90 (3H, s), 4.37 (2H, d, J=6.0 Hz), 5.42 (1H, t, J=6.0 Hz), 8.04-8.09 (1H, m), 8.24-8.29 (2H, m).

B) Methyl 4-amino-2-(3-hydroxypropyl)benzoate

A mixture of methyl 2-(3-hydroxyprop-1-yn-1-yl)-4-nitrobenzoate (55.0 g), 10% palladium on carbon (11.0 g, water content: about 50%), and methanol (1100 mL) was stirred under a hydrogen atmosphere at room temperature for 23 hours. The catalyst was removed by filtration, and the filtrate was then concentrated under reduced pressure. Ethyl acetate/diisopropyl ether (200 mL/200 mL) was added to the residue, followed by concentration under reduced pressure to obtain the title compound (48.4 g).

MS: [M+Na]$^+$ 232.0.

C) 4-((Tert-butoxycarbonyl)amino)-2-(3-hydroxypropyl)benzoic acid

A 2 M sodium hydroxide aqueous solution (625 mL) was added to a mixture of methyl 4-amino-2-(3-hydroxypropyl)benzoate (130.8 g) and methanol (1300 mL) at room temperature, followed by stirring at 50° C. for 5 hours. After cooling, di-tert-butyl dicarbonate (290 mL) was added to the reaction mixture while maintaining the internal temperature to 5° C. or less, followed by stirring at room temperature for 15 hours. Water (1300 mL), 2 N hydrochloric acid (625 mL), water (650 mL), and a seed crystal were added to the reaction mixture (internal temperature: 5° C. or less), followed by stirring at the same temperature for 2.5 hours. The precipitated solid was collected by filtration and was washed with water and heptane. A mixture of the resulting solid, diisopropyl ether (900 mL), and heptane (600 mL) was stirred at room temperature for 2 hours. The precipitated solid was collected by filtration and was washed with diisopropyl ether/heptane (3:2), followed by drying under reduced pressure at 40° C. to obtain the title compound (154 g).

MS: [M+Na]$^+$318.1.

D) Benzyl 4-((tert-butoxycarbonyl)amino)-2-(3-hydroxypropyl)benzoate

Benzyl bromide (74.2 mL) and diisopropylethylamine (182 mL) were added to a mixture of 4-((tert-butoxycarbonyl)amino)-2-(3-hydroxypropyl)benzoic acid (153.5 g) and DMF (1500 mL) at room temperature, followed by stirring for 22 hours. Water (2250 mL) was added to the reaction mixture (internal temperature: 10° C. or less), followed by stirring at 0° C. for 2 hours. The precipitated solid was collected by filtration and was washed with water and heptane. The resulting solid was dissolved in ethyl acetate, followed by drying over anhydrous magnesium sulfate. The solvent was then distilled under reduced pressure. Heptane and diisopropyl ether were added to the residue, followed by concentration under reduced pressure. Diisopropyl ether (1000 mL) was then added thereto, followed by stirring at room temperature for 2 hours. The precipitated solid was collected by filtration and was washed with diisopropyl ether to obtain the title compound (163 g).

MS: [M+Na]$^+$408.1.

E) 2,3-Bis(benzyloxy)benzoic acid

Benzyl bromide (141 mL) was added to a mixture of methyl 2,3-dihydroxybenzoate (100 g), potassium carbonate (247 g), tetrabutylammonium bromide (9.59 g), and acetone (1000 mL) at 0° C., followed by stirring at room temperature overnight. The reaction mixture was concentrated under reduced pressure, and water (400 mL) was added to the residue at 0° C., followed by stirring. The precipitated solid was collected by filtration and was washed with water/isopropyl alcohol (400 mL/100 mL) to obtain methyl 2,3-bis(benzyloxy)benzoate as a crude product.

An 8 N sodium hydroxide aqueous solution (149 mL) was added to a mixture of the methyl 2,3-bis(benzyloxy)benzoate prepared by the above-described method, methanol (400 mL), and THF (400 mL) at room temperature, followed by stirring at 50° C. for 1 hour. After completion of the reaction, 6 N hydrochloric acid (280 mL) was added to the reaction mixture to make the mixture acidic, and cold water (500 mL) was then added thereto. The precipitated solid was collected by filtration and was washed with cold water and diisopropyl ether to obtain the title compound (220 g).
MS: [M+Na]$^+$ 357.1.

F) 3-(Benzyloxy)-2-hydroxybenzoic acid

Piperidine (177 mL) was added to a mixture of 2,3-bis(benzyloxy)benzoic acid (199 g) and DMA (320 mL) at room temperature, followed by stirring under a nitrogen atmosphere at 150° C. for 2 hours. Piperidine (60 mL) was further added to the reaction mixture, followed by further stirring under a nitrogen atmosphere at 150° C. for 2 hours. 6 N hydrochloric acid (350 mL) was added to the reaction mixture at 0° C. to adjust the pH to 2 to 3. The precipitated solid was collected by filtration and was washed with cold water, followed by drying under reduced pressure at 50° C. to obtain the title compound (173 g) as a crude product.
The resulting solid was distributed between ethyl acetate and water (800 mL: 200 mL), and the organic layer was washed with water, 1 M hydrochloric acid, and a saturated saline solution and was then dried over anhydrous magnesium sulfate. The solvent was distilled under reduced pressure. The resulting solid was washed with heptane/ethyl acetate (5:1, 500 mL) and was dried under reduced pressure to obtain the title compound (114 g).
MS: [M+H]$^+$ 245.0.

G) (S)-Di-tert-butyl 2-(3-(benzyloxy)-2-hydroxybenzamide)succinate

WSC hydrochloride (179 g) and HOBt.H$_2$O (143 g) were added to a mixture of 3-(benzyloxy)-2-hydroxybenzoic acid (151.9 g), N,N-diisopropylethylamine (326 mL), and DMF (1500 mL). The mixture was stirred at room temperature for 10 minutes, and (S)-di-tert-butyl 2-aminosuccinate hydrochloride (210 g) was added thereto, followed by stirring at room temperature for 23 hours. To the reaction mixture, (S)-di-tert-butyl 2-aminosuccinate hydrochloride (21.0 g), N,N-diisopropylethylamine (32.6 mL), HOBt.H$_2$O (14.3 g), and WSC hydrochloride (17.9 g) were added at room temperature, followed by stirring at 40° C. for 5 hours. To the reaction mixture, ethyl acetate (1500 mL), a saturated sodium hydrogen carbonate aqueous solution (1500 mL), and water (1500 mL) were added (internal temperature: 25° C. or less), and the mixture was then poured into water (750 mL) for distribution. The aqueous layer was extracted with ethyl acetate (1000 mL). The organic layer combined was washed with 1 M hydrochloric acid (750 mL×2) and a saturated saline solution (750 mL×2) and was then dried over anhydrous sodium sulfate, and the solvent was distilled under reduced pressure. The residue was purified by silica gel column chromatography (ethyl acetate/hexane) to obtain the title compound (233.1 g).
MS: [M+H]$^+$ 472.3.

H) (S)-Di-tert-butyl 2-(3-(benzyloxy)-2-(3-(2-((benzyloxy)carbonyl)-5-((tert-butoxycarbonyl)amino)phenyl)propoxy)benzamide)succinate 1,1'-(Azodicarbonyl)dipiperidine (96.3 g) and tributylphosphine (94 mL) were added to a mixture of (S)-di-tert-butyl 2-(3-(benzyloxy)-2-hydroxybenzamide)succinate (90 g), benzyl 4-((tert-butoxycarbonyl)amino)-2-(3-hydroxypropyl)benzoate (73.6 g), and toluene (900 mL) (internal temperature: 35° C. or less), followed by stirring at room temperature for 16 hours. Hexane (900 mL) was added to the reaction mixture at room temperature, followed by stirring at the same temperature for 1 hour. The insoluble matter was removed by filtration, and the filtrate was then concentrated under reduced pressure. The residue was purified by silica gel column chromatography (from ethyl acetate/hexane to toluene), and a mixture of the resulting solid and diisopropyl ether/heptane (600 mL: 300 mL) was stirred at room temperature for 1 hour. The precipitated solid was collected by filtration, washed with diisopropyl ether/heptane (2:1), and dried to obtain the title compound (133 g).
MS: [M+H]$^+$ 839.4.

I) (S)-4-((tert-Butoxycarbonyl)amino)-2-(3-(2-((1,4-di-tert-butoxy-1,4-dioxobutan-2-yl)carbamoyl)-6-hydroxyphenoxy)propyl)benzoic acid A mixture of (S)-di-tert-butyl 2-(3-(benzyloxy)-2-(3-(2-((benzyloxy)carbonyl)-5-((tert-butoxycarbonyl)amino)phenyl)propoxy)benzamide)succinate (75.2 g), 10% palladium on carbon (7.5 g, water content: about 50%), and THF (1050 mL) was stirred under a hydrogen atmosphere at room temperature for 4 hours. The catalyst was removed by filtration, and the filtrate was then concentrated under reduced pressure to obtain the title compound (62.7 g).
MS: [M+H]$^+$ 659.2.

J) (S)-Di-tert-butyl 2-(10-((tert-butoxycarbonyl)amino)-13-oxo-6,7,8,13-tetrahydrodibenzo[b,f][1,4]dioxecine-4-carboxamide)succinate WSC hydrochloride (73.9 g) and N,N-dimethyl-4-aminopyridine (1.569 g) were added to a mixture of (S)-4-((tert-butoxycarbonyl)amino)-2-(3-(2-((1,4-di-tert-butoxy-1,4-dioxobutan-2-yl)carbamoyl)-6-hydroxyphenoxy)propyl)benzoic acid (169 g) and pyridine (4250 mL) (internal temperature: 10° C. or less), followed by stirring at room temperature for 15 hours. After completion of the reaction, 0.5 N hydrogen chloride/cyclopentyl methyl ether/diisopropyl ether (200 mL, a solution prepared by adding diisopropyl ether to 4 N hydrogen chloride in cyclopentyl methyl ether (25 mL) to give a volume of 200 mL) was added to the reaction mixture (internal temperature: 5° C. or less), and the solvent was distilled under reduced pressure. The residue was distributed between ethyl acetate (1700 mL) and a 20% citric acid aqueous solution (1700 mL), and the aqueous layer was re-extracted with ethyl acetate (1000 mL). The organic layer combined was washed with a 20% citric acid aqueous solution (1700 mL×2) and a saturated saline solution (1000 mL) and was then dried over anhydrous magnesium sulfate, and the solvent was distilled under reduced pressure. The residue was purified by silica gel column chromatography (ethyl acetate/hexane) to obtain the title compound (142.6 g).
MS: [M+H]$^+$ 641.3.

K) (S)-2-(10-Amino-13-oxo-6,7,8,13-tetrahydrodibenzo[b,f][1,4]dioxecine-4-carboxamide)succinic acid hydrochloride Four normal hydrogen chloride in cyclopentyl methyl ether (800 mL) was added to a mixture of (S)-di-tert-butyl 2-(10-((tert-butoxycarbonyl)amino)-13-oxo-6,7,8,13-tetrahydrodibenzo[b,f][1,4]dioxecine-4-carboxamide)succinate (156.6 g), acetic acid (800 mL), and tert-butyl alcohol (160 mL) at room temperature, and a seed crystal was then added thereto at 40° C., followed by stirring at the same temperature for 14 hours. Isopropyl acetate (1600 mL) was added to the reaction mixture (internal temperature: 25° C. or less), followed by stirring at room temperature for 1 hour. The precipitated solid was collected by filtration and was washed with isopropyl acetate to obtain the title compound (100 g).
MS: [M+H]$^+$ 429.1.

L) N-((10-Carbamimidamido-13-oxo-6,7,8,13-tetrahydrodibenzo[b,f][1,4]dioxecin-4-yl)carbonyl)-L-aspartic acid Four normal hydrogen chloride in cyclopentyl methyl ether (420 mL) and cyanamide (70.5 g) were added to a mixture of (S)-2-(10-amino-13-oxo-6,7,8,13-tetrahydrodibenzo[b,f][1,4]dioxecine-4-carboxamide)succinic acid hydrochloride (259.6 g) and tert-butyl alcohol (2600 mL) at room temperature, followed by stirring at 40° C. for 17 hours. Water (1300 mL) was added to the reaction mixture (internal temperature: 30° C. or less), and the mixture was then distributed between toluene/ethyl acetate (650 mL/650 mL) and water (2600 mL). The organic layer was extracted with water (1300 mL), and an aqueous solution (860 mL) of ammonium acetate (172 g) was added to the combined aqueous layer at room temperature, followed by stirring at room temperature for 3 hours. The precipitated solid was collected by filtration, washed with water (1300 mL) and acetone (520 mL), and dried to obtain the title compound (253 g) as a crude product.

The crude product (272.3 g) of the title compound was dissolved in acetic acid (1790 mL) and water (80 mL) at an internal temperature of 50° C., and the insoluble matter was removed by filtration (washed with 100 mL of acetic acid). Acetone/acetic acid (2025 mL/675 mL) was added to the filtrate at room temperature, and a seed crystal was then added thereto, followed by stirring at the same temperature overnight. The precipitated solid was collected by filtration, washed with acetone/acetic acid (1000 mL/1000 mL) and acetone (2000 mL), and dried under reduced pressure at 50° C. for 2 hours to obtain the title compound (206.9 g) as a solid.

The resulting solid (206.4 g) was dissolved in acetic acid (1000 mL) and water (100 mL) at an internal temperature of 50° C., and water (3000 mL) was added thereto at the same temperature. A seed crystal was then added to the solution, followed by stirring at the same temperature for 2 hours and at room temperature overnight. The precipitated solid was collected by filtration, washed with acetic acid/water (100 mL/300 mL), water (1000 mL), and acetone (1000 mL), air dried for 3 hours, and then dried under reduced pressure at 50° C. for 2 hours to obtain the title compound (176.0 g) as crystals.

The resulting solid (176.0 g) was filtered and was then pulverized with a jet mill to obtain the title compound (172.3 g) as crystals.

$^1$H NMR (300 MHz, DMSO-d$_6$) δ 2.01 (1H, brs), 2.14 (1H, brs), 2.55-2.68 (1H, m), 2.69-2.82 (1H, m), 3.31 (2H, brs), 3.88-4.04 (1H, m), 4.05-4.23 (1H, m), 4.31-4.48 (1H, m), 7.16-7.40 (3H, m), 7.64 (1H, dd, J=8.0, 1.7 Hz), 7.72-8.29 (6H, m), 9.12 (1H, d, J=6.1 Hz).

Optical purity: 99% ee

One having a longer retention time under the following optical analysis conditions:

Column: CHIRALPAK QNAX (trade name), 4.6 mm ID×250 mmL Mobile phase: methanol/acetic acid/ammonium acetate=980/20/5 (v/v/w)

Example 2

N-((10-Carbamimidamido-13-oxo-6,7,8,13-tetrahydrodibenzo[b,f][1,4]dioxecin-4-yl)carbonyl)-D-aspartic acid A) tert-Butyl 3-(benzyloxy)-2-hydroxybenzoate N,N-Dimethylformamide di-t-butyl acetal (50 mL) and toluene (200 mL) were added to a mixture of 3-(benzyloxy)-2-hydroxybenzoic acid (9.40 g) and toluene (200 mL) at room temperature, followed by heating to reflux for 1 hour. The reaction mixture was concentrated under reduced pressure, and the residue was then purified by silica gel column chromatography (ethyl acetate/hexane) to obtain the title compound (8.58 g).
MS: [M+Na]$^+$323.1.

B) tert-Butyl 3-(benzyloxy)-2-(3-(2-((benzyloxy) carbonyl)-5-((tert-butoxycarbonyl)amino)phenyl) propoxy)benzoate Methanesulfonyl chloride (2.5 mL) and triethylamine (10 mL) were added to a mixture of benzyl 4-((tert-butoxycarbonyl)amino)-2-(3-((methylsulfonyl)oxy)propyl)benzoate (11.32 g) and THF (165 mL) at 0° C., followed by stirring at room temperature for 1 hour. A saturated ammonium chloride aqueous solution was added to the reaction mixture at 0° C., followed by extraction with ethyl acetate. The organic layer was washed with a saturated saline solution and was then dried over anhydrous sodium sulfate, and the solvent was distilled under reduced pressure to obtain benzyl 4-((tert-butoxycarbonyl)amino)-2-(3-((methylsulfonyl)oxy) propyl)benzoate as a crude product.

Potassium carbonate (10.14 g) was added to a mixture of the crude product of benzyl 4-((tert-butoxycarbonyl)amino)-2-(3-((methylsulfonyl)oxy)propyl)benzoate, tert-butyl 3-(benzyloxy)-2-hydroxybenzoate (8.8184 g), and DMF (250 mL) at room temperature, followed by stirring at 80° C. for 18 hours. Ethyl acetate and 1 N hydrochloric acid were added to the reaction mixture at 0° C., followed by extraction with ethyl acetate. The organic layer was washed with water and a saturated saline solution and was then dried over anhydrous sodium sulfate, and the solvent was distilled under reduced pressure. The residue was purified by silica gel column chromatography (ethyl acetate/hexane) to obtain the title compound (16.77 g).
MS: [M+Na]$^+$690.3.

C) 2-(3-(2-(tert-Butoxycarbonyl)-6-hydroxyphenoxy)propyl)-4-((tert-butoxycarbonyl)amino)benzoic acid A mixture of tert-butyl 3-(benzyloxy)-2-(3-(2-((benzyloxy)carbonyl)-5-((tert-butoxycarbonyl)amino)phenyl) propoxy)benzoate (14.54 g), 10% palladium on carbon (1.45 g, water content: about 55%), and THF (150 mL) was stirred under a hydrogen atmosphere at room temperature for 4 hours. The catalyst was removed by filtration, and the filtrate was then concentrated under reduced pressure (toluene azeotrope, twice) to obtain the title compound (10.80 g).
MS: [M+Na]$^+$ 510.2.

D) tert-Butyl 10-((tert-butoxycarbonyl)amino)-13-oxo-6,7,8,13-tetrahydrodibenzo[b,f][1,4]dioxecine-4-carboxylate WSC hydrochloride (3.81 g) and N,N-dimethyl-4-aminopyridine (0.081 g) were added to a mixture of 2-(3-(2-(tert-butoxycarbonyl)-6-hydroxyphenoxy)propyl)-4-((tert-butoxycarbonyl)amino)benzoic acid (6.46 g) and pyridine (165 mL) at 0° C., followed by stirring at room temperature for 12 hours. Water was added to the reaction mixture at 0° C., followed by extraction with ethyl acetate. The organic layer was washed with 1 N hydrochloric acid (three times) and with saturated sodium bicarbonate water and a saturated saline solution and was then dried over anhydrous sodium sulfate, and the solvent was distilled under reduced pressure. The residue was purified by silica gel column chromatography (ethyl acetate/hexane) to obtain the title compound (5.03 g).
MS: [M+Na]$^+$ 492.1.

E) 10-Amino-13-oxo-6,7,8,13-tetrahydrodibenzo[b,f][1,4]dioxecine-4-carboxylic acid hydrochloride Concentrated hydrochloric acid (1.915 mL) was added to a mixture of tert-butyl 10-((tert-butoxycarbonyl)amino)-13-oxo-6,7,8,13-tetrahydrodibenzo[b,f][1,4]dioxecine-4-carboxylate (2.96 g) and acetic acid (30 mL) at room temperature, followed by stirring at 50° C. for 6 hours. The reaction mixture was concentrated under reduced pressure to obtain the title compound (2.240 g).
MS: [M+H]$^+$ 314.1.

F) (R)-Dibenzyl 2-(10-amino-13-oxo-6,7,8,13-tetrahydrodibenzo[b,f][1,4]dioxecine-4-carboxamide)succinate (R)-Dibenzyl 2-aminosuccinate hydrochloride (719 mg), N,N-diisopropylethylamine (1.196 mL), HOBt.H$_2$O (315 mg), and WSC hydrochloride (394 mg) were added to a mixture of 10-amino-13-oxo-6,7,8,13-tetrahydrodibenzo[b,f][1,4]dioxecine-4-carboxylic acid hydrochloride (479 mg) and DMF (5 mL) at 0° C., followed by stirring at room temperature for 6 hours. Water was added to the reaction mixture at 0° C., followed by extraction with ethyl acetate. The organic layer was washed with a saturated sodium hydrogen carbonate aqueous solution and a saturated saline solution and was then dried over anhydrous sodium sulfate, and the solvent was distilled under reduced pressure. The residue was purified by silica gel column chromatography (ethyl acetate/hexane) to obtain the title compound (781 mg).
MS: [M+H]$^+$ 609.2.

G) (R)-2-(10-Amino-13-oxo-6,7,8,13-tetrahydrodibenzo[b,f][1,4]dioxecine-4-carboxamide)succinic acid A mixture of (R)-dibenzyl 2-(10-amino-13-oxo-6,7,8,13-tetrahydrodibenzo[b,f][1,4]dioxecine-4-carboxamide)succinate (749.6 mg), 10% palladium on carbon (75 mg, water content: about 55%), and THF (8 mL) was stirred under a hydrogen atmosphere at room temperature for 6 hours. The catalyst was removed by filtration, and the filtrate was then concentrated under reduced pressure to obtain the title compound (529 mg).
MS: [M+H]$^+$ 429.1.

H) N-((10-Carbamimidamido-13-oxo-6,7,8,13-tetrahydrodibenzo[b,f][1,4]dioxecin-4-yl)carbonyl)-D-aspartic acid Four normal hydrogen chloride in cyclopentyl methyl ether (1.230 mL) and cyanamide (155 mg) were added to a mixture of (R)-2-(10-amino-13-oxo-6,7,8,13-tetrahydrodibenzo[b,f][1,4]dioxecine-4-carboxamide)succinic acid (527 mg) and tert-butyl alcohol (5 mL) at room temperature, followed by stirring at 60° C. for 5 hours. Ethyl acetate (5 mL), toluene (5 mL), and water (10 mL) were added to the reaction mixture, followed by extraction with water (water: 10 mL). Ammonium acetate (284 mg) was added to the aqueous layer at room temperature, followed by stirring at the same temperature for 2 hours. The precipitated solid was collected by filtration, washed with water, and dried under reduced pressure at 50° C. to obtain the title compound (566.4 mg) as a crude product.

The crude product (545.3 mg) of the title compound was dissolved in acetic acid (5.5 mL) at room temperature. Acetone (5.50 mL) was added to the solution at room temperature, and a seed crystal was then added thereto, followed by stirring at the same temperature overnight. Acetone (5.50 mL) was added to the resulting suspension, and the precipitated solid was then collected by filtration, washed with acetone, air dried for 2 hours, and dried under reduced pressure at 50° C. for 2 hours to obtain the title compound (487 mg). The resulting solid (440.8 mg) was dissolved in acetic acid (4.4 mL) and water (0.4 mL) at 50° C., and water (5.5 mL) was added thereto at the same temperature. A seed crystal was then added to the solution, followed by stirring at room temperature overnight. Water (1.1 mL) was added to this mixture, followed by stirring at room temperature for 72 hours. The precipitated solid was collected by filtration, washed with acetic acid/water (2:3), water, and acetonitrile, and dried under reduced pressure at 50° C. to obtain the title compound (230 mg).

$^1$H NMR (300 MHz, DMSO-d$_6$) δ 2.00 (1H, brs), 2.14 (1H, brs), 2.54-2.67 (1H, m), 2.68-2.81 (1H, m), 3.32 (2H, brs), 3.85-4.03 (1H, m), 4.05-4.22 (1H, m), 4.29-4.46 (1H, m), 7.15-7.39 (3H, m), 7.64 (1H, dd, J=7.9, 1.7 Hz), 7.70-8.37 (6H, m), 9.12 (1H, d, J=6.2 Hz).

Optical purity: >99% ee
One having a shorter retention time under the following optical analysis conditions:
Column: CHIRALPAK QNAX (trade name) 4.6 mm ID×250 mmL
Mobile phase: methanol/acetic acid/ammonium acetate=980/20/5 (v/v/w)

Example 3

N-((10-Carbamimidamido-13-oxo-6,7,8,13-tetrahydrodibenzo[b,f][1,4]dioxecin-4-yl)carbonyl)aspartic acid

A) Benzyl 4-((tert-butoxycarbonyl)amino)-2-(3-((methylsulfonyl)oxy)propyl)benzoate Methanesulfonyl chloride (1.0 mL) and triethylamine (4.0 mL) were added to a mixture of benzyl 4-((tert-butoxycarbonyl)amino)-2-(3-((methylsulfonyl)oxy)propyl)benzoate (3.62 g) and THF (60 mL) at 0° C., followed by stirring at room temperature for 1 hour. A saturated ammonium chloride aqueous solution was added to the reaction mixture at 0° C., followed by extraction with ethyl acetate. The organic layer was washed with a saturated saline solution and was then dried over anhydrous sodium sulfate, and the solvent was distilled under reduced pressure. The residue was purified by silica gel column chromatography (ethyl acetate/hexane) to obtain the title compound (4.02 g).

MS: [M+Na]$^+$ 486.3.

B) Di-tert-butyl 2-(3-(benzyloxy)-2-(3-(2-((benzyloxy)carbonyl)-5-((tert-butoxycarbonyl)amino)phenyl)propoxy)benzamide)succinate A mixture of benzyl 4-((tert-butoxycarbonyl)amino)-2-(3-((methylsulfonyl)oxy)propyl)benzoate (1.1553 g) and DMF (12 mL) was added to a mixture of (S)-di-tert-butyl 2-(3-(benzyloxy)-2-hydroxybenzamide)succinate (1.4461 g), potassium carbonate (1.0 g), and DMF (12 mL) at room temperature, followed by stirring at 80° C. overnight. The reaction mixture was poured into a mixture of ethyl acetate and a saturated ammonium chloride aqueous solution at 0° C., and was partitioned. The organic layer was washed with water and a saturated saline solution and was then dried over anhydrous sodium sulfate, and the solvent was distilled under reduced pressure. The residue was purified by silica gel column chromatography (ethyl acetate/hexane) to obtain the title compound (1.682 g).

MS: [M+H]$^+$ 839.4.

C) 4-((tert-Butoxycarbonyl)amino)-2-(3-(2-((1,4-di-tert-butoxy-1,4-dioxobutan-2-yl)carbamoyl)-6-hydroxyphenoxy)propyl)benzoic acid A mixture of di-tert-butyl 2-(3-(benzyloxy)-2-(3-(2-((benzyloxy)carbonyl)-5-((tert-butoxycarbonyl)amino)phenyl)propoxy)benzamide)succinate (7.12 g), 10% palladium on carbon (750 mg, water content: about 55%), and THF (105 mL) was stirred under a hydrogen atmosphere at room temperature for 3 hours. The catalyst was removed by filtration, and the filtrate was then concentrated under reduced pressure. Toluene was added to the residue, followed by concentration under reduced pressure to obtain the title compound (5.80 g).

MS: [M+H]$^+$ 659.3.

D) Di-tert-butyl 2-(10-((tert-butoxycarbonyl)amino)-13-oxo-6,7,8,13-tetrahydrodibenzo[b,f][1,4]dioxecine-4-carboxamide)succinate WSC hydrochloride (0.732 g) and N,N-dimethyl-4-aminopyridine (15.9 mg) were added to a mixture of 4-((tert-butoxycarbonyl)amino)-2-(3-(2-((1,4-di-tert-butoxy-1,4-dioxobutan-2-yl)carbamoyl)-6-hydroxyphenoxy)propyl)benzoic acid (1.6774 g) and pyridine (42 mL) at 0° C., followed by stirring at room temperature for 8 hours. Water (50 mL) was added to the reaction mixture at 0° C., followed by extraction with ethyl acetate (120 mL). The organic layer was washed with 1 N hydrochloric acid (100 mL×3), water, a saturated sodium hydrogen carbonate aqueous solution (50 mL), and a saturated saline solution (50 mL) and was then dried over anhydrous sodium sulfate, and the solvent was distilled under reduced pressure. The residue was purified by silica gel column chromatography (ethyl acetate/hexane) to obtain the title compound (1.404 g).

MS: [M+H]$^+$ 641.3.

E) 2-(10-Amino-13-oxo-6,7,8,13-tetrahydrodibenzo[b,f][1,4]dioxecine-4-carboxamide)succinic acid hydrochloride Four normal hydrogen chloride in cyclopentyl methyl ether (8 mL) was added to a mixture of di-tert-butyl 2-(10-((tert-butoxycarbonyl)amino)-13-oxo-6,7,8,13-tetrahydrodibenzo[b,f][1,4]dioxecine-4-carboxamide)succinate (1.39 g) and acetic acid (8 mL) at room temperature, followed by stirring at 40° C. for 3 hours. The reaction mixture was concentrated under reduced pressure. A mixture of the residue and diisopropyl ether/ethyl acetate (20 mL/2 mL) was stirred at room temperature for 1 hour, and the precipitated solid was then collected by filtration, washed with diisopropyl ether, and dried under reduced pressure to obtain the title compound (0.990 g).

MS: [M+H]$^+$ 429.1.

F) N-((10-Carbamimidamido-13-oxo-6,7,8,13-tetrahydrodibenzo[b,f][1,4]dioxecin-4-yl)carbonyl)aspartic acid

MS: [M+H]$^+$ 471.1.

Four normal hydrogen chloride in cyclopentyl methyl ether (1.510 mL) and cyanamide (254 mg) were added to a mixture of (2-(10-amino-13-oxo-6,7,8,13-tetrahydrodibenzo[b,f][1,4]dioxecine-4-carboxamide)succinic acid hydrochloride (936.0 mg) and tert-butyl alcohol (10 mL) at room temperature, followed by stirring at 60° C. for 3 hours. Toluene (10 mL), water (20 mL), and ethyl acetate (10 mL) were added to the reaction mixture, followed by extraction with water (water: 5 mL×2). Ammonium acetate (466 mg) was added to the aqueous layer at room temperature, followed by stirring at the same temperature for 2 hours. The precipitated solid was collected by filtration, washed with water, and dried under reduced pressure at 50° C. to obtain the title compound (852 mg).

$^1$H NMR (300 MHz, DMSO-d$_6$) δ 2.02 (1H, brs), 2.15 (1H, brs), 2.55-2.66 (1H, m), 2.67-2.79 (1H, m), 3.05-3.55 (2H, m), 3.96 (1H, t, J=8.0 Hz), 4.08-4.23 (1H, m, J=6.3 Hz), 4.29-4.44 (1H, m), 7.22-7.37 (3H, m), 7.64 (1H, dd, J=8.0, 1.7 Hz), 7.69-8.15 (6H, m), 9.10 (1H, d, J=5.9 Hz).

Example 6

N-((10-Carbamimidamido-13-oxo-6,7,8,13-tetrahydrodibenzo[b,f][1,4]dioxecin-4-yl)carbonyl)-3-sulfo-L-alanine A) (R)-2-(10-Guanidino-13-oxo-6,7,8,13-tetrahydrodibenzo[b,f][1,4]dioxecine-4-carboxamide)-3-methoxy-3-oxopropane-1-sulfonic acid A mixture of 10-guanidino-13-oxo-6,7,8,13-tetrahydrodibenzo[b,f][1,4]dioxecine-4-carboxylic acid hydrochloride (160 mg), (R)-2-amino-3-methoxy-3-oxopropane-1-sulfonic acid (112 mg), WSC hydrochloride (117 mg), HOBt.H$_2$O (94 mg), diisopropylethylamine (0.285 mL), and DMF (2 mL) was stirred at room temperature for 5 hours. The reaction mixture was purified by HPLC (C18, mobile phase: water/acetonitrile (system containing 0.1% TFA)), acetonitrile was removed from the obtained fraction under reduced pressure, and an ammonium acetate aqueous solution was added to the remaining aqueous solution at room temperature to adjust the pH to about 4. The resulting solid was collected by filtration to obtain the title compound (56.0 mg) as crude crystals.

MS: [M+H]$^+$ 521.1.

B) N-((10-Carbamimidamido-13-oxo-6,7,8,13-tetrahydrodibenzo[b,f][1,4]dioxecin-4-yl)carbonyl)-3-sulfo-L-alanine A mixture of (R)-2-(10-guanidino-13-oxo-6,7,8,13-tetrahydrodibenzo[b,f][1,4]dioxecine-4-carboxamide)-3-methoxy-3-oxopropane-1-sulfonic acid (45 mg), 6 M hydrochloric acid (0.5 mL), and acetic acid (0.5 mL) was stirred at 40° C. for 22 hours. The reaction mixture was concentrated under reduced pressure, and an ammonium acetate aqueous solution was then added to a mixture of the residue and water (1.5 mL) to adjust the pH to about 4. The mixture was stirred at room temperature for 2 hours, and the precipitated solid was collected by filtration and was washed with water to obtain the title compound (14.4 mg).

$^1$H NMR (400 MHz, DMSO-$d_6$) δ 2.01 (2H, brs), 2.90-3.03 (2H, m), 3.14-3.29 (2H, m), 4.08 (2H, dd, J=17.7, 5.0 Hz), 4.46-4.56 (1H, m), 7.20-7.30 (3H, m), 7.32-8.59 (8H, m), 9.06 (1H, brs).

Example 11

3-(((10-Carbamimidamido-13-oxo-6,7,8,13-tetrahydrodibenzo[b,f][1,4]dioxecin-4-yl)carbonyl)amino)pentanedioic acid

A) Dibenzyl 3-(10-amino-13-oxo-6,7,8,13-tetrahydrodibenzo[b,f][1,4]dioxecine-4-carboxamide)pentanedioate A mixture of 10-amino-13-oxo-6,7,8,13-tetrahydrodibenzo[b,f][1,4]dioxecine-4-carboxylic acid hydrochloride (133 mg), dibenzyl 3-aminopentanedioate hydrochloride (207 mg), WSC hydrochloride (109 mg), HOBt.H$_2$O (87 mg), diisopropylethylamine (0.331 mL), and DMF (2 mL) was stirred at room temperature for 2 hours. Water was added to the reaction mixture at 0° C., followed by extraction with ethyl acetate. The extract was washed with 1 N hydrochloric acid, water, and a saturated saline solution and was then dried over anhydrous magnesium sulfate, and the solvent was distilled under reduced pressure. The residue was purified by silica gel column chromatography (ethyl acetate/hexane) to obtain the title compound (241 mg).

MS: [M+H]$^+$ 623.3.

B) 3-(10-Amino-13-oxo-6,7,8,13-tetrahydrodibenzo[b,f][1,4]dioxecine-4-carboxamide)pentanedioic acid Ten percent palladium on carbon (25 mg, water content: about 55%) was added to a mixture of dibenzyl 3-(10-amino-13-oxo-6,7,8,13-tetrahydrodibenzo[b,f][1,4]dioxecine-4-carboxamide)pentanedioate (237 mg) and THF (5 mL), followed by stirring under a hydrogen atmosphere at room temperature for 3 hours. The insoluble matter was removed by filtration, and the filtrate was then concentrated under reduced pressure to obtain the title compound (173 mg).

MS: [M+H]$^+$ 443.1.

C) 3-(((10-Carbamimidamido-13-oxo-6,7,8,13-tetrahydrodibenzo[b,f][1,4]dioxecin-4-yl)carbonyl)amino)pentanedioic acid Four mole hydrogen chloride in cyclopentyl methyl ether (0.285 mL) and cyanamide (47.9 mg) were added to a mixture of 3-(10-amino-13-oxo-6,7,8,13-tetrahydrodibenzo[b,f][1,4]dioxecine-4-carboxamide)pentanedioic acid (168 mg) and tert-butyl alcohol (3 mL) at room temperature, followed by stirring at 60° C. for 4 hours. The reaction mixture was concentrated under reduced pressure, the residue was then purified by HPLC (C18, mobile phase: water/acetonitrile (system containing 0.1% TFA)), and the solvent was distilled from the obtained fraction under reduced pressure. An aqueous solution (1.5 mL) of ammonium acetate (117 mg) was added to a mixture of the residue and water (1.5 mL) at room temperature, followed by stirring at the same temperature for 1.5 hours. The precipitated solid was collected by filtration and was washed with water to obtain the title compound (100 mg).

$^1$H NMR (400 MHz, DMSO-$d_6$) δ 1.92 (2H, d, J=10.5 Hz), 2.55 (4H, d, J=5.7 Hz), 3.24 (2H, brs), 3.87 (2H, brs), 4.50 (1H, d, J=6.4 Hz), 7.18 (1H, d, J=8.3 Hz), 7.23-7.32 (2H, m), 7.60 (1H, dd, J=7.9, 1.5 Hz), 7.75 (1H, d, J=8.4 Hz), 7.85 (1H, d, J=8.4 Hz), 8.16 (4H, brs), 8.98 (1H, brs).

Example 13

N-((9-Carbamimidamido-6-oxo-11,12-dihydro-6H-dibenzo[b,f][1,4]dioxonin-1-yl)carbonyl)-L-aspartic acid trifluoroacetate

A) 3-(Benzyloxy)-2-hydroxybenzaldehyde 2,3-Dihydroxybenzaldehyde (20 g) was added to a mixture of sodium hydride (60%, 8.34 g) and DMSO (300 mL) at room temperature, followed by stirring at room temperature for 1 hour. Benzyl bromide (24.78 g) was added thereto at room temperature, followed by stirring at room temperature for 3 hours. The reaction mixture was poured into iced water and was made acidic with 1 N hydrochloric acid. The precipitated solid was collected by filtration and was dried under reduced pressure to obtain a crude product. The crude product was purified by HPLC (C18, mobile phase: water/acetonitrile (system containing 0.1% formic acid)) to obtain the title compound (5.2 g).

MS: [M−H]$^-$ 227.12.

B) Methyl 4-nitro-2-vinylbenzoate

A mixture of methyl 2-bromo-4-nitrobenzoate (30 g) and THF (270 mL) was subjected to deaeration for 10 minutes and replacement with argon. Palladium(II) chloride (408 mg), triphenylphosphine (1.81 g), and potassium vinyltrifluoroborate (15.4 g) were added thereto at room temperature, followed by deaeration for 10 minutes. Cesium carbonate (112.5 g) and water (30 mL) were then added to the mixture at room temperature, followed by stirring at 85° C. for 18 hours. The mixture was cooled to room temperature and was then poured into iced water. The mixture was extracted with ethyl acetate, and the extract was washed with a saturated saline solution, and was then dried over anhydrous sodium sulfate, filtered, and concentrated under reduced pressure. The residue was purified by silica gel column chromatography (ethyl acetate/petroleum ether) to obtain the title compound (31.4 g).

$^1$H NMR (400 MHz, CDCl$_3$) δ 3.96 (3H, s), 5.53 (1H, d, J=10.76 Hz), 5.83 (1H, d, J=17.61 Hz), 7.43 (1H, dd, J=17.36, 11.00 Hz), 8.01 (1H, d, J=8.80 Hz), 8.11-8.13 (1H, m), 8.41 (1H, s).

C) Methyl 4-amino-2-vinylbenzoate

An iron powder (101 g) was added to a mixture of methyl 4-nitro-2-vinylbenzoate (38 g) and ethyl acetate (1 L) at room temperature, and ammonium chloride (59.4 g) and water (200 mL) were then added thereto at room temperature, followed by stirring at 75° C. for 48 hours. The reaction mixture was cooled to room temperature and was filtered through Celite (trade name). The filtrate was washed with a saturated saline solution, and the organic layer was dried over anhydrous sodium sulfate, filtered, and concentrated under reduced pressure to obtain the title compound (32 g).

MS: [M+H]$^+$ 178.12.

D) Methyl 4-((tert-butoxycarbonyl)amino)-2-vinylbenzoate

Triethylamine (70 mL), 4-dimethylaminopyridine (catalyst quantity), and di-tert-butyl dicarbonate (42.78 mL) were added to a mixture of methyl 4-amino-2-vinylbenzoate (30 g) and THF (300 mL) at 0° C., followed by stirring at room temperature for 18 hours. The mixture was diluted with water, followed by extraction with ethyl acetate. The organic layer was washed with water and a saturated saline solution, and was then dried over anhydrous sodium sulfate, filtered, and concentrated under reduced pressure. The residue was purified by silica gel column chromatography (ethyl acetate/petroleum ether) to obtain the title compound (18 g).

MS: [M+H]$^+$ 278.12.

E) Methyl 4-((tert-butoxycarbonyl)amino)-2-(2-hydroxyethyl)benzoate

9-Borabicyclo[3.3.1]nonane (0.5 M THF solution, 180 mL) was added dropwise to a mixture of methyl 4-((tert-butoxycarbonyl)amino)-2-vinylbenzoate (5 g) and THF (50 mL) at 0° C., followed by stirring at room temperature for 18 hours. A 1 N sodium hydroxide aqueous solution (10 mL) and 30% hydrogen peroxide (15 mL) were added to the mixture, followed by stirring at room temperature for 2 hours. The reaction mixture was diluted with water, followed by extraction with ethyl acetate. The organic layer was washed with water and a saturated saline solution, and was then dried over anhydrous sodium sulfate, filtered, and concentrated under reduced pressure. The residue was purified by silica gel column chromatography (ethyl acetate/petroleum ether) to obtain the title compound (3 g).

MS: [M+H]$^+$ 296.50.

F) Methyl 4-((tert-butoxycarbonyl)amino)-2-(2-((methylsulfonyl)oxy)ethyl)benzoate Methanesulfonyl chloride (1.73 g) was added to a mixture of methyl 4-((tert-butoxycarbonyl)amino)-2-(2-hydroxyethyl)benzoate (3 g) and dichloromethane (25 mL) at 0° C., and a mixture of triethylamine (3.08 g) and dichloromethane (20 mL) was then added thereto at 0° C., followed by stirring at room temperature for 1 hour. The mixture was diluted with water, followed by extraction with dichloromethane. The organic layer was washed with water and a saturated saline solution, and the organic layer was then dried over anhydrous sodium sulfate, filtered, and concentrated under reduced pressure to obtain the title compound (3 g).

MS: [M+H]$^+$ 374.19.

G) Methyl 2-(2-(2-(benzyloxy)-6-formylphenoxy)ethyl)-4-((tert-butoxycarbonyl)amino)benzoate Potassium carbonate (5.54 g) was added to a mixture of methyl 4-((tert-butoxycarbonyl)amino)-2-(2-((methylsulfonyl)oxy)ethyl)benzoate (7.5 g), 3-(benzyloxy)-2-hydroxybenzaldehyde (3.05 g), and DMF (100 mL) at 0° C., followed by stirring at 90° C. for 18 hours. The reaction mixture was cooled to room temperature and was then poured into iced water, and the aqueous layer was extracted with ethyl acetate. The organic layer was washed with water and a saturated saline solution, and was then dried over anhydrous sodium sulfate, filtered, and concentrated under reduced pressure. The residue was purified by silica gel column chromatography (ethyl acetate/petroleum ether) to obtain the title compound (3 g).

MS: [M+H]$^+$ 506.17.

H) 3-(Benzyloxy)-2-(2-(5-((tert-butoxycarbonyl)amino)-2-(methoxycarbonyl)phenyl)ethoxy)benzoic acid An aqueous solution (15 mL) of sodium dihydrogen phosphate (4.06 g), sodium chlorite (1.06 g), and 2-methyl-2-butene (3.32 g) were added to a mixture of methyl 2-(2-(2-(benzyloxy)-6-formylphenoxy)ethyl)-4-((tert-butoxycarbonyl)amino)benzoate (3 g), tert-butanol (25 mL), and dichloromethane (15 mL) at 0° C., followed by stirring at room temperature for 2 hours. The reaction mixture was diluted with water, followed by extraction with ethyl acetate. The organic layer was washed with water and a saturated saline solution, and the organic layer was then dried over anhydrous sodium sulfate, filtered, and concentrated under reduced pressure to obtain the title compound (3.2 g).

MS: [M+H]$^+$ 522.19.

I) tert-Butyl 3-(benzyloxy)-2-(2-(5-((tert-butoxycarbonyl)amino)-2-(methoxycarbonyl)phenyl)ethoxy)benzoate N,N-Dimethylformamide di-tert-butylacetal (7.2 mL) was added to a mixture of 3-(benzyloxy)-2-(2-(5-((tert-butoxycarbonyl)amino)-2-(methoxycarbonyl)phenyl)ethoxy)benzoic acid (6.2 g) and toluene (15 mL) at room temperature, followed by heating to reflux for 18 hours. The reaction mixture was concentrated under reduced pressure, and the residue was purified by silica gel column chromatography (ethyl acetate/petroleum ether) to obtain the title compound (4 g).

MS: [M−H]$^−$ 576.30.

J) 2-(2-(2-(Benzyloxy)-6-(tert-butoxycarbonyl)phenoxy)ethyl)-4-((tert-butoxycarbonyl)amino)benzoic acid Lithium hydroxide (1.45 g) was added to a mixture of tert-butyl 3-(benzyloxy)-2-(2-(5-((tert-butoxycarbonyl)amino)-2-(methoxycarbonyl)phenyl)ethoxy)benzoate (4 g) and THF/methanol/water (2:1:1, 20 mL) at 0° C., followed by stirring at room temperature for 18 hours. After neutralization with 1 N hydrochloric acid, extraction with ethyl acetate was performed. The organic layer was washed with water and a saturated saline solution, and the organic layer was then dried over anhydrous sodium sulfate, filtered, and concentrated under reduced pressure to obtain the title compound (1.4 g).

MS: [M−H]$^−$ 562.33.

K) 4-((tert-Butoxycarbonyl)amino)-2-(2-(2-(tert-butoxycarbonyl)-6-hydroxyphenoxy)ethyl)benzoic acid Palladium on carbon (100 mg) was added to a mixture of 2-(2-(2-(benzyloxy)-6-(tert-butoxycarbonyl)phenoxy)

ethyl)-4-((tert-butoxycarbonyl)amino)benzoic acid (1.4 g) and ethanol (20 mL), followed by stirring under a hydrogen atmosphere at room temperature for 6 hours. The reaction mixture was filtered through Celite (trade name), the filtrate was concentrated under reduced pressure to obtain the title compound (1.2 g).
MS: [M−H]$^+$ 472.29.

L) tert-Butyl 9-((tert-butoxycarbonyl)amino)-6-oxo-11,12-dihydro-6H-dibenzo[b,f][1,4]dioxonine-1-carboxylate Methyl-6-nitrobenzoic acid (0.96 g) and dimethylaminopyridine (0.284 g) were added to a mixture of 4-((tert-butoxycarbonyl)amino)-2-(2-(2-(tert-butoxycarbonyl)-6-hydroxyphenoxy)ethyl)benzoic acid (1.1 g) and dichloromethane (10 mL) at room temperature, followed stirring at room temperature for 16 hours. After completion of the reaction, concentration was performed under reduced pressure. The residue was purified by silica gel column chromatography (ethyl acetate/petroleum ether) to obtain the title compound (0.43 g).
MS: [M−H]$^−$ 454.30.

M) 9-Amino-6-oxo-11,12-dihydro-6H-dibenzo[b,f][1,4]dioxonine-1-carboxylic acid

A mixture of tert-butyl 9-((tert-butoxycarbonyl)amino)-6-oxo-11,12-dihydro-6H-dibenzo[b,f][1,4]dioxonine-1-carboxylate (0.43 g) and TFA (2 mL) was stirred at room temperature for 2 hours. The reaction mixture was concentrated under reduced pressure. The residue was washed with hexane and pentane to obtain the title compound (0.30 g).
MS: [M+H]$^+$ 300.14.

N) 9-(N',N''-Bis(tert-butoxycarbonyl)carbamimidamido)-6-oxo-11,12-dihydro-6H-dibenzo[b,f][1,4]dioxonine-1-carboxylic acid N,N'-Bis(tert-butoxycarbonyl)-1H-pyrazole-1-carboxyamidine (378 mg) was added to a mixture of 9-amino-6-oxo-11,12-dihydro-6H-dibenzo[b,f][1,4]dioxonine-1-carboxylic acid (300 mg) and acetonitrile (5 mL) at room temperature, followed by stirring at room temperature for 4 hours. The reaction mixture was concentrated under reduced pressure. The residue was purified by silica gel column chromatography (ethyl acetate/petroleum ether) to obtain the title compound (0.30 g).
MS: [M+H]$^+$ 554.32.

O) Di-tert-butyl N-((9-(N',N''-bis(tert-butoxycarbonyl)carbamimidamido)-6-oxo-11,12-dihydro-6H-dibenzo[b,f][1,4]dioxonin-1-yl)carbonyl)-L-aspartate WSC hydrochloride (0.105 g), HOBt (0.059 g), and N,N'-diisopropylethylamine (0.095 g) were added to a mixture of 9-(N',N''-bis(tert-butoxycarbonyl)carbamimidamido)-6-oxo-11,12-dihydro-6H-dibenzo[b,f][1,4]dioxonine-1-carboxylic acid (0.20 g) and THF (10 mL) at 0° C., followed by stirring at room temperature for 30 minutes. Subsequently, di-tert-butyl L-aspartate hydrochloride (0.125 g) was added thereto at 0° C., followed by stirring at room temperature for 18 hours. The reaction mixture was diluted with water, followed by extraction with ethyl acetate. The organic layer was washed with water and a saturated saline solution, and was then dried over anhydrous sodium sulfate, filtered, and concentrated under reduced pressure. The residue was purified by silica gel column chromatography (ethyl acetate/petroleum ether) to obtain the title compound (150 mg).
MS: [M+H]$^+$ 769.48.

P) N-((9-Carbamimidamido-6-oxo-11,12-dihydro-6H-dibenzo[b,f][1,4]dioxonin-1-yl)carbonyl)-L-aspartic acid trifluoroacetate Di-tert-butyl N-((9-(N',N''-bis(tert-butoxycarbonyl)carbamimidamido)-6-oxo-11,12-dihydro-6H-dibenzo[b,f][1,4]dioxonin-1-yl)carbonyl)-L-aspartate (0.150 g) was added to TFA (2 mL) cooled to 0° C., followed by stirring at room temperature for 2 hours. The reaction mixture was concentrated under reduced pressure, and the resulting solid was washed with pentane to obtain the title compound (65 mg).
$^1$H NMR (400 MHz, DMSO-d$_6$) δ 2.81 (2H, d, J=5.38 Hz), 3.20-3.22 (2H, m), 4.24-4.31 (2H, m), 4.74-4.79 (1H, m), 7.30-7.36 (3H, m), 7.55 (1H, dd, J=8.07, 1.71 Hz), 7.61 (1H, dd, J=7.83, 1.47 Hz), 7.70 (4H, s), 7.84 (1H, d, J=9.2 Hz), 8.56 (1H, d, J=8.31 Hz), 10.01 (1H, s), 12.48 (1H, brs), 12.91 (1H, brs).

Example 18

N-((10-Carbamimidamido-13-oxo-6,7,8,13-tetrahydrodibenzo[b,f][1,4]dioxecin-4-yl)carbonyl)-L-glutamic acid A) (S)-Dibenzyl 2-(10-amino-13-oxo-6,7,8,13-tetrahydrodibenzo[b,f][1,4]dioxecine-4-carboxamide)pentanedioate A mixture of 10-amino-13-oxo-6,7,8,13-tetrahydrodibenzo[b,f][1,4]dioxecine-4-carboxylic acid hydrochloride (100 mg), L-glutamic acid dibenzyl ester hydrochloride (156 mg), WSC hydrochloride (82 mg), HOBt.H$_2$O (65.7 mg), diisopropylethylamine (0.250 mL), and DMF (2 mL) was stirred at room temperature for 3 hours. Water was added to the reaction mixture at 0° C., followed by extraction with ethyl acetate. The extract was washed with 1 N hydrochloric acid, water, and a saturated saline solution, and was then dried over anhydrous magnesium sulfate, and the solvent was distilled under reduced pressure. The residue was purified by silica gel column chromatography (ethyl acetate/hexane) to obtain the title compound (159 mg).
MS: [M+H]$^+$ 623.3.

B) (S)-2-(10-Amino-13-oxo-6,7,8,13-tetrahydrodibenzo[b,f][1,4]dioxecine-4-carboxamide)pentanedioic acid Ten percent palladium on carbon (32 mg, water content: about 55%) was added to a mixture of (S)-dibenzyl 2-(10-amino-13-oxo-6,7,8,13-tetrahydrodibenzo[b,f][1,4]dioxecine-4-carboxamide)pentanedioate (156 mg) and THF (3 mL), followed by stirring under a hydrogen atmosphere at room temperature for 4 hours. The insoluble matter was removed by filtration, and the resulting filtrate was then concentrated under reduced pressure to obtain the title compound (120 mg).
MS: [M+H]$^+$ 443.1.

C) N-((10-Carbamimidamido-13-oxo-6,7,8,13-tetrahydrodibenzo[b,f][1,4]dioxecin-4-yl)carbonyl)-L-glutamic acid Four mole hydrogen chloride in cyclopentyl methyl ether (0.188 mL) and cyanamide (31.5 mg) were added to a mixture of (S)-2-(10-amino-13-oxo-6,7,8,13-tetrahydrodibenzo[b,f][1,4]dioxecine-4-carboxamide)pentanedioic acid (111 mg) and tert-butyl alcohol (2 mL) at room temperature, followed by stirring at 60° C. for 4 hours. The reaction mixture was concentrated under reduced pressure, and the residue was then purified by HPLC (C18, mobile phase:
water/acetonitrile (system containing 0.1% TFA)). The solvent was distilled from the obtained fraction under reduced pressure. An aqueous solution (1.5 mL) of ammonium acetate (57.8 mg) was added to a mixture of the residue and water (1.5 mL) at room temperature, followed by stirring at the same temperature for 1.5 hours. The precipitated solid was collected by filtration and was washed with water to obtain the title compound (33.2 mg).
$^1$H NMR (400 MHz, DMSO-d$_6$) δ 1.85-2.35 (7H, m), 3.41-3.52 (1H, m, J=8.9 Hz), 3.99-4.09 (1H, m), 4.16-4.30 (2H, m), 7.23 (1H, d, J=1.8 Hz), 7.32 (1H, t, J=8.0 Hz), 7.37 (1H, dd, J=8.4, 1.8 Hz), 7.66 (1H, dd, J=7.9, 1.7 Hz), 7.74-8.64 (6H, m), 9.00 (1H, d, J=6.5 Hz), 12.29 (2H, brs).

Example 19

N-((9-Carbamimidamido-6-oxo-6,11-dihydrodibenzo[b,f][1,4]dioxocin-1-yl)carbonyl)-L-aspartic acid trifluoroacetate A) 2-(Trimethylsilyl)ethyl 2-methyl-4-nitrobenzoate 4-Dimethylaminopyridine (67.4 g) and WSC hydrochloride (95.46 g) were added to a mixture of 2-methyl-4-nitrobenzoic acid (50 g) and dichloromethane (600 mL) at room temperature, followed by stirring at room temperature for 30 minutes. 2-(Trimethylsilyl)ethanol (58.79 g) was then added thereto at room temperature, followed by stirring at room temperature for 5 hours. After completion of the reaction, the reaction mixture was diluted with water, followed by extraction with ethyl acetate. The organic layer was washed with water and a saturated saline solution, and was then dried over anhydrous sodium sulfate, filtered, and concentrated under reduced pressure. The residue was purified by silica gel column chromatography (ethyl acetate/petroleum ether) to obtain the title compound (75 g).
$^1$H NMR (400 MHz, CDCl$_3$) δ 0.08 (9H, s), 1.13-1.17 (2H, m), 2.68 (3H, s), 4.41-4.45 (2H, m), 7.95 (1H, d, J=8.7 Hz), 8.05-8.08 (1H, m), 8.10 (1H, s).

B) 2-(Trimethylsilyl)ethyl 2-(bromomethyl)-4-nitrobenzoate

N-Bromosuccinimide (47.5 g) and 2,2'-azobisisobutyronitrile (4.38 g) were added to a mixture of 2-(trimethylsilyl)ethyl 2-methyl-4-nitrobenzoate (75 g) and carbon tetrachloride (150 mL) at room temperature, followed by irradiation with an UV halogen lamp to reflux for 18 hours. The mixture was filtered through Celite (trade name), and the filtrate was diluted with water, followed by extraction with dichloromethane. The organic layer was washed with water and a saturated saline solution, and was then dried over anhydrous sodium sulfate, filtered, and concentrated under reduced pressure. The residue was purified by silica gel column chromatography (ethyl acetate/petroleum ether) to obtain the title compound (35 g).
$^1$H NMR (400 MHz, CDCl$_3$) δ 0.09 (9H, s), 1.16-1.21 (2H, m), 4.46-4.51 (2H, m), 4.97 (2H, s), 8.09 (1H, d, J=8.3 Hz), 8.20 (1H, dd, J=2.2, 8.6 Hz), 8.32 (1H, d, J=2.4 Hz).

C) 1,2-Bis(methoxymethoxy)benzene

A mixture of pyrocatechol (50 g) and DMF (250 mL) was added dropwise to a mixture of 60% sodium hydride (54.3 g) and DMF (250 mL) at 0° C., followed by stirring at room temperature for 30 minutes. Subsequently, chloromethyl methyl ether (91.4 g) was added thereto at room temperature, followed by stirring at room temperature for 3 hours. The reaction mixture was poured into iced water, and the aqueous layer was extracted with ethyl acetate. The organic layer was washed with water and a saturated saline solution, and was then dried over anhydrous sodium sulfate, filtered, and concentrated under reduced pressure to obtain the title compound (90 g).
$^1$H NMR (300 MHz, CDCl$_3$) δ 3.52 (6H, s), 5.23 (4H, s), 6.94-6.98 (2H, m), 7.14-7.18 (2H, m).

D) 2,3-Bis(methoxymethoxy)benzaldehyde

Normal-Butyllithium (1.6 M hexane solution, 502 mL) was added to a mixture of 1,2-bis(methoxymethoxy)benzene (90 g) and diethyl ether (900 mL) at 0° C., followed by stirring at 0° C. for 3 hours. DMF (64.5 g) was then added thereto at 0° C., followed by stirring at 0° C. for 10 minutes. An ammonium chloride aqueous solution was added to the reaction mixture, and the aqueous layer was extracted with diethyl ether. The organic layer was washed with water and a saturated saline solution, and was then dried over anhydrous sodium sulfate, filtered, and concentrated under reduced pressure. The residue was purified by silica gel column chromatography (ethyl acetate/petroleum ether) to obtain the title compound (51 g).
MS: [M−H]$^-$ 225.18.

E) 2-Hydroxy-3-(methoxymethoxy)benzaldehyde

Montmorillonite K10 (trade name, 51 g) was added to a mixture of 2,3-bis(methoxymethoxy)benzaldehyde (51 g) and benzene (500 mL), followed by stirring at room temperature for 3 hours. After completion of the reaction, insoluble matter was removed by filtration through Celite (trade name), and the filtrate was concentrated under reduced pressure. The residue was purified by silica gel column chromatography (ethyl acetate/petroleum ether) to obtain the title compound (10 g).
MS (M+H)$^+$: 183.13.

F) 2-(Trimethylsilyl)ethyl 2-((2-formyl-6-(methoxymethoxy)phenoxy)methyl)-4-nitrobenzoate A mixture of 2-hydroxy-3-(methoxymethoxy)benzaldehyde (5.0 g) and DMF (20 mL) was added to a mixture of 60% sodium hydride (1.2 g) and DMF (20 mL) at 0° C., followed by stirring for 30 minutes. Subsequently, a mixture of 2-(trimethylsilyl)ethyl 2-(bromomethyl)-4-nitrobenzoate (19.8 g) and DMF (20 mL) was added dropwise thereto at 0° C., followed by stirring at room temperature for 18 hours. After completion of the reaction, the mixture was poured into iced water, and the aqueous layer was diluted with ethyl acetate. The organic layer was washed with cold water and a saturated saline solution, and was then dried over anhydrous sodium sulfate, filtered, and concentrated under reduced pressure. The residue was purified by silica gel column chromatography (ethyl acetate/petroleum ether) to obtain the title compound (7 g).
$^1$H NMR (400 MHz, CDCl$_3$) δ 0.06-0.1 (9H, m), 1.09-1.13 (2H, m), 3.47 (3H, s), 4.37-4.41 (2H, m), 5.21 (2H, s), 5.62 (2H, s), 7.19 (1H, t, J=1.5 Hz), 7.44 (1H, dd, J=1.5, 8.3 Hz), 7.53 (1H, dd, J=1.5, 7.8 Hz), 8.15-8.18 (1H, m), 8.22-8.25 (1H, m), 8.89 (1H, d, J=2.0 Hz), 10.37 (1H, s).

G) 3-(Methoxymethoxy)-2-((5-nitro-2-((2-(trimethylsilyl)ethoxy)carbonyl)benzyl)oxy)benzoic acid A mixture of sodium chlorite (2.74 g), sodium dihydrogen phosphate (10.45 g), and water (15 mL) was added to a mixture of 2-(trimethylsilyl)ethyl 2-((2-formyl-6-(methoxymethoxy)phenoxy)methyl)-4-nitrobenzoate (7 g) and tert-butanol/dichloromethane (10:3, 70 mL) at 0° C., and 2-methyl-2-butene (8.48 g) was then added thereto, followed by stirring at room temperature for 18 hours. After completion of the reaction, the mixture was concentrated under reduced pressure, and water was added to the residue, followed by extraction with ethyl acetate. The organic layer was washed with water and a saturated saline solution, and was then dried over anhydrous sodium sulfate, filtered, and concentrated under reduced pressure. The residue was washed with pentane to obtain the title compound (6.0 g).
MS (M−H)⁻: 476.22.

H) tert-Butyl 3-(methoxymethoxy)-2-((5-nitro-2-((2-(trimethylsilyl)ethoxy)carbonyl)benzyl)oxy)benzoate N,N-Dimethylformamide di-tert-butylacetal (7.66 g) was added to a mixture of 3-(methoxymethoxy)-2-((5-nitro-2-((2-(trimethylsilyl)ethoxy)carbonyl)benzyl)oxy)benzoic acid (6 g) and toluene (60 mL) at room temperature, followed by stirring at 100° C. for 3 hours. The reaction mixture was cooled to room temperature, N,N-dimethylformamide di-tert-butylacetal (7.66 g) was added thereto, and the mixture was stirred at 100° C. for 24 hours, followed by concentration under reduced pressure. The residue was diluted with water, followed by extraction with ethyl acetate. The organic layer was washed with water and a saturated saline solution, and was then dried over anhydrous sodium sulfate, filtered, and concentrated under reduced pressure. The residue was purified by silica gel column chromatography (ethyl acetate/petroleum ether) to obtain the title compound (4 g).
MS (M+H)⁺: 534.29.

I) tert-Butyl 2-((5-amino-2-((2-(trimethylsilyl)ethoxy)carbonyl)benzyl)oxy)-3-(methoxymethoxy)benzoate Iron (3.1 g) and ammonium chloride (1.85 g) were added to a mixture of tert-butyl 3-(methoxymethoxy)-2-((5-nitro-2-((2-(trimethylsilyl)ethoxy)carbonyl)benzyl)oxy)benzoate (3.7 g) and ethanol/water (4:1, 50 mL) at room temperature, followed by stirring at 80° C. for 4 hours. After completion of the reaction, the reaction mixture was filtered through Celite (trade name), and the filtrate was concentrated under reduced pressure. The residue was diluted with water, followed by extraction with ethyl acetate. The organic layer was washed with water and a saturated saline solution, and was then dried over anhydrous sodium sulfate, filtered, and concentrated under reduced pressure. The residue was purified by silica gel column chromatography (ethyl acetate/petroleum ether) to obtain the title compound (3.4 g).
MS (M+H)⁺: 504.18.

J) tert-Butyl 2-((5-amino-2-((2-(trimethylsilyl)ethoxy)carbonyl)benzyl)oxy)-3-hydroxybenzoate One normal hydrogen chloride in 2-propanol (19.68 mL) was added dropwise to a mixture of tert-butyl 2-((5-amino-2-((2-(trimethylsilyl)ethoxy)carbonyl)benzyl)oxy)-3-(methoxymethoxy)benzoate (3.3 g) and 2-propanol (15 mL) at 0° C., followed by stirring at room temperature for 4 hours. The mixture was diluted with water, followed by extraction with ethyl acetate. The organic layer was washed with water and a saturated saline solution, and was then dried over anhydrous sodium sulfate, filtered, and concentrated under reduced pressure. The residue was purified by neutral silica gel column chromatography (ethyl acetate/petroleum ether) to obtain the title compound (2.47 g).
MS (M+H)⁺: 460.21.

K) 4-Amino-2-((2-(tert-butoxycarbonyl)-6-hydroxyphenoxy)methyl)benzoic acid

Tetra-n-butylammonium fluoride (1 M THF solution, 16.14 mL) was added dropwise to a mixture of tert-butyl 2-((5-amino-2-((2-(trimethylsilyl)ethoxy)carbonyl)benzyl)oxy)-3-hydroxybenzoate (2.47 g) and THF (20 mL) at 0° C., followed by stirring at room temperature for 18 hours. After completion of the reaction, the mixture was diluted with water, followed by extraction with ethyl acetate. The organic layer was washed with water and a saturated saline solution, and was then dried over anhydrous sodium sulfate, filtered, and concentrated under reduced pressure. The residue was purified by neutral silica gel column chromatography (methanol/dichloromethane) to obtain the title compound (1.55 g).
MS (M+H)⁺: 360.10.

L) tert-Butyl 9-amino-6-oxo-6,11-dihydrodibenzo[b,f][1,4]dioxocine-1-carboxylate 2-Methyl-6-nitrobenzoic acid (0.575 g) and 4-dimethylaminopyridine (0.154 g) were added to a mixture of 4-amino-2-((2-(tert-butoxycarbonyl)-6-hydroxyphenoxy)methyl)benzoic acid (0.5 g) and dichloromethane (10 mL) at room temperature, followed by stirring at room temperature for 36 hours and then concentration under reduced pressure. The residue was purified by neutral silica gel column chromatography (ethyl acetate/petroleum ether) to obtain the title compound (0.35 g).
MS (M+H)⁺: 342.18.

M) 9-Amino-6-oxo-6,11-dihydrodibenzo[b,f][1,4]dioxocine-1-carboxylic acid tert-Butyl 9-amino-6-oxo-6,11-dihydrodibenzo[b,f][1,4]dioxocine-1-carboxylate (0.3 g) was added to TFA (3 mL) at 0° C., followed by stirring at room temperature for 2 hours. The mixture was then concentrated under reduced pressure. Dichloromethane was added to the residue, followed by concentration to obtain the title compound (0.34 g).
MS (M+H)⁺: 286.07.

N) 9-(N',N''-Bis(tert-butoxycarbonyl)carbamimidamido)-6-oxo-6,11-dihydrodibenzo[b,f][1,4]dioxocine-1-carboxylic acid N,N'-Bis(tert-butoxycarbonyl)-1H-pyrazole-1-carboxamidine (264 mg) and triethylamine (172 mg) were added to a mixture of 9-amino-6-oxo-6,11-dihydrodibenzo[b,f][1,4]dioxocine-1-carboxylic acid (340 mg) and acetonitrile (10 mL) at room temperature, followed by stirring at room temperature for 12 hours. Ethyl acetate was added thereto, and the mixture was washed with water and a saturated saline solution, and was then dried over anhydrous sodium sulfate, filtered, and concentrated under reduced pressure. The residue was purified by neutral silica gel column chromatography (methanol/dichloromethane) to obtain the title compound (0.19 g).
MS (M+H)+: 528.24.

O) Di-tert-butyl N-((9-(N',N''-bis(tert-butoxycarbonyl)carbamimidamido)-6-oxo-6,11-dihydrodibenzo[b,f][1,4]dioxocin-1-yl)carbonyl)-L-aspartate WSC hydrochloride (0.146 g), HOBt (0.082 g), and N,N'-diisopropylethylamine (0.16 mL) were added to a mixture of 9-(N',N''-bis(tert-butoxycarbonyl)carbamimidamido)-6-oxo-6,11-dihydrodibenzo[b,f][1,4]dioxocine-1-carboxylic acid (0.27 g) and THF (10 mL) at 0° C., followed by stirring at room temperature for 30 minutes. Subsequently, di-tert-butyl L-aspartate hydrochloride (0.174 g) was added thereto at 0° C., followed by stirring at room temperature for 18 hours. After completion of the reaction, the reaction mixture was diluted with water, followed by extraction with ethyl acetate. The organic layer was washed with water and a saturated saline solution, and was then dried over anhydrous sodium sulfate, filtered, and concentrated under reduced pressure. The residue was purified by silica gel column chromatography (neutral, ethyl acetate/petroleum ether) to obtain the title compound (160 mg).
MS (M+H)+: 755.45.

P) N-((9-Carbamimidamido-6-oxo-6,11-dihydrodibenzo[b,f][1,4]dioxocin-1-yl)carbonyl)-L-aspartic acid trifluoroacetate Di-tert-butyl N-((9-(N',N''-bis(tert-butoxycarbonyl)carbamimidamido)-6-oxo-6,11-dihydrodibenzo[b,f][1,4]dioxocin-1-yl)carbonyl)-L-aspartate (0.160 g) was added to iced TFA (2 mL), followed by stirring room temperature for 3 hours. The reaction mixture was concentrated under reduced pressure, and ethyl acetate was added to the residue, followed by concentration under reduced pressure. The resulting solid was washed with hexane to obtain the title compound (110 mg).
$^1$H NMR (400 MHz, DMSO-d$_6$) δ 2.78-2.90 (2H, m), 4.77-4.82 (1H, m), 5.41-5.48 (2H, m), 7.11-7.18 (2H, m), 7.28 (1H, dd, J=2.0, 8.3 Hz), 7.36 (1H, dd, J=1.5, 7.8 Hz), 7.45 (1H, dd, J=1.5, 7.8 Hz), 7.60-7.64 (5H, m), 8.78 (1H, d, J=8.3 Hz), 9.89 (1H, brs), 12.42-13.05 (2H, m).

Example 22

3-(10-Carbamimidamido-13-oxo-6,7,8,13-tetrahydrodibenzo[b,f][1,4]dioxecin-4-yl)-5-(carboxymethyl)-4,5-dihydro-1,2-oxazole-5-carboxylic acid A) 2-((tert-Butyl(dimethyl)silyl)oxy)-3-((4-methoxybenzyl)oxy)benzaldehyde A mixture of 2-hydroxy-3-((4-methoxybenzyl)oxy)benzaldehyde (2.00 g), tert-butyldimethylchlorosilane (1.401 g), imidazole (0.633 g), and DMF (20 mL) was stirred at room temperature for 2 hours. Water was added to the reaction mixture, followed by extraction with hexane/ethyl acetate. The extract was washed with water and a saturated saline solution and was dried over anhydrous magnesium sulfate. The solvent was then distilled under reduced pressure to obtain the title compound (3.33 g).
MS: [M+H]+ 373.2.

B) (E)-1-(2-((tert-Butyl(dimethyl)silyl)oxy)-3-((4-methoxybenzyl)oxy)phenyl)-N-hydroxymethanimine A mixture of 2-((tert-butyl(dimethyl)silyl)oxy)-3-((4-methoxybenzyl)oxy)benzaldehyde (3.33 g), hydroxylammonium chloride (0.683 g), sodium hydrogen carbonate (0.826 g), water (3 mL), and ethanol (27 mL) was stirred at room temperature overnight. Water was added to the reaction mixture, followed by extraction with ethyl acetate. The extract was washed with a saturated saline solution and was dried over anhydrous magnesium sulfate, and the solvent was then distilled under reduced pressure to obtain the title compound (2.85 g).
MS: [M+H]+ 388.2.

C) tert-Butyl 5-(2-tert-butoxy-2-oxoethyl)-3-(2-((tert-butyl(dimethyl)silyl)oxy)-3-((4-methoxybenzyl)oxy)phenyl)-4,5-dihydro-1,2-oxazole-5-carboxylate A sodium hypochlorite aqueous solution (5%, 24.09 g) was added to a mixture of (E)-1-(2-((tert-butyl(dimethyl)silyl)oxy)-3-((4-methoxybenzyl)oxy)phenyl)-N-hydroxymethanimine (2.85 g), di-tert-butyl 2-methylenesuccinate (1.782 g), and THF (30 mL) at 0° C., followed by stirring at room temperature for 6 hours. Water was added to the reaction mixture, followed by extraction with ethyl acetate. The extract was washed with a saturated saline solution and was dried over anhydrous magnesium sulfate, and the solvent was then distilled under reduced pressure to obtain the title compound (4.35 g).
MS: [M+H]+ 628.3.

D) tert-Butyl 5-(2-tert-butoxy-2-oxoethyl)-3-(2-hydroxy-3-((4-methoxybenzyl)oxy)phenyl)-4,5-dihydro-1,2-oxazole-5-carboxylate Tetra-n-butylammonium fluoride (1 M THF solution, 8.31 mL) was added to a mixture of tert-butyl 5-(2-tert-butoxy-2-oxoethyl)-3-(2-((tert-butyl(dimethyl)silyl)oxy)-3-((4-methoxybenzyl)oxy)phenyl)-4,5-dihydro-1,2-oxazole-5-carboxylate (4.35 g) and THF (50 mL) at 0° C., followed by stirring at the same temperature for 1 hour. To the reaction mixture, 0.1 M hydrochloric acid was added, followed by extraction with ethyl acetate. The extract was washed with a saturated saline solution and was dried over anhydrous magnesium sulfate, and the solvent was then distilled under reduced pressure. The residue was purified by silica gel column chromatography (ethyl acetate/hexane) to obtain the title compound (2.51 g).
MS: [M+H]+ 514.3.

E) tert-Butyl 3-(2-(3-(2-((benzyloxy)carbonyl)-5-((tert-butoxycarbonyl)amino)phenyl)propoxy)-3-((4-methoxybenzyl)oxy)phenyl)-5-(2-tert-butoxy-2-oxoethyl)-4,5-dihydro-1,2-oxazole-5-carboxylate A mixture of benzyl 4-((tert-butoxycarbonyl)amino)-2-(3-((methylsulfonyl)oxy)propyl)benzoate (2.39 g) and DMF (25 mL) was added to a mixture of tert-butyl 5-(2-tert-butoxy-2-oxoethyl)-3-(2-hydroxy-3-((4-methoxybenzyl)oxy)phenyl)-4,5-dihydro-1,2-oxazole-5-carboxylate (2.51 g), potassium carbonate (2.026 g), and DMF (25 mL) at room temperature, followed by stirring at 80° C. overnight. Water was added to the reaction mixture, followed by extraction with ethyl acetate. The extract was washed with a saturated saline solution and was dried over anhydrous magnesium sulfate, and the solvent was then distilled under reduced pressure. The residue was purified by silica gel column chromatography (ethyl acetate/hexane) to obtain the title compound (2.95 g).

MS: [M+H]$^+$ 881.4.

F) 4-((tert-Butoxycarbonyl)amino)-2-(3-(2-(5-(tert-butoxycarbonyl)-5-(2-tert-butoxy-2-oxoethyl)-4,5-dihydro-1,2-oxazol-3-yl)-6-hydroxyphenoxy)propyl)benzoic acid Under a hydrogen atmosphere, a mixture of tert-butyl 3-(2-(3-(2-((benzyloxy)carbonyl)-5-((tert-butoxycarbonyl)amino)phenyl)propoxy)-3-((4-methoxybenzyl)oxy)phenyl)-5-(2-tert-butoxy-2-oxoethyl)-4,5-dihydro-1,2-oxazole-5-carboxylate (2.65 g), 10% palladium on carbon (water content: about 55%, 1.5 g), and THF (30 mL) was stirred at room temperature for 5.5 hours. The catalyst was removed by filtration, and the filtrate was then concentrated under reduced pressure. About three-fourth of the residue was purified by silica gel column chromatography (ethyl acetate/hexane) to obtain the title compound (561 mg).

MS: [M+H]$^+$ 671.3.

G) tert-Butyl 3-(10-((tert-butoxycarbonyl)amino)-13-oxo-6,7,8,13-tetrahydrodibenzo[b,f][1,4]dioxecin-4-yl)-5-(2-tert-butoxy-2-oxoethyl)-4,5-dihydro-1,2-oxazole-5-carboxylate 2-Methyl-6-nitrobenzoic anhydride (123 mg) and N,N-dimethyl-4-aminopyridine (219 mg) were added to a mixture of 4-((tert-butoxycarbonyl)amino)-2-(3-(2-(5-(tert-butoxycarbonyl)-5-(2-tert-butoxy-2-oxoethyl)-4,5-dihydro-1,2-oxazol-3-yl)-6-hydroxyphenoxy)propyl)benzoic acid (200 mg) and toluene (300 mL) at 100° C., followed by stirring at the same temperature for 15 minutes. 2-Methyl-6-nitrobenzoic anhydride (61.6 mg) was further added thereto, followed by stirring at 100° C. for 30 minutes. The reaction mixture was concentrated under reduced pressure, and 0.1 M hydrochloric acid was then added to the residue, followed by extraction with ethyl acetate. The extract was washed with a 0.28% ammonia aqueous solution three times and then with 0.1 M hydrochloric acid and a saturated saline solution and was dried over anhydrous magnesium sulfate, and the solvent was then distilled under reduced pressure. The residue was purified by silica gel column chromatography (ethyl acetate/hexane, then NH, ethyl acetate/hexane) to obtain the title compound (82 mg).

MS: [M+Na]$^+$ 675.3.

H) 3-(10-Amino-13-oxo-6,7,8,13-tetrahydrodibenzo[b,f][1,4]dioxecin-4-yl)-5-(carboxymethyl)-4,5-dihydro-1,2-oxazole-5-carboxylic acid trifluoroacetate A mixture of tert-butyl 3-(10-((tert-butoxycarbonyl)amino)-13-oxo-6,7,8,13-tetrahydrodibenzo[b,f][1,4]dioxecin-4-yl)-5-(2-tert-butoxy-2-oxoethyl)-4,5-dihydro-1,2-oxazole-5-carboxylate (105 mg) and TFA (2 mL) was stirred at room temperature for 1 hour. The reaction mixture was concentrated under reduced pressure, and diethyl ether was then added to the residue, followed by concentration under reduced pressure. The residue was washed with hexane to obtain the title compound (63.3 mg).

MS: [M+H]$^+$ 441.1.

I) 3-(10-Carbamimidamido-13-oxo-6,7,8,13-tetrahydrodibenzo[b,f][1,4]dioxecin-4-yl)-5-(carboxymethyl)-4,5-dihydro-1,2-oxazole-5-carboxylic acid Four mole hydrogen chloride in cyclopropyl methyl ether (0.083 mL) was added to a mixture of 3-(10-amino-13-oxo-6,7,8,13-tetrahydrodibenzo[b,f][1,4]dioxecin-4-yl)-5-(carboxymethyl)-4,5-dihydro-1,2-oxazole-5-carboxylic acid trifluoroacetate (61.5 mg), cyanamide (13.99 mg), and tert-butyl alcohol (2 mL) at room temperature, followed by stirring at 60° C. for 3 hours. Cyanamide (28.0 mg) and 4 M hydrogen chloride in cyclopropyl methyl ether (0.166 mL) was further added thereto, followed by stirring at 60° C. for 30 minutes. The reaction mixture was concentrated under reduced pressure, and the residue was then purified by HPLC (C18, mobile phase: water/acetonitrile (system containing 0.1% TFA)), and the obtained fraction was concentrated under reduced pressure. An ammonium acetate aqueous solution was added to the residue to adjust the pH to about 4. The suspension was stirred at room temperature for 1 hour, and the solid was then collected by filtration and was washed with water and acetone to obtain the title compound (16.10 mg).

$^1$H NMR (400 MHz, DMSO-d$_6$) δ 1.86-2.08 (2H, m), 2.74 (2H, brs), 3.15-3.53 (3H, m), 3.84-3.94 (2H, m), 3.99 (1H, d, J=17.1 Hz), 6.78-8.62 (10H, m).

Example 23

3-(10-Carbamimidamido-13-oxo-6,7,8,13-tetrahydrodibenzo[b,f][1,4]dioxecin-4-yl)-5-(carboxymethyl)-4,5-dihydro-1,2-oxazole-5-carboxylic acid (optical isomer)

A) tert-Butyl 3-(2-(3-(2-((benzyloxy)carbonyl)-5-((tert-butoxycarbonyl)amino)phenyl)propoxy)-3-hydroxyphenyl)-5-(2-tert-butoxy-2-oxoethyl)-4,5-dihydro-1,2-oxazole-5-carboxylate A mixture of 4-((tert-butoxycarbonyl)amino)-2-(3-(2-(5-(tert-butoxycarbonyl)-5-(2-tert-butoxy-2-oxoethyl)-4,5-dihydro-1,2-oxazol-3-yl)-6-hydroxyphenoxy)propyl)benzoic acid (363 mg), benzyl bromide (0.071 mL), N,N-diisopropylethylamine (0.208 mL), and DMF (4 mL) was stirred at room temperature overnight. To the reaction mixture, 0.1 M hydrochloric acid was added, followed by extraction with ethyl acetate. The extract was washed with a saturated saline solution and was dried over anhydrous magnesium sulfate, and the solvent was then distilled under reduced pressure. The residue was purified by silica gel column chromatography (ethyl acetate/hexane) to obtain the title compound (330 mg).

MS: [M+H]$^+$ 761.3.

B) tert-Butyl 3-(2-(3-(2-((benzyloxy)carbonyl)-5-((tert-butoxycarbonyl)amino)phenyl)propoxy)-3-hydroxyphenyl)-5-(2-tert-butoxy-2-oxoethyl)-4,5-dihydro-1,2-oxazole-5-carboxylate (optical isomer)

Racemates (1.896 g) of tert-butyl 3-(2-(3-(2-((benzyloxy)carbonyl)-5-((tert-butoxycarbonyl)amino)phenyl)propoxy)-3-hydroxyphenyl)-5-(2-tert-butoxy-2-oxoethyl)-4,5-dihydro-1,2-oxazole-5-carboxylate were isolated by HPLC (column: CHIRALPAK IC, 20 mm ID×250 mmL, mobile phase: carbon dioxide/ethanol=770/230), and a racemate having a longer retention time was obtained as the title compound (684 mg).
MS: [M+H]$^+$ 761.3.

C) 4-((tert-Butoxycarbonyl)amino)-2-(3-(2-(5-(tert-butoxycarbonyl)-5-(2-tert-butoxy-2-oxoethyl)-4,5-dihydro-1,2-oxazol-3-yl)-6-hydroxyphenoxy)propyl)benzoic acid (optical isomer)

Under a hydrogen atmosphere, a mixture of tert-butyl 3-(2-(3-(2-((benzyloxy)carbonyl)-5-((tert-butoxycarbonyl)amino)phenyl)propoxy)-3-hydroxyphenyl)-5-(2-tert-butoxy-2-oxoethyl)-4,5-dihydro-1,2-oxazole-5-carboxylate (optical isomer) (795 mg), 10% palladium on carbon (water content: about 55%, 80 mg), and THF (8 mL) was stirred at room temperature for 1.5 hours. The catalyst was removed by filtration, and the filtrate was then concentrated under reduced pressure. The residue was purified by silica gel column chromatography (ethyl acetate/hexane) to obtain the title compound (642 mg).
MS: [M+H]$^+$ 671.3.

D) tert-Butyl 3-(10-((tert-butoxycarbonyl)amino)-13-oxo-6,7,8,13-tetrahydrodibenzo[b,f][1,4]dioxecin-4-yl)-5-(2-tert-butoxy-2-oxoethyl)-4,5-dihydro-1,2-oxazole-5-carboxylate (optical isomer)

2-Methyl-6-nitrobenzoic anhydride (395 mg) and N,N-dimethyl-4-aminopyridine (140 mg) were added to a mixture of 4-((tert-butoxycarbonyl)amino)-2-(3-(2-(5-(tert-butoxycarbonyl)-5-(2-tert-butoxy-2-oxoethyl)-4,5-dihydro-1,2-oxazol-3-yl)-6-hydroxyphenoxy)propyl)benzoic acid (optical isomer) (642 mg) and toluene (950 mL) at 100° C., followed by stirring at the same temperature for 24 hours. The reaction mixture was cooled to room temperature and was then washed with a saturated sodium hydrogen carbonate aqueous solution, 0.1 M hydrochloric acid, and a saturated saline solution and was dried over anhydrous magnesium sulfate, and the solvent was then distilled under reduced pressure. The residue was purified by silica gel column chromatography (NH, ethyl acetate/hexane) to obtain the title compound (338 mg).
MS: [M+H]$^+$ 653.3.

E) 3-(10-Carbamimidamido-13-oxo-6,7,8,13-tetrahydrodibenzo[b,f][1,4]dioxecin-4-yl)-5-(carboxymethyl)-4,5-dihydro-1,2-oxazole-5-carboxylic acid (optical isomer)

A mixture of tert-butyl 3-(10-((tert-butoxycarbonyl)amino)-13-oxo-6,7,8,13-tetrahydrodibenzo[b,f][1,4]dioxecin-4-yl)-5-(2-tert-butoxy-2-oxoethyl)-4,5-dihydro-1,2-oxazole-5-carboxylate (optical isomer) (338 mg) and 1 M hydrogen chloride in acetic acid (4 mL) was stirred at room temperature overnight. The reaction mixture was concentrated under reduced pressure, and the residue was then washed with diethyl ether. Four mole hydrogen chloride in cyclopropyl methyl ether (0.577 mL) was added to a mixture of the resulting solid (231 mg), cyanamide (97 mg), and tert-butyl alcohol (5 mL) at room temperature. The reaction mixture was stirred at 60° C. for 4 hours, and the reaction mixture was then concentrated under reduced pressure. Water (10 mL) and then an aqueous solution (2 mL) of ammonium acetate (178 mg) were added dropwise to the residue, followed by stirring at room temperature for 3 hours. The precipitated solid was collected by filtration and was washed with water and acetone. The resulting solid was purified by HPLC (C18, mobile phase: water/acetonitrile (system containing 0.1% TFA)), and the obtained fraction was concentrated under reduced pressure. An ammonium acetate aqueous solution was added to the residue to adjust the pH to about 4. The suspension was stirred at room temperature for 1 hour, and the precipitated solid was then collected by filtration and was washed with water and acetone to obtain the title compound (134 mg).
$^1$H NMR (400 MHz, DMSO-d$_6$) δ 1.92-2.09 (2H, m), 2.77 (2H, s), 3.21-3.43 (3H, m), 3.85-3.98 (2H, m), 4.03 (1H, d, J=17.4 Hz), 7.21-7.33 (3H, m), 7.54-7.61 (2H, m), 7.75 (4H, brs), 7.90 (1H, d, J=8.8 Hz).

Example 24

3-(10-Carbamimidamido-13-oxo-6,7,8,13-tetrahydrodibenzo[b,f][1,4]dioxecin-4-yl)-5-(carboxymethyl)-4,5-dihydro-1,2-oxazole-5-carboxylic acid (optical isomer)

A) tert-Butyl 3-(2-(3-(2-((benzyloxy)carbonyl)-5-((tert-butoxycarbonyl)amino)phenyl)propoxy)-3-hydroxyphenyl)-5-(2-tert-butoxy-2-oxoethyl)-4,5-dihydro-1,2-oxazole-5-carboxylate (optical isomer)

Racemates (1.896 g) of tert-butyl 3-(2-(3-(2-((benzyloxy)carbonyl)-5-((tert-butoxycarbonyl)amino)phenyl)propoxy)-3-hydroxyphenyl)-5-(2-tert-butoxy-2-oxoethyl)-4,5-dihydro-1,2-oxazole-5-carboxylate were isolated by HPLC (column: CHIRALPAK IC, 20 mm ID×250 mmL, mobile phase: carbon dioxide/ethanol=770/230), and a racemate having a shorter retention time was obtained as the title compound (883 mg).
MS: [M+H]$^+$ 761.3.

B) 4-((tert-Butoxycarbonyl)amino)-2-(3-(2-(5-(tert-butoxycarbonyl)-5-(2-tert-butoxy-2-oxoethyl)-4,5-dihydro-1,2-oxazol-3-yl)-6-hydroxyphenoxy)propyl)benzoic acid (optical isomer)

Under a hydrogen atmosphere, a mixture of tert-butyl 3-(2-(3-(2-((benzyloxy)carbonyl)-5-((tert-butoxycarbonyl)amino)phenyl)propoxy)-3-hydroxyphenyl)-5-(2-tert-butoxy-2-oxoethyl)-4,5-dihydro-1,2-oxazole-5-carboxylate (optical isomer) (142 mg), 10% palladium on carbon (water content: about 55%, 14 mg), and THF (2 mL) was stirred at room temperature for 1.5 hours. The catalyst was removed by filtration, and the filtrate was then concentrated under reduced pressure. The residue was purified by silica gel column chromatography (ethyl acetate/hexane) to obtain the title compound (90.2 mg).
MS: [M+H]$^+$ 671.3.

C) tert-Butyl 3-(10-((tert-butoxycarbonyl)amino)-13-oxo-6,7,8,13-tetrahydrodibenzo[b,f][1,4]dioxecin-4-yl)-5-(2-tert-butoxy-2-oxoethyl)-4,5-dihydro-1,2-oxazole-5-carboxylate (optical isomer)

2-Methyl-6-nitrobenzoic anhydride (55.6 mg) and N,N-dimethyl-4-aminopyridine (19.71 mg) were added to a toluene (130 mL) solution of 4-((tert-butoxycarbonyl)amino)-2-(3-(2-(5-(tert-butoxycarbonyl)-5-(2-tert-butoxy-2-oxoethyl)-4,5-dihydro-1,2-oxazol-3-yl)-6-hydroxyphenoxy)propyl)benzoic acid (optical isomer) (90.2 mg) at 100° C., followed by stirring at the same temperature for 24 hours. The reaction mixture was cooled to room temperature and was then washed with 0.1 M hydrochloric acid and a saturated saline solution and dried over anhydrous magnesium sulfate, and the solvent was then distilled under reduced pressure. The residue was purified by silica gel column chromatography (NH, ethyl acetate/hexane) to obtain the title compound (47.0 mg).

MS: [M+H]$^+$ 653.3.

D) 3-(10-Carbamimidamido-13-oxo-6,7,8,13-tetrahydrodibenzo[b,f][1,4]dioxecin-4-yl)-5-(carboxymethyl)-4,5-dihydro-1,2-oxazole-5-carboxylic acid (optical isomer)

A mixture of tert-butyl 3-(10-((tert-butoxycarbonyl)amino)-13-oxo-6,7,8,13-tetrahydrodibenzo[b,f][1,4]dioxecin-4-yl)-5-(2-tert-butoxy-2-oxoethyl)-4,5-dihydro-1,2-oxazole-5-carboxylate (optical isomer) (47.0 mg) and 1 M hydrogen chloride in acetic acid (1 mL) was stirred at room temperature overnight. The reaction mixture was concentrated under reduced pressure, and the residue was then washed with diethyl ether. Four mole hydrogen chloride in cyclopropyl methyl ether (0.059 mL) was added to a mixture of the resulting solid (23.8 mg), cyanamide (10.00 mg), and tert-butyl alcohol (1 mL) at room temperature. The reaction mixture was stirred at 60° C. for 4 hours, and the reaction mixture was then concentrated under reduced pressure. Water (3 mL) and then an aqueous solution (2 mL) of ammonium acetate (18.33 mg) were added dropwise to the residue, followed by stirring at room temperature for 3 hours. The solid was collected by filtration and was washed with water and acetone to obtain a crude product (18.0 mg) of the title compound. This crude product was combined with a crude product (99.0 mg) of the title compound obtained by the same procedure, the combined crude product was purified by HPLC (C18, mobile phase: water/acetonitrile (system containing 0.1% TFA)), and the obtained fraction was concentrated under reduced pressure. An ammonium acetate aqueous solution was added to the residue to adjust the pH to about 4. The suspension was stirred at room temperature for 1 hour, and the solid was then collected by filtration and was washed with water and acetone to obtain the title compound (29.0 mg).

$^1$H NMR (400 MHz, DMSO-d$_6$) δ 1.88-2.09 (2H, m), 2.76 (2H, s), 3.14-3.40 (3H, m), 3.85-3.97 (2H, m), 4.01 (1H, d, J=17.4 Hz), 7.21-7.32 (3H, m), 7.54-7.60 (2H, m), 7.69 (4H, brs), 7.91 (1H, d, J=8.2 Hz).

Example 26

N-((9-Carbamimidamido-12-oxo-5,6,7,12-tetrahydro-4H-thieno[3,2-c][2]benzooxecin-2-yl)carbonyl)-L-aspartic acid

A) 5-Allyl-4-hydroxythiophene-2-carboxylic acid

A mixture of methyl 5-allyl-4-hydroxythiophene-2-carboxylate (424 mg), 1 N sodium hydroxide aqueous solution (7 mL), and methanol (5 mL) was stirred at room temperature for 1 day. One normal hydrochloric acid was added to the reaction mixture at 0° C. to make the mixture acidic, followed by extraction with ethyl acetate. The extract was washed with water and a saturated saline solution and was then dried over anhydrous magnesium sulfate, and the solvent was distilled under reduced pressure to obtain the title compound (366 mg).

$^1$H NMR (400 MHz, DMSO-d$_6$) δ 3.39 (2H, dt, J=6.5, 1.3 Hz), 5.02-5.16 (2H, m), 5.90 (1H, ddt, J=16.8, 10.1, 6.4 Hz), 7.20 (1H, s), 9.49 (1H, s), 12.77 (1H, brs).

B) Benzyl 5-allyl-4-hydroxythiophene-2-carboxylate

Benzyl bromide (0.258 mL) was added to methyl 5-allyl-4-hydroxythiophene-2-carboxylate (365 mg) and a DMF (4 mL) solution of diisopropylethylamine (0.571 mL) at room temperature, followed by stirring at the same temperature overnight. Water was added to the reaction mixture, followed by extraction with ethyl acetate. The extract was washed with a saturated saline solution and was dried over anhydrous magnesium sulfate, and the solvent was then distilled under reduced pressure. The residue was purified by silica gel column chromatography (ethyl acetate/hexane) to obtain the title compound (462 mg).

$^1$H NMR (400 MHz, DMSO-d$_6$) δ 3.41 (2H, dt, J=6.5, 1.3 Hz), 5.04-5.16 (2H, m), 5.27 (2H, s), 5.90 (1H, ddt, J=16.9, 10.1, 6.5 Hz), 7.28-7.30 (1H, m), 7.33-7.43 (5H, m), 9.62 (1H, s).

C) Benzyl 5-allyl-4-((2-allyl-4-nitrobenzoyl)oxy)thiophene-2-carboxylate

DMF (0.013 mL) was added to a mixture of 2-allyl-4-nitrobenzoic acid (695 mg), oxalyl chloride (0.440 mL), and THF (4 mL) at room temperature, followed by stirring at the same temperature for 1 hour and then concentration under reduced pressure. A mixture of the residue and DMF (1 mL) was added to a pyridine (2 mL) solution of benzyl 5-allyl-4-hydroxythiophene-2-carboxylate (460 mg) at room temperature, followed by stirring at 50° C. overnight. One mole hydrochloric acid (3 mL) was added to the reaction mixture, followed by extraction with ethyl acetate. The extract was washed with 0.28% aqueous ammonia (5 mL×2), 1 M hydrochloric acid (4 mL), and a saturated saline solution and was dried over anhydrous magnesium sulfate, and the solvent was then distilled under reduced pressure. The residue was purified by silica gel column chromatography (ethyl acetate/hexane) to obtain the title compound (661 mg).

$^1$H NMR (400 MHz, DMSO-d$_6$) δ 3.56 (2H, d, J=6.5 Hz), 3.85 (2H, d, J=6.4 Hz), 5.03-5.19 (4H, m), 5.34 (2H, s), 5.85-6.09 (2H, m), 7.33-7.49 (5H, m), 7.88 (1H, s), 8.22-8.33 (3H, m).

D) Benzyl 9-nitro-12-oxo-7,12-dihydro-4H-benzo[h]thieno[3,2-b]oxecine-2-carboxylate A second-generation Grubbs catalyst (36.3 mg) was added to a toluene (330 mL) solution of benzyl 5-allyl-4-((2-allyl-4-nitrobenzoyl)oxy)thiophene-2-carboxylate (660 mg) at 80° C., followed by stirring at the same temperature for 1 hour and then concentration under reduced pressure. The residue was purified by silica gel column chromatography (ethyl acetate/hexane) to obtain the title compound (527 mg).

$^1$H NMR (400 MHz, DMSO-d$_6$) δ 3.27-3.29 (2H, m, J=2.3 Hz), 3.33-3.35 (2H, m), 5.34 (2H, s), 5.52 (2H, t, J=6.0 Hz), 7.34-7.49 (5H, m), 7.82 (1H, s), 7.94 (1H, d, J=8.3 Hz), 8.26 (1H, dd, J=8.5, 2.3 Hz), 8.43 (1H, d, J=2.2 Hz).

E) 9-Amino-12-oxo-5,6,7,12-tetrahydro-4H-benzo[h]thieno[3,2-b]oxecine-2-carboxylic acid A mixture of (E)-benzyl 9-nitro-12-oxo-7,12-dihydro-4H-benzo[h]thieno[3,2-b]oxecine-2-carboxylate (200 mg), 20% palladium hydroxide on carbon (70 mg, water content: about 50%), and THF (3 mL) was stirred under a hydrogen atmosphere at room temperature for 5 hours. The insoluble matter was removed by filtration, and the resulting filtrate was then concentrated under reduced pressure to obtain the title compound (147 mg).
MS: [M+H]$^+$ 318.0.

F) 9-Guanidino-12-oxo-5,6,7,12-tetrahydro-4H-benzo[h]thieno[3,2-b]oxecine-2-carboxylic acid trifluoroacetate Four mole hydrogen chloride in cyclopentyl methyl ether (0.343 mL) was added to a mixture of 9-amino-12-oxo-5,6,7,12-tetrahydro-4H-benzo[h]thieno[3,2-b]oxecine-2-carboxylic acid (145 mg), cyanamide (57.6 mg), and tert-butanol (2 mL) at room temperature, followed by stirring at 60° C. for 16 hours. Subsequently, cyanamide (38.4 mg) was added to the reaction mixture, and the mixture was further stirred at 60° C. overnight and was then concentrated under reduced pressure. The residue was purified by HPLC (C18, mobile phase: water/acetonitrile (system containing 0.1% TFA)) to obtain the title compound (182 mg).
MS: [M+H]$^+$ 360.1.

G) (S)-Di-tert-butyl 2-(9-guanidino-12-oxo-5,6,7,12-tetrahydro-4H-benzo[h]thieno[3,2-b]oxecine-2-carboxamide)succinate trifluoroacetate A mixture of 9-guanidino-12-oxo-5,6,7,12-tetrahydro-4H-benzo[h]thieno[3,2-b]oxecine-2-carboxylic acid trifluoroacetate (90 mg), (S)-di-tert-butyl 2-aminosuccinate hydrochloride (80 mg), WSC hydrochloride (54.7 mg), HOBt.H$_2$O (43.7 mg), diisopropylethylamine (0.100 mL), and DMF (2 mL) was stirred at room temperature overnight. The reaction mixture was purified by HPLC (C18, mobile phase: water/acetonitrile (system containing 0.1% TFA)) to obtain the title compound (122 mg).
MS: [M+H]$^+$ 587.2.

H) N-((9-Carbamimidamido-12-oxo-5,6,7,12-tetrahydro-4H-thieno[3,2-c][2]benzooxecin-2-yl)carbonyl)-L-aspartic acid A mixture of (S)-di-tert-butyl 2-(9-guanidino-12-oxo-5,6,7,12-tetrahydro-4H-benzo[h]thieno[3,2-b]oxecine-2-carboxamide)succinate trifluoroacetate (122 mg) and trifluoroacetic acid (1 mL) was stirred at room temperature for 1 hour and was then concentrated under reduced pressure. The reaction mixture was purified by HPLC (C18, mobile phase: water/acetonitrile (system containing 0.1% TFA)), and the obtained fraction was concentrated under reduced pressure. To a mixture of the residue and water (1.5 mL), an aqueous solution of ammonium acetate (40.3 mg) was added at room temperature to adjust the pH to about 4, followed by stirring at the same temperature for 1 hour. The precipitated solid was collected by filtration and was washed with water to obtain the title compound (64.9 mg).
$^1$H NMR (400 MHz, DMSO-d$_6$) δ 1.48 (1H, brs), 1.60 (1H, brs), 1.71 (2H, brs), 2.31-2.42 (1H, m), 2.65-2.77 (1H, m), 2.94-3.17 (4H, m), 4.40 (1H, brs), 7.21-7.30 (2H, m), 7.63 (4H, brs), 7.95 (1H, d, J=8.9 Hz), 8.13 (1H, s), 8.48 (1H, d, J=6.5 Hz).

Example 30

N-((9-Carbamimidamido-6-oxo-6,11,12,13-tetrahydrodibenzo[b,g]oxonin-1-yl)carbonyl)-L-aspartic acid trifluoroacetate A) (E)-Benzyl 2-(3-(2-(benzyloxy)-6-formylphenyl)prop-1-enyl)-4-nitrobenzoate (1,1'-Bis(diphenylphosphino)ferrocene)palladium(II) dichloride (899 mg), benzyl 2-bromo-4-nitrobenzoate (4.9 g), and cesium carbonate (12 g) were added to a toluene (50 mL) solution of 2-allyl-3-(benzyloxy)benzaldehyde (3.1 g) at room temperature, followed by stirring at 110° C. for 18 hours. The reaction mixture was diluted with ethyl acetate, washed water and a saturated saline solution, and was then dried over anhydrous sodium sulfate, and the solvent was distilled under reduced pressure. The residue was purified by silica gel column chromatography (ethyl acetate/petroleum ether) to obtain the title compound (2.84 g).
MS: [M+H]$^+$ 508.1.

B) (E)-3-(Benzyloxy)-2-(3-(2-(benzyloxycarbonyl)-5-nitrophenyl)allyl)benzoic acid Sodium chlorite (1 g), a solution of sodium of dihydrogen phosphate (3.83 g) in water (10 mL), and 2-methyl-2-butene (3.13 g) were added to a t-butanol/dichloromethane (30/10 mL) solution of (E)-benzyl 2-(3-(2-(benzyloxy)-6-formylphenyl)prop-1-enyl)-4-nitrobenzoate (8.8 g) at 0° C., followed by stirring at room temperature for 5 hours. The reaction mixture solution was concentrated under reduced pressure, and the residue was diluted with ethyl acetate. The organic layer was washed with water and a saturated saline solution and was then dried over anhydrous sodium sulfate, and the solvent was distilled under reduced pressure. The residue was washed with diethyl ether/pentane to obtain the title compound (2.5 g).
MS: [M+H]$^+$ 524.4.

C) (S,E)-Di-tert-butyl 2-(3-(benzyloxy)-2-(3-(2-(benzyloxycarbonyl)-5-nitrophenyl)allyl)benzamide)succinate WSC hydrochloride (1.33 g), HOBt (756 mg), N,N-diisopropylethylamine (1.7 mL), and L-aspartic acid hydrochloride (1.6 g) were added to a tetrahydrofuran (10 mL) solution of (E)-3-(benzyloxy)-2-(3-(2-(benzyloxycarbonyl)-5-nitrophenyl)allyl)benzoic acid (2.5 g) at 0° C., followed by stirring at room temperature for 18 hours. The reaction mixture was diluted with water, followed by extraction with ethyl acetate. The extract was washed with water and a saturated saline solution and was then dried over anhydrous sodium sulfate, and the solvent was distilled under reduced pressure. The residue was purified by silica gel column chromatography (ethyl acetate/petroleum ether) to obtain the title compound (2.4 g).
MS: [M+H]$^+$ 751.6.

D) (S)-4-Amino-2-(3-(2-(1,4-di-tert-butoxy-1,4-dioxobutan-2-ylcarbamoyl)-6-hydroxyphenyl)propyl)benzoic acid A catalyst quantity of palladium on carbon was added to a THF (100 mL) solution of (S,E)-di-tert-butyl 2-(3-(benzyloxy)-2-(3-(2-(benzyloxycarbonyl)-5-nitrophenyl)allyl)benzamide)succinate (2.4 g) at room temperature, followed by stirring under a hydrogen atmosphere of 70 psi for 18 hours. The reaction mixture was filtered through Celite, and the filtrate was concentrated under reduced pressure, and the residue was washed with pentane to obtain the title compound (1.6 g).
MS: [M+H]$^+$ 543.2.

E) (S)-Di-tert-butyl 2-(9-amino-6-oxo-6,11,12,13-tetrahydrodibenzo[b,g]oxonine-1-carboxamide)succinate 2-Methyl-6-nitrobenzoic anhydride (304 mg) and a catalyst quantity of N,N-dimethyl-4-aminopyridine were added to a dichloromethane (10 mL) solution of (S)-4-amino-2-(3-(2-(1,4-di-tert-butoxy-1,4-dioxobutan-2-ylcarbamoyl)-6-hydroxyphenyl)propyl)benzoic acid (400 mg) at room temperature, followed by stirring at the same temperature for 24 hours. The reaction mixture was concentrated under reduced pressure. The residue was purified by silica gel column chromatography (ethyl acetate/petroleum ether) to obtain the title compound (200 mg).

MS: [M+H]$^+$ 525.5.

F) (S)-2-(9-Amino-6-oxo-6,11,12,13-tetrahydrodibenzo[b,g]oxonine-1-carboxamide)succinic acid trifluoroacetate A mixture of (S)-di-tert-butyl 2-(9-amino-6-oxo-6,11,12,13-tetrahydrodibenzo[b,g]oxonine-1-carboxamide)succinate (300 mg) and TFA (3 mL) was stirred at room temperature for 2 hours. The reaction mixture was concentrated under reduced pressure to obtain the title compound (350 mg).

MS: [M+H]$^+$ 413.3.

G) N-((9-Carbamimidamido-6-oxo-6,11,12,13-tetrahydrodibenzo[b,g]oxonin-1-yl)carbonyl)-L-aspartic acid trifluoroacetate Four normal hydrochloric acid in cyclopentyl methyl ether (0.87 mL) and cyanamide (150 mg) were added to a t-butanol (5 mL) solution of (S)-2-(9-amino-6-oxo-6,11,12,13-tetrahydrodibenzo[b,g]oxonine-1-carboxamide)succinic acid trifluoroacetate (350 mg) at room temperature, followed by stirring at 80° C. for 5 hours. The reaction mixture was concentrated under reduced pressure and was then purified by HPLC to obtain the title compound (73 mg).

$^1$H NMR (300 MHz, DMSO-d$_6$) δ 1.95 (2H, s), 2.65 (1H, d, J=8.4 Hz), 2.76 (3H, d, J=5.3 Hz), 2.89 (2H, s), 4.65 (1H, td, J=8.2, 5.3 Hz), 7.09 (3H, s), 7.21 (1H, t, J=7.7 Hz), 7.29 (1H, dd, J=8.1, 1.5 Hz), 7.49 (3H, s), 7.58 (1H, d, J=8.9 Hz), 8.67 (1H, d, J=7.9 Hz), 9.76 (1H, s), 12.3 (1H, s), 12.79 (1H, s).

Example 37

N-((3-Carbamimidamido-14-oxo-5,7,8,14-tetrahydro-6H-dibenzo[b,h]oxecin-9-yl)carbonyl)-L-aspartic acid

A) Allyl 3-(allyloxy)-4-bromobenzoate

Allyl bromide (4.2 mL) was added to a mixture of 4-bromo-3-hydroxybenzoic acid (5 g), potassium carbonate (8.0 g), and DMF (50 mL) at 0° C., followed by stirring at room temperature overnight. The reaction mixture was distributed between ethyl acetate and 1 N hydrochloric acid. The organic layer was washed with water and a saturated saline solution and was then dried over anhydrous sodium sulfate, and the solvent was distilled under reduced pressure. The residue was purified by silica gel column chromatography (ethyl acetate/hexane) to obtain the title compound (6.74 g).

$^1$H NMR (300 MHz, DMSO-d$_6$) δ 4.76 (2H, dt, J=4.9, 1.6 Hz), 4.81 (2H, dt, J=5.4, 1.5 Hz), 5.30 (2H, ddq, J=10.5, 6.1, 1.5 Hz), 5.35-5.53 (2H, m), 5.94-6.18 (2H, m), 7.50 (1H, dd, J=8.2, 1.9 Hz), 7.57 (1H, d, J=1.8 Hz), 7.77 (1H, d, J=8.2 Hz).

B) Benzyl 2-allyl-4-bromo-3-hydroxybenzoate

A mixture of allyl 3-(allyloxy)-4-bromobenzoate (3.056 g) and N-methylpyrrolidone (15 mL) was stirred under microwave irradiation at 200° C. for 6 hours. The reaction mixture was poured into water, followed by extraction with ethyl acetate. The organic layer was washed with water and a saturated saline solution and was then dried over anhydrous sodium sulfate, and the solvent was distilled under reduced pressure.

A 2 N sodium hydroxide aqueous solution (30 mL) was added to a mixture of the resulting residue and THF/methanol (30 mL/30 mL) at 0° C., followed by stirring at 60° C. overnight. The reaction mixture was distributed between ethyl acetate and 1 N hydrochloric acid. The organic layer was washed with a saturated saline solution and was then dried over anhydrous sodium sulfate, and the solvent was distilled under reduced pressure to obtain 2-allyl-4-bromo-3-hydroxybenzoic acid (2.97 g) as a crude product.

Benzyl bromide (1.3 mL) was added to a mixture of the crude product of 2-allyl-4-bromo-3-hydroxybenzoic acid (2.64 g), potassium hydrogen carbonate (1.54 g), and DMF (60 mL) at 0° C., followed by stirring at room temperature overnight. On normal hydrochloric acid was added to the reaction mixture at room temperature, followed by extraction with ethyl acetate. The organic layer was washed with water and a saturated saline solution and was then dried over anhydrous sodium sulfate, and the solvent was distilled under reduced pressure. The residue was purified by silica gel column chromatography (ethyl acetate/hexane) to obtain the title compound (2.165 g).

$^1$H NMR (300 MHz, DMSO-d$_6$) δ 3.70 (2H, d, J=6.1 Hz), 4.74-4.98 (2H, m), 5.29 (2H, s), 5.83 (1H, ddt, J=16.8, 10.5, 6.1 Hz), 7.20 (1H, d, J=8.4 Hz), 7.27-7.57 (6H, m), 9.39 (1H, brs).

C) Benzyl 2-allyl-3-((2-allyl-4-nitrobenzoyl)oxy)-4-bromobenzoate

Oxalyl chloride (1.62 mL) and DMF (0.200 mL) were added to a mixture of 2-allyl-4-nitrobenzoic acid (2.54 g) and THF (25 mL) at room temperature, followed by stirring at room temperature for 1 hour. The reaction mixture was then concentrated. A mixture of benzyl 2-allyl-4-bromo-3-hydroxybenzoate (2.13 g) and DMF (7 mL) and pyridine (2 mL) were added to a mixture of the residue and DMF (3 mL) at room temperature, followed by stirring at 60° C. for 48 hours. The reaction mixture was poured into water/ethyl acetate, followed by extraction. The organic layer was washed with 0.25% aqueous ammonia, water, 1 N hydrochloric acid, and a saturated saline solution and was then dried over anhydrous sodium sulfate, and the solvent was distilled under reduced pressure. The residue was purified by silica gel column chromatography (ethyl acetate/hexane) to obtain the title compound (2.93 g).

$^1$H NMR (300 MHz, DMSO-d$_6$) δ 3.45-3.81 (2H, m), 3.88 (2H, d, J=6.1 Hz), 4.78 (1H, dd, J=17.2, 1.6 Hz), 4.91 (1H, dd, J=10.2, 1.5 Hz), 5.00-5.18 (2H, m), 5.35 (2H, s), 5.78 (1H, ddt, J=16.8, 10.4, 6.1 Hz), 6.02 (1H, ddt, J=16.9, 10.4, 6.5 Hz), 7.29-7.55 (5H, m), 7.70-7.80 (1H, m), 7.80-7.90 (1H, m), 8.25-8.37 (2H, m), 8.41-8.51 (1H, m).

D) Benzyl 12-bromo-3-nitro-14-oxo-8,14-dihydro-5H-dibenzo[b,h]oxecine-9-carboxylate A second-generation Hoveyda-Grubbs catalyst (0.0220 g) was added to a mixture of benzyl 2-allyl-3-((2-allyl-4-nitrobenzoyl)oxy)-4-bromobenzoate (1.8865 g) and toluene (190 mL) at 100° C., followed by stirring at the same temperature for 1 hour. The reaction mixture was concentrated. The residue was washed with toluene/diisopropyl ether (4 mL/40 mL) to obtain the title compound (1.521 g).

$^1$H NMR (300 MHz, DMSO-$d_6$) δ 3.53 (1H, d, J=14.6 Hz), 3.74 (1H, d, J=11.4 Hz), 3.90-4.12 (1H, m), 4.49-4.73 (1H, m), 5.27-5.46 (2H, m), 5.47-5.69 (2H, m), 7.31-7.58 (5H, m), 7.64-7.76 (1H, m), 7.77-7.91 (2H, m), 8.28 (1H, dd, J=8.4, 2.0 Hz), 8.42 (1H, s).

E) 3-Amino-14-oxo-6,7,8,14-tetrahydro-5H-dibenzo[b,h]oxecine-9-carboxylic acid hydrobromate A mixture of benzyl 12-bromo-3-nitro-14-oxo-8,14-dihydro-5H-dibenzo[b,h]oxecine-9-carboxylate (700 mg), 20% palladium hydroxide (140 mg, water content: about 50%), and 2-propanol (28 mL) was stirred under a hydrogen atmosphere at room temperature for 6 hours. Twenty percent palladium hydroxide (143.4 mg, water content: about 50%) was added to the reaction mixture, followed by stirring under a hydrogen atmosphere at room temperature overnight. The catalyst was removed by filtration, and the filtrate was then concentrated under reduced pressure. Twenty percent palladium hydroxide (140.0 mg, water content: about 50%) was added to a mixture of the residue and 2-propanol (28 mL), followed by stirring under a hydrogen atmosphere at room temperature for 6 hours. Twenty percent palladium hydroxide (210.4 mg, water content: about 50%) was added to the reaction mixture, followed by stirring under a hydrogen atmosphere at room temperature overnight. The catalyst was removed by filtration, and the filtrate was then concentrated under reduced pressure. The residue was washed with hexane to obtain the title compound (416 mg).

MS: [M+H]$^+$ 312.1.

F) (S)-Di-tert-butyl 2-(3-guanidino-14-oxo-6,7,8,14-tetrahydro-5H-dibenzo[b,h]oxecine-9-carboxamide) succinate Four normal hydrogen chloride in cyclopentyl methyl ether (0.724 mL) and cyanamide (122 mg) were added to a mixture of 3-amino-14-oxo-6,7,8,14-tetrahydro-5H-dibenzo[b,h]oxecine-9-carboxylic acid hydrobromate (180.4 mg) and tert-butyl alcohol (10 mL) at room temperature, followed by stirring at 60° C. for 6 hours. The reaction mixture was concentrated. To a mixture of the residue and DMF (5 mL), (S)-di-tert-butyl 2-aminosuccinate hydrochloride (245 mg), N,N-diisopropylethylamine (0.304 mL), WSC hydrochloride (167 mg), and HOBt.H$_2$O (133 mg) were added at 0° C., followed by stirring at room temperature for 66 hours. To the reaction mixture, (S)-di-tert-butyl 2-aminosuccinate hydrochloride (245 mg), diisopropylethylamine (0.304 mL), WSC hydrochloride (167 mg), and HOBt.H$_2$O (133 mg) were added at 0° C., followed by stirring at room temperature for 22 hours. Water was added to the reaction mixture at 0° C., followed by extraction with ethyl acetate. The organic layer was washed with a saturated sodium hydrogen carbonate aqueous solution and a saturated saline solution and was then dried over anhydrous sodium sulfate, and the solvent was distilled under reduced pressure. The residue was purified by silica gel column chromatography (NH, methanol/ethyl acetate) to obtain the title compound (199 mg).

MS: [M+H]$^+$ 581.3.

G) N-((3-Carbamimidamido-14-oxo-5,7,8,14-tetrahydro-6H-dibenzo[b,h]oxecin-9-yl)carbonyl)-L-aspartic acid A mixture of (S)-di-tert-butyl 2-(3-guanidino-14-oxo-6,7,8,14-tetrahydro-5H-dibenzo[b,h]oxecine-9-carboxamide) succinate (193.4 mg) and trifluoroacetic acid (5 mL) was stirred at room temperature for 30 minutes. The reaction mixture was concentrated. The residue was dissolved in water/acetonitrile/TFA (20 mL/2 mL/1 mL), and a 1 M ammonium acetate aqueous solution was then added thereto to adjust the pH of the solution to 4, followed by stirring at room temperature for 1 hour. The precipitated solid was collected by filtration, washed with water, and dried under reduced pressure at 50° C. to obtain the title compound (137 mg).

$^1$H NMR (300 MHz, DMSO-$d_6$) δ 1.45-1.70 (2H, m), 1.79 (2H, brs), 2.40-2.61 (1H, m), 2.76 (1H, dd, J=15.9, 7.8 Hz), 3.01 (2H, brs), 3.17 (2H, brs), 4.39-4.56 (1H, m), 7.14 (1H, s), 7.19 (1H, dd, J=7.6, 1.0 Hz), 7.27 (1H, dd, J=8.4, 1.9 Hz), 7.34 (1H, t, J=7.9 Hz), 7.68 (1H, dd, J=8.2, 1.0 Hz), 7.91 (5H, d, J=8.4 Hz), 8.18 (1H, d, J=7.9 Hz).

Example 40

N-((3-Carbamimidamido-15-oxo-5,7,8,10,11,15-hexahydro-6H-12,14-dioxabenzo[5,6]cyclodeca[1,2-f]inden-9-yl)carbonyl)-L-aspartic acid A) Ethyl 6-(allyloxy)-2,3-dihydro-1-benzofuran-4-carboxylate A mixture of ethyl 6-hydroxy-2,3-dihydro-1-benzofuran-4-carboxylate (1.00 g), 3-bromopropene (0.436 mL), potassium carbonate (0.697 g), and acetonitrile (10 mL) was stirred at 70° C. for 2 hours. The precipitate was removed by filtration, and the filtrate was then concentrated under reduced pressure. The residue was purified by silica gel column chromatography (ethyl acetate/hexane) to obtain the title compound (1.150 g).

MS: [M+H]$^+$ 249.1.

B) Ethyl 5-allyl-6-hydroxy-2,3-dihydro-1-benzofuran-4-carboxylate

A mixture of ethyl 6-(allyloxy)-2,3-dihydro-1-benzofuran-4-carboxylate (1.15 g) and N-methyl-2-pyrrolidone (4.5 mL) was heated under microwave irradiation at 200° C. for 2 hours. Water was added to the reaction mixture, followed by extraction with ethyl acetate. The extract was washed with a saturated saline solution and was dried over anhydrous magnesium sulfate, and the solvent was then distilled under reduced pressure. The residue was purified by silica gel column chromatography (ethyl acetate/hexane) to obtain the title compound (0.778 g).

MS: [M+H]$^+$ 249.1.

C) 5-Allyl-6-hydroxy-2,3-dihydro-1-benzofuran-4-carboxylic acid

A mixture of ethyl 5-allyl-6-hydroxy-2,3-dihydro-1-benzofuran-4-carboxylate (778 mg), THF (10 mL), ethanol (10 mL), and 1 M sodium hydroxide aqueous solution (10 mL) was stirred at 50° C. for 3 hours. The reaction mixture was neutralized with 6 M hydrochloric acid at 0° C., followed by extraction with ethyl acetate. The extract was washed with a saturated saline solution and was dried over anhydrous magnesium sulfate, and the solvent was then distilled under reduced pressure. Ethanol (5 mL) and an 8 M sodium hydroxide aqueous solution (5 mL) were added to the residue, followed by stirring at 100° C. for 3 hours. The reaction mixture was neutralized with 6 M hydrochloric acid at 0° C., followed by extraction with ethyl acetate. The extract was washed with a saturated saline solution and was dried over anhydrous magnesium sulfate, and the solvent was then distilled under reduced pressure to obtain the title compound (0.778 g).

MS: [M+H]$^+$ 221.1.

D) Benzyl 5-allyl-6-hydroxy-2,3-dihydro-1-benzofuran-4-carboxylate

A mixture of 5-allyl-6-hydroxy-2,3-dihydro-1-benzofuran-4-carboxylic acid (777 mg), benzyl bromide (0.462 mL), N,N-diisopropylethylamine (1.356 mL), and DMF (10 mL) was stirred at room temperature overnight. Water was added to the reaction mixture, followed by extraction with ethyl acetate. The extract was washed with a saturated saline solution and was dried over anhydrous magnesium sulfate, and the solvent was then distilled under reduced pressure. The residue was purified by silica gel column chromatography (ethyl acetate/hexane) to obtain the title compound (680 mg).

$^1$H NMR (400 MHz, DMSO-d$_6$) δ 3.09 (2H, t, J=8.7 Hz), 3.38 (2H, d, J=6.1 Hz), 4.45 (2H, t, J=8.6 Hz), 4.74-4.84 (2H, m), 5.28 (2H, s), 5.70-5.87 (1H, m), 6.41 (1H, s), 7.30-7.46 (5H, m), 9.56 (1H, s).

E) Benzyl 5-allyl-6-((2-allyl-4-nitrobenzoyl)oxy)-2,3-dihydro-1-benzofuran-4-carboxylate DMF (0.136 mL) was added to a mixture of 2-allyl-4-nitrobenzoic acid (908 mg), THF (10 mL), and oxalyl chloride (0.575 ml) at room temperature, followed by stirring at the same temperature for 1.5 hours. The reaction mixture was concentrated under reduced pressure, DMF (1 mL) was then added to the residue, and a pyridine (3 mL) solution of benzyl 5-allyl-6-hydroxy-2,3-dihydro-1-benzofuran-4-carboxylate (680 mg) was then added thereto at room temperature, followed by stirring at 50° C. for 12 hours. One mole hydrochloric acid was added to the reaction mixture, followed by extraction with ethyl acetate. The extract was washed with a 0.28% ammonia aqueous solution twice, 1 M hydrochloric acid, and a saturated saline solution and was dried over anhydrous magnesium sulfate, and the solvent was then distilled under reduced pressure. The residue was purified by silica gel column chromatography (ethyl acetate/hexane) to obtain the title compound (880 mg).

MS: [M+H]$^+$ 500.2.

F) Benzyl 3-nitro-15-oxo-5,10,11,15-tetrahydro-8H-12,14-dioxabenzo[5,6]cyclodeca[1,2-f]indene-9-carboxylate A second-generation Grubbs catalyst (74.4 mg) was added to a toluene (450 mL) solution of benzyl 5-allyl-6-((2-allyl-4-nitrobenzoyl)oxy)-2,3-dihydro-1-benzofuran-4-carboxylate (876 mg) at 80° C., followed by stirring at the same temperature for 20 minutes. The reaction mixture was concentrated under reduced pressure, and the residue was purified by silica gel column chromatography (ethyl acetate/hexane) to obtain the title compound (615 mg).

$^1$H NMR (400 MHz, DMSO-d$_6$) δ 2.44-4.70 (8H, m), 5.31-5.57 (4H, m), 6.99 (1H, s), 7.33-7.46 (3H, m), 7.47-7.53 (2H, m), 7.90 (1H, d, J=8.4 Hz), 8.22-8.29 (1H, m), 8.33-8.41 (1H, m).

G) 3-Amino-15-oxo-5,7,8,10,11,15-hexahydro-6H-12,14-dioxabenzo[5,6]cyclodeca[1,2-f]indene-9-carboxylic acid Under a hydrogen atmosphere, a mixture of benzyl 3-nitro-15-oxo-5,10,11,15-tetrahydro-8H-12,14-dioxabenzo[5,6]cyclodeca[1,2-f]indene-9-carboxylate (615 mg), 10% palladium on carbon (300 mg, water content: about 55%), and THF (13 mL) was stirred at room temperature overnight. The catalyst was removed by filtration, and the filtrate was then concentrated under reduced pressure to obtain the title compound (577 mg).

MS: [M+H]$^+$ 354.1.

H) Di-tert-butyl N-((3-carbamimidamido-15-oxo-5,7,8,10,11,15-hexahydro-6H-12,14-dioxabenzo[5,6]cyclodeca[1,2-f]inden-9-yl)carbonyl)-L-aspartate Four mole hydrogen chloride in cyclopropyl methyl ether (1.225 mL) was added to a mixture of 3-amino-15-oxo-5,7,8,10,11,15-hexahydro-6H-12,14-dioxabenzo[5,6]cyclodeca[1,2-f]indene-9-carboxylic acid (577 mg), cyanamide (206 mg), and tert-butyl alcohol (36 mL) at room temperature, followed by stirring at 70° C. for 22 hours. The reaction mixture was concentrated under reduced pressure. To the residue, di-tert-butyl L-aspartate hydrochloride (274 mg), WSC (151 mg), HOBt.H$_2$O (149 mg), N,N-diisopropylethylamine (0.424 mL), and DMF (3 mL) were added, followed by stirring at room temperature for 4 hours and then at 60° C. for 2 hours. Water was added to the reaction mixture, followed by extraction with ethyl acetate. The extract was washed with a saturated saline solution and was dried over anhydrous magnesium sulfate, and the solvent was then distilled under reduced pressure. The residue was purified by silica gel column chromatography (NH, ethyl acetate/hexane and then methanol/ethyl acetate) to obtain the title compound (209 mg).

MS: [M+H]$^+$ 623.3.

I) N-((3-Carbamimidamido-15-oxo-5,7,8,10,11,15-hexahydro-6H-12,14-dioxabenzo[5,6]cyclodeca[1,2-f]inden-9-yl)carbonyl)-L-aspartic acid A mixture of di-tert-butyl N-((3-carbamimidamido-15-oxo-5,7,8,10,11,15-hexahydro-6H-12,14-dioxabenzo[5,6]cyclodeca[1,2-f]inden-9-yl)carbonyl)-L-aspartate (209 mg) and TFA (2 mL) was stirred at room temperature for 1 hour. The reaction mixture was concentrated under reduced pressure, and water (5 mL) was then added to the residue. An ammonium acetate aqueous solution was then added thereto to adjust the pH to about 4. The mixture was stirred at room temperature for 1 hour, and the solid was then collected by filtration and was washed with water and acetone to obtain the title compound (167 mg).

$^1$H NMR (400 MHz, DMSO-d$_6$) δ 1.40-1.87 (4H, m), 2.37-2.56 (1H, m), 2.75 (1H, dd, J=16.6, 8.4 Hz), 2.82-2.97 (2H, m), 3.03-3.20 (4H, m), 4.40-4.51 (1H, m), 4.56 (2H, t, J=8.8 Hz), 7.04-7.14 (2H, m), 7.18-7.27 (1H, m), 7.30-8.45 (6H, m).

Example 42

N-(3-(3-Carbamimidamido-16-oxo-6,7,8,9-tetrahydro-16H-dibenzo[b,f][1,4,8]trioxacyclododecin-11-yl)propanoyl)aspartic acid trifluoroacetate

A) Benzyl 2-(4-bromobutoxy)-4-nitrobenzoate

A mixture of benzyl 2-hydroxy-4-nitrobenzoate (6.0 g), potassium carbonate (6.0 g), 1,4-dibromobutane (18.0 g), and DMF (120 mL) was stirred at 60° C. overnight. Water (500 mL) was added to the reaction mixture at room temperature, followed by extraction with ethyl acetate (200 mL×2). The organic layer was dried over anhydrous sodium sulfate and was concentrated. The residue was purified by silica gel column chromatography (ethyl acetate/petroleum ether) to obtain the title compound (8.0 g).

$^1$H NMR (400 MHz, DMSO-dd: δ 1.82-1.90 (4H, m), 3.54 (2H, t, J=6.4 Hz), 4.23 (2H, t, J=6.0 Hz), 5.35 (2H, s), 7.37-7.48 (5H, m), 7.85-7.96 (3H, m).

B) (E)-Di-tert-butyl 2-(3-(3-(benzyloxy)-2-(4-(2-((benzyloxy)carbonyl)-5-nitrophenoxy)butoxy)phenyl)acrylamide)succinate A mixture of benzyl 2-(4-bromobutoxy)-4-nitrobenzoate (8.0 g), potassium carbonate (5.4 g), (S,E)-di-tert-butyl 2-(3-(3-(benzyloxy)-2-hydroxyphenyl)acrylamide)succinate (9.76 g), and DMF (100 mL) was stirred at 60° C. overnight. Water (500 mL) was added to the reaction mixture at room temperature, followed by extraction with ethyl acetate (200 mL×2). The organic layer was dried over anhydrous sodium sulfate and was concentrated. The residue was purified by silica gel column chromatography (ethyl acetate/petroleum ether) to obtain the title compound (12.0 g).

MS: [M+H]$^+$ 825.2.

C) 4-Amino-2-(4-(2-(3-((1,4-di-tert-butoxy-1,4-dioxobutan-2-yl)amino)-3-oxopropyl)-6-hydroxyphenoxy)butoxy)benzoic acid A mixture of (E)-di-tert-butyl 2-(3-(3-(benzyloxy)-2-(4-(2-((benzyloxy)carbonyl)-5-nitrophenoxy)butoxy)phenyl)acrylamide)succinate (12.0 g), 10% palladium on carbon (3.0 g), and THF (120 mL) was stirred under a hydrogen atmosphere at room temperature overnight. The catalyst was removed by filtration, and the filtrate was then concentrated under reduced pressure to obtain the title compound (9.0 g).

MS: [M+H]$^+$ 617.2.

D) 2-(4-(2-(3-((1,4-Di-tert-butoxy-1,4-dioxobutan-2-yl)amino)-3-oxopropyl)-6-hydroxyphenoxy)butoxy)-4-guanidinobenzoic acid trifluoroacetate Four normal hydrogen chloride in cyclopentyl methyl ether (3.65 mL) and cyanamide (1.84 g) were added to a mixture of 4-amino-2-(4-(2-(3-((1,4-di-tert-butoxy-1,4-dioxobutan-2-yl)amino)-3-oxopropyl)-6-hydroxyphenoxy)butoxy)benzoic acid (9.0 g) and dioxane (100 mL) at room temperature, followed by stirring at 60° C. overnight. The reaction mixture was concentrated, and the residue was purified by HPLC (C18, mobile phase: water/acetonitrile (system containing 0.1% TFA)) to obtain the title compound (4.3 g).

MS: [M+H]$^+$ 659.2.

E) Di-tert-butyl 2-(3-(3-guanidino-16-oxo-7,8,9,16-tetrahydro-6H-dibenzo[b,f][1,4,8]trioxacyclododecin-11-yl)propanamide)succinate trifluoroacetate A mixture of 2-(4-(2-(3-((1,4-di-tert-butoxy-1,4-dioxobutan-2-yl)amino)-3-oxopropyl)-6-hydroxyphenoxy)butoxy)-4-guanidinobenzoic acid trifluoroacetate (2.0 g), 2-methyl-6-nitrobenzoic anhydride (1.25 g), N,N-dimethyl-4-aminopyridine (784 mg), and dichloromethane (800 mL) was stirred at room temperature overnight. The reaction mixture was concentrated, and the residue was purified by HPLC (C18, mobile phase: water/acetonitrile (system containing 0.1% TFA)) to obtain the title compound (250 mg).

MS: [M+H]$^+$ 641.3.

F) N-(3-(3-Carbamimidamido-16-oxo-6,7,8,9-tetrahydro-16H-dibenzo[b,f][1,4,8]trioxacyclododecin-11-yl)propanoyl)aspartic acid trifluoroacetate TFA (2.0 mL) was added to a mixture of di-tert-butyl 2-(3-(3-guanidino-16-oxo-7,8,9,16-tetrahydro-6H-dibenzo[b,f][1,4,8]trioxacyclododecin-11-yl)propanamide)succinate trifluoroacetate (120 mg) and dichloromethane (10 mL) at room temperature, followed by stirring at the same temperature overnight. The reaction mixture was concentrated, and the residue was purified by HPLC (C18, mobile phase: water/acetonitrile (system containing 0.1% TFA)) to obtain the title compound (55.0 mg).

$^1$H NMR (400 MHz, DMSO-d$_6$): δ 1.96-2.02 (4H, m), 2.42-2.63 (3H, m), 2.63-2.67 (1H, m), 2.84-2.88 (2H, m), 4.11-4.13 (2H, m), 4.22-4.24 (2H, m), 4.51-4.53 (1H, m), 6.90-6.93 (1H, m), 7.00 (1H, s), 7.06-7.10 (1H, m), 7.14-7.15 (1H, m), 7.27-7.29 (1H, m), 7.67-7.74 (5H, m), 8.23-8.24 (1H, m), 10.0 (1H, s), 12.65 (1H, brs).

Example 43

N-(3-(3-Carbamimidamido-15-oxo-7,8-dihydro-6H,15H-dibenzo[b,f][1,4,8]trioxacycloundecin-10-yl)propanoyl)aspartic acid trifluoroacetate A) Benzyl 2-(3-bromopropoxy)-4-nitrobenzoate A mixture of benzyl 2-hydroxy-4-nitrobenzoate (6.0 g), potassium carbonate (6.0 g), 1,3-dibromobutane (18.0 g), and DMF (120 mL) was stirred at 60° C. overnight. Water (500 mL) was added to the reaction mixture at room temperature, followed by extraction with ethyl acetate (200 mL×2). The organic layer was dried over anhydrous sodium sulfate and was concentrated. The residue was purified by silica gel column chromatography (ethyl acetate/petroleum ether) to obtain the title compound (7.8 g).

$^1$H NMR (400 MHz, DMSO-d$_6$): δ 2.19 (2H, q, J=6.0 Hz), 3.53 (2H, t, J=6.4 Hz), 4.26 (2H, t, J=6.0 Hz), 5.33-5.34 (2H, m), 7.33-7.47 (5H, m), 7.85-7.93 (3H, m).

B) (E)-Di-tert-butyl 2-(3-(3-(benzyloxy)-2-(3-(2-((benzyloxy)carbonyl)-5-nitrophenoxy)propoxy)phenyl)acrylamide)succinate A mixture of benzyl 2-(4-bromobutoxy)-4-nitrobenzoate (6.0 g), potassium carbonate (4.2 g), (S,E)-di-tert-butyl 2-(3-(3-(benzyloxy)-2-hydroxyphenyl)acrylamide)succinate (7.56 g), and DMF (100 mL) was stirred at 60° C. overnight. Water (500 mL) was added to the reaction mixture at room temperature, followed by extraction with ethyl acetate (200 mL×2). The organic layer was dried over anhydrous sodium sulfate and was concentrated. The residue was purified by silica gel column chromatography (ethyl acetate/petroleum ether) to obtain the title compound (10.0 g).

MS: [M+H]$^+$ 811.2.

C) 4-Amino-2-(3-(2-(3-((1,4-di-tert-butoxy-1,4-dioxobutan-2-yl)amino)-3-oxopropyl)-6-hydroxyphenoxy)propoxy)benzoic acid A mixture of (E)-di-tert-butyl 2-(3-(3-(benzyloxy)-2-(3-(2-((benzyloxy)carbonyl)-5-nitrophenoxy)propoxy)phenyl)

acrylamide)succinate (10.0 g), 10% palladium on carbon (3.0 g), and THF (120 mL) was stirred under a hydrogen atmosphere at room temperature overnight. The catalyst was removed by filtration, and the filtrate was then concentrated under reduced pressure to obtain the title compound (8.0 g).

MS: [M+H]$^+$ 603.2.

D) (S)-2-(3-(2-(3-((1,4-Di-tert-butoxy-1,4-dioxobutan-2-yl)amino)-3-oxopropyl)-6-hydroxyphenoxy)propoxy)-4-guanidinobenzoic acid trifluoroacetate Four normal hydrogen chloride in cyclopentyl methyl ether (3.1 mL) and cyanamide (1.55 g) were added to a mixture of 4-amino-2-(3-(2-(3-((1,4-di-tert-butoxy-1,4-dioxobutan-2-yl)amino)-3-oxopropyl)-6-hydroxyphenoxy)propoxy)benzoic acid (7.4 g) and dioxane (100 mL) at room temperature, followed by stirring at 60° C. overnight. The reaction mixture was concentrated, and the residue was purified by HPLC (C18, mobile phase: water/acetonitrile (system containing 0.1% TFA)) to obtain the title compound (3.0 g).

MS: [M+H]$^+$ 645.2.

E) Di-tert-butyl 2-(3-(3-guanidino-15-oxo-6,7,8,15-tetrahydrodibenzo[b,f][1,4,8]trioxacycloundecin-10-yl)propanamide)succinate trifluoroacetate A mixture of (S)-2-(3-(2-(3-((1,4-di-tert-butoxy-1,4-dioxobutan-2-yl)amino)-3-oxopropyl)-6-hydroxyphenoxy)propoxy)-4-guanidinobenzoic acid trifluoroacetate (2.0 g), 2-methyl-6-nitrobenzoic anhydride (1.28 g), N,N-dimethyl-4-aminopyridine (802 mg), and dichloromethane (800 mL) was stirred at room temperature overnight. The reaction mixture was concentrated, and the residue was purified by HPLC (C18, mobile phase: water/acetonitrile (system containing 0.1% TFA)) to obtain the title compound (700 mg).

MS: [M+H]$^+$ 627.2.

F) N-(3-(3-Carbamimidamido-15-oxo-7,8-dihydro-6H,15H-dibenzo[b,f][1,4,8]trioxacycloundecin-10-yl)propanoyl)aspartic acid trifluoroacetate TFA (2.0 mL) was added to a mixture of di-tert-butyl 2-(3-(3-guanidino-15-oxo-6,7,8,15-tetrahydrodibenzo[b,f][1,4,8]trioxacycloundecin-10-yl)propanamide)succinate trifluoroacetate (300 mg) and dichloromethane (10 mL) at room temperature, followed by stirring at the same temperature overnight. The reaction mixture was concentrated, and the residue was purified by HPLC (C18, mobile phase: water/acetonitrile (system containing 0.1% TFA)) to obtain the title compound (137.0 mg).

$^1$H NMR (400 MHz, DMSO-d$_6$): δ 2.10-2.12 (2H, m), 2.43-2.53 (3H, m), 2.60-2.62 (1H, m), 2.86-2.92 (2H, m), 4.14-4.20 (4H, m), 4.45 (1H, brs), 7.11-7.21 (5H, m), 7.67-7.70 (4H, m), 7.79 (1H, d, J=8.4 Hz), 8.20 (1H, brs), 10.0 (1H, brs), 12.6 (1H, brs).

Example 44

N-(3-(11-Carbamimidamido-14-oxo-7,8,9,14-tetrahydro-6H-dibenzo[b,f][1,4]dioxacycloundecin-4-yl)propanoyl)-L-aspartic acid trifluoroacetate A) 2-Hydroxy-3-((2-(trimethylsilyl)ethoxy)methoxy)benzaldehyde 2,3-Dihydroxybenzaldehyde (10 g) was added to a mixture of 60% sodium hydride (6.37 g) and DMF (100 mL) at 0° C., followed by stirring at room temperature for 30 minutes. A mixture of 2-(trimethylsilyl)ethoxymethyl chloride and DMF (50 mL) was then added thereto at 0° C., followed by stirring at room temperature overnight. The reaction mixture was poured into a mixture of ethyl acetate and 1 N hydrochloric acid at 0° C. for distribution. The organic layer was washed with water and a saturated saline solution and was then dried over anhydrous sodium sulfate, and the solvent was distilled under reduced pressure. The residue was purified by silica gel column chromatography (ethyl acetate/hexane) to obtain the title compound (10.57 g).

$^1$H NMR (300 MHz, DMSO-d$_6$) δ −0.03 (9H, s), 0.89 (2H, dd, J=8.6, 7.7 Hz), 3.75 (2H, dd, J=8.6, 7.6 Hz), 5.27 (2H, s), 6.89 (1H, t, J=7.9 Hz), 7.33 (2H, ddd, J=10.2, 8.0, 1.5 Hz), 10.07-10.42 (2H, m).

B) (E)-Methyl 3-(2-hydroxy-3-((2-(trimethylsilyl)ethoxy)methoxy)phenyl)acrylate

Methyl 2-(triphenylphosphoranylidene)acetate (1.06 g) was added to a mixture of 2-hydroxy-3-((2-(trimethylsilyl)ethoxy)methoxy)benzaldehyde (706.4 mg) and toluene (14 mL) at room temperature, followed by stirring at the same temperature overnight. The reaction mixture was concentrated. The residue was purified by silica gel column chromatography (ethyl acetate/hexane) to obtain the title compound (762 mg).

$^1$H NMR (300 MHz, DMSO-d$_6$) δ −0.02 (9H, s), 0.79-0.97 (2H, m), 3.65-3.82 (5H, m), 5.23 (2H, s), 6.59 (1H, d, J=16.1 Hz), 6.77 (1H, t, J=8.0 Hz), 7.11 (1H, dd, J=8.0, 1.3 Hz), 7.27 (1H, dd, J=7.9, 1.2 Hz), 7.90 (1H, d, J=16.1 Hz), 9.41 (1H, s).

C) (E)-3-(2-Hydroxy-3-((2-(trimethylsilyl)ethoxy)methoxy)phenyl)acrylic acid

Two normal sodium hydroxide aqueous solution (7 mL) was added to a mixture of (E)-methyl 3-(2-hydroxy-3-((2-(trimethylsilyl)ethoxy)methoxy)phenyl)acrylate (732.0 mg) and THF/methanol (7 mL/7 mL) at 0° C., followed by stirring at room temperature overnight. The reaction mixture was distributed between ethyl acetate and 1 N hydrochloric acid. The organic layer was washed with a saturated saline solution and was then dried over anhydrous sodium sulfate, and the solvent was distilled under reduced pressure to obtain 2-allyl-4-bromo-3-hydroxybenzoic acid (700 mg).

$^1$H NMR (300 MHz, DMSO-d$_6$) δ −0.02 (9H, s), 0.61-1.11 (2H, m), 3.75 (2H, t, J=8.2 Hz), 5.23 (2H, s), 6.49 (1H, d, J=16.1 Hz), 6.77 (1H, t, J=7.9 Hz), 7.10 (1H, d, J=8.0 Hz), 7.23 (1H, d, J=7.8 Hz), 7.83 (1H, d, J=16.1 Hz), 9.33 (1H, brs), 12.22 (1H, brs).

D) (S,E)-Dibenzyl 2-(3-(2-hydroxy-3-((2-(trimethylsilyl)ethoxy)methoxy)phenyl)acrylamide)succinate (S)-Dibenzyl 2-aminosuccinate hydrochloride (932 mg), N,N-diisopropylethylamine (1.0 mL), WSC hydrochloride (511 mg), and HOBt.H$_2$O (408 mg) were added to a mixture of (E)-3-(2-hydroxy-3-((2-(trimethylsilyl)ethoxy)methoxy)phenyl)acrylic acid (689.1 mg) and DMF (10 mL) at 0° C., followed by stirring at room temperature overnight. Water was added to the reaction mixture at 0° C., followed by extraction with ethyl acetate. The organic layer was washed with 1 N hydrochloric acid, water, a saturated sodium hydrogen carbonate aqueous solution, and a saturated saline solution and was then dried over anhydrous sodium sulfate, and the solvent was distilled under reduced pressure. The residue was purified by silica gel column chromatography (ethyl acetate/hexane) to obtain the title compound (1.311 g).

MS: [M+H]$^+$ 606.3.

E) (S,E)-Dibenzyl 2-(3-(2-(allyloxy)-3-((2-(trimethylsilyl)ethoxy)methoxy)phenyl)acrylamide)succinate Allyl bromide (0.200 mL) was added to a mixture of (S,E)-dibenzyl 2-(3-(2-hydroxy-3-((2-(trimethylsilyl)ethoxy)methoxy)phenyl)acrylamide)succinate (1.28 g), potassium carbonate (0.876 g), and DMF (13 mL) at 0° C., followed by stirring at room temperature for 4 hours. The reaction mixture was poured into a mixture of ethyl acetate and a saturated ammonium chloride aqueous solution at 0° C. for distribution. The organic layer was washed with water and a saturated saline solution and was then dried over anhydrous sodium sulfate, and the solvent was distilled under reduced pressure. The residue was purified by silica gel column chromatography (ethyl acetate/hexane) to obtain the title compound (1.301 g).

MS: [M+H]$^+$ 646.2.

F) (S,E)-Dibenzyl 2-(3-(2-(allyloxy)-3-hydroxyphenyl) acrylamide)succinate

Trifluoroacetic acid (13 mL) was added to a mixture of (S,E)-dibenzyl 2-(3-(2-(allyloxy)-3-((2-(trimethylsilyl)ethoxy)methoxy)phenyl)acrylamide)succinate (1.24 g) and triethylsilane (1.0 mL) at 0° C., followed by stirring at room temperature for 1 hour. The reaction mixture was concentrated and was distributed between ethyl acetate and a saturated sodium hydrogen carbonate aqueous solution. The organic layer was washed with a saturated saline solution and was then dried over anhydrous sodium sulfate, and the solvent was distilled under reduced pressure. The residue was purified by silica gel column chromatography (ethyl acetate/hexane) to obtain the title compound (0.899 g).

MS: [M+H]$^+$ 516.2.

G) (S,E)-Dibenzyl 2-(3-(3-((2-allyl-4-nitrobenzoyl)oxy)-2-(allyloxy)phenyl)acrylamide)succinate Oxalyl chloride (0.444 mL) and DMF (0.065 mL) were added to a mixture of 2-allyl-4-nitrobenzoic acid (701 mg) and (7.5 mL) at room temperature, followed by stirring at room temperature for 1 hour. The reaction mixture was then concentrated. A mixture of (S,E)-dibenzyl 2-(3-(2-(allyloxy)-3-hydroxyphenyl)acrylamide)succinate (871.7 mg) and DMF (3 mL) was added to a mixture of the residue, DMF (2 mL), and pyridine (1 mL) at room temperature, followed by stirring at room temperature for 1 hour, at 40° C. for 18 hours, and at 60° C. for 24 hours. The reaction mixture was poured into water/ethyl acetate, followed by extraction with ethyl acetate. The organic layer was washed with 0.25% aqueous ammonia, water, 1 N hydrochloric acid, and a saturated saline solution and was then dried over anhydrous sodium sulfate, and the solvent was distilled under reduced pressure. The residue was purified by silica gel column chromatography (ethyl acetate/hexane) to obtain the title compound (739 mg).

MS: [M+H]$^+$ 705.2.

H) (S)-Dibenzyl 2-((2E)-3-(11-nitro-14-oxo-9,14-dihydro-6H-dibenzo[b,f][1,4]dioxacycloundecin-4-yl)acrylamide)succinate A second-generation Hoveyda-Grubbs catalyst (60.7 mg) was added to a mixture of (S,E)-dibenzyl 2-(3-(3-((2-allyl-4-nitrobenzoyl)oxy)-2-(allyloxy)phenyl)acrylamide)succinate (681.0 mg) and toluene (700 mL) at 100° C., followed by stirring at the same temperature for 1 hour. The reaction mixture was concentrated, and the residue was purified by silica gel column chromatography (ethyl acetate/hexane) to obtain the title compound (275 mg).

MS: [M+H]$^+$ 677.2.

I) (S)-2-(3-(11-Amino-14-oxo-7,8,9,14-tetrahydro-6H-dibenzo[b,f][1,4]dioxacycloundecin-4-yl)propanamide)succinic acid A mixture of (S)-dibenzyl 2-((2E)-3-(11-nitro-14-oxo-9,14-dihydro-6H-dibenzo[b,f][1,4]dioxacycloundecin-4-yl)acrylamide)succinate (264.0 mg), 10% palladium on carbon (153.4 mg, water content: about 55%), and THF (10 mL) was stirred under a hydrogen atmosphere at room temperature overnight. The catalyst was removed by filtration, and the filtrate was then concentrated under reduced pressure to obtain the title compound (208 mg).

MS: [M+Na]$^+$ 493.2.

J) N-(3-(11-Carbamimidamido-14-oxo-7,8,9,14-tetrahydro-6H-dibenzo[b,f][1,4]dioxacycloundecin-4-yl)propanoyl)-L-aspartic acid trifluoroacetate Four normal hydrogen chloride in cyclopentyl methyl ether (0.293 mL) and cyanamide (49.2 mg) were added to a mixture of (S)-2-(3-(11-amino-14-oxo-7,8,9,14-tetrahydro-6H-dibenzo[b,f][1,4]dioxacycloundecin-4-yl)propanamide)succinic acid (184 mg) and tert-butyl alcohol (5 mL) at room temperature, followed by stirring at 60° C. for 3 hours. The reaction mixture was concentrated, and the residue was purified by HPLC (C18, mobile phase: water/acetonitrile (system containing 0.1% TFA)). The resulting solid was then washed with diethyl ether to obtain the title compound (170 mg).

$^1$H NMR (300 MHz, DMSO-d$_6$) δ 1.69-1.86 (2H, m), 1.88-2.00 (2H, m), 2.07-2.23 (2H, m), 2.40-2.56 (1H, m), 2.58-2.71 (1H, m), 2.79 (2H, t, J=6.3 Hz), 2.94 (2H, dd, J=7.7, 5.4 Hz), 4.04-4.20 (2H, m), 4.42-4.55 (1H, m), 6.77-6.91 (1H, m), 7.01 (2H, d, J=7.9 Hz), 7.13-7.34 (2H, m), 7.71 (4H, brs), 8.06 (2H, d, J=8.4 Hz), 12.85 (2H, brs).

Example 47

N-(3-(10-Carbamimidamido-13-oxo-6,7,8,13-tetrahydrodibenzo[b,f][1,4]dioxecin-4-yl)propanoyl)aspartic acid A) (S,E)-Di-tert-butyl 2-(3-(3-(benzyloxy)-2-hydroxyphenyl)acrylamide)succinate (S)-Di-tert-butyl 2-aminosuccinate hydrochloride (2.189 g), diisopropylethylamine (2.83 mL), WSC hydrochloride (1.489 g), and HOBt.H$_2$O (1.190 g) were added to a mixture of (E)-3-(3-(benzyloxy)-2-hydroxyphenyl)acrylic acid (1.75 g) and DMF (150 mL) at 0° C., followed by stirring at room temperature overnight and then at 60° C. for 2 hours. Water was added to the reaction mixture at 0° C., followed by extraction with ethyl acetate. The organic layer was washed with 1 N hydrochloric acid, water, a saturated sodium hydrogen carbonate aqueous solution, and a saturated saline solution and was then dried over anhydrous sodium sulfate, and the solvent was distilled under reduced pressure. The residue was purified by silica gel column chromatography (ethyl acetate/hexane) to obtain the title compound (3.00 g).

MS: [M+H]$^+$ 498.3.

B) (E)-Di-tert-butyl 2-(3-(3-(benzyloxy)-2-(3-(2-((benzyloxy)carbonyl)-5-((tert-butoxycarbonyl)amino)phenyl)propoxy)phenyl)acrylamide)succinate A mixture of benzyl 4-((tert-butoxycarbonyl)amino)-2-(3-((methylsulfonyl)oxy)propyl)benzoate (547.3 mg) and DMF (7 mL) was added to a mixture of (S,E)-di-tert-butyl 2-(3-(3-(benzyloxy)-2-hydroxyphenyl)acrylamide)succinate (705 mg), potassium carbonate (490 mg), and DMF (8 mL) at room temperature, followed by stirring at 80° C. for 12 hours. The reaction mixture was cooled to room temperature and was poured into a mixture of ethyl acetate and a saturated ammonium chloride aqueous solution at 0° C. for distribution. The organic layer was washed with water and a saturated saline solution and was then dried over anhydrous sodium sulfate, and the solvent was distilled under reduced pressure. The residue was purified by silica gel column chromatography (ethyl acetate/hexane) to obtain the title compound (921 mg).

$^1$H NMR (300 MHz, DMSO-$d_6$) δ 1.38 (9H, s), 1.37 (9H, s), 1.47 (9H, s), 1.81-1.97 (2H, m), 2.53-2.82 (2H, m), 2.89-3.06 (2H, m), 3.92 (2H, t, J=6.4 Hz), 4.59-4.73 (1H, m), 5.13 (2H, s), 5.25 (2H, s), 6.75 (1H, d, J=16.0 Hz), 7.01-7.58 (15H, m), 7.67-7.91 (2H, m), 8.44 (1H, d, J=8.2 Hz), 9.60 (1H, s).

C) 4-((tert-Butoxycarbonyl)amino)-2-(3-(2-(3-((1,4-di-tert-butoxy-1,4-dioxobutan-2-yl)amino)-3-oxopropyl)-6-hydroxyphenoxy)propyl)benzoic acid A mixture of (E)-di-tert-butyl 2-(3-(3-(benzyloxy)-2-(3-(2-((benzyloxy)carbonyl)-5-((tert-butoxycarbonyl)amino)phenyl)propoxy)phenyl)acrylamide)succinate (854.8 mg), 10% palladium on carbon (97.8 mg, water content: about 55%), and THF (20 mL) was stirred under a hydrogen atmosphere at room temperature overnight. The catalyst was removed by filtration, and the filtrate was then concentrated under reduced pressure. The residue was purified by silica gel column chromatography (ethyl acetate/hexane) to obtain the title compound (614 mg).

MS: [M+H]$^+$ 687.3.

D) Di-tert-butyl 2-(3-(10-((tert-butoxycarbonyl)amino)-13-oxo-6,7,8,13-tetrahydrodibenzo[b,f][1,4]dioxecin-4-yl)propanamide)succinate 2-Methyl-6-nitrobenzoic anhydride (380 mg) and N,N-dimethyl-4-aminopyridine (68.4 mg) were added to a mixture of 4-((tert-butoxycarbonyl)amino)-2-(3-(2-(3-((1,4-di-tert-butoxy-1,4-dioxobutan-2-yl)amino)-3-oxopropyl)-6-hydroxyphenoxy)propyl)benzoic acid (252.8 mg) and THF (350 mL) at room temperature. The mixture was stirred at 60° C. for 1 hour, followed by heating to reflux for 20 hours. The reaction mixture was concentrated, and the residue was distributed between ethyl acetate and water. The organic layer was washed with a saturated saline solution and was then dried over anhydrous sodium sulfate, and the solvent was distilled under reduced pressure. The residue was purified by silica gel column chromatography (ethyl acetate/hexane) to obtain the title compound (152 mg).

MS: [M+H]$^+$ 669.4.

E) 2-(3-(10-Amino-13-oxo-6,7,8,13-tetrahydrodibenzo[b,f][1,4]dioxecin-4-yl)propanamide)succinic acid trifluoroacetate A mixture of di-tert-butyl 2-(3-(10-((tert-butoxycarbonyl)amino)-13-oxo-6,7,8,13-tetrahydrodibenzo[b,f][1,4]dioxecin-4-yl)propanamide)succinate (146.3 mg) and TFA (5 mL) was stirred at room temperature for 1 hour. The reaction mixture was concentrated under reduced pressure, and the residue was washed with diethyl ether to obtain the title compound (59.0 mg).

MS: [M+H]$^+$ 457.2.

F) N-(3-(10-Carbamimidamido-13-oxo-6,7,8,13-tetrahydrodibenzo[b,f][1,4]dioxecin-4-yl)propanoyl) aspartic acid trifluoroacetate Four normal hydrogen chloride in cyclopentyl methyl ether (0.112 mL) and cyanamide (18.9 mg) were added to a mixture of 2-(3-(10-amino-13-oxo-6,7,8,13-tetrahydrodibenzo[b,f][1,4]dioxecin-4-yl)propanamide)succinic acid trifluoroacetate (51.3 mg) and tert-butyl alcohol (0.5 mL) at room temperature, followed by stirring at 60° C. for 2 hours. The reaction mixture was concentrated, and the residue was purified by HPLC (C18, mobile phase: water/acetonitrile (system containing 0.1% TFA)) to obtain the title compound (48.0 mg).

MS: [M+H]$^+$ 499.2.

G) N-(3-(10-Carbamimidamido-13-oxo-6,7,8,13-tetrahydrodibenzo[b,f][1,4]dioxecin-4-yl)propanoyl) aspartic acid One mole ammonium acetate aqueous solution was added to a water/TFA (2.0 mL/0.02 mL) solution of N-(3-(10-carbamimidamido-13-oxo-6,7,8,13-tetrahydrodibenzo[b,f][1,4]dioxecin-4-yl)propanoyl)aspartic acid trifluoroacetate (40.0 mg) to adjust the pH of the solution to 5, followed by stirring at room temperature for 30 minutes. The precipitated solid was collected by filtration, washed with water, and dried under reduced pressure at 50° C. to obtain the title compound (31.6 mg).

$^1$H NMR (300 MHz, DMSO-$d_6$) δ 1.97 (2H, brs), 2.19-2.51 (4H, m), 2.86 (2H, t, J=7.7 Hz), 3.31 (2H, brs), 3.92 (2H, brs), 4.13-4.29 (1H, m), 7.02-7.12 (1H, m), 7.13-7.19 (1H, m), 7.20-7.37 (3H, m), 7.43-8.05 (4H, m), 7.74 (1H, d, J=7.1 Hz), 7.88 (1H, d, J=8.3 Hz).

Example 48

N-(3-(9-Carbamimidamido-6-oxo-11,12-dihydro-6H-[2]benzoxocino[4,3-b]pyridin-2-yl)propanoyl)-L-aspartic acid trifluoroacetate A) Benzyl 2-bromo-4-nitrobenzoate A mixture of 2-bromo-4-nitrobenzoic acid (4.1 g), (bromomethyl)benzene (3.4 g), potassium carbonate (4.6 g), and acetonitrile (60 mL) was stirred at 80° C. for 1.5 hours. The reaction mixture was filtered, and the filtrate was then concentrated under reduced pressure. The residue was purified by silica gel column chromatography (ethyl acetate/petroleum ether) to obtain the title compound (5.4 g).

$^1$H NMR (400 MHz, CDCl$_3$) δ 5.41 (2H, s), 7.37-7.48 (5H, m), 7.92 (1H, d, J=8.4 Hz), 8.18 (1H, dd, J=8.4 Hz, 2.0 Hz), 8.49 (1H, d, J=2.0 Hz).

B) Ethyl 3-(5-hydroxypyridin-2-yl)acrylate

A mixture of 5-hydroxypicolinaldehyde (20.8 g), [(ethoxycarbonyl)methylene]triphenylphosphorane (76.5 g), and tetrahydrofuran (1000 mL) was stirred under a nitrogen atmosphere at 50° C. overnight. The reaction mixture was concentrated under reduced pressure. The residue was purified by silica gel column chromatography (ethyl acetate/petroleum ether) to obtain the title compound (19.5 g).
MS: [M+H]+ 193.9.

C) Ethyl 3-(5-hydroxypyridin-2-yl)propanoate

A mixture of ethyl 3-(5-hydroxypyridin-2-yl)acrylate (19.5 g), 10% palladium on carbon (2.0 g), and methanol (500 mL) was stirred under a hydrogen atmosphere overnight. The reaction mixture was filtered, and the filtrate was then concentrated under reduced pressure to obtain the title compound (17.0 g).
MS: [M+H]+ 196.2.

D) Ethyl 3-(5-hydroxy-6-iodopyridin-2-yl)propanoate

A mixture of ethyl 3-(5-hydroxypyridin-2-yl)propanoate (17.0 g) and tetrahydrofuran (90 mL) was added to a mixture of sodium hydrogen carbonate (8.8 g) and water (90 mL), followed by stirring at room temperature for 0.5 hours. Subsequently, iodine (26.6 g) was gradually added thereto, followed by stirring at room temperature overnight. The reaction mixture was diluted with water, followed by extraction with ethyl acetate. The extract was washed with a saturated saline solution and was then dried over anhydrous sodium sulfate, and the solvent was distilled under reduced pressure. The residue was purified by silica gel column chromatography (ethyl acetate/petroleum ether) to obtain the title compound (17.1 g).
MS: [M+H]+ 321.8.

E) Ethyl 3-(5-(benzyloxy)-6-iodopyridin-2-yl)propanoate

A mixture of ethyl 3-(5-hydroxy-6-iodopyridin-2-yl)propanoate (17.1 g), (bromomethyl)benzene (9.9 g), potassium carbonate (14.62 g), and acetonitrile (200 mL) was heated to reflux for 2 hours. The insoluble matter was removed by filtration, and the filtrate was then concentrated under reduced pressure to obtain the title compound (22.0 g).
MS: [M+H]+ 412.0.

F) 3-(5-(Benzyloxy)-6-iodopyridin-2-yl)propanoic acid

A mixture of ethyl 3-(5-(benzyloxy)-6-iodopyridin-2-yl)propanoate (22.0 g), a 1 M sodium hydroxide aqueous solution (107 mL), methanol (110 mL), and tetrahydrofuran (110 mL) was stirred for 1.5 hours. A 1 M hydrochloric acid aqueous solution was added to the reaction mixture to adjust the pH to 2 to 3, followed by extraction with ethyl acetate. The extract was washed with a saturated saline solution and was then dried over anhydrous sodium sulfate, and the solvent was distilled under reduced pressure to obtain the title compound (18.5 g).
MS: [M+H]+ 384.0.

G) (S)-Di-tert-butyl 2-(3-(5-(benzyloxy)-6-iodopyridin-2-yl)propanamide)succinate A mixture of (S)-di-tert-butyl 2-aminosuccinate hydrochloride (16.35 g), O-(benzotriazol-1-yl)-N,N,N',N'-tetramethyluronium hexafluorophosphate (21.97 g), and triethylamine (13.4 mL) was added to a mixture of 3-(5-(benzyloxy)-6-iodopyridin-2-yl)propanoic acid (18.5 g) and DMF (200 mL), followed by stirring at room temperature overnight. After completion of the reaction, the reaction mixture was diluted with water, followed by extraction with ethyl acetate. The extract was washed with a saturated saline solution and was then dried over anhydrous sodium sulfate, and the solvent was distilled under reduced pressure. The residue was purified by silica gel column chromatography (ethyl acetate/petroleum ether) to obtain the title compound (26.9 g).
$^1$H NMR (400 MHz, DMSO-$d_6$) δ 1.36 (9H, s), 1.38 (9H, s), 2.46-2.52 (3H, m), 2.60-2.66 (1H, m), 2.85 (2H, t, J=7.6 Hz), 4.43-4.50 (1H, m), 5.22 (2H, s), 7.20 (1H, d, J=8.4 Hz), 7.31-7.36 (2H, m), 7.42 (2H, t, J=7.2 Hz), 7.49 (2H, d, J=6.8 Hz), 8.29 (1H, d, J=8.0 Hz).

H) (S)-Di-tert-butyl 2-(3-(5-(benzyloxy)-6-((trimethylsilyl)ethynyl)pyridin-2-yl)propanamide)succinate A mixture of (S)-di-tert-butyl 2-(3-(5-(benzyloxy)-6-iodopyridin-2-yl)propanamide)succinate (26.9 g), ethynyltrimethylsilane (8.64 g), bis(triphenylphosphine)palladium (II) dichloride (3.09 g), copper(I) iodide (1.68 g), triethylamine (12.2 mL), and DMF (150 mL) was stirred under a nitrogen atmosphere at 80° C. overnight. The reaction mixture was diluted with water, followed by extraction with ethyl acetate. The extract was washed with a saturated saline solution and was then dried over anhydrous sodium sulfate, and the solvent was distilled under reduced pressure. The residue was purified by silica gel column chromatography (ethyl acetate/petroleum ether) to obtain the title compound (24.0 g).
MS: [M+H]+ 581.2.

I) (S)-Di-tert-butyl 2-(3-(5-(benzyloxy)-6-ethynylpyridin-2-yl)propanamide)succinate A mixture of (S)-di-tert-butyl 2-(3-(5-(benzyloxy)-6-((trimethylsilyl)ethynyl)pyridin-2-yl)propanamide)succinate (12.0 g), potassium carbonate (5.71 g), and methanol (100 mL) was stirred at room temperature for 0.5 hours. The reaction mixture was diluted with water, followed by extraction with ethyl acetate. The extract was washed with a saturated saline solution and was then dried over anhydrous sodium sulfate, and the solvent was distilled under reduced pressure to obtain the title compound (8.0 g).
MS: [M+H]+ 508.8.

J) (S)-Di-tert-butyl 2-(3-(5-(benzyloxy)-6-((2-((benzyloxy)carbonyl)-5-nitrophenyl)ethynyl)pyridin-2-yl)propanamide)succinate A mixture of (S)-di-tert-butyl 2-(3-(5-(benzyloxy)-6-ethynylpyridin-2-yl)propanamide)succinate (3.9 g), benzyl 2-bromo-4-nitrobenzoate (2.57 g), tetrakis(triphenylphosphine)palladium(0) (0.889 g), triethylamine (2.13 mL), and DMF (50 mL) was stirred under a nitrogen atmosphere at 110° C. overnight. The reaction mixture was diluted with water, followed by extraction with ethyl acetate. The extract was washed with a saturated saline solution and was then dried over anhydrous sodium sulfate, and the solvent was distilled under reduced pressure. The residue was purified by silica gel column chromatography (ethyl acetate/petroleum ether) to obtain the title compound (5.0 g).
MS: [M+H]+ 764.1.

K) (S)-4-Amino-2-(2-(6-(3-((1,4-di-tert-butoxy-1,4-dioxobutan-2-yl)amino)-3-oxopropyl)-3-hydroxypyridin-2-yl)ethyl)benzoic acid Ten percent palladium on carbon (0.36 g) was added to a mixture of (S)-di-tert-butyl 2-(3-(5-(benzyloxy)-6-((2-((benzyloxy)carbonyl)-5-nitrophenyl)ethynyl)pyridin-2-yl)propanamide)succinate (1.2 g) and tetrahydrofuran (30 mL), followed by stirring under a hydrogen atmosphere at room temperature overnight. The reaction mixture was filtered, and the filtrate was then concentrated under reduced pressure to obtain the title compound (0.83 g).

MS: [M+H]$^+$ 558.2.

L) (S)-2-(2-(6-(3-((1,4-Di-tert-butoxy-1,4-dioxobutan-2-yl)amino)-3-oxopropyl)-3-hydroxypyridin-2-yl)ethyl)-4-guanidinobenzoic acid A mixture of (S)-4-amino-2-(2-(6-(3-((1,4-di-tert-butoxy-1,4-dioxobutan-2-yl)amino)-3-oxopropyl)-3-hydroxypyridin-2-yl)ethyl)benzoic acid (0.300 g), cyanamide (0.113 g), 4 M hydrochloric acid in dioxane (0.27 mL), and dioxane (20 mL) was stirred at 50° C. for 4.5 hours. After completion of the reaction, the reaction mixture was concentrated under reduced pressure and was purified by HPLC to obtain the title compound (0.280 g).

MS: [M+H]$^+$ 600.3.

M) (S)-Di-tert-butyl 2-(3-(9-(3-(tert-butoxycarbonyl)guanidino)-6-oxo-11,12-dihydro-6H-benzo[6,7]oxocino[3,2-b]pyridin-2-yl)propanamide)succinate A mixture of (S)-2-(2-(6-(3-((1,4-di-tert-butoxy-1,4-dioxobutan-2-yl)amino)-3-oxopropyl)-3-hydroxypyridin-2-yl)ethyl)-4-guanidinobenzoic acid (0.230 g), 1-[3-(dimethylamino)propyl]-3-ethyl carbodiimide (0.110 g), and pyridine (5 mL) was stirred at room temperature for 5 hours. Subsequently, 4-dimethylaminopyridine (0.005 g) and di-tert-butyl dicarbonate (0.207 mg) were added thereto, followed by stirring at room temperature for 3 hours. The reaction mixture was concentrated under reduced pressure, and the residue was purified by silica gel column chromatography (ethyl acetate/petroleum ether) to obtain the title compound (0.14 g).

MS: [M+H]$^+$ 782.3.

N) N-(3-(9-Carbamimidamido-6-oxo-11,12-dihydro-6H-[2]benzoxocino[4,3-b]pyridin-2-yl)propanoyl)-L-aspartic acid trifluoroacetate A mixture of (S)-di-tert-butyl 2-(3-(9-(3-(tert-butoxycarbonyl)guanidino)-6-oxo-11,12-dihydro-6H-benzo[6,7]oxocino[3,2-b]pyridin-2-yl)propanamide)succinate (0.140 g), trifluoroacetic acid (5 mL), and dichloromethane (10 mL) was stirred overnight. The reaction mixture was concentrated under reduced pressure, and the residue was washed with dichloromethane to obtain the title compound (0.14 g).

$^1$H NMR (400 MHz, MeOD) δ 2.58 (2H, t, J=7.2 Hz), 2.69-2.72 (2H, m), 2.96 (2H, t, J=7.2 Hz), 3.31-3.37 (4H, m), 4.56-4.61 (1H, m), 7.09 (1H, d, J=8.0 Hz), 7.14-7.17 (2H, m), 7.39 (1H, d, J=8.0 Hz), 7.46 (1H, d, J=8.4 Hz).

Example 50

N-(3-(9-Carbamimidamido-6-oxo-12,13-dihydro-6H-dibenzo[b,f][1,5]dioxonin-2-yl)propanoyl)-L-aspartic acid trifluoroacetate

A) (E)-tert-Butyl 3-(4-hydroxy-3-(2-hydroxyethyl)phenyl)acrylate

A mixture of 4-bromo-2-(2-hydroxyethyl)phenol (2.33 g), tert-butyl acrylate (2.35 mL), potassium phosphate (2.73 g), palladium acetate (0.048 g), and DMF (30 mL) was stirred at 90° C. overnight. To the reaction mixture, 0.1 N hydrochloric acid was added at room temperature. The mixture was filtered through Celite (trade name), and the filtrate was extracted with ethyl acetate. The extract was washed with water and a saturated saline solution and was then dried over magnesium sulfate, and the solvent was distilled under reduced pressure. The residue was purified by silica gel column chromatography (ethyl acetate/hexane) to obtain the title compound (1.76 g).

$^1$H NMR (300 MHz, CDCl$_3$) δ 1.52 (9H, s), 2.87-2.95 (2H, m), 3.96-4.07 (3H, m), 6.21 (1H, d, J=15.9 Hz), 6.90 (1H, d, J=8.3 Hz), 7.23 (1H, d, J=2.3 Hz), 7.33 (1H, dd, J=8.5, 2.1 Hz), 7.50 (1H, d, J=15.9 Hz), 8.29 (1H, brs).

B) (E)-tert-Butyl 3-(4-(benzyloxy)-3-(2-hydroxyethyl)phenyl)acrylate

A mixture of (E)-tert-butyl 3-(4-hydroxy-3-(2-hydroxyethyl)phenyl)acrylate (1.76 g), benzyl bromide (0.83 mL), potassium carbonate (1.10 g), and acetone (30 mL) was stirred at room temperature overnight. The reaction mixture was neutralized with 1 N hydrochloric acid, followed by extraction with ethyl acetate. The extract was washed with water and a saturated saline solution and was then dried over magnesium sulfate, and the solvent was distilled under reduced pressure. The residue was purified by silica gel column chromatography (ethyl acetate/hexane) to obtain the title compound (1.57 g).

$^1$H NMR (300 MHz, CDCl$_3$) δ 1.53 (9H, s), 2.95 (2H, t, J=6.4 Hz), 3.87 (2H, q, J=6.4 Hz), 5.11 (2H, s), 6.25 (1H, d, J=15.9 Hz), 6.92 (1H, d, J=8.3 Hz), 7.29-7.46 (7H, m), 7.52 (1H, d, J=15.9 Hz).

C) (E)-Benzyl 2-(2-(benzyloxy)-5-(3-(tert-butoxy)-3-oxoprop-1-en-1-yl)phenetoxy)-4-nitrobenzoate A mixture of benzyl 2-hydroxy-4-nitrobenzoate (1.27 g), (E)-tert-butyl 3-(4-(benzyloxy)-3-(2-hydroxyethyl)phenyl)acrylate (1.57 g), 2-(tributylphosphoranylidene)acetonitrile (1.39 g), and toluene (15 mL) was stirred at 80° C. overnight. The reaction mixture was purified by silica gel column chromatography (ethyl acetate/hexane) to obtain the title compound (1.76 g).

$^1$H NMR (300 MHz, CDCl$_3$) δ 1.50 (9H, s), 3.19 (2H, t, J=6.8 Hz), 4.32 (2H, t, J=6.8 Hz), 5.15 (2H, s), 5.34 (2H, s), 6.30 (1H, d, J=15.9 Hz), 6.91 (1H, d, J=8.3 Hz), 7.29-7.48 (12H, m), 7.52 (1H, d, J=15.9 Hz), 7.70-7.79 (2H, m), 7.82-7.91 (1H, m).

D) (E)-3-(4-(Benzyloxy)-3-(2-(2-((benzyloxy)carbonyl)-5-nitrophenoxy)ethyl)phenyl)acrylic acid A mixture of (E)-benzyl 2-(2-(benzyloxy)-5-(3-(tert-butoxy)-3-oxoprop-1-en-1-yl)phenetoxy)-4-nitrobenzoate (1.76 g), TFA (3 mL), and toluene (5 mL) was stirred at room temperature for 1 hour. The reaction mixture was concentrated under reduced pressure to obtain the title compound (1.50 g).

MS: [M+H]⁺ 554.3.

E) (S,E)-Di-tert-butyl 2-(3-(4-(benzyloxy)-3-(2-(2-((benzyloxy)carbonyl)-5-nitrophenoxy)ethyl)phenyl)acrylamide)succinate A mixture of (E)-3-(4-(benzyloxy)-3-(2-(2-((benzyloxy)carbonyl)-5-nitrophenoxy)ethyl)phenyl)acrylic acid (1.50 g), L-aspartic acid hydrochloride (0.916 g), WSC (0.719 mL), HOBt.H₂O (0.622 g), triethylamine (1.13 mL), and DMF (12 mL) was stirred at room temperature for 3 days. Water was added to the reaction mixture, followed by extraction with ethyl acetate. The extract was washed with water and a saturated saline solution and was then dried over magnesium sulfate, and the solvent was distilled under reduced pressure. The residue was purified by silica gel column chromatography (ethyl acetate/hexane) to obtain the title compound (1.98 g).

MS: [M+H]⁺ 781.4.

F) (S,E)-Di-tert-butyl 2-(3-(3-(2-(5-amino-2-((benzyloxy)carbonyl)phenoxy)ethyl)-4-(benzyloxy)phenyl)acrylamide)succinate Acetic acid (1.58 mL) was added to a mixture of (S,E)-di-tert-butyl 2-(3-(4-(benzyloxy)-3-(2-(2-((benzyloxy)carbonyl)-5-nitrophenoxy)ethyl)phenyl)acrylamide)succinate (1.80 g), a zinc powder (1.51 g), and methanol (10 mL) at room temperature, followed by stirring at the same temperature overnight. A saturated sodium hydrogen carbonate aqueous solution and ethyl acetate were added to the reaction mixture, and the insoluble matter was removed by filtration. The solvent was distilled under reduced pressure, and the residue was extracted with ethyl acetate. The extract was washed with water and a saturated saline solution and was then dried over magnesium sulfate, and the solvent was distilled under reduced pressure. The residue was purified by silica gel column chromatography (ethyl acetate/hexane) to obtain the title compound (1.63 g).

MS: [M+H]⁺ 751.4.

G) (S)-Di-tert-butyl 2-((E)-3-(4-(benzyloxy)-3-(2-(2-((benzyloxy)carbonyl)-5-((Z)-2,3-bis(tert-butoxycarbonyl)guanidino)phenoxy)ethyl)phenyl)acrylamide) succinate A mixture of (S,E)-di-tert-butyl 2-(3-(3-(2-(5-amino-2-((benzyloxy)carbonyl)phenoxy)ethyl)-4-(benzyloxy)phenyl)acrylamide)succinate (1.63 g), N,N'-bis-tert-butoxycarbonylthiourea (3.00 g), 1-ethyl-3-(3-dimethylaminopropyl)carbodiimide (1.92 mL), triethylamine (1.51 mL), and acetonitrile (8 mL) was stirred at room temperature for 3 days. The solvent was distilled under reduced pressure, and the residue was purified by silica gel column chromatography (ethyl acetate/hexane) to obtain the title compound (195 mg).

H) (S,Z)-4-(2,3-Bis(tert-butoxycarbonyl)guanidino)-2-(5-(3-((1,4-di-tert-butoxy-1,4-dioxobutan-2-yl)amino)-3-oxopropyl)-2-hydroxyphenetoxy)benzoic acid A mixture of (S)-di-tert-butyl 2-((E)-3-(4-(benzyloxy)-3-(2-(2-((benzyloxy)carbonyl)-5-((Z)-2,3-bis(tert-butoxycarbonyl)guanidino)phenoxy)ethyl)phenyl)acrylamide) succinate (195 mg), 10% palladium on carbon (20.9 mg), and THF (5 mL) was stirred under a hydrogen atmosphere at room temperature for 3 hours. The insoluble matter was removed by filtration, and the solvent was distilled under reduced pressure. The residue was purified by silica gel column chromatography (ethyl acetate/hexane) to obtain the title compound (105 mg).

MS: [M+H-Boc]⁺715.4.

I) (S,Z)-Di-tert-butyl 2-(3-(9-(2,3-bis(tert-butoxycarbonyl)guanidino)-6-oxo-12,13-dihydro-6H-dibenzo[b,f][1,5]dioxonin-2-yl)propanamide)succinate A THF (10 mL) solution of (S,Z)-4-(2,3-bis(tert-butoxycarbonyl)guanidino)-2-(5-(3-((1,4-di-tert-butoxy-1,4-dioxobutan-2-yl)amino)-3-oxopropyl)-2-hydroxyphenetoxy)benzoic acid (87.6 mg) was added to a mixture of 2-methyl-6-nitrobenzoic anhydride (55.5 mg), N,N-dimethyl-4-aminopyridine (39.4 mg), and THF (70 mL) at room temperature using a syringe pump over 12 hours. A saturated sodium hydrogen carbonate aqueous solution was added to the reaction mixture, followed by extraction with ethyl acetate. The extract was washed with a saturated saline solution and was then dried over magnesium sulfate, and the solvent was distilled under reduced pressure. The residue was purified by silica gel column chromatography (ethyl acetate/hexane) to obtain the title compound (81 mg).

MS: [M+H]⁺ 797.5.

J) N-(3-(9-Carbamimidamido-6-oxo-12,13-dihydro-6H-dibenzo[b,f][1,5]dioxonin-2-yl)propanoyl)-L-aspartic acid trifluoroacetate A mixture of (S,Z)-di-tert-butyl 2-(3-(9-(2,3-bis(tert-butoxycarbonyl)guanidino)-6-oxo-12,13-dihydro-6H-dibenzo[b,f][1,5]dioxonin-2-yl)propanamide)succinate (81 mg) and TFA (1 mL) was stirred at room temperature for 2 hours. The solvent was distilled under reduced pressure, and diisopropyl ether was added to the residue. The precipitate was collected by filtration, washed with diisopropyl ether and was then dried under reduced pressure. The resulting solid was recrystallized from dimethyl sulfoxide/ethyl acetate to obtain the title compound (24 mg).

¹H NMR (300 MHz, DMSO-d₆) δ 2.31 (2H, t, J=7.6 Hz), 2.53-2.74 (4H, m), 2.99 (2H, brs), 4.29 (2H, brs), 4.43-4.59 (1H, m), 6.86 (1H, dd, J=8.3, 1.9 Hz), 6.92 (1H, d, J=1.5 Hz), 6.94 (2H, s), 7.06 (1H, s), 7.41 (1H, d, J=8.3 Hz), 7.52 (4H, s), 8.19 (1H, d, J=7.9 Hz), 9.73 (1H, s).

Example 52

N-(3-(3-Carbamimidamido-14-oxo-6,7-dihydro-14H-dibenzo[b,h][1,4,7]trioxecin-9-yl)propanoyl) aspartic acid trifluoroacetate A) (E)-Di-tert-butyl 2-(3-(3-(benzyloxy)-2-(2-((tert-butyldimethylsilyl)oxy)ethoxy)phenyl)acrylamide) succinate (2-Bromoethoxy) (tert-butyl)dimethylsilane (0.944 mL) and tetrabutylammonium iodide (0.542 g) were added to a mixture of (S,E)-di-tert-butyl 2-(3-(3-(benzyloxy)-2-hydroxyphenyl)acrylamide)succinate (1.46 g), potassium carbonate (2.028 g), and DMF (40 mL) at 0° C., followed by stirring at 80° C. for 3 hours. The reaction mixture was poured into a mixture of ethyl acetate and a saturated ammonium chloride aqueous solution at 0° C. for distribution. The organic layer was washed with water and a saturated saline solution and was then dried over anhydrous sodium sulfate, and the solvent was distilled under reduced pressure. The residue was purified by silica gel column chromatography (ethyl acetate/hexane) to obtain the title compound (1.920 g).

$^1$H NMR (300 MHz, DMSO-d$_6$) δ −0.05-0.05 (6H, m), 0.67-0.95 (9H, m), 1.23-1.63 (18H, m), 2.53-2.81 (2H, m), 3.76-3.90 (2H, m), 3.97-4.14 (2H, m), 4.62 (1H, q, J=7.1 Hz), 5.04-5.23 (2H, m), 6.71 (1H, d, J=16.0 Hz), 6.99-7.24 (3H, m), 7.27-7.59 (5H, m), 7.68-7.87 (1H, m), 8.38 (1H, d, J=8.0 Hz).

B) (E)-Di-tert-butyl 2-(3-(3-(benzyloxy)-2-(2-hydroxyethoxy)phenyl)acrylamide)succinate Tetrabutylammonium fluoride (1 M THF solution, 4.35 mL) was added to a mixture of (E)-di-tert-butyl 2-(3-(3-(benzyloxy)-2-(2-((tert-butyldimethylsilyl)oxy)ethoxy)phenyl)acrylamide)succinate (1.90 g) and THF (100 mL) at 0° C., followed by stirring at room temperature for 2 hours. Water was added to the reaction mixture, followed by extraction with ethyl acetate. The organic layer was washed with a saturated saline solution and was then dried over anhydrous sodium sulfate, and the solvent was distilled under reduced pressure. The residue was purified by silica gel column chromatography (ethyl acetate/hexane) to obtain the title compound (1.50 g).

MS: [M+H]$^+$ 542.3.

C) (E)-Di-tert-butyl 2-(3-(3-(benzyloxy)-2-(2-((methylsulfonyl)oxy)ethoxy)phenyl)acrylamide) succinate Methanesulfonyl chloride (0.319 mL) and triethylamine (1.150 mL) were added to a mixture of (E)-di-tert-butyl 2-(3-(3-(benzyloxy)-2-(2-hydroxyethoxy)phenyl)acrylamide)succinate (1.49 g) and THF (100 mL) at 0° C., followed by stirring at room temperature for 1 hour. A saturated ammonium chloride aqueous solution was added to the reaction mixture at 0° C., followed by extraction with ethyl acetate. The organic layer was washed with a saturated saline solution and was then dried over anhydrous sodium sulfate, and the solvent was distilled under reduced pressure. The residue was purified by silica gel column chromatography (ethyl acetate/hexane) to obtain the title compound (1.70 g).

MS: [M+H]$^+$ 620.2.

D) (E)-Di-tert-butyl 2-(3-(3-(benzyloxy)-2-(2-(2-((benzyloxy)carbonyl)-5-nitrophenoxy)ethoxy)phenyl)acrylamide)succinate A mixture of (E)-di-tert-butyl 2-(3-(3-(benzyloxy)-2-(2-((methylsulfonyl)oxy)ethoxy)phenyl)acrylamide)succinate (1.70 g) and DMF (30 mL) was added to a mixture of benzyl 2-hydroxy-4-nitrobenzoate (1.499 g), potassium carbonate (1.137 g), and DMF (30 mL) at room temperature, followed by stirring at 80° C. overnight. The reaction mixture was poured into a mixture of ethyl acetate and a saturated ammonium chloride aqueous solution at 0° C. for distribution. The organic layer was washed with water and a saturated saline solution and was then dried over anhydrous sodium sulfate, and the solvent was distilled under reduced pressure. The residue was purified by silica gel column chromatography (ethyl acetate/hexane) to obtain the title compound (2.030 g).

MS: [M+H]$^+$ 797.3.

E) 4-Amino-2-(2-(2-(3-((1,4-di-tert-butoxy-1,4-dioxobutan-2-yl)amino)-3-oxopropyl)-6-hydroxyphenoxy)ethoxy)benzoic acid A mixture of (E)-di-tert-butyl 2-(3-(3-(benzyloxy)-2-(2-(2-((benzyloxy)carbonyl)-5-nitrophenoxy)ethoxy)phenyl)acrylamide)succinate (1.99 g), 10% palladium on carbon (200 mg, water content: about 55%), and THF (100 mL) was stirred under a hydrogen atmosphere at room temperature overnight. The catalyst was removed by filtration, and the filtrate was then concentrated under reduced pressure to obtain the title compound (1.459 g).

MS: [M+H]$^+$ 589.3.

F) 2-(2-(2-(3-((1,4-Di-tert-butoxy-1,4-dioxobutan-2-yl)amino)-3-oxopropyl)-6-hydroxyphenoxy)ethoxy)-4-guanidinobenzoic acid trifluoroacetate 1H-Pyrazole-1-carboximidamide hydrochloride (378 mg) and triethylamine (0.96 mL) were added to a mixture of 4-amino-2-(2-(2-(3-((1,4-di-tert-butoxy-1,4-dioxobutan-2-yl)amino)-3-oxopropyl)-6-hydroxyphenoxy)ethoxy)benzoic acid (404 mg) and acetonitrile (10 mL) at room temperature, followed by heating to reflux overnight. 1H-pyrazole-1-carboximidamide hydrochloride (378 mg) and triethylamine (0.96 mL) were added to the reaction mixture at room temperature, followed by heating to reflux overnight. The reaction mixture was concentrated. By the same procedure, a reaction of 4-amino-2-(2-(2-(3-((1,4-di-tert-butoxy-1,4-dioxobutan-2-yl)amino)-3-oxopropyl)-6-hydroxyphenoxy)ethoxy)benzoic acid (404 mg) was performed. The residues were combined, and acetonitrile was added thereto, followed by stirring. The insoluble matter was removed by filtration, and the filtrate was then concentrated. The residue was purified by HPLC (C18, mobile phase: water/acetonitrile (system containing 0.1% TFA)) to obtain the title compound (297 mg).

MS: [M+H]$^+$ 631.3.

G) Di-tert-butyl 2-(3-(3-guanidino-14-oxo-7,14-dihydro-6H-dibenzo[b,h][1,4,7]trioxecin-9-yl)propanamide)succinate trifluoroacetate Dicyclohexylcarbodiimide (209 mg) and N,N-dimethyl-4-aminopyridine (61.9 mg) were added to a mixture of 2-(2-(2-(3-((1,4-di-tert-butoxy-1,4-dioxobutan-2-yl)amino)-3-oxopropyl)-6-hydroxyphenoxy)ethoxy)-4-guanidinobenzoic acid trifluoroacetate (251.6 mg), pyridine (0.041 mL), and THF (250 mL) at 40° C., followed by stirring at 40° C. for 14 hours. The reaction mixture was concentrated, and acetonitrile (5 mL) was added to the residue, followed by stirring. The precipitated solid was removed by filtration, and the filtrate was then concentrated. The residue was purified by HPLC (C18, mobile phase: water/acetonitrile (system containing 0.1% TFA)) to obtain the title compound (98 mg).

MS: [M+H]$^+$ 613.3.

H) N-(3-(9-Carbamimidamido-6-oxo-11,12-dihydro-6H-dibenzo[b,f]oxocin-3-yl)propanoyl)aspartic acid trifluoroacetate A mixture of di-tert-butyl 2-(3-(3-guanidino-14-oxo-7,14-dihydro-6H-dibenzo[b,h][1,4,7]trioxecin-9-yl)propanamide)succinate trifluoroacetate (97.9 mg) and TFA (5 mL) was stirred at room temperature for 30 minutes. The reaction mixture was concentrated under reduced pressure, and the residue was washed with diethyl ether to obtain the title compound (61.6 mg).

$^1$H NMR (300 MHz, DMSO-d$_6$) δ 2.34-2.75 (4H, m), 2.79-2.98 (2H, m), 4.21 (2H, brs), 4.29 (2H, brs), 4.50 (1H, d, J=7.8 Hz), 7.07-7.20 (3H, m), 7.22-7.30 (1H, m), 7.63-7.89 (6H, m), 8.21 (1H, d, J=7.6 Hz).

Example 57

N-(3-(9-Carbamimidamido-6-oxo-11,12-dihydro-6H-dibenzo[b,f]oxocin-1-yl)propanoyl)-L-aspartic acid trifluoroacetate A) Ethyl (2E)-3-(2-iodo-3-methoxyphenyl)acrylate Sixty percent sodium hydride (3.7 g) was gradually added to a THF (300 mL) solution of ethyl (diethoxyphosphoryl) acetate (18.8 g) at 0° C. The mixture was stirred for 20 minutes, and a THF (100 mL) solution of 2-iodo-3-methoxybenzaldehyde (20.0 g) was then added dropwise thereto at 0° C., followed by stirring at room temperature for 1 hour. Iced water (200 mL) was added to the reaction mixture. The organic layer was separated, and the aqueous layer was then extracted with ethyl acetate (100 mL×2). The combined organic layer was washed with a saturated saline solution. The solvent was then distilled under reduced pressure to obtain the title compound (24.0 g).

MS: [M+H]$^+$ 333.1.

B) Ethyl (2E)-3-(3-hydroxy-2-iodophenyl)acrylate

Under a nitrogen atmosphere a dichloromethane (100 mL) solution of boron tribromide (44.8 g) was added dropwise to a dichloromethane (250 mL) solution of ethyl (2E)-3-(2-iodo-3-methoxyphenyl)acrylate (24.0 g) at −70° C. The temperature of the mixture was raised to room temperature and was stirred at the same temperature for 1 hour. Methanol (150 mL) was added dropwise to the reaction mixture at −70° C., and water and dichloromethane were added thereto. The aqueous layer was extracted with dichloromethane (100 mL×2). The combined organic layer was then washed with a saturated saline solution, and the solvent was distilled under reduced pressure to obtain the title compound (20.0 g).

MS: [M+H]$^+$ 319.1.

C) Ethyl (2E)-3-(3-(benzyloxy)-2-iodophenyl)acrylate

Benzyl bromide (11 g) was added to a mixture of ethyl (2E)-3-(3-hydroxy-2-iodophenyl)acrylate (18 g), potassium carbonate (9.4 g), and acetonitrile (300 mL), followed by stirring at 60° C. for 4 hours. Water (200 mL) was added to the reaction mixture, followed by extraction with ethyl acetate (150 mL×3). The extract was washed with a saturated saline solution and was dried over anhydrous sodium sulfate, and the solvent was then distilled under reduced pressure to obtain the title compound (29 g).

MS: [M+H]$^+$ 409.1.

D) (2E)-3-(3-(Benzyloxy)-2-iodophenyl)acrylic acid

Sodium hydroxide (15.6 g) was dissolved in water (80 mL), and the solution was added to a methanol (80 mL)/THF (80 mL) solution of ethyl (2E)-3-(3-(benzyloxy)-2-iodophenyl)acrylate (31.7 g). The mixture was stirred at room temperature overnight, and 2 M hydrochloric acid was then added to the reaction mixture to adjust the pH to 2. The solid was collected by filtration and was washed with methanol to obtain the title compound (19.8 g).

MS: [M+H]$^+$ 381.1.

E) Di-tert-butyl N-((2E)-3-(3-(benzyloxy)-2-iodophenyl)prop-2-enoyl)-L-aspartate A mixture of (2E)-3-(3-(benzyloxy)-2-iodophenyl)acrylic acid (8 g), di-tert-butyl L-aspartate hydrochloride (6.5 g), O-(benzotriazol-1-yl)-N,N,N',N'-tetramethyluronium hexafluorophosphate (10 g), triethylamine (4.2 g), DMF (150 mL) was stirred at room temperature for 2 hours. Water (200 mL) was added to the reaction mixture, followed by extraction with ethyl acetate (150 mL×3). The extract was washed with a saturated saline solution and was dried over anhydrous sodium sulfate, and the solvent was then distilled under reduced pressure. The residue was purified by silica gel column chromatography (ethyl acetate/petroleum ether) to obtain the title compound (10.8 g).

MS: [M+H]$^+$ 608.3.

F) Di-tert-butyl N-((2E)-3-(3-(benzyloxy)-2-((trimethylsilyl)ethynyl)phenyl)prop-2-enoyl)-L-aspartate Under a nitrogen atmosphere, a mixture of di-tert-butyl N-((2E)-3-(3-(benzyloxy)-2-iodophenyl)prop-2-enoyl)-L-aspartate (5.5 g), ethynyl(trimethyl)silane (4.4 g), tetrakis (triphenylphosphine)palladium (1.12 g), copper(I) iodide (342 mg), triethylamine (1.8 g), and DMF (100 mL) was stirred at 50° C. overnight. Water (200 mL) was added to the reaction mixture, followed by extraction with ethyl acetate (100 mL×3). The extract was washed with a saturated saline solution and was dried over anhydrous sodium sulfate, and the solvent was then distilled under reduced pressure. The residue was purified by silica gel column chromatography (ethyl acetate/petroleum ether) to obtain the title compound (3.5 g).

$^1$H NMR (500 MHz, DMSO-d$_6$): δ 0.25 (9H, s), 1.41 (9H, s), 1.42 (9H, s), 2.60-2.75 (2H, m), 4.65 (1H, q, J=7.0 Hz), 5.21 (2H, s), 6.84 (1H, d, J=15.5 Hz), 7.18 (1H, d, J=8.0 Hz), 7.30-7.35 (2H, m), 7.38-7.43 (3H, m), 7.53 (1H, d, J=7.0 Hz), 7.90 (1H, d, J=16.0 Hz), 8.48 (1H, d, J=8.0 Hz).

G) Di-tert-butyl N-((2E)-3-(3-(benzyloxy)-2-ethynylphenyl)prop-2-enoyl)-L-aspartate Tetra-n-butylammonium fluoride (783 mg) was added to a THF (50 mL) solution of di-tert-butyl N-((2E)-3-(3-(benzyloxy)-2-((trimethylsilyl)ethynyl)phenyl)prop-2-enoyl)-L-aspartate (3.5 g), followed by stirring at room temperature for 1 hour. Water (100 mL) was added to the reaction mixture, followed by extraction with ethyl acetate (50 mL×3). The extract was washed with a saturated saline solution and was dried over anhydrous sodium sulfate, and the solvent was then distilled under reduced pressure to obtain the title compound (3.02 g).

MS: [M+H]$^+$ 506.8.

H) Di-tert-butyl N-((2E)-3-(3-(benzyloxy)-2-((2-((benzyloxy)carbonyl)-5-nitrophenyl)ethynyl)phenyl)prop-2-enoyl)-L-aspartate Under a nitrogen atmosphere, a mixture of di-tert-butyl N-((2E)-3-(3-(benzyloxy)-2-ethynylphenyl)prop-2-enoyl)-

L-aspartate (2.0 g), benzyl 2-bromo-4-nitrobenzoate (1.34 g), tetrakis(triphenylphosphine)palladium (498 mg), triethylamine (808 mg), and DMF (8 mL) was stirred under microwave irradiation at 130° C. for 2 hours. Water (50 mL) was added to the reaction mixture, followed by extraction with ethyl acetate (40 mL×3). The extract was washed with a saturated saline solution and was dried over anhydrous sodium sulfate, and the solvent was then distilled under reduced pressure. The residue was purified by silica gel column chromatography (ethyl acetate/petroleum ether/ethyl acetate) to obtain the title compound (2.4 g).

$^1$H NMR (500 MHz, DMSO-d$_6$): δ 1.37 (18H, s), 2.69-2.73 (2H, m), 4.65 (1H, q, J=7.0 Hz), 5.27 (2H, s), 5.43 (2H, s), 6.90 (1H, d, J=15.5 Hz), 7.24 (1H, d, J=8.0 Hz), 7.28-7.33 (4H, m), 7.36-7.45 (5H, m), 7.49 (1H, t, J=8.0 Hz), 7.55 (2H, d, J=7.0 Hz), 8.99 (1H, d, J=15.5 Hz), 8.16 (1H, d, J=9.0 Hz), 8.30-8.33 (2H, m), 8.49 (1H, d, J=8.5 Hz).

I) 4-Amino-2-(2-(2-(3-(((2S)-1,4-di-tert-butoxy-1,4-dioxobutan-2-yl)amino)-3-oxopropyl)-6-hydroxyphenyl)ethyl)benzoic acid Under a hydrogen atmosphere, a mixture of di-tert-butyl N-((2E)-3-(3-(benzyloxy)-2-((2-((benzyloxy)carbonyl)-5-nitrophenyl)ethynyl)phenyl)prop-2-enoyl)-L-aspartate (1.2 g), 20% palladium hydroxide on carbon (600 mg), and ethyl acetate (200 mL) was stirred at room temperature for 48 hours. The catalyst was removed by filtration, and the filtrate was then concentrated under reduced pressure to obtain the title compound (641 mg).

MS: [M+H]$^+$ 557.0.

J) 4-Carbamimidamido-2-(2-(2-(3-(((2S)-1,4-di-tert-butoxy-1,4-dioxobutan-2-yl)amino)-3-oxopropyl)-6-hydroxyphenyl)ethyl)benzoic acid A mixture of 4-amino-2-(2-(2-(3-(((2S)-1,4-di-tert-butoxy-1,4-dioxobutan-2-yl)amino)-3-oxopropyl)-6-hydroxyphenyl)ethyl)benzoic acid (300 mg), 1H-pyrazole-1-carboximidamide hydrochloride (526 mg), triethylamine (364 mg), and acetonitrile (10 mL) was stirred at 60° C. for 48 hours. The reaction mixture was concentrated under reduced pressure, and the residue was then purified by HPLC to obtain the title compound (209 mg).

MS: [M+H]$^+$ 599.3.

K) Di-tert-butyl N-(3-(9-carbamimidamido-6-oxo-11,12-dihydro-6H-dibenzo[b,f]oxocin-1-yl)propanoyl)-L-aspartate A mixture of 4-carbamimidamido-2-(2-(2-(3-(((2S)-1,4-di-tert-butoxy-1,4-dioxobutan-2-yl)amino)-3-oxopropyl)-6-hydroxyphenyl)ethyl)benzoic acid (299 mg), WSC (384 mg), and pyridine (10 mL) solution was stirred at room temperature overnight. Water was added to the reaction mixture, followed by concentration under reduced pressure. The residue was purified by HPLC to obtain the title compound (115 mg).

MS: [M+H]$^+$ 581.3.

L) N-(3-(9-Carbamimidamido-6-oxo-11,12-dihydro-6H-dibenzo[b,f]oxocin-1-yl)propanoyl)-L-aspartic acid trifluoroacetate Di-tert-butyl N-(3-(9-carbamimidamido-6-oxo-11,12-dihydro-6H-dibenzo[b,f]oxocin-1-yl)propanoyl)-L-aspartate (95 mg) was added to trifluoroacetic acid (5 mL), followed by stirring at room temperature for 4 hours. The trifluoroacetic acid was distilled under reduced pressure, and the residue was then purified by HPLC (C18, mobile phase: water/acetonitrile (system containing 0.1% TFA)) to obtain the title compound (50.5 mg).

$^1$H NMR (500 MHz, DMSO-d$_6$) δ 2.35 (2H, t, J=7.5 Hz), 2.50-2.67 (2H, m), 2.82 (2H, t, J=8.0 Hz), 3.13 (2H, t, J=7.5 Hz), 3.23 (2H, t, J=7.5 Hz), 4.52 (1H, d, J=7.0 Hz), 6.92 (1H, d, J=8.0 Hz), 6.98-7.09 (4H, m), 7.38 (1H, d, J=8.0 Hz), 7.53 (4H, s), 8.25 (1H, d, J=8.0 Hz), 9.75 (1H, brs), 12.60 (2H, brs).

Example 58

1-(6-Oxo-11,12-dihydro-6H-dibenzo[b,f]oxocin-9-yl)guanidine trifluoroacetate

A) Benzyl 2-((2-(benzyloxy)phenyl)ethynyl)-4-nitrobenzoate

A mixture of 2-bromo-4-nitrobenzoic acid (12.3 g), (bromomethyl)benzene (6.5 mL), potassium carbonate (10.0 g), and acetonitrile (150 mL) was heated to reflux for 2 hours. The solid was removed by filtration, and the filtrate was concentrated under reduced pressure. The residue was purified by silica gel column chromatography (petroleum ether/ethyl acetate) to obtain benzyl 2-bromo-4-nitrobenzoate (17 g). Under a nitrogen atmosphere, a mixture of 1-(benzyloxy)-2-ethynylbenzene (1.78 g), benzyl 2-bromo-4-nitrobenzoate (2.53 g), bis(triphenylphosphine)palladium(II) dichloride (302 mg), triethylamine (3.6 mL), and DMF (40 mL) was stirred under microwave irradiation at 130° C. for 0.5 hours. Water (200 mL) was added to the reaction mixture, followed by extraction with ethyl acetate (100 mL×3). The extract was washed with a saturated saline solution and was dried over anhydrous sodium sulfate, and the solvent was then distilled under reduced pressure. The residue was purified by silica gel column chromatography (dichloromethane/petroleum ether) to obtain the title compound (2.51 g).

MS: [M+NH$_4$]$^+$481.1.

B) 4-Amino-2-(2-(2-hydroxyphenyl)ethyl)benzoic acid

Under a hydrogen atmosphere, a mixture of benzyl 2-((2-(benzyloxy)phenyl)ethynyl)-4-nitrobenzoate (1.87 g), 20% palladium hydroxide on carbon (250 mg), THF (50 mL), and methanol (50 mL) was stirred at room temperature overnight. The catalyst was removed by filtration, and the filtrate was then concentrated under reduced pressure.

The residue was purified by HPLC to obtain the title compound (1.00 g).

MS: [M+H]$^+$ 258.0.

C) 4-Carbamimidamido-2-(2-(2-hydroxyphenyl)ethyl)benzoic acid hydrochloride

Cyanamide (1.59 g) and 4 M hydrogen chloride in 1,4-dioxane (13.5 mL) were added to a 1,4-dioxane (50 mL) solution of 4-amino-2-(2-(2-hydroxyphenyl)ethyl)benzoic acid (1.00 g), and the resulting mixture was stirred at 80° C. for 2 hours. The reaction mixture was concentrated under reduced pressure, and the residue was then purified by HPLC to obtain the title compound (584 mg).

MS: [M+H]$^+$ 300.1.

D) 1-(6-Oxo-11,12-dihydro-6H-dibenzo[b,f]oxocin-9-yl)guanidine trifluoroacetate WSC (500 mg) was added to a pyridine (25 mL) solution of 4-carbamimidamido-2-(2-(2-hydroxyphenyl)ethyl)benzoic acid hydrochloride (500 mg), and the resulting mixture was stirred at room temperature for 3 hours. The reaction mixture was concentrated under reduced pressure, and the residue was then purified by HPLC (C18, mobile phase: water/acetonitrile (system containing TFA)) to obtain the title compound (215.4 mg).

$^1$H-NMR (500 MHz, DMSO-$d_6$): δ 3.12-3.15 (2H, m), 3.18-3.21 (2H, m), 7.05-7.10 (4H, m), 7.14-7.17 (2H, m), 7.40 (1H, d, J=8.0 Hz), 7.51-7.65 (4H, brs), 9.74-9.87 (1H, brs).

Example 59

6-Oxo-11,12-dihydro-6H-dibenzo[b,f]oxocine-2-carboximidamide trifluoroacetate

A) Benzyl 2-((2-(benzyloxy)-5-cyanophenyl)ethynyl)benzoate

A mixture of benzyl 2-ethynylbenzoate (1.00 g), 4-(benzyloxy)-3-bromobenzonitrile (1.22 g), bis(triphenylphosphine)palladium(II) dichloride (0.30 g), triethylamine (1.20 mL), and DMF (6.00 mL) was stirred under microwave irradiation at 150° C. for 40 minutes. The reaction mixture was filtered, and the filtrate was then added to water (400 mL), followed by extraction with ethyl acetate (100 mL×3). The filtrate was concentrated under reduced pressure, and the residue was then purified by silica gel column chromatography (ethyl acetate/petroleum ether) to obtain the title compound (0.60 g).

MS: [M+H]$^+$ 444.1.

B) Benzyl 2-((2-(benzyloxy)-5-carbamimidoylphenyl)ethynyl)benzoate trifluoroacetate Under a nitrogen atmosphere, lithium hexamethyldisilazane (1 M, 9.03 mL) was added to a THF (15 mL) solution of benzyl 2-((2-(benzyloxy)-5-cyanophenyl)ethynyl)benzoate (800 mg) under ice cooling, and the resulting mixture was stirred at room temperature for 3.5 hours. The reaction mixture was added to 2 M hydrochloric acid (100 mL), followed by extraction with ethyl acetate (100 mL×3). The extract was washed with a saturated saline solution and was dried over anhydrous sodium sulfate, and the solvent was then distilled under reduced pressure. The residue was purified by HPLC (C18, mobile phase: water/acetonitrile (system containing TFA)) to obtain the title compound (383 mg).

$^1$H-NMR (500 MHz, DMSO-$d_6$): δ 5.32 (2H, s), 5.36 (2H, s), 7.28-7.45 (9H, m), 7.51 (2H, d, J=7.0 Hz), 7.55-7.59 (1H, m), 7.62-7.68 (2H, m), 7.83-7.86 (2H, m), 7.98 (1H, dd, J$_1$=8.0 Hz, J$_2$=1.0 Hz), 9.04 (2H, s), 9.22 (2H, s).

C) Benzyl 2-((2-(benzyloxy)-5-(N-(tert-butoxycarbonyl)carbamimidoyl)phenyl)ethynyl)benzoate A mixture of benzyl 2-((2-(benzyloxy)-5-carbamimidoylphenyl)ethynyl)benzoate trifluoroacetate (190 mg), di-tert-butyl dicarbonate (108 mg), triethylamine (0.12 mL), and THF (10 mL) was stirred at room temperature overnight. The reaction mixture was added to water (300 mL), followed by extraction with ethyl acetate (50 mL×3). The filtrate was concentrated under reduced pressure, and the residue was then purified by silica gel column chromatography (ethyl acetate/petroleum ether) to obtain the title compound (220 mg).

MS: [M+H]$^+$ 560.7.

D) 2-(2-(5-(N-(Tert-butoxycarbonyl)carbamimidoyl)-2-hydroxyphenyl)ethyl)benzoic acid Under a hydrogen atmosphere, a mixture of benzyl 2-((2-(benzyloxy)-5-(N-(tert-butoxycarbonyl)carbamimidoyl)phenyl)ethynyl)benzoate (240 mg), 10% palladium on carbon (25 mg), and THF (20 mL) was stirred at room temperature overnight. The reaction mixture was filtered, and the filtrate was then concentrated under reduced pressure to obtain the title compound (142 mg).

MS: [M+H]$^+$ 385.0.

E) tert-Butyl ((6-oxo-11,12-dihydro-6H-dibenzo[b,f]oxocin-2-yl)carbonoimidoyl)carbamate Under a nitrogen atmosphere, N,N'-dicyclohexylcarbodiimide (91 mg) was added to a THF (10 mL) solution of 2-(2-(5-(N-(tert-butoxycarbonyl)carbamimidoyl)-2-hydroxyphenyl)ethyl)benzoic acid (113 mg) and N,N-dimethyl-4-aminopyridine (36 mg) at room temperature, and the resulting mixture was stirred at room temperature for 3 hours. Water (200 mL) was added to the reaction mixture, followed by extraction with ethyl acetate (100 mL×3). The extract was washed with a saturated saline solution and was dried over anhydrous sodium sulfate, and the solvent was then distilled under reduced pressure. The residue was purified by silica gel column chromatography (ethyl acetate/petroleum ether) to obtain the title compound (80 mg).

$^1$H-NMR (500 MHz, CDCl$_3$): δ 1.44 (9H, s), 3.11-3.21 (4H, m), 6.99 (2H, t, J=8.5 Hz), 7.05-7.09 (1H, m), 7.17-7.21 (1H, m), 7.25 (1H, dd, J$_1$=7.5 Hz, J$_2$=1.0 Hz), 7.42 (1H, dd, J$_1$=8.5 Hz, J$_2$=2.0 Hz), 7.59 (1H, d, J=2.5 Hz).

F) 6-Oxo-11,12-dihydro-6H-dibenzo[b,f]oxocine-2-carboximidamide trifluoroacetate A mixture of tert-butyl ((6-oxo-11,12-dihydro-6H-dibenzo[b,f]oxocin-2-yl)carbonoimidoyl)carbamate (80 mg), TFA (2.0 mL), and dichloromethane (10 mL) was stirred at room temperature for 0.5 hours, followed by concentration under reduced pressure. The residue was purified by HPLC (C18, mobile phase: water/acetonitrile (system containing 10 nM TFA)) to obtain the title compound (53.6 mg).

$^1$H-NMR (400 MHz, DMSO-$d_6$): δ 3.19-3.28 (4H, m), 7.23 (2H, t, J=8.0 Hz), 7.35-7.39 (3H, m), 7.57 (1H, dd, J$_1$=8.4 Hz, J$_2$=2.0 Hz), 7.64 (1H, d, J=2.4 Hz), 9.08 (2H, s), 9.21 (2H, s).

Example 61

N-(3-(2-Carbamimidoyl-6-oxo-11,12-dihydro-6H-dibenzo[b,f]oxocin-10-yl)propanoyl)-L-aspartic acid trifluoroacetate

A) 4-(Benzyloxy)-3-bromobenzonitrile

Benzyl bromide (16.52 g) was added to a mixture of 3-bromo-4-hydroxybenzonitrile (25 g), potassium carbonate (20.94 g), and DMF (300 mL) at room temperature, followed by stirring at 50° C. overnight. Water was added to the reaction mixture at 0° C., followed by extraction with ethyl acetate. The organic layer was washed with water and a saturated saline solution, dried over anhydrous magnesium sulfate, and concentrated under reduced pressure. The resulting solid was recrystallized from ethyl acetate/hexane to obtain the title compound (28.8 g).

$^1$H NMR (300 MHz, CDCl$_3$) δ 5.23 (2H, s), 6.97 (1H, d, J=8.3 Hz), 7.31-7.49 (5H, m), 7.55 (1H, dd, J=8.6, 1.8 Hz), 7.77-7.95 (1H, m).

B) 4-Benzyloxy-3-vinylbenzonitrile

A mixture of 4-(benzyloxy)-3-bromobenzonitrile (10 g), potassium trifluoro(vinyl)borate (6.97 g), triethylamine (14.52 mL), (1,1'-bis(diphenylphosphino)ferrocene) dichloropalladium-dichloromethane complex (1.417 g), DMA (100 mL) was stirred at 130° C. for 1 hour. The mixture was cooled to room temperature and was then diluted with ethyl acetate, washed with water and a saturated saline solution, dried over anhydrous magnesium sulfate, and concentrated under reduced pressure. The residue was purified by silica gel column chromatography (NH, ethyl acetate/hexane) to obtain the title compound (6.77 g).

$^1$H NMR (300 MHz, CDCl$_3$) δ 5.16 (2H, s), 5.33-5.44 (1H, m), 5.79 (1H, dd, J=17.7, 0.7 Hz), 6.97 (1H, d, J=8.6 Hz), 6.99-7.11 (1H, m), 7.31-7.46 (5H, m), 7.50 (1H, dd, J=8.5, 2.0 Hz), 7.76 (1H, d, J=2.2 Hz).

C) 3-Bromo-3-(bromomethyl)benzoic acid

N-Bromosuccinimide (13.04 g) was added to a mixture of 2-bromo-3-methylbenzoic acid (15 g), 2,2'-azobisisobutyronitrile (0.573 g), and benzotrifluoride (150 mL) at room temperature, followed by stirring at 90° C. for 3 hours. The mixture was concentrated under reduced pressure, and the residue was then diluted with a saturated sodium hydrogen carbonate aqueous solution. The aqueous layer was washed with ethyl acetate and was made acidic with 6 N hydrochloric acid. This aqueous layer was extracted with ethyl acetate, and the extract was washed with water and a saturated saline solution, dried over anhydrous magnesium sulfate, and concentrated under reduced pressure to obtain the title compound (20.5 g).

$^1$H NMR (300 MHz, CDCl$_3$) δ 4.70 (2H, s), 7.36-7.45 (1H, m), 7.65 (1H, dd, J=7.7, 1.7 Hz), 7.78-7.87 (1H, m).

D) Benzyl 2-bromo-3-(hydroxymethyl)benzoate

Benzyl bromide (9 mL) was added to a mixture of 3-bromo-3-(bromomethyl)benzoic acid (15.94 g), potassium carbonate (11.44 g), and DMF (200 mL) at room temperature, followed by stirring at room temperature overnight. Water was added to the reaction mixture at 0° C., followed by extraction with ethyl acetate. The organic layer was washed with water and a saturated saline solution, dried over anhydrous magnesium sulfate, and concentrated under reduced pressure. The residue was purified by silica gel column chromatography (ethyl acetate/hexane) to obtain the title compound (12.50 g).

$^1$H NMR (300 MHz, CDCl$_3$) δ 1.97-2.08 (1H, m), 4.81 (2H, d, J=6.0 Hz), 5.33-5.43 (2H, m), 7.30-7.50 (6H, m), 7.57-7.69 (2H, m).

E) Benzyl 2-bromo-3-(((tert-butyl(dimethyl)silyl)oxy)methyl)benzoate

A mixture of benzyl 2-bromo-3-(hydroxymethyl)benzoate (4.82 g), imidazole (2.349 g), DMF (30 mL), and tert-butyldimethylsilyl chloride (3.35 mL) was stirred at room temperature overnight. The reaction mixture was poured into water, followed by extraction with ethyl acetate. The organic layer was washed with water and a saturated saline solution, dried over anhydrous magnesium sulfate, and concentrated under reduced pressure. The residue was purified by silica gel column chromatography (ethyl acetate/hexane) to obtain the title compound (6.21 g).

$^1$H NMR (300 MHz, CDCl$_3$) δ 0.09-0.19 (6H, m), 0.92-1.01 (9H, m), 4.73-4.81 (2H, m), 5.34-5.40 (2H, m), 7.30-7.43 (4H, m), 7.43-7.50 (2H, m), 7.56-7.63 (1H, m), 7.66-7.74 (1H, m).

F) Benzyl 2-((EZ)-2-(2-(benzyloxy)-5-cyanophenyl)vinyl)-3-(((tert-butyl(dimethyl)silyl)oxy)methyl)benzoate Palladium acetate (0.052 g) was added to a mixture of benzyl 2-bromo-3-(((tert-butyl(dimethyl)silyl)oxy)methyl)benzoate (2 g), 4-(benzyloxy)-3-vinylbenzonitrile (1.621 g), potassium phosphate (1.267 g), and DMA (30 mL) at room temperature, followed by stirring under a nitrogen atmosphere at 130° C. for 30 minutes. Water was added to the mixture at room temperature, followed by extraction with ethyl acetate. The organic layer was separated and was then washed with water and a saturated saline solution, dried over anhydrous magnesium sulfate, and concentrated under reduced pressure. The residue was purified by silica gel column chromatography (ethyl acetate/hexane) to obtain the title compound (2.34 g).

$^1$H NMR (300 MHz, CDCl$_3$) δ 0.02 (6H, s), 0.90 (9H, s), 4.75 (2H, s), 5.14 (2H, s), 5.24 (2H, s), 6.75 (1H, d, J=16.6 Hz), 6.95 (1H, d, J=8.6 Hz), 7.22-7.44 (12H, m), 7.50 (1H, dd, J=8.5, 2.0 Hz), 7.69-7.76 (2H, m), 7.79 (1H, d, J=7.5 Hz).

G) Benzyl 2-((EZ)-2-(2-(benzyloxy)-5-carbamimidoylphenyl)vinyl)-3-(hydroxymethyl)benzoate Lithium bis(trimethylsilyl)amide (1 M, THF solution, 19.5 mL) was added dropwise to a mixture of benzyl 2-((EZ)-2-(2-(benzyloxy)-5-cyanophenyl)vinyl)-3-(((tert-butyl(dimethyl)silyl)oxy)methyl)benzoate (2.3 g) and THF (10 mL) at 0° C., followed by stirring at room temperature for 3 hours. Two normal hydrochloric acid (30 mL) was added dropwise to the reaction mixture at 0° C., followed by stirring at room temperature for 1 hour. After dilution with THF/ethyl acetate (1:1), the aqueous layer was made basic with a saturated sodium hydrogen carbonate aqueous solution. The organic layer was separated, and the aqueous layer was extracted with THF/ethyl acetate (1:1). The combined organic layers was washed with a saturated saline solution, dried over anhydrous magnesium sulfate, and concentrated under reduced pressure to obtain the title compound (1.921 g).

MS: [M+H]$^+$ 493.3.

H) Benzyl 2-(2-(benzyloxy)-5-((EZ)-N'-(tert-butoxycarbonyl)carbamimidoyl)styryl)-3-(hydroxymethyl)benzoate Triethylamine (0.815 mL) was added to a mixture of benzyl 2-((EZ)-2-(2-(benzyloxy)-5-carbamimidoylphenyl)vinyl)-3-(hydroxymethyl)benzoate (1.921 g), di-tert-butyl dicarbonate (1.087 mL), and THF (10 mL) at 0° C. Subsequently, 1 N sodium hydroxide (5 mL) was added thereto, followed by stirring at 0° C. for 1 hour. Water was added to the reaction mixture at room temperature, followed by extraction with ethyl acetate. The organic layer was separated, washed with water and a saturated saline solution, dried over anhydrous magnesium sulfate, and concentrated under reduced pressure. The residue was purified by silica gel column chromatography (ethyl acetate/hexane) to obtain the title compound (1.55 g).

MS: [M+H]+ 593.4.

I) Benzyl 2-((EZ)-2-(2-(benzyloxy)-5-(N'-(tert-butoxycarbonyl)carbamimidoyl)phenyl)vinyl)-3-formylbenzoate 1,1,1-Triacetoxy-1,1-dihydro-1,2-benziodoxol-3(1H)-one (1.664 g) was added to a mixture of benzyl 2-(2-(benzyloxy)-5-((EZ)-N'-(tert-butoxycarbonyl)carbamimidoyl)styryl)-3-(hydroxymethyl)benzoate (1.55 g) and acetonitrile (20 mL) at room temperature, followed by stirring at room temperature for 30 minutes. A saturated sodium hydrogen carbonate aqueous solution and sodium thiosulfate were added to the mixture, followed by stirring for 20 minutes. The mixture was extracted with ethyl acetate, and the extract was washed with a saturated sodium hydrogen carbonate aqueous solution and a saturated saline solution, dried over anhydrous magnesium sulfate, and concentrated under reduced pressure. The residue was purified by silica gel column chromatography (ethyl acetate/hexane) to obtain the title compound (1.07 g).

MS: [M+H]+ 591.3.

J) Benzyl 2-((EZ)-2-(2-(benzyloxy)-5-(N'-(tert-butoxycarbonyl)carbamimidoyl)phenyl)vinyl)-3-((1E)-3-tert-butoxy-3-oxoprop-1-en-1-yl)benzoate Acetonitrile (5 mL) was added to lithium chloride (45.6 mg) that was dried under reduced pressure. Benzyl 2-((EZ)-2-(2-(benzyloxy)-5-(N'-(tert-butoxycarbonyl)carbamimidoyl)phenyl)vinyl)-3-formylbenzoate (0.53 g) and tert-butyl (diethoxyphosphoryl)acetate ester (0.232 mL) were further added to the mixture at 0° C., followed by stirring under a nitrogen atmosphere at 0° C. for 5 minutes. 1,8-Diazabicyclo[5.4.0]unde-7-cene was then added thereto at 0° C., followed by stirring under a nitrogen atmosphere at room temperature overnight. Water was added to the reaction mixture at room temperature, followed by extraction with ethyl acetate. The organic layer was separated and was then washed with water and a saturated saline solution, dried over anhydrous magnesium sulfate, and concentrated under reduced pressure. The residue was purified by silica gel column chromatography (ethyl acetate/hexane) to obtain the title compound (0.552 g).

MS: [M+H]+ 689.4.

K) (2E)-3-(2-((EZ)-2-(2-(Benzyloxy)-5-(N'-(tert-butoxycarbonyl)carbamimidoyl)phenyl)vinyl)-3-((benzyloxy)carbonyl)phenyl)acrylic acid A mixture of benzyl 2-((EZ)-2-(2-(benzyloxy)-5-(N'-(tert-butoxycarbonyl)carbamimidoyl)phenyl)vinyl)-3-((1E)-3-tert-butoxy-3-oxoprop-1-en-1-yl)benzoate (0.55 g) and TFA (5 mL) was stirred at room temperature for 1 hour and was concentrated under reduced pressure. THF (5 mL) and water (5 mL) were added to the residue, and 1 N sodium hydroxide (7.98 mL) and then di-tert-butyl dicarbonate (0.222 mL) were added thereto at 0° C., followed by stirring at 0° C. for 1 hour. The reaction mixture was diluted with ethyl acetate, washed with water and a saturated saline solution, dried over anhydrous magnesium sulfate, and concentrated under reduced pressure to obtain the title compound (0.643 g).

MS: [M+H]+ 633.3.

L) Di-tert-butyl N-((2E)-3-(2-((EZ)-2-(2-(benzyloxy)-5-(N'-(tert-butoxycarbonyl)carbamimidoyl)phenyl)vinyl)-3-((benzyloxy)carbonyl)phenyl)prop-2-enoyl)-L-aspartate N,N'-Diisopropylethylamine (0.243 mL) was added to a mixture of (2E)-3-(2-((EZ)-2-(2-(benzyloxy)-5-(N'-(tert-butoxycarbonyl)carbamimidoyl)phenyl)vinyl)-3-((benzyloxy)carbonyl)phenyl)acrylic acid (506 mg), di-tert-butyl L-aspartate hydrochloride (338 mg), WSC hydrochloride (0.245 g), HOBt.H₂O (0.196 g), and DMF (5 mL) at room temperature, followed by stirring overnight. Water was added to the reaction mixture, followed by extraction with ethyl acetate. The extract was then washed with water, a saturated sodium hydrogen carbonate aqueous solution, and a saturated saline solution, dried over anhydrous magnesium sulfate, and concentrated under reduced pressure. The residue was purified by silica gel column chromatography (ethyl acetate/hexane) to obtain the title compound (0.246 g).

MS: [M+H-(Boc)]+ 760.4.

M) 2-(2-(5-(N'-(tert-Butoxycarbonyl)carbamimidoyl)-2-hydroxyphenyl)ethyl)-3-(3-(((2S)-1,4-di-tert-butoxy-1,4-dioxobutan-2-yl)amino)-3-oxopropyl)benzoic acid A mixture of di-tert-butyl N-((2E)-3-(2-((EZ)-2-(2-(benzyloxy)-5-(N'-(tert-butoxycarbonyl)carbamimidoyl)phenyl)vinyl)-3-((benzyloxy)carbonyl)phenyl)prop-2-enoyl)-L-aspartate (240 mg), 10% palladium on carbon (29.7 mg), and methanol (5 mL) was stirred under a hydrogen atmosphere at room temperature for 1 hour. The reaction mixture was filtered, and the filtrate was concentrated under reduced pressure to obtain the title compound (191 mg).

MS: [M+H]+ 684.4.

N) Di-tert-butyl N-(3-(2-(N'-(tert-butoxycarbonyl)carbamimidoyl)-6-oxo-11,12-dihydro-6H-dibenzo[b,f]oxocin-10-yl)propanoyl)-L-aspartate 4-Dimethylaminopyridine (34.2 mg) was added to a mixture of 2-(2-(5-(N'-(tert-butoxycarbonyl)carbamimidoyl)-2-hydroxyphenyl)ethyl)-3-(3-(((2S)-1,4-di-tert-butoxy-1,4-dioxobutan-2-yl)amino)-3-oxopropyl)benzoic acid (191 mg), WSC hydrochloride (0.081 g), and THF (10 mL) at 0° C., followed by stirring at room temperature for 5 hours. Water was added to the reaction mixture at room temperature, followed by extraction with ethyl acetate. The organic layer was separated and was then washed with a saturated sodium hydrogen carbonate aqueous solution, water, and a saturated saline solution, dried over anhydrous magnesium sulfate, and concentrated under reduced pressure. The residue was purified by silica gel column chromatography (ethyl acetate/hexane) to obtain the title compound (0.076 g).

MS: [M+H]+ 666.4.

O) N-(3-(2-Carbamimidoyl-6-oxo-11,12-dihydro-6H-dibenzo[b,f]oxocin-10-yl)propanoyl)-L-aspartic acid trifluoroacetate A mixture of di-tert-butyl N-(3-(2-(N'-(tert-butoxycarbonyl)carbamimidoyl)-6-oxo-11,12-dihydro-6H-dibenzo[b,f]

oxocin-10-yl)propanoyl)-L-aspartate (26 mg) and TFA (2 mL) was stirred at room temperature for 2 hours and was then concentrated under reduced pressure. Diisopropyl ether was added to the residue, and the resulting solid was collected by filtration to obtain the title compound (19.60 mg).

$^1$H NMR (300 MHz, DMSO-$d_6$) δ 2.39 (2H, t, J=7.7 Hz), 2.52-2.60 (1H, m), 2.60-2.72 (1H, m), 2.85 (2H, t, J=7.7 Hz), 4.48-4.59 (1H, m), 7.08-7.28 (3H, m), 7.35 (1H, d, J=8.6 Hz), 7.56 (1H, dd, J=8.5, 2.4 Hz), 7.62 (1H, d, J=2.2 Hz), 8.31 (1H, d, J=7.9 Hz), 9.05 (2H, s), 9.18 (2H, s).

Example 62

N-((2-Carbamimidoyl-6-oxo-11,12-dihydro-6H-dibenzo[b,f]oxocin-10-yl)carbonyl)-L-aspartic acid trifluoroacetate A) 2-((EZ)-2-(2-(Benzyloxy)-5-(N'-(tert-butoxycarbonyl)carbamimidoyl)phenyl)vinyl)-3-((benzyloxy)carbonyl)benzoic acid Sodium chlorite (0.155 g) was added to a mixture of benzyl 2-((EZ)-2-(2-(benzyloxy)-5-(N'-(tert-butoxycarbonyl)carbamimidoyl)phenyl)vinyl)-3-formylbenzoate (0.505 g), sodium dihydrogen phosphate (308 mg), 2-methyl-2-butene (0.453 mL), acetonitrile (10 mL), and water (2.0 mL) at 0° C., followed by stirring at 0° C. for 1 hour and at room temperature for 1 hour. Sodium dihydrogen phosphate (0.103 g), 2-methyl-2-butene (0.151 mL), and sodium chlorite (0.052 g) were further added thereto, followed by stirring at room temperature for 1 hour. At 0° C., 1 N hydrochloric acid was added thereto, followed by extraction with ethyl acetate. The organic layer was separated and was then washed with water and a saturated saline solution, dried over anhydrous magnesium sulfate, and concentrated under reduced pressure to obtain the title compound (516 mg).
MS: [M+H]$^+$ 607.3.

B) Di-tert-butyl N-(2-((EZ)-2-(2-(benzyloxy)-5-(N'-(tert-butoxycarbonyl)carbamimidoyl)phenyl)vinyl)-3-((benzyloxy)carbonyl)benzoyl)-L-aspartate N,N'-Diisopropylethylamine (0.198 mL) was added to a mixture of 2-((EZ)-2-(2-(benzyloxy)-5-(N'-(tert-butoxycarbonyl)carbamimidoyl)phenyl)vinyl)-3-((benzyloxy)carbonyl)benzoic acid (516 mg), di-tert-butyl L-aspartate hydrochloride (0.287 g), WSC hydrochloride (0.212 g), HOBt.H$_2$O (0.169 g), and DMF (5 mL) at room temperature, followed by stirring overnight. Water was added to the reaction mixture, followed by extraction with ethyl acetate. The organic layer was separated, washed with water, a saturated sodium bicarbonate water, and a saturated saline solution, dried over anhydrous magnesium sulfate, and concentrated under reduced pressure. The residue was purified by silica gel column chromatography (ethyl acetate/hexane) to obtain the title compound (0.546 g).
MS: [M+H−(Boc)]$^+$ 734.4.

C) 2-(2-(5-(N'-(tert-Butoxycarbonyl)carbamimidoyl)-2-hydroxyphenyl)ethyl)-3-(((2S)-1,4-di-tert-butoxy-1,4-dioxobutan-2-yl)carbamoyl)benzoic acid A mixture of di-tert-butyl N-(2-((EZ)-2-(2-(benzyloxy)-5-(N'-(tert-butoxycarbonyl)carbamimidoyl)phenyl)vinyl)-3-((benzyloxy)carbonyl)benzoyl)-L-aspartate (546 mg), 10% palladium on carbon (300 mg), and methanol (5 mL) was stirred under a hydrogen atmosphere at room temperature for 1 hour. The reaction mixture was filtered, and the filtrate was concentrated under reduced pressure to obtain the title compound (426 mg).
MS: [M+H]$^+$ 656.4.

D) Di-tert-butyl N-((2-(N'-(tert-butoxycarbonyl)carbamimidoyl)-6-oxo-11,12-dihydro-6H-dibenzo[b,f]oxocin-10-yl)carbonyl)-L-aspartate 4-Dimethylaminopyridine (79 mg) was added to a mixture of 2-(2-(5-(N'-(tert-butoxycarbonyl)carbamimidoyl)-2-hydroxyphenyl)ethyl)-3-(((2S)-1,4-di-tert-butoxy-1,4-dioxobutan-2-yl)carbamoyl)benzoic acid (426 mg), WSC hydrochloride (0.187 g), and THF (10 mL) at 0° C., followed by stirring at room temperature for 5 hours. Water was added to the reaction mixture at room temperature, followed by extraction with ethyl acetate. The organic layer was separated and was then washed with a saturated sodium hydrogen carbonate aqueous solution, water, and a saturated saline solution, dried over anhydrous magnesium sulfate, and concentrated under reduced pressure. The residue was purified by silica gel column chromatography (ethyl acetate/hexane) to obtain the title compound (0.120 g).
MS: [M+H]$^+$ 638.4.

E) N-((2-Carbamimidoyl-6-oxo-11,12-dihydro-6H-dibenzo[b,f]oxocin-10-yl)carbonyl)-L-aspartic acid trifluoroacetate A mixture of di-tert-butyl N-((2-(N'-(tert-butoxycarbonyl)carbamimidoyl)-6-oxo-11,12-dihydro-6H-dibenzo[b,f]oxocin-10-yl)carbonyl)-L-aspartate (120 mg) and TFA (3 mL) was stirred at room temperature for 2 hours, followed by concentration under reduced pressure. Diisopropyl ether was added to the residue, and the resulting solid was collected by filtration to obtain the title compound (93 mg).
$^1$H NMR (300 MHz, DMSO-$d_6$) δ 2.60-2.76 (1H, m), 2.78-2.93 (1H, m), 3.25 (4H, dd, J=12.6, 3.5 Hz), 4.72 (1H, td, J=8.1, 5.2 Hz), 7.25-7.43 (3H, m), 7.47 (1H, dd, J=7.3, 1.7 Hz), 7.52-7.64 (2H, m), 8.77 (1H, d, J=7.9 Hz), 9.09 (2H, s), 9.19 (2H, s).

Example 65

N$^2$-((10-Carbamimidamido-13-oxo-6,7,8,13-tetrahydrodibenzo[b,f][1,4]dioxecin-4-yl)carbonyl)-N$^2$-(carboxymethyl)-L-asparagine A) (S)-tert-Butyl 4-amino-2-((2-(tert-butoxy)-2-oxoethyl)amino)-4-oxobutanoate N,N-Diisopropylethylamine (1.113 mL) was added to a mixture of L-asparagine tert-butyl ester (500 mg) and THF (5 mL) at 0° C., and a mixture of tert-butyl bromoacetate (0.493 mL) and THF (5 mL) was then added thereto, followed by stirring at room temperature overnight. The reaction mixture was concentrated under reduced pressure. Ethyl acetate was added to the residue, and the insoluble matter was removed by filtration. The filtrate was concentrated under reduced pressure, and the residue was purified by silica gel column chromatography (ethyl acetate/hexane) to obtain the title compound (532.7 mg).
MS: [M+H]$^+$ 303.1.

B) 10-Guanidino-13-oxo-6,7,8,13-tetrahydrodibenzo[b,f][1,4]dioxecine-4-carboxylic acid Four mole hydrogen chloride in cyclopentyl methyl ether (7.51 mL) and cyanamide (1.262 g) were added to a mixture of 10-amino-13-oxo-6,7,8,13-tetrahydrodibenzo[b,f][1,4]dioxecine-4-carboxylic acid hydrochloride (2.10 g) and tert-butyl alcohol (40 mL) at room temperature, followed by stirring at 70° C. for 18 hours. Ethyl acetate (40 mL) was added to the reaction mixture at room temperature, followed by stirring at the same temperature for 30 minutes. The precipitated solid was collected by filtration and was washed with water and ethyl acetate to obtain the title compound (2.09 g).

C) N²-((10-Carbamimidamido-13-oxo-6,7,8,13-tetrahydrodibenzo [b,f][1,4]dioxecin-4-yl)carbonyl)-N²-(carboxymethyl)-L-asparagine A mixture of 10-guanidino-13-oxo-6,7,8,13-tetrahydrodibenzo[b,f][1,4]dioxecine-4-carboxylic acid hydrochloride (100 mg), N,N'-dicyclohexylcarbodiimide (63.2 mg), and pyridine (2 mL) was stirred at room temperature for 1 day. The reaction mixture was concentrated under reduced pressure, and acetonitrile was then added to the residue. The insoluble matter was removed by filtration, and the filtrate was concentrated under reduced pressure. The residue was purified by HPLC (C18, mobile phase: water/acetonitrile (system containing 0.1% TFA)), and the obtained fraction was concentrated under reduced pressure. A mixture of the residue, 4 M hydrogen chloride in cyclopentyl methyl ether (2 mL), and acetic acid (2 mL) was stirred at 40° C. for 5 hours. The reaction mixture was concentrated under reduced pressure, and the residue was then purified by HPLC (C18, mobile phase: water/acetonitrile (system containing 0.1% TFA)). The obtained fraction was concentrated under reduced pressure. An aqueous solution of ammonium acetate (60.1 mg) was added to a mixture of the residue and water at room temperature, followed by stirring at the same temperature for 30 minutes. The precipitated solid was collected by filtration and was washed with water and acetonitrile to obtain the title compound (23.0 mg).
¹H NMR (400 MHz, DMSO-d₆) δ 1.90-1.99 (2H, m), 2.89 (2H, brs), 3.20 (2H, brs), 3.53 (1H, brs), 3.72-3.94 (3H, m), 4.07 (1H, brs), 6.90 (1H, brs), 6.97 (1H, d, J=8.3 Hz), 7.20 (2H, t, J=7.6 Hz), 7.28-7.33 (1H, m), 7.41-7.54 (2H, m), 7.61 (4H, brs), 7.86 (1H, s), 9.87 (1H, brs).

Example 67

N-((3-Carbamimidamido-11-methoxy-14-oxo-5,7,8,14-tetrahydro-6H-dibenzo[b,h]oxecin-9-yl)carbonyl)-L-aspartic acid A) Ethyl 3-(allyloxy)-5-methoxybenzoate 3-Bromopropene (2.395 mL) was added to a mixture of ethyl 3-hydroxy-5-methoxybenzoate (3.62 g), potassium carbonate (3.82 g), and DMF (40 mL) at room temperature, followed by stirring at the same temperature overnight. Water was added to the reaction mixture, followed by extraction with ethyl acetate. The organic layer was washed with a saturated saline solution and was then dried over anhydrous magnesium sulfate, and the solvent was distilled under reduced pressure. The residue was purified by silica gel column chromatography (ethyl acetate/hexane) to obtain the title compound (4.16 g).
MS: [M+H]⁺ 237.1.

B) Ethyl 2-allyl-3-hydroxy-5-methoxybenzoate

A mixture of ethyl 3-(allyloxy)-5-methoxybenzoate (200 mg) and NMP (1.0 mL) was stirred under microwave irradiation at 200° C. for 5 hours. Water was added to the reaction mixture, followed by extraction with ethyl acetate. The organic layer was washed with water and a saturated saline solution and was then dried over anhydrous magnesium sulfate, and the solvent was distilled under reduced pressure. The same procedure was performed twice using ethyl 3-(allyloxy)-5-methoxybenzoate (1.92 g) and NMP (10 mL), followed by post-treatment, respectively. Three residues were combined, followed by purification by silica gel column chromatography (ethyl acetate/hexane) to obtain the title compound (2.73 g).
MS: [M+H]⁺ 237.1.

C) (S)-Dibenzyl 2-(2-allyl-3-hydroxy-5-methoxybenzamide)succinate

A mixture of ethyl 2-allyl-3-hydroxy-5-methoxybenzoate (1 g), 2 N sodium hydroxide aqueous solution (7 mL), and methanol (7 mL) was stirred at room temperature overnight and was then stirred at 50° C. for 5 hours. A 2 N sodium hydroxide aqueous solution (4 mL) was added to the reaction mixture at room temperature, followed by stirring 50° C. overnight. One normal hydrochloric acid (22 mL) was added to the reaction mixture at 0° C. to make the mixture acidic, followed by extraction with ethyl acetate. The organic layer was washed with water and a saturated saline solution and was then dried over anhydrous magnesium sulfate, and the solvent was distilled under reduced pressure. A mixture of the residue, (S)-dibenzyl 2-aminosuccinate hydrochloride (2.220 g), WSC hydrochloride (1.216 g), HOBt·H₂O (0.972 g), N,N-diisopropylethylamine (2.216 mL), and DMF (9 mL) was stirred at room temperature overnight. Water was added to the reaction mixture, followed by extraction with ethyl acetate. The organic layer was washed with 1 N hydrochloric acid and a saturated saline solution and was then dried over anhydrous magnesium sulfate, and the solvent was distilled under reduced pressure. The residue was purified by silica gel column chromatography (ethyl acetate/hexane) to obtain the title compound (2.10 g).
MS: [M+H]⁺ 504.3.

D) (S)-Dibenzyl 2-(2-allyl-3-((2-allyl-4-nitrobenzoyl)oxy)-5-methoxybenzamide)succinate Two drops of DMF were added to a mixture of 2-allyl-4-nitrobenzoic acid (741 mg), oxalyl chloride (0.469 mL), and THF (7 mL) at room temperature, and the mixture was stirred at the same temperature for 1 hour and was then concentrated under reduced pressure. A mixture of the residue and DMF (1 mL) was added to a mixture of (S)-dibenzyl 2-(2-allyl-3-hydroxy-5-methoxybenzamide)succinate (900 mg) and pyridine (3 mL) at room temperature, followed by stirring at 50° C. overnight. One mole hydrochloric acid (3 mL) was added to the reaction mixture, followed by extraction with ethyl acetate. The extract was washed with 0.28% aqueous ammonia (5 mL×2), 1 M hydrochloric acid (4 mL), and a saturated saline solution and was dried over anhydrous magnesium sulfate, and the solvent was then distilled under reduced pressure. The residue was purified by silica gel column chromatography (ethyl acetate/hexane) to obtain the title compound (969.4 mg).
MS: [M+H]⁺ 693.3.

E) (S)-Dibenzyl 2-(11-methoxy-3-nitro-14-oxo-8,14-dihydro-5H-dibenzo[b,h]oxecine-9-carboxamide)succinate A second-generation Grubbs catalyst (18.43 mg) was added to a mixture of (S)-dibenzyl 2-(2-allyl-3-((2-allyl-4- nitrobenzoyl)oxy)-5-methoxybenzamide)succinate (500 mg) and toluene (250 mL) at 80° C., followed by stirring at the same temperature for 4 hours. After concentration under reduced pressure, the residue was purified by silica gel column chromatography (ethyl acetate/hexane) to obtain the title compound (203 mg).

MS: [M+H]$^+$ 665.3.

F) (S)-2-(3-Amino-11-methoxy-14-oxo-6,7,8,14-tetrahydro-5H-dibenzo[b,h]oxecine-9-carboxamide) succinic acid A mixture of (S)-dibenzyl 2-(11-methoxy-3-nitro-14-oxo-8,14-dihydro-5H-dibenzo[b,h]oxecine-9-carboxamide)succinate (200 mg), 10% palladium on carbon (60 mg, water content: about 55%), and THF (5 mL) was stirred under a hydrogen atmosphere at room temperature for 1 day. The catalyst was removed by filtration, and the filtrate was then concentrated under reduced pressure. A mixture of the residue, 10% palladium on carbon (100 mg, water content: about 55%), and THF (5 mL) was stirred under a hydrogen atmosphere at room temperature for 7 hours. The catalyst was removed by filtration, and the filtrate was then concentrated under reduced pressure. A mixture of the residue, 20% palladium hydroxide on carbon (100 mg, water content: about 50%), and THF (5 mL) was stirred under a hydrogen atmosphere at room temperature overnight. The catalyst was removed by filtration, and the filtrate was then concentrated under reduced pressure to obtain the title compound (153.2 mg).

MS: [M+H]$^+$ 457.2.

G) N-((3-Carbamimidamido-11-methoxy-14-oxo-5,7,8,14-tetrahydro-6H-dibenzo[b,h]oxecin-9-yl)carbonyl)-L-aspartic acid Four mole hydrogen chloride in cyclopentyl methyl ether (0.250 mL) was added to a mixture of (S)-2-(3-amino-11-methoxy-14-oxo-6,7,8,14-tetrahydro-5H-dibenzo[b,h]oxecine-9-carboxamide)succinic acid (152 mg), cyanamide (70.0 mg), and tert-butyl alcohol (2 mL) at room temperature, followed by stirring at 60° C. overnight. The reaction mixture was concentrated under reduced pressure, and the residue was purified by HPLC (C18, mobile phase: water/acetonitrile (system containing 0.1% TFA)). The obtained fraction was concentrated under reduced pressure. An aqueous solution (1 mL) of ammonium acetate (77 mg) was added to a mixture of the residue and water (1.5 mL) at room temperature, followed by stirring at the same temperature for 1 hour. The precipitated solid was collected by filtration and was washed with water to obtain the title compound (83.5 mg).

$^1$H NMR (400 MHz, DMSO-d$_6$) δ 1.59 (2H, brs), 1.73 (2H, brs), 2.46 (1H, d, J=4.5 Hz), 2.66-2.78 (1H, m), 2.91 (2H, brs), 3.08-3.22 (2H, m), 3.80 (3H, s), 4.38-4.46 (1H, m), 6.80 (1H, d, J=2.3 Hz), 7.15 (1H, s), 7.25 (1H, d, J=8.6 Hz), 7.31 (1H, d, J=2.4 Hz), 7.79 (4H, brs), 7.92 (1H, d, J=8.4 Hz), 8.13 (1H, d, J=7.8 Hz).

Example 68

1-(13-Oxo-6,7,8,13-tetrahydrodibenzo[b,f][1,4]dioxecin-10-yl)guanidine trifluoroacetate

A) Benzyl 2-(3-(2-(benzyloxy)phenoxy)propyl)-4-((tert-butoxycarbonyl)amino)benzoate Methanesulfonyl chloride (0.221 mL) and triethylamine (0.904 mL) were added to a mixture of benzyl 4-((tert-butoxycarbonyl)amino)-2-(3-((methylsulfonyl)oxy)propyl)benzoate (1.0 g) and THF (15 mL) at 0° C., followed by stirring at room temperature for 1 hour. A saturated ammonium chloride aqueous solution was added to the reaction mixture at 0° C., followed by extraction with ethyl acetate. The organic layer was washed with a saturated saline solution and was then dried over anhydrous sodium sulfate, and the solvent was distilled under reduced pressure.

Potassium carbonate (0.895 g) was added to a mixture of the crude product (1.3875 g) of benzyl 4-((tert-butoxycarbonyl)amino)-2-(3-((methylsulfonyl)oxy)propyl)benzoate, 2-(benzyloxy)phenol (0.454 mL), and DMF (12 mL) at room temperature, followed by stirring at 80° C. overnight. Ethyl acetate and 1 N hydrochloric acid were added to the reaction mixture at 0° C., followed by extraction with ethyl acetate. The organic layer was washed with water and a saturated saline solution and was then dried over anhydrous sodium sulfate, and the solvent was distilled under reduced pressure. The residue was purified by silica gel column chromatography (ethyl acetate/hexane) to obtain the title compound (1.202 g).

MS: [M+Na]$^+$ 590.4.

B) 4-((tert-Butoxycarbonyl)amino)-2-(3-(2-hydroxyphenoxy)propyl)benzoic acid A mixture of benzyl 2-(3-(2-(benzyloxy)phenoxy)propyl)-4-((tert-butoxycarbonyl)amino)benzoate (1.0694 g), 10% palladium on carbon (0.102 g, water content: about 55%), and THF (10 mL) was stirred under a hydrogen atmosphere at room temperature for 2 hours. The catalyst was removed by filtration, and the filtrate was then concentrated under reduced pressure to obtain the title compound (0.788 g).

MS: [M+Na]$^+$ 410.2.

C) tert-Butyl (13-oxo-6,7,8,13-tetrahydrodibenzo[b,f][1,4]dioxecin-10-yl)carbamate WSC hydrochloride (494 mg) and N,N-dimethyl-4-aminopyridine (10.5 mg) were added to a mixture of 4-((tert-butoxycarbonyl)amino)-2-(3-(2-hydroxyphenoxy)propyl)benzoic acid (665.1 mg) and pyridine (70 mL) at 0° C., followed by stirring at room temperature overnight. N,N-Dimethyl-4-aminopyridine (10.5 mg) was added to the reaction mixture at room temperature, followed by stirring at the same temperature overnight. The reaction mixture was concentrated under reduced pressure, and ethyl acetate was then added to the residue. The mixture was washed with 1 N hydrochloric acid, water, and a saturated saline solution and was then dried over anhydrous sodium sulfate, and the solvent was distilled under reduced pressure. The residue was purified by silica gel column chromatography (ethyl acetate/hexane) to obtain the title compound (418 mg).

$^1$H NMR (300 MHz, DMSO-d$_6$) δ 1.47 (9H, s), 1.88-2.06 (2H, m), 3.11 (2H, t, J=6.4 Hz), 3.72 (2H, t, J=5.6 Hz), 7.01-7.16 (3H, m), 7.24 (1H, dd, J=8.5, 2.1 Hz), 7.32-7.44 (2H, m), 7.52 (1H, d, J=2.1 Hz), 9.61 (1H, s).

D) 10-Amino-7,8-dihydrodibenzo[b,f][1,4]dioxecin-13(6H)-one hydrochloride

Four normal hydrogen chloride in cyclopentyl methyl ether (4 mL) was added to a mixture of tert-butyl (13-oxo-6,7,8,13-tetrahydrodibenzo[b,f][1,4]dioxecin-10-yl)carbamate (435.0 mg) and acetic acid (8 mL) at room temperature, followed by stirring at the same temperature for 2 hours. The reaction mixture was concentrated under reduced pressure to obtain the title compound (359 mg).
MS: [M+H]$^+$ 270.0.

E) 1-(13-Oxo-6,7,8,13-tetrahydrodibenzo[b,f][1,4] dioxecin-10-yl)guanidine trifluoroacetate Four normal hydrogen chloride in cyclopentyl methyl ether (0.743 mL) and cyanamide (125 mg) were added to a mixture of 10-amino-7,8-dihydrodibenzo[b,f][1,4]dioxecin-13(6H)-one hydrochloride (303.0 mg) and tert-butyl alcohol (9 mL) at room temperature, followed by stirring at 60° C. overnight. The reaction mixture was concentrated, and the residue was purified by HPLC (C18, mobile phase: water/acetonitrile (system containing 0.1% TFA)) to obtain the title compound (407 mg).
$^1$H NMR (300 MHz, DMSO-d$_6$) δ 1.94-2.13 (2H, m), 3.13 (2H, t, J=6.4 Hz), 3.76 (2H, t, J=5.7 Hz), 6.99-7.19 (4H, m), 7.28 (1H, d, J=2.1 Hz), 7.34-7.43 (1H, m), 7.50 (1H, d, J=8.2 Hz), 7.65 (4H, s), 9.94 (1H, s).

Example 69

N-((10-Carbamimidoyl-14-oxo-5,7,8,14-tetrahydro-6H-dibenzo[b,h]oxecin-3-yl)carbonyl)-L-aspartic acid trifluoroacetate A) Ethyl 3-allyl-4-hydroxybenzimidate hydrochloride Acetyl chloride (13.26 mL) was added to a mixture of 3-allyl-4-hydroxybenzonitrile (3.71 g) and ethanol (14.65 mL) at 0° C., followed by stirring at room temperature for 3 hours, at 50° C. overnight, and then at 70° C. overnight. The precipitated solid was collected by filtration and was washed with ethyl acetate to obtain the title compound (3.98 g).
$^1$H NMR (400 MHz, DMSO-d$_6$) δ 1.47 (3H, t, J=7.0 Hz), 3.34 (2H, d, J=6.5 Hz), 4.55 (2H, q, J=6.9 Hz), 5.00-5.12 (2H, m), 5.90-6.06 (1H, m), 7.03 (1H, d, J=8.4 Hz), 7.80-7.90 (2H, m), 10.65 (1H, brs), 11.06 (1H, s), 11.32 (1H, brs).

B) tert-Butyl ((3-allyl-4-((tert-butoxycarbonyl)oxy)phenyl)(imino)methyl)carbamate A mixture of ethyl 3-allyl-4-hydroxybenzimidate hydrochloride (680 mg) and 7 M ammonia in methanol (7 mL) was stirred at room temperature for 3 days. The reaction mixture was concentrated under reduced pressure, and a saturated sodium hydrogen carbonate aqueous solution/water (1/1) was added to the residue, followed by washing with ethyl acetate. Di-tert-butyl dicarbonate (2.61 mL) was added to a mixture of the aqueous layer (about 10 mL), an 8 M sodium hydroxide aqueous solution (1.405 mL), and ethanol (5 mL) at 0° C., followed by stirring at room temperature for 8 hours. The reaction mixture was neutralized with 1 M hydrochloric acid at 0° C., followed by extraction with ethyl acetate. The organic layer was washed with a saturated saline solution and was dried over anhydrous magnesium sulfate, and the solvent was then distilled under reduced pressure. The residue was purified by silica gel column chromatography (ethyl acetate/hexane) to obtain the title compound (718 mg).
MS: [M+H]$^+$ 377.2.

C) tert-Butyl ((3-allyl-4-hydroxyphenyl) (imino)methyl)carbamate

A mixture of tert-butyl ((3-allyl-4-((tert-butoxycarbonyl)oxy)phenyl) (imino)methyl)carbamate (718 mg), a 4 M sodium hydroxide aqueous solution (1.192 mL), and ethanol (4 mL) was stirred at 60° C. for 30 minutes. The reaction mixture was neutralized with 1 M hydrochloric acid at 0° C., followed by extraction with ethyl acetate. The organic layer was washed with a saturated saline solution and was dried over anhydrous magnesium sulfate, and the solvent was then distilled under reduced pressure to obtain the title compound (642 mg).
MS: [M+H-tBu]$^+$ 221.0.

D) (S)-Di-tert-butyl 2-(3-iodo-4-(methoxycarbonyl)benzamide)succinate

A mixture of 1-methyl 2-iodoterephthalate (5.00 g), (S)-di-tert-butyl 2-aminosuccinate hydrochloride (5.06 g), WSC hydrochloride (3.76 g), HOBt.H$_2$O (3.00 g), triethylamine (5.24 mL), N,N-dimethyl-4-aminopyridine (0.200 g), and DMF (80 mL) was stirred at room temperature for 3 days. Water was added to the reaction mixture, followed by extraction with ethyl acetate. The organic layer was washed with a saturated saline solution and was dried over anhydrous magnesium sulfate, and the solvent was then distilled under reduced pressure. The residue was purified by silica gel column chromatography (ethyl acetate/hexane) to obtain the title compound (8.66 g).
MS: [M+Na]$^+$ 556.2.

E) (S)-4-((1,4-Di-tert-butoxy-1,4-dioxobutan-2-yl)carbamoyl)-2-iodobenzoic acid

A mixture of (S)-di-tert-butyl 2-(3-iodo-4-(methoxycarbonyl)benzamide)succinate (10.2 g), THF (40 mL), methanol (40 mL), and a 4 M lithium hydroxide aqueous solution (5 mL) was stirred at 0° C. for 3 hours. Water (15 mL) was added to the reaction mixture, followed by stirring at 0° C. for 3 hours. One mole hydrochloric acid was added to the reaction mixture at 0° C. to make the mixture acidic, and a saturated saline solution was then added thereto, followed by extraction with ethyl acetate. The organic layer was washed with a saturated saline solution and was dried over anhydrous magnesium sulfate, and the solvent was then distilled under reduced pressure. The residue was purified by silica gel column chromatography (ethyl acetate/hexane) to obtain the title compound (1.92 g).
MS: [M+H]$^+$ 520.2.

F) (S)-Di-tert-butyl 2-(4-((2-allyl-4-(N-(tert-butoxycarbonyl)carbamimidoyl)phenoxy)carbonyl)-3-iodobenzamide)succinate A mixture of tert-butyl ((3-allyl-4-hydroxyphenyl) (imino)methyl)carbamate (266 mg), (S)-4-((1,4-di-tert-butoxy-1,4-dioxobutan-2-yl)carbamoyl)-2-iodobenzoic acid (500 mg), N,N'-dicyclohexylcarbodiimide (238 mg), N,N-dimethyl-4-aminopyridine (11.76 mg), and pyridine (5 mL) was stirred at room temperature for 3 hours. One mole hydrochloric acid was added to the reaction mixture, followed by extraction with ethyl acetate. The organic layer was washed with a saturated saline solution and was dried over anhydrous magnesium sulfate, and the solvent was then distilled under reduced pressure. The residue was purified by silica gel column chromatography (ethyl acetate/hexane) to obtain the title compound (516 mg).
MS: [M+H]$^+$ 778.8.

G) (S)-Di-tert-butyl 2-(3-allyl-4-((2-allyl-4-(N-(tert-butoxycarbonyl)carbamimidoyl)phenoxy)carbonyl)benzamide)succinate A mixture of (S)-di-tert-butyl 2-(4-((2-allyl-4-(N-(tert-butoxycarbonyl)carbamimidoyl)phenoxy)carbonyl)-3-iodobenzamide)succinate (516 mg), 2-allyl-4,4,5,5-tetramethyl-1,3,2-dioxaborolane (167 mg), [1,1'-bis(diphenylphosphino)ferrocene]palladium(II) dichloride (48.6 mg), cesium fluoride (151 mg), and THF (5 mL) was heated to reflux under a nitrogen atmosphere for 4 hours. To the reaction mixture, THF (5 mL), 2-allyl-4,4,5,5-tetramethyl-1,3,2-dioxaborolane (167 mg), [1,1'-bis(diphenylphosphino)ferrocene]palladium(II) dichloride (48.6 mg), and cesium fluoride (151 mg) were added, followed by heating to reflux for 2.5 hours. To the reaction mixture, 0.1 M hydrochloric acid was added, followed by extraction with ethyl acetate. The organic layer was washed with a saturated saline solution and was dried over anhydrous magnesium sulfate, and the solvent was then distilled under reduced pressure. The residue was purified by silica gel column chromatography (ethyl acetate/hexane) to obtain the title compound (216 mg).

MS: [M+H]$^+$ 692.0.

H) (S)-Di-tert-butyl 2-(10-(N-(tert-butoxycarbonyl)carbamimidoyl)-14-oxo-8,14-dihydro-5H-dibenzo[b,h]oxecine-3-carboxamide)succinate A second-generation Grubbs catalyst (26.5 mg) was added in small portions to a mixture of (S)-di-tert-butyl 2-(3-allyl-4-((2-allyl-4-(N-(tert-butoxycarbonyl)carbamimidoyl)phenoxy)carbonyl)benzamide)succinate (216 mg) and toluene (300 mL) at 80° C., followed by stirring at the same temperature for 30 minutes. The reaction mixture was concentrated under reduced pressure, and the residue was purified by silica gel column chromatography (ethyl acetate/hexane) to obtain the title compound (81 mg).

MS: [M+H]$^+$ 664.0.

I) ((S)-Di-tert-butyl 2-(10-(N-(tert-butoxycarbonyl)carbamimidoyl)-14-oxo-6,7,8,14-tetrahydro-5H-dibenzo[b,h]oxecine-3-carboxamide)succinate A mixture of (S)-di-tert-butyl 2-(10-(N-(tert-butoxycarbonyl)carbamimidoyl)-14-oxo-8,14-dihydro-5H-dibenzo[b,h]oxecine-3-carboxamide)succinate (80.6 mg), 10% palladium on carbon (10 mg, water content: about 55%), and THF (2 mL) was stirred under a hydrogen atmosphere at room temperature overnight. The catalyst was removed by filtration, and the filtrate was then concentrated under reduced pressure. A mixture of the residue, 10% palladium on carbon (20 mg, water content: about 55%), and THF (2 mL) was stirred under a hydrogen atmosphere at room temperature for 8 hours. Ten percent palladium on carbon (80 mg, water content: about 55%) was added to the reaction mixture, followed by stirring under a hydrogen atmosphere at room temperature overnight. The catalyst was removed by filtration, and the filtrate was then concentrated under reduced pressure. The residue was purified by silica gel column chromatography (ethyl acetate/hexane) and then further purified by HPLC (C18, mobile phase: water/acetonitrile (system containing 0.1% TFA)), and the obtained fraction was neutralized with a saturated sodium hydrogen carbonate aqueous solution. A saturated saline solution was added thereto, followed by extraction with ethyl acetate. The organic layer was washed with a saturated saline solution, 0.1 M hydrochloric acid, and a saturated saline solution and was then dried over anhydrous magnesium sulfate, and the solvent was distilled under reduced pressure to obtain the title compound (27.0 mg).

MS: [M+H]$^+$ 666.3.

J) N-((10-Carbamimidoyl-14-oxo-5,7,8,14-tetrahydro-6H-dibenzo[b,h]oxecin-3-yl)carbonyl)-L-aspartic acid trifluoroacetate A mixture of ((S)-di-tert-butyl 2-(10-(N-(tert-butoxycarbonyl)carbamimidoyl)-14-oxo-6,7,8,14-tetrahydro-5H-dibenzo[b,h]oxecine-3-carboxamide)succinate (27.0 mg) and TFA (1 mL) was stirred at room temperature for 1 hour. The reaction mixture was concentrated under reduced pressure, and the residue was washed with diethyl ether to obtain the title compound (14.40 mg).

$^1$H NMR (400 MHz, DMSO-d$_6$) δ 1.56-1.70 (2H, m), 1.70-1.82 (2H, m), 2.57-2.69 (1H, m), 2.81 (1H, dd, J=16.1, 7.7 Hz), 2.96-3.07 (2H, m), 3.18-3.45 (2H, m), 4.55-4.76 (1H, m), 7.76-7.81 (1H, m), 7.83-7.93 (4H, m), 7.99 (1H, d, J=7.9 Hz), 8.67-8.89 (1H, m), 9.07 (2H, brs), 9.30 (2H, brs).

Example 71

3-((((10-Carbamimidamido-13-oxo-6,7,8,13-tetrahydrodibenzo[b,f][1,4]dioxecin-4-yl)carbonyl) (carboxymethyl)amino)methyl)benzoic acid

A) tert-Butyl 3-((10-amino-N-(2-(tert-butoxy)-2-oxoethyl)-13-oxo-6,7,8,13-tetrahydrodibenzo[b,f][1,4]dioxecine-4-carboxamide)methyl)benzoate N,N-Diisopropylethylamine (0.200 mL), WSC hydrochloride (110 mg), and HOBt.H$_2$O (88 mg, 0.58 mmol) were added to a mixture of 10-amino-13-oxo-6,7,8,13-tetrahydrodibenzo[b,f][1,4]dioxecine-4-carboxylic acid hydrochloride (134.4 mg), tert-butyl 3-(((2-(tert-butoxy)-2-oxoethyl)amino)methyl)benzoate (125 mg), and DMF (1 mL) at 0° C., followed by stirring at room temperature for 2 hours. Water was added to the reaction mixture at 0° C., followed by extraction with ethyl acetate. The organic layer was washed with a saturated sodium hydrogen carbonate aqueous solution and a saturated saline solution and was then dried over anhydrous sodium sulfate, and the solvent was distilled under reduced pressure. The residue was purified by silica gel column chromatography (ethyl acetate/hexane) to obtain the title compound (213 mg).

MS: [M+H]$^+$ 617.3.

B) 3-((10-Amino-N-(carboxymethyl)-13-oxo-6,7,8,13-tetrahydrodibenzo[b,f][1,4]dioxecine-4-carboxamide)methyl)benzoic acid hydrochloride Four normal hydrogen chloride in cyclopentyl methyl ether (4 mL) was added to a mixture of tert-butyl 3-((10-amino-N-(2-(tert-butoxy)-2-oxoethyl)-13-oxo-6,7,8,13-tetrahydrodibenzo[b,f][1,4]dioxecine-4-carboxamide)methyl)benzoate (202.7 mg) and acetic acid (4 mL) at room temperature, followed by stirring at the same temperature overnight. Ethyl acetate (4 mL) was added to the reaction mixture at room temperature, followed by stirring at the same temperature for 30 minutes. The precipitated solid was collected by filtration and was washed with ethyl acetate to obtain the title compound (151 mg).

MS: [M+H]$^+$ 505.2.

C) 3-((((10-Carbamimidamido-13-oxo-6,7,8,13-tetrahydrodibenzo[b,f][1,4]dioxecin-4-yl)carbonyl) (carboxymethyl)amino)methyl)benzoic acid Four normal hydrogen chloride in cyclopentyl methyl ether (0.189 mL) and cyanamide (31.7 mg) were added to a mixture of 3-((10-amino-N-(carboxymethyl)-13-oxo-6,7,8, 13-tetrahydrodibenzo[b,f][1,4]dioxecine-4-carboxamide) methyl)benzoic acid hydrochloride (136.0 mg) and tert-butyl alcohol (2 mL) at room temperature, followed by stirring at 60° C. for 6 hours. To the reaction mixture, 4 N hydrogen chloride in cyclopentyl methyl ether (0.189 mL) and cyanamide (31.7 mg) were added at room temperature, followed by stirring at 70° C. for 3 hours. To the reaction mixture, ethyl acetate and toluene were added, followed by extraction with water. Ammonium acetate (116 mg) was added to the aqueous layer at room temperature, followed by stirring at the same temperature for 90 minutes. The precipitated solid was collected by filtration and was washed with water and acetonitrile to obtain the title compound (113 mg).

$^1$H NMR (300 MHz, DMSO-$d_6$) δ 1.60-2.03 (2H, m), 3.11 (2H, brs), 3.49 (2H, brs), 3.90 (2H, brs), 3.98-4.41 (1H, m), 4.42-5.38 (1H, m), 7.05-7.29 (4H, m), 7.30-7.61 (3H, m), 7.66-8.03 (3H, m), 8.32 (4H, brs), 12.61 (2H, s).

Example 76

N-((3-Carbamimidamido-15-oxo-5,6,7,8,9,15-hexahydrodibenzo[b,i]hexacycloundecin-10-yl)carbonyl)-L-aspartic acid

A) Benzyl 2-allyl-4-bromo-3-((2-(trimethylsilyl) ethoxy)methoxy)benzoate

Sixty percent sodium hydride (0.333 g) was added to a mixture of benzyl 2-allyl-4-bromo-3-hydroxybenzoate (2.63 g) and DMF (30 mL) at 0° C. The reaction mixture was stirred at room temperature for 30 minutes, and 2-(trimethylsilyl)ethoxymethyl chloride (1.609 mL) was then added thereto, followed by stirring at room temperature for 30 minutes. Water was added to the reaction mixture, followed by extraction with ethyl acetate. The organic layer was washed with a saturated saline solution and was dried over anhydrous magnesium sulfate, and the solvent was then distilled under reduced pressure. The residue was purified by silica gel column chromatography (ethyl acetate/hexane) to obtain the title compound (3.39 g).

$^1$H NMR (400 MHz, DMSO-$d_6$) δ 0.00 (9H, s), 0.89-0.97 (2H, m), 3.76 (2H, d, J=6.0 Hz), 3.80-3.89 (2H, m), 4.83 (1H, d, J=17.1 Hz), 4.92 (1H, d, J=10.1 Hz), 5.09 (2H, s), 5.29 (2H, s), 5.76-5.91 (1H, m), 7.31-7.51 (6H, m), 7.66 (1H, d, J=8.4 Hz).

B) Benzyl 4-bromo-2-(3-hydroxypropyl)-3-((2-(trimethylsilyl)ethoxy)methoxy)benzoate A borane-THF complex (7.81 mL, 1 M THF solution) was added to a mixture of benzyl 2-allyl-4-bromo-3-((2-(trimethylsilyl)ethoxy)methoxy)benzoate (3.39 g) and THF (40 mL) at 0° C., followed by stirring at 0° C. for 2 hours. To the reaction mixture, a 2 M sodium hydroxide aqueous solution (3.73 mL) and a 30% hydrogen peroxide solution (0.966 g) were added, followed by stirring at 0° C. for 3 hours. One mole hydrochloric acid (7.46 mL) was added to the reaction mixture at 0° C., followed by extraction with ethyl acetate. The organic layer was washed with a saturated saline solution and was dried over anhydrous magnesium sulfate, and the solvent was then distilled under reduced pressure. The residue was purified by silica gel column chromatography (ethyl acetate/hexane) to obtain the title compound (2.40 g).

$^1$H NMR (400 MHz, DMSO-$d_6$) δ 0.01 (9H, s), 0.87-0.99 (2H, m), 1.49-1.72 (2H, m), 2.89-3.00 (2H, m), 3.32-3.40 (2H, m), 3.77-3.90 (2H, m), 4.42 (1H, t, J=5.1 Hz), 5.09 (2H, s), 5.32 (2H, s), 7.33-7.50 (6H, m), 7.61 (1H, d, J=8.4 Hz).

C) Benzyl 4-bromo-2-(3-oxopropyl)-3-((2-(trimethylsilyl)ethoxy)methoxy)benzoate Dess-Martin periodinane (2.260 g) was added in small portions to a mixture of benzyl 4-bromo-2-(3-hydroxypropyl)-3-((2-(trimethylsilyl)ethoxy)methoxy)benzoate (2.40 g) and acetonitrile (25 mL) at 0° C., followed by stirring at the same temperature for 4 hours. To the reaction mixture, ethyl acetate, a saturated sodium hydrogen carbonate aqueous solution, and a sodium thiosulfate aqueous solution were added at 0° C., followed by stirring at the same temperature for 20 minutes. The precipitate was removed by filtration, and the filtrate was then extracted with ethyl acetate. The organic layer was washed with a saturated saline solution and was dried over anhydrous magnesium sulfate, and the solvent was then distilled under reduced pressure. The residue was purified by silica gel column chromatography (ethyl acetate/hexane) to obtain the title compound (1.940 g).

$^1$H NMR (400 MHz, DMSO-$d_6$) δ 0.00 (9H, s), 0.83-0.97 (2H, m), 2.65 (2H, t, J=7.8 Hz), 3.18 (2H, t, J=7.7 Hz), 3.73-3.85 (2H, m), 5.12 (2H, s), 5.32 (2H, s), 7.33-7.49 (5H, m), 7.52 (1H, d, J=8.4 Hz), 7.66 (1H, d, J=8.4 Hz), 9.63 (1H, s).

D) Butyl 4-bromo-2-(but-3-en-1-yl)-3-hydroxybenzoate and ethyl 4-bromo-2-(but-3-en-1-yl)-3-hydroxybenzoate Under a nitrogen atmosphere, n-butyllithium (1.6 M hexane solution, 4.91 mL) was added to a mixture of methyltriphenylphosphonium bromide (3.09 g) and THF (20 mL) at 0° C., followed by stirring at the same temperature for 2 hours. A mixture of benzyl 4-bromo-2-(3-oxopropyl)-3-((2-(trimethylsilyl)ethoxy)methoxy)benzoate (1.94 g) and THF (10 mL) was added thereto, followed by stirring at room temperature overnight. Water was added to the reaction mixture, followed by extraction with ethyl acetate. The organic layer was washed with a saturated saline solution and was dried over anhydrous magnesium sulfate, and the solvent was then distilled under reduced pressure. The residue was purified by silica gel column chromatography (ethyl acetate/hexane) to obtain a mixture (1.25 g) of benzyl 4-bromo-2-(but-3-en-1-yl)-3-((2-(trimethylsilyl)ethoxy) methoxy)benzoate and butyl 4-bromo-2-(but-3-en-1-yl)-3-((2-(trimethylsilyl)ethoxy)methoxy)benzoate. To a mixture of this mixture and triethylsilane (1.25 mL), TFA (12 mL) was added at 0° C., followed by stirring at the same temperature for 2 hours. The reaction mixture was concentrated under reduced pressure, and the residue was distributed between ethyl acetate and a saturated sodium hydrogen carbonate aqueous solution. The organic layer was washed with a saturated saline solution and was dried over anhydrous magnesium sulfate, and the solvent was then distilled under reduced pressure. The residue was purified by silica gel column chromatography (ethyl acetate/hexane) and then further by HPLC (C18, mobile phase: water/acetonitrile (system containing 0.1% TFA)). The obtained fraction was neutralized with a saturated sodium hydrogen carbonate aqueous solution, followed by extraction with ethyl acetate. The extract was washed with a saturated saline solution and was then dried over anhydrous magnesium sulfate, and the solvent was distilled under reduced pressure to obtain butyl 4-bromo-2-(but-3-en-1-yl)-3-hydroxybenzoate (310 mg) and ethyl 4-bromo-2-(but-3-en-1-yl)-3-hydroxybenzoate (98.1 mg). Butyl 4-bromo-2-(but-3-en-1-yl)-3-hydroxybenzoate $^1$H NMR (400 MHz, DMSO-$d_6$) δ 0.92 (3H, t, J=7.4 Hz), 1.29-1.48 (2H, m), 1.60-1.74 (2H, m), 2.15-2.26 (2H, m), 2.91-3.04 (2H, m), 4.23 (2H, t, J=6.5 Hz), 4.90-5.05 (2H, m), 5.85 (1H, ddt, J=17.0, 10.4, 6.5 Hz), 7.15 (1H, d, J=8.3 Hz), 7.48 (1H, d, J=8.4 Hz), 9.31 (1H, s). Ethyl 4-bromo-2-(but-3-en-1-yl)-3-hydroxybenzoate $^1$H NMR (400 MHz, DMSO-$d_6$) δ 1.23-1.36 (3H, m), 2.13-2.28 (2H, m), 2.87-3.02 (2H, m), 4.27 (2H, q, J=6.9 Hz), 4.86-5.07 (2H, m), 5.86 (1H, ddt, J=17.0, 10.4, 6.5 Hz), 7.15 (1H, d, J=8.3 Hz), 7.47 (1H, d, J=8.4 Hz), 9.30 (1H, s).

E) Benzyl 4-bromo-2-(but-3-en-1-yl)-3-hydroxybenzoate

A mixture of butyl 4-bromo-2-(but-3-en-1-yl)-3-hydroxybenzoate (310 mg), ethyl 4-bromo-2-(but-3-en-1-yl)-3-hydroxybenzoate (98.1 mg), ethanol (4 mL), and a 4 M sodium hydroxide aqueous solution (4 mL) was stirred at 50° C. overnight. The reaction mixture was neutralized with 6 M hydrochloric acid at 0° C., followed by extraction with ethyl acetate. The organic layer was washed with a saturated saline solution and was dried over anhydrous magnesium sulfate, and the solvent was then distilled under reduced pressure. N,N-Diisopropylethylamine (0.454 mL) and benzyl bromide (0.155 mL) were added to a mixture of the residue and DMF (4 mL) at 0° C., followed by stirring at 0° C. for 5 hours and then at room temperature overnight. To the reaction mixture, 0.1 M hydrochloric acid was added, followed by extraction with ethyl acetate. The organic layer was washed with a saturated saline solution and was dried over anhydrous magnesium sulfate, and the solvent was then distilled under reduced pressure. The residue was purified by silica gel column chromatography (ethyl acetate/hexane) and further by HPLC (C18, mobile phase: water/acetonitrile (system containing 0.1% TFA)), and the obtained fraction was neutralized with a saturated sodium hydrogen carbonate aqueous solution, followed by extraction with ethyl acetate. The organic layer was washed with a saturated saline solution and was then dried over anhydrous magnesium sulfate, and the solvent was distilled under reduced pressure to obtain the title compound (249 mg).
$^1$H NMR (400 MHz, DMSO-$d_6$) δ 2.11-2.23 (2H, m), 2.88-3.03 (2H, m), 4.81-5.00 (2H, m), 5.30 (2H, s), 5.76 (1H, ddt, J=17.0, 10.3, 6.5 Hz), 7.14-7.22 (1H, m), 7.29-7.62 (6H, m), 9.33 (1H, s).

F) Benzyl 3-((2-allyl-4-nitrobenzoyl)oxy)-4-bromo-2-(but-3-en-1-yl)benzoate

One drop of DMF was added to a mixture of 2-allyl-4-nitrobenzoic acid (263 mg), THF (3 mL), and oxalyl chloride (0.166 mL) at room temperature, followed by stirring at the same temperature for 15 minutes. The reaction mixture was concentrated under reduced pressure. To the residue, a mixture of benzyl 4-bromo-2-(but-3-en-1-yl)-3-hydroxybenzoate (229 mg), DMF (3 mL), and pyridine (3 mL) was added at 0° C., followed by stirring at 50° C. for 30 minutes. One mole hydrochloric acid was added to the reaction mixture at 0° C., followed by extraction with ethyl acetate. The organic layer was washed with 0.28% aqueous ammonia, 1 M hydrochloric acid, and a saturated saline solution and was dried over anhydrous magnesium sulfate, and the solvent was then distilled under reduced pressure. The residue was purified by silica gel column chromatography (ethyl acetate/hexane) to obtain the title compound (290 mg).
$^1$H NMR (400 MHz, DMSO-$d_6$) δ 2.06-2.27 (2H, m), 2.63-2.85 (1H, m), 2.98-3.16 (1H, m), 3.80-3.96 (2H, m), 4.75-4.92 (2H, m), 5.01-5.15 (2H, m), 5.36 (2H, s), 5.66 (1H, ddt, J=16.7, 10.4, 6.6 Hz), 6.02 (1H, ddt, J=16.9, 10.3, 6.4 Hz), 7.34-7.45 (3H, m), 7.46-7.54 (2H, m), 7.72-7.77 (1H, m), 7.79-7.86 (1H, m), 8.27-8.35 (2H, m), 8.45 (1H, d, J=8.1 Hz).

G) Benzyl 13-bromo-3-nitro-15-oxo-5,8,9,15-tetrahydrodibenzo[b,i][1]oxacycloundecine-10-carboxylate A second-generation Hoveyda-Grubbs catalyst (16.56 mg) was added to a mixture of benzyl 3-((2-allyl-4-nitrobenzoyl)oxy)-4-bromo-2-(but-3-en-1-yl)benzoate (290 mg) and toluene (300 mL) at 80° C., followed by stirring at the same temperature for 30 minutes. The reaction mixture was concentrated under reduced pressure, and the residue was purified by silica gel column chromatography (ethyl acetate/hexane) to obtain the title compound (235 mg).
$^1$H NMR (400 MHz, CDCl$_3$) δ 2.13-2.58 (2H, m), 2.68-2.87 (1H, m), 3.24-3.51 (2H, m), 3.78-4.08 (1H, m), 5.24-5.83 (4H, m), 7.32-7.49 (5H, m), 7.57-7.65 (1H, m), 7.70-7.90 (2H, m), 8.13-8.29 (2H, m).

H) 3-Amino-15-oxo-5,6,7,8,9,15-hexahydrodibenzo[b,i][1]oxacycloundecine-10-carboxylic acid hydrobromate A mixture of benzyl 13-bromo-3-nitro-15-oxo-5,8,9,15-tetrahydrodibenzo[b,i][1]oxacycloundecine-10-carboxylate (235 mg), 20% palladium hydroxide on carbon (200 mg, water content: about 50%), and 2-propanol (3 mL) was stirred under a hydrogen atmosphere at room temperature overnight. The catalyst was removed by filtration, and the filtrate was then concentrated under reduced pressure to obtain the title compound (216 mg).
MS: [M+H]$^+$ 326.2.

I) (S)-Dibenzyl 2-(3-amino-15-oxo-5,6,7,8,9,15-hexahydrodibenzo[b,i][1]oxacycloundecine-10-carboxamide)succinate A mixture of 3-amino-15-oxo-5,6,7,8,9,15-hexahydrodibenzo[b,i][1]oxacycloundecine-10-carboxylic acid hydrobromate (216 mg), (S)-dibenzyl 2-aminosuccinate hydrochloride (223 mg), WSC hydrochloride (122 mg), HOBt.H$_2$O (98 mg), N,N-diisopropylethylamine (0.464 mL), and DMF (3 mL) was stirred at room temperature overnight. Water was added to the reaction mixture, followed by extraction with ethyl acetate. The extract was washed with a saturated saline solution and was dried over anhydrous magnesium sulfate, and the solvent was then distilled under reduced pressure. The residue was purified by silica gel column chromatography (ethyl acetate/hexane) to obtain the title compound (170 mg).
MS: [M+H]$^+$ 621.2.

J) (S)-2-(3-Amino-15-oxo-5,6,7,8,9,15-hexahydrod-ibenzo[b,i][1]oxacycloundecine-10-carboxamide) succinic acid Under a hydrogen atmosphere, a mixture of (S)-dibenzyl 2-(3-amino-15-oxo-5,6,7,8,9,15-hexahydrodibenzo[b,i][1] oxacycloundecine-10-carboxamide)succinate (170 mg), 10% palladium on carbon (34 mg, water content: about 55%), and THF (2 mL) was stirred at room temperature for 6 hours. The catalyst was removed by filtration, and the filtrate was then concentrated under reduced pressure to obtain the title compound (137 mg).
MS: [M+H]$^+$ 441.2.

K) N-((3-Carbamimidamido-15-oxo-5,6,7,8,9,15-hexahydrodibenzo[b,i]hexacycloundecin-10-yl)carbonyl)-L-aspartic acid A solution (0.233 mL) of 4 M hydrogen chloride in cyclopropyl methyl ether was added to a mixture of (S)-2-(3-amino-15-oxo-5,6,7,8,9,15-hexahydrodibenzo[b,i][1]ox-acycloundecine-10-carboxamide)succinic acid (137 mg), cyanamide (39.2 mg), and tert-butyl alcohol (3 mL) at room temperature, followed by stirring at 60° C. for 4 hours. The reaction mixture was concentrated under reduced pressure. To the residue, water (3 mL) and then an aqueous solution prepared from ammonium acetate (71.9 mg) and water (2 mL) were added dropwise, followed by stirring at room temperature for 3 hours. The precipitated solid was collected by filtration and was washed with water and acetone. The resulting solid was purified by HPLC (C18, mobile phase: water/acetonitrile (system containing 0.1% TFA)), and the obtained fraction was concentrated under reduced pressure. An ammonium acetate aqueous solution was added to the residue to adjust the pH to about 4, followed by stirring at room temperature overnight. The precipitated solid was collected by filtration and was washed with water and acetone to obtain the title compound (64.4 mg).
MS: [M+H]$^+$ 483.2.
$^1$H NMR (400 MHz, DMSO-d$_6$) δ 1.00-1.38 (2H, m), 1.52-1.84 (4H, m), 2.51-2.58 (1H, m), 2.69-3.16 (3H, m), 3.24-3.43 (2H, m), 4.40-4.54 (1H, m), 7.13 (1H, brs), 7.17-7.24 (2H, m), 7.26-7.36 (2H, m), 7.59-8.12 (5H, m), 8.17 (1H, d, J=6.7 Hz).

Example 77

N-((3-Carbamimidamido-16-oxo-5,7,8,9,10,16-hexahydro-6H-dibenzo[b,j]oxacyclododecin-11-yl)carbonyl)-L-aspartic acid

A) Methyl 2-(3-hydroxypropyl)-4-nitrobenzoate

A borane-THF complex (1 M THF solution, 9.80 mL) was added to a THF (20 mL) solution of methyl 2-allyl-4-nitrobenzoate (1.97 g) at 0° C., followed by stirring at the same temperature for 2 hours. A 2 M sodium hydroxide aqueous solution (4.68 mL) and 30% hydrogen peroxide solution (1.212 g) were added to the reaction mixture, followed by stirring at 0° C. for 1.5 hours. One mole hydrochloric acid (9.36 mL) was added to the reaction mixture at 0° C., followed by extraction with ethyl acetate. The organic layer was washed with a saturated saline solution and was dried over anhydrous magnesium sulfate, and the solvent was then distilled under reduced pressure. The residue was purified by silica gel column chromatography (ethyl acetate/hexane) to obtain the title compound (1.360 g).
$^1$H NMR (400 MHz, DMSO-d$_6$) δ 1.65-1.76 (2H, m), 2.92-3.03 (2H, m), 3.37-3.47 (2H, m), 3.89 (3H, s), 4.51 (1H, t, J=5.1 Hz), 7.96 (1H, d, J=8.4 Hz), 8.10-8.21 (2H, m).

B) Methyl 4-nitro-2-(3-oxopropyl)benzoate

Dess-Martin periodinane (2.65 g) was added in small portions to an acetonitrile (30 mL) solution of methyl 2-(3-hydroxypropyl)-4-nitrobenzoate (1.36 g) at 0° C., followed by stirring at 0° C. for 1 hour and then at room temperature for 5 hours. To the reaction mixture, ethyl acetate, a saturated sodium hydrogen carbonate aqueous solution, and a sodium thiosulfate aqueous solution were added at 0° C., followed by stirring at the same temperature for 20 minutes. The precipitate was removed by filtration, and the filtrate was extracted with ethyl acetate. The organic layer was washed with a saturated saline solution and was dried over anhydrous magnesium sulfate, and the solvent was then distilled under reduced pressure. The residue was purified by silica gel column chromatography (ethyl acetate/hexane) to obtain the title compound (1.060 g).
$^1$H NMR (400 MHz, DMSO-d$_6$) δ 2.84 (2H, t, J=7.5 Hz), 3.21 (2H, t, J=7.5 Hz), 3.89 (3H, s), 8.00 (1H, d, J=8.6 Hz), 8.16 (1H, dd, J=8.6, 2.3 Hz), 8.25 (1H, d, J=2.3 Hz), 9.71 (1H, s).

C) Methyl 2-(but-3-en-1-yl)-4-nitrobenzoate

Under a nitrogen atmosphere, n-butyllithium (1.6 M hexane solution, 2.93 mL) was added to a mixture of methyltriphenylphosphonium bromide (1.916 g) and THF (20 mL) at 0° C., followed by stirring at the same temperature for 1 hour. A mixture of methyl 4-nitro-2-(3-oxopropyl) benzoate (1.06 g) and THF (10 mL) was added to the reaction mixture, followed by stirring at 0° C. for 1 hour and then at room temperature overnight. Water was added to the reaction mixture, followed by extraction with ethyl acetate. The organic layer was washed with a saturated saline solution and was dried over anhydrous magnesium sulfate, and the solvent was then distilled under reduced pressure. The residue was purified by silica gel column chromatography (ethyl acetate/hexane) to obtain the title compound (0.347 g).
MS: [M+H]$^+$ 236.0.

D) 2-(But-3-en-1-yl)-4-nitrobenzoic acid

A mixture of methyl 2-(but-3-en-1-yl)-4-nitrobenzoate (347 mg), THF (3 mL), methanol (3 mL), and a 1 M sodium hydroxide aqueous solution (3 mL) was stirred at room temperature for 4 hours. The reaction mixture was neutralized with 1 M hydrochloric acid at 0° C., followed by extraction with ethyl acetate. The organic layer was washed with water and a saturated saline solution and was dried over anhydrous magnesium sulfate, and the solvent was then distilled under reduced pressure to obtain the title compound (302 mg).
$^1$H NMR (400 MHz, DMSO-d$_6$) δ 2.23-2.41 (2H, m), 3.03-3.13 (2H, m), 4.92-5.04 (2H, m), 5.84 (1H, ddt, J=17.0, 10.3, 6.6 Hz), 7.96 (1H, d, J=8.6 Hz), 8.11 (1H, dd, J=8.4, 2.3 Hz), 8.17 (1H, d, J=2.3 Hz), 13.59 (1H, s).

E) Benzyl 4-bromo-2-(but-3-en-1-yl)-3-((2-(but-3-en-1-yl)-4-nitrobenzoyl)oxy)benzoate One drop of DMF was added to a mixture of 2-(but-3-en-1-yl)-4-nitrobenzoic acid (183 mg), THF (3 mL), and oxalyl chloride (0.109 mL), followed by stirring at room temperature for 15 minutes and then concentration under reduced pressure. To the residue, a mixture of benzyl 4-bromo-2-(but-3-en-1-yl)-3-hydroxybenzoate (249 mg), DMF (2 mL), and pyridine (2 mL) was added at 0° C., followed by stirring at 50° C. for 1 hour. To the reaction mixture, a mixture of an acid chloride separately prepared by the same method above from 2-(but-3-en-1-yl)-4-nitrobenzoic acid (83 mg) and oxalyl chloride (0.045 mL) and DMF (1 mL) was added at 0° C., followed by stirring at 50° C. for 30 minutes. One mole hydrochloric acid was added to the reaction mixture at 0° C., followed by extraction with ethyl acetate. The extract was washed with 0.28% aqueous ammonia, 1 M hydrochloric acid, and a saturated saline solution and was dried over anhydrous magnesium sulfate, and the solvent was then distilled under reduced pressure. The residue was purified by silica gel column chromatography (ethyl acetate/hexane) to obtain the title compound (280 mg).

$^1$H NMR (400 MHz, DMSO-$d_6$) δ 2.08-2.29 (2H, m), 2.32-2.43 (2H, m), 2.66-2.84 (1H, m), 3.00-3.15 (1H, m), 3.19 (2H, t, J=7.6 Hz), 4.80-4.89 (2H, m), 4.93-5.03 (2H, m), 5.36 (2H, s), 5.57-5.74 (1H, m), 5.85 (1H, ddt, J=17.0, 10.3, 6.5 Hz), 7.33-7.52 (5H, m), 7.74-7.78 (1H, m), 7.79-7.87 (1H, m), 8.28 (1H, dd, J=8.6, 2.3 Hz), 8.33 (1H, d, J=2.3 Hz), 8.43 (1H, d, J=8.6 Hz).

F) 3-Amino-16-oxo-6,7,8,9,10,16-hexahydro-5H-dibenzo[b,j][1]oxacyclododecine-11-carboxylic acid hydrobromate A second-generation Hoveyda-Grubbs catalyst (15.59 mg) was added to a mixture of benzyl 4-bromo-2-(but-3-en-1-yl)-3-((2-(but-3-en-1-yl)-4-nitrobenzoyl)oxy)benzoate (280 mg) and toluene (800 mL) at 90° C., followed by stirring at the same temperature for 30 minutes. A second-generation Hoveyda-Grubbs catalyst (15.59 mg) was added to the reaction mixture at 90° C., followed by stirring at the same temperature for 30 minutes, followed by concentration under reduced pressure. The residue was purified by silica gel column chromatography (ethyl acetate/hexane). A mixture of the residue, 20% palladium hydroxide on carbon (70 mg, water content: about 50%), and 2-propanol (3 mL) was stirred under a hydrogen atmosphere at room temperature for 3 days. The catalyst was removed by filtration, and the filtrate was then concentrated under reduced pressure. A mixture of the residue, 20% palladium hydroxide on carbon (70 mg, water content: about 50%), and 2-propanol (3 mL) was stirred at room temperature overnight. The catalyst was removed by filtration, and the filtrate was then concentrated under reduced pressure to obtain the title compound (53.0 mg).

MS: [M+H]$^+$ 340.1.

G) (S)-Dibenzyl 2-(3-amino-16-oxo-6,7,8,9,10,16-hexahydro-5H-dibenzo[b,j][1]oxacyclododecine-11-carboxamide)succinate A mixture of 3-amino-16-oxo-6,7,8,9,10,16-hexahydro-5H-dibenzo[b,j][1]oxacyclododecine-11-carboxylic acid hydrobromate (53.0 mg), (S)-dibenzyl 2-aminosuccinate hydrochloride (52.9 mg), WSC hydrochloride (29.0 mg), HOBt.H$_2$O (23.17 mg), N,N-diisopropylethylamine (0.110 mL), and DMF (1 mL) was stirred at room temperature overnight. Water was added to the reaction mixture, followed by extraction with ethyl acetate. The organic layer was washed with a saturated saline solution and was dried over anhydrous magnesium sulfate, and the solvent was then distilled under reduced pressure. The residue was purified by silica gel column chromatography (ethyl acetate/hexane) to obtain the title compound (39.5 mg).

MS: [M+H]$^+$ 635.3.

H) (S)-2-(3-Amino-16-oxo-6,7,8,9,10,16-hexahydro-5H-dibenzo[b,j][1]oxacyclododecine-11-carboxamide)succinic acid A mixture of (S)-dibenzyl 2-(3-amino-16-oxo-6,7,8,9,10,16-hexahydro-5H-dibenzo[b,j][1]oxacyclododecine-11-carboxamide)succinate (39.5 mg), 10% palladium on carbon (10 mg, water content: about 55%), and THF (1 mL) was stirred under a hydrogen atmosphere at room temperature overnight. The catalyst was removed by filtration, and the filtrate was then concentrated under reduced pressure to obtain the title compound (40.0 mg).

MS: [M+H]$^+$ 455.2.

I) N-((3-Carbamimidamido-16-oxo-5,7,8,9,10,16-hexahydro-6H-dibenzo[b,j]oxacyclododecin-11-yl)carbonyl)-L-aspartic acid A solution (0.233 mL) of 4 M hydrogen chloride in cyclopropyl methyl ether was added to a mixture of (S)-2-(3-amino-16-oxo-6,7,8,9,10,16-hexahydro-5H-dibenzo[b,j][1]oxacyclododecine-11-carboxamide)succinic acid (40.0 mg), cyanamide (11.10 mg), and tert-butyl alcohol (1 mL) at room temperature, followed by stirring at 60° C. for 6 hours. The reaction mixture was concentrated under reduced pressure. To a mixture of the residue and water (3 mL), an aqueous solution prepared from ammonium acetate (20.35 mg) and water (2 mL) was added, followed by stirring at room temperature for 1 hour. The precipitated solid was collected by filtration and was washed with water and acetone. The resulting solid was purified by HPLC (C18, mobile phase: water/acetonitrile (system containing 0.1% TFA)), and the obtained fraction was concentrated under reduced pressure. An ammonium acetate aqueous solution was added to the residue to adjust the pH to about 4, followed by stirring at room temperature overnight. The precipitated solid was collected by filtration and was washed with water and acetone to obtain the title compound (11.20 mg).

MS: [M+H]$^+$ 497.2.

$^1$H NMR (400 MHz, DMSO-$d_6$) δ 0.98-1.19 (4H, m), 1.38-1.67 (4H, m), 2.46-2.57 (1H, m), 2.60-2.67 (2H, m), 2.70-2.79 (1H, m), 2.88-3.07 (2H, m), 4.38-4.55 (1H, m), 7.15-7.27 (3H, m), 7.27-7.39 (2H, m), 7.93 (5H, d, J=8.7 Hz), 8.17-8.25 (1H, m).

Example 79

N-(3-(3-Carbamimidamido-14-oxo-7,8-dihydro-6H,14H-dibenzo[b,f][1,5]dioxecin-9-yl)propanoyl)-L-aspartic acid A) (E)-tert-Butyl 3-(3-(benzyloxy)-2-formylphenyl)acrylate Tripotassium phosphate (6.5 g) and palladium acetate (0.110 g) were added to a mixture of 2-(benzyloxy)-6-bromobenzaldehyde (7.14 g), tert-butyl acrylate (7.18 mL), and DMF (72 mL) at room temperature, followed by stirring under a nitrogen atmosphere at 100° C. for 12 hours. A saturated ammonium chloride aqueous solution was added to the reaction mixture at 0° C., followed by extraction with ethyl acetate. The organic layer was washed with water and a saturated saline solution and was then dried over anhydrous sodium sulfate, and the solvent was distilled under reduced pressure. The residue was purified by silica gel column chromatography (ethyl acetate/hexane) to obtain the title compound (7.68 g).

MS: [M+Na]$^+$361.2.

B) (E)-tert-Butyl 3-(3-(benzyloxy)-2-((E)-3-ethoxy-3-oxoprop-1-en-1-yl)phenyl)acrylate 1,8-Diazabicyclo[5.4.0]unde-7-cene (5.5 mL) was added to a mixture of (E)-tert-butyl 3-(3-(benzyloxy)-2-formylphenyl)acrylate (7.68 g), triethyl carboxymethylphosphonate (6.75 mL), lithium chloride (1.45 g), and acetonitrile (150 mL) at 0° C., followed by stirring at room temperature for 6 hours. Water was added to the reaction mixture at 0° C., followed by extraction with ethyl acetate. The organic layer was washed with a saturated saline solution and was then dried over anhydrous sodium sulfate, and the solvent was distilled under reduced pressure. The residue was purified by silica gel column chromatography (ethyl acetate/hexane) to obtain the title compound (6.57 g).

MS: [M+Na]$^+$ 431.2.

C) tert-Butyl 3-(2-(3-ethoxy-3-oxopropyl)-3-hydroxyphenyl)propanoate

A mixture of (E)-tert-butyl 3-(3-(benzyloxy)-2-((E)-3-ethoxy-3-oxoprop-1-en-1-yl)phenyl)acrylate (6.57 g), a palladium on carbon-ethylenediamine complex (742 mg), and toluene (130 mL) was stirred under a hydrogen atmosphere at room temperature for 6 hours. The catalyst was removed by filtration, and the filtrate was then concentrated under reduced pressure. The residue was purified by silica gel column chromatography (ethyl acetate/hexane) to obtain a mixture (5.60 g) of mono-enones.

A mixture of the mono-enone mixture (5.60 g), 10% palladium on carbon (0.700 g, water content: about 55%), and THF (130 mL) was stirred under a hydrogen atmosphere at room temperature overnight. The catalyst was removed by filtration, and the filtrate was then concentrated under reduced pressure to obtain the title compound (4.63 g).

MS: [M+Na]$^+$ 345.2.

D) tert-Butyl 3-(3-(benzyloxy)-2-(3-ethoxy-3-oxopropyl)phenyl)propanoate

Benzyl bromide (1.9 mL) was added to a mixture of tert-butyl 3-(2-(3-ethoxy-3-oxopropyl)-3-hydroxyphenyl) propanoate (4.63 g), potassium carbonate (2.5 g), and DMF (50 mL) at 0° C., followed by stirring at room temperature for 8 hours. The reaction mixture was poured into a mixture of ethyl acetate and 1 N hydrochloric acid at 0° C., followed by extraction with ethyl acetate. The organic layer was washed with water and a saturated saline solution and was then dried over anhydrous sodium sulfate, and the solvent was distilled under reduced pressure. The residue was purified by silica gel column chromatography (ethyl acetate/hexane) to obtain the title compound (5.13 g).

MS: [M+Na]$^+$ 435.2.

E) 3-(3-(Benzyloxy)-2-(3-ethoxy-3-oxopropyl)phenyl)propanoic acid

Four normal hydrogen chloride in ethyl acetate (30 mL) was added to a mixture of tert-butyl 3-(3-(benzyloxy)-2-(3-ethoxy-3-oxopropyl)phenyl)propanoate (5.03 g) and ethyl acetate (30 mL) at 0° C., followed by stirring at room temperature for 24 hours. Four normal hydrogen chloride in ethyl acetate (15 mL) was added to the reaction mixture at 0° C., followed by stirring at room temperature overnight. The reaction mixture was concentrated under reduced pressure, and the residue was purified by silica gel column chromatography (ethyl acetate/hexane) to obtain the title compound (1.905 g).

MS: [M+Na]$^+$ 379.1.

F) 3-(3-(Benzyloxy)-2-(3-hydroxypropyl)phenyl) propanoic acid

Lithium triethylborohydride (0.113 g) was added to a mixture of 3-(3-(benzyloxy)-2-(3-ethoxy-3-oxopropyl)phenyl)propanoic acid (1.8413 g), THF (20 mL), and ethanol (2 mL) at 0° C. twice, followed by stirring at room temperature for 2 hours. One normal hydrochloric acid was added to the reaction mixture at 0° C., followed by extraction with ethyl acetate. The organic layer was washed with a saturated saline solution and was then dried over anhydrous sodium sulfate, and the solvent was distilled under reduced pressure to obtain the title compound (1.613 g).

MS: [M+H]$^+$ 337.1.

G) (S)-Di-tert-butyl 2-(3-(3-(benzyloxy)-2-(3-hydroxypropyl)phenyl)propanamide)succinate (S)-Di-tert-butyl 2-aminosuccinate hydrochloride (1.710 g), N,N-diisopropylethylamine (2.20 mL), HOBt.H$_2$O (0.929 g), and WSC hydrochloride (1.163 g) were added to a mixture of 3-(3-(benzyloxy)-2-(3-hydroxypropyl)phenyl) propanoic acid (1.59 g) and DMF (32 mL) at 0° C., followed by stirring at room temperature overnight. Water was added to the reaction mixture at 0° C., followed by extraction with ethyl acetate. The organic layer was washed with 1 N hydrochloric acid, water, a saturated sodium hydrogen carbonate aqueous solution, and a saturated saline solution and was then dried over anhydrous sodium sulfate, and the solvent was distilled under reduced pressure. The residue was purified by silica gel column chromatography (ethyl acetate/hexane) to obtain the title compound (2.65 g).

MS: [M+H]$^+$ 542.4.

H) (S)-Di-tert-butyl 2-(3-(3-(benzyloxy)-2-(3-(2-((benzyloxy)carbonyl)-5-((tert-butoxycarbonyl) amino)phenoxy)propyl)phenyl)propanamide)succinate 1,1'-(Azodicarbonyl)dipiperidine (726 mg), tributylphosphine (0.709 mL), and toluene (5 mL) were added to a mixture of (S)-di-tert-butyl 2-(3-(3-(benzyloxy)-2-(3-hydroxypropyl)phenyl)propanamide)succinate (519.2 mg), benzyl 4-((tert-butoxycarbonyl)amino)-2-hydroxybenzoate (329 mg), and toluene (25 mL) at room temperature, followed by stirring at the same temperature for 6 hours. Hexane (30 mL) was added to the reaction mixture at room temperature, followed by stirring at the same temperature for 1 hour. The insoluble matter was removed by filtration, and the filtrate was then concentrated under reduced pressure. The residue was purified by silica gel column chromatography (ethyl acetate/hexane) to obtain the title compound (696 mg).

MS: [M+H]$^+$ 867.2.

I) (S)-4-((tert-Butoxycarbonyl)amino)-2-(3-(2-(3-((1,4-di-tert-butoxy-1,4-dioxobutan-2-yl)amino)-3-oxopropyl)-6-hydroxyphenyl)propoxy)benzoic acid A mixture of (S)-di-tert-butyl 2-(3-(3-(benzyloxy)-2-(3-(2-((benzyloxy)carbonyl)-5-((tert-butoxycarbonyl)amino)phenoxy)propyl)phenyl)propanamide)succinate (798.8 mg), 10% palladium on carbon (80 mg, water content: about 55%), and THF (12 mL) was stirred under a hydrogen atmosphere at room temperature for 8 hours. The catalyst was removed by filtration, and the filtrate was then concentrated under reduced pressure to obtain the title compound (666 mg).

MS: [M+H]$^+$ 687.2.

J) (S)-Di-tert-butyl 2-(3-(3-((tert-butoxycarbonyl)amino)-14-oxo-6,7,8,14-tetrahydrodibenzo[b,f][1,5]dioxecin-9-yl)propanamide)succinate WSC hydrochloride (277 mg) and N,N-dimethyl-4-aminopyridine (25.0 mg) were added to a mixture of (S)-4-((tert-butoxycarbonyl)amino)-2-(3-(2-(3-((1,4-di-tert-butoxy-1,4-dioxobutan-2-yl)amino)-3-oxopropyl)-6-hydroxyphenyl)propoxy)benzoic acid (495.9 mg) and pyridine (25 mL) at 0° C., followed by stirring at room temperature overnight. Four normal hydrogen chloride in cyclopentyl methyl ether (0.511 mL) was added to the reaction mixture at 0° C., and the solvent was distilled under reduced pressure. Ethyl acetate was added to the residue, and the mixture was washed with 1 N hydrochloric acid, water, and a saturated saline solution and was then dried over anhydrous sodium sulfate. The solvent was distilled under reduced pressure. The residue was purified by silica gel column chromatography (ethyl acetate/hexane) to obtain the title compound (251 mg).

MS: [M+Na]$^+$ 691.2.

K) (S)-2-(3-(3-Amino-14-oxo-6,7,8,14-tetrahydrodibenzo[b,f][1,5]dioxecin-9-yl)propanamide)succinic acid hydrochloride A mixture of (S)-di-tert-butyl 2-(3-(3-((tert-butoxycarbonyl)amino)-14-oxo-6,7,8,14-tetrahydrodibenzo[b,f][1,5]dioxecin-9-yl)propanamide)succinate (323.0 mg), 4 N hydrogen chloride in cyclopentyl methyl ether (3 mL), and acetic acid (3 mL) was stirred at room temperature for 1 hour. Acetic acid (6 mL) was added to the reaction mixture at room temperature, followed by stirring at the same temperature overnight. The reaction mixture was concentrated to obtain the title compound (259 mg).

MS: [M+H]$^+$ 457.2.

L) (S)-2-(3-(3-Guanidino-14-oxo-6,7,8,14-tetrahydrodibenzo[b,f][1,5]dioxecin-9-yl)propanamide)succinic acid A mixture of (S)-2-(3-(3-amino-14-oxo-6,7,8,14-tetrahydrodibenzo[b,f][1,5]dioxecin-9-yl)propanamide)succinic acid hydrochloride (135.7 mg), 4 N hydrogen chloride in cyclopentyl methyl ether (0.206 mL), cyanamide (34.7 mg), and tert-butyl alcohol (5 mL) was stirred at 60° C. for 12 hours. Toluene, ethyl acetate, and water were added to the reaction mixture, followed by extraction with water. A mixture of ammonium acetate (63.7 mg) and water (2 mL) was added to the aqueous layer at room temperature, followed by stirring at the same temperature for 2 hours. The precipitated solid was collected by filtration and was washed with water and acetonitrile to obtain the title compound (99 mg).

$^1$H NMR (300 MHz, DMSO-d$_6$) δ 2.14 (2H, d, J=5.7 Hz), 2.23-2.34 (1H, m), 2.36-2.54 (3H, m), 2.75-3.12 (4H, m), 3.58-3.74 (1H, m), 3.75-3.89 (1H, m), 4.21 (1H, ddd, J=10.1, 6.9, 3.4 Hz), 6.79 (1H, d, J=1.9 Hz), 6.95 (1H, dd, J=8.3, 1.9 Hz), 7.00-7.09 (3H, m), 7.47-7.89 (6H, m).

Example 91

3-(10-Carbamimidamido-13-oxo-6,7,8,13-tetrahydrodibenzo[b,f][1,4]dioxecin-4-yl)propanoic acid trifluoroacetate

A) tert-Butyl 3-(3-(benzyloxy)-2-hydroxyphenyl)acrylate tert-Butyl 2-(triphenylphosphoranylidene)acetate (2.15 g) was added to a mixture of 3-(benzyloxy)-2-hydroxybenzaldehyde (1.09 g) and toluene (20 mL) at room temperature, followed by stirring at the same temperature overnight. The reaction mixture was concentrated under reduced pressure, and the residue was purified by silica gel column chromatography (ethyl acetate/hexane) to obtain the title compound (1.400 g).

$^1$H NMR (300 MHz, DMSO-d$_6$) δ 1.48 (9H, s), 5.13-5.23 (2H, m), 5.85 (0.1H, d, J=12.5 Hz), 6.46 (0.9H, d, J=16.1 Hz), 6.63-6.79 (1H, m), 7.03 (1H, dd, J=8.1, 1.3 Hz), 7.17 (1H, dd, J=7.9, 1.1 Hz), 7.26-7.44 (3H, m), 7.45-7.56 (2H, m), 7.81 (1H, d, J=16.2 Hz), 9.30 (1H, s).

B) Benzyl 2-(3-(2-(benzyloxy)-6-(3-(tert-butoxy)-3-oxoprop-1-en-1-yl)phenoxy)propyl)-4-((tert-butoxycarbonyl)amino)benzoate 1,1'-(Azodicarbonyl)dipiperidine (2.165 g), tributylphosphine (2.13 mL), and toluene (84 mL) were added to a mixture of tert-butyl 3-(3-(benzyloxy)-2-hydroxyphenyl)acrylate (1.40 g), benzyl 4-((tert-butoxycarbonyl)amino)-2-(3-hydroxypropyl)benzoate (1.70 g), and toluene (28 mL) at room temperature, followed by stirring at the same temperature overnight. Hexane (112 mL) was added to the reaction mixture at room temperature, followed by stirring at the same temperature for 1 hour. The insoluble matter was removed by filtration, and the filtrate was then concentrated under reduced pressure. The residue was purified by silica gel column chromatography (ethyl acetate/hexane) to obtain the title compound (2.75 g).

MS: [M+Na]$^+$ 716.3.

C) 2-(3-(2-(3-(tert-Butoxy)-3-oxopropyl)-6-hydroxyphenoxy)propyl)-4-((tert-butoxycarbonyl)amino)benzoic acid A mixture of benzyl 2-(3-(2-(benzyloxy)-6-(3-(tert-butoxy)-3-oxoprop-1-en-1-yl)phenoxy)propyl)-4-((tert-butoxycarbonyl)amino)benzoate (2.75 g), 10% palladium on carbon (283.1 mg, water content: about 55%), and THF (60 mL) was stirred under a hydrogen atmosphere at room temperature overnight. The catalyst was removed by filtration, and the filtrate was then concentrated under reduced pressure to obtain the title compound (2.180 g).

MS: [M+Na]$^+$ 538.2.

D) tert-Butyl 3-(10-((tert-butoxycarbonyl)amino)-13-oxo-6,7,8,13-tetrahydrodibenzo[b,f][1,4]dioxecin-4-yl)propanoate WSC hydrochloride (1.21 g) and N,N-dimethyl-4-aminopyridine (26.8 mg) were added to a mixture of 2-(3-(2-(3-(tert-butoxy)-3-oxopropyl)-6-hydroxyphenoxy)propyl)-4-((tert-butoxycarbonyl)amino)benzoic acid (2.17 g) and pyridine (55 mL) at 0° C., followed by stirring at room temperature overnight. The reaction mixture was distilled under reduced pressure. Ethyl acetate was added to the residue, and the mixture was washed with 1 N hydrochloric acid, water, and a saturated saline solution and was then dried over anhydrous sodium sulfate. The solvent was distilled under reduced pressure. The residue was purified by silica gel column chromatography (ethyl acetate/hexane) to obtain the title compound (1.540 g).
MS: [M+Na]$^+$ 520.2.

E) 3-(10-Amino-13-oxo-6,7,8,13-tetrahydrodibenzo[b,f][1,4]dioxecin-4-yl)propanoic acid hydrochloride A mixture of tert-butyl 3-(10-((tert-butoxycarbonyl)amino)-13-oxo-6,7,8,13-tetrahydrodibenzo[b,f][1,4]dioxecin-4-yl)propanoate (1.54 g), 4 N hydrogen chloride in cyclopentyl methyl ether (16 mL), and acetic acid (16 mL) was stirred at room temperature overnight. The reaction mixture was concentrated to obtain the title compound (1.140 g).
MS: [M+Na]$^+$ 364.0.

F) 3-(10-Carbamimidamido-13-oxo-6,7,8,13-tetrahydrodibenzo[b,f][1,4]dioxecin-4-yl)propanoic acid trifluoroacetate Four normal hydrogen chloride in cyclopentyl methyl ether (0.300 mL) and cyanamide (50.2 mg) were added to a mixture of 3-(10-amino-13-oxo-6,7,8,13-tetrahydrodibenzo[b,f][1,4]dioxecin-4-yl)propanoic acid hydrochloride (150.4 mg) and tert-butyl alcohol (3 mL) at room temperature, followed by stirring at 60° C. for 18 hours. To the reaction mixture, 4 N hydrogen chloride in cyclopentyl methyl ether (0.300 mL) and cyanamide (50.2 mg) were added at room temperature, followed by stirring at 60° C. for 6 hours. The reaction mixture was concentrated, and the residue was purified by HPLC (C18, mobile phase: water/acetonitrile (system containing 0.1% TFA)) to obtain the title compound (165 mg).
$^1$H NMR (300 MHz, DMSO-d$_6$) δ 1.91-2.06 (2H, m), 2.52-2.59 (2H, m), 2.78-2.97 (2H, m), 3.21-3.39 (2H, m), 3.93 (2H, t, J=5.2 Hz), 7.02-7.22 (2H, m), 7.23-7.39 (3H, m), 7.71 (4H, s), 7.90 (1H, d, J=8.2 Hz), 10.06 (1H, s), 12.16 (1H, brs).

Example 94

N-((10-Carbamimidamido-13-oxo-6,7,8,13-tetrahydrodibenzo[b,f][1,4]dioxecin-4-yl)carbonyl)-N-(carboxymethyl)-O-methyl-L-tyrosine

A) (S)-tert-Butyl 2-((2-(tert-butoxy)-2-oxoethyl)amino)-3-(4-hydroxyphenyl)propanoate tert-Butyl bromoacetate (4.5 mL) was added to a mixture of (S)-tert-butyl 2-amino-3-(4-hydroxyphenyl)propanoate (6.00 g), N,N-diisopropylethylamine (9.0 mL), and acetonitrile (90 mL) at 0° C., followed by stirring at room temperature for 66 hours. Water was added to the reaction mixture at 0° C., followed by extraction with ethyl acetate. The organic layer was washed with a saturated saline solution and was then dried over anhydrous sodium sulfate, and the solvent was distilled under reduced pressure. The residue was purified by silica gel column chromatography (ethyl acetate/hexane) to obtain the title compound (7.60 g).
MS: [M+H]$^+$ 352.1.

B) (S)-tert-Butyl 2-((2-(tert-butoxy)-2-oxoethyl)amino)-3-(4-methoxyphenyl)propanoate 1,1'-(Azodicarbonyl)dipiperidine (1.436 g), tributylphosphine (1.404 mL), and toluene (40 mL) were added to a mixture of (S)-tert-butyl 2-((2-(tert-butoxy)-2-oxoethyl)amino)-3-(4-hydroxyphenyl)propanoate (1.00 g), methanol (0.576 mL), and toluene (20 mL) at room temperature, followed by stirring at the same temperature overnight. Hexane (60 mL) was added to the reaction mixture at room temperature, followed by stirring at the same temperature for 1 hour. The insoluble matter was removed by filtration, and the filtrate was then concentrated under reduced pressure. The residue was purified by silica gel column chromatography (ethyl acetate/hexane) to obtain the title compound (1.020 g).
MS: [M+H]$^+$ 366.1.

C) (S)-tert-Butyl 2-(N-(2-(tert-butoxy)-2-oxoethyl)-10-guanidino-13-oxo-6,7,8,13-tetrahydrodibenzo[b,f][1,4]dioxecine-4-carboxamide)-3-(4-methoxyphenyl)propanoate N,N'-Dicyclohexylcarbodiimide (182 mg) was added to a mixture of 10-guanidino-13-oxo-6,7,8,13-tetrahydrodibenzo[b,f][1,4]dioxecine-4-carboxylic acid hydrochloride (172.8 mg), (S)-tert-butyl 2-((2-(tert-butoxy)-2-oxoethyl)amino)-3-(4-methoxyphenyl)propanoate (189.7 mg), pyridine (1.5 mL), and DMF (1.5 mL) at room temperature, followed by stirring at 50° C. for 2 hours. The reaction mixture was concentrated under reduced pressure, and the residue was then purified by silica gel column chromatography (NH, ethyl acetate/hexane) to obtain the title compound (211 mg).
MS: [M+H]$^+$ 703.4.

D) N-((10-carbamimidamido-13-oxo-6,7,8,13-tetrahydrodibenzo[b,f][1,4]dioxecin-4-yl)carbonyl)-N-(carboxymethyl)-O-methyl-L-tyrosine A mixture of (S)-tert-butyl 2-(N-(2-(tert-butoxy)-2-oxoethyl)-10-guanidino-13-oxo-6,7,8,13-tetrahydrodibenzo[b,f][1,4]dioxecine-4-carboxamide)-3-(4-methoxyphenyl)propanoate (207.0 mg), 4 N hydrogen chloride in cyclopentyl methyl ether (1 mL), and acetic acid (1 mL) was stirred at room temperature overnight. The reaction mixture was concentrated under reduced pressure, and a 1 M ammonium acetate aqueous solution was then added to a mixture of the residue and water to adjust the pH to 4, followed by stirring at room temperature for 2 hours. The precipitated solid was collected by filtration and was washed with water and acetonitrile. The resulting crude product was purified by HPLC (C18, mobile phase: water/acetonitrile (system containing 0.1% TFA)), and the obtained fraction was concentrated under reduced pressure. Water and a 1 M ammonium acetate aqueous solution were added to the residue at room temperature to adjust the pH of the mixture to 4, followed by stirring at room temperature for 2 hours. The precipitated solid was collected by filtration and was washed with water and acetonitrile to obtain the title compound (21.3 mg) as crude crystals.

$^1$H NMR (300 MHz, DMSO-d$_6$) δ 1.60-2.17 (2H, m), 2.66-3.58 (6H, m), 3.60-4.24 (6H, m), 6.68-7.10 (4H, m), 7.10-7.37 (4H, m), 7.39-7.54 (1H, m), 7.55-8.03 (5H, m), 10.00 (2H, brs).

Example 99

1-((10-Carbamimidamido-13-oxo-6,7,8,13-tetrahydrodibenzo[b,f][1,4]dioxecin-4-yl)carbonyl)-L-prolyl-L-aspartic acid A) (S)-tert-Butyl 1-(10-amino-13-oxo-6,7,8,13-tetrahydrodibenzo[b,f][1,4]dioxecine-4-carbonyl)pyrrolidine-2-carboxylate A mixture of 10-amino-13-oxo-6,7,8,13-tetrahydrodibenzo[b,f][1,4]dioxecine-4-carboxylic acid hydrochloride (200 mg), L-proline tert-butyl ester hydrochloride (178 mg), WSC hydrochloride (164 mg), HOBt.H$_2$O (131 mg), N,N-diisopropylethylamine (0.499 mL), and DMF (3 mL) was stirred at room temperature for 5 hours. Water was added to the reaction mixture at 0° C., followed by extraction with ethyl acetate. The organic layer was washed with 1 N hydrochloric acid, water, and a saturated saline solution and was then dried over anhydrous magnesium sulfate, and the solvent was distilled under reduced pressure. The residue was purified by silica gel column chromatography (ethyl acetate/hexane) to obtain the title compound (238 mg).

MS: [M+H]$^+$ 467.2.

B) (S)-1-(10-Amino-13-oxo-6,7,8,13-tetrahydrodibenzo[b,f][1,4]dioxecine-4-carbonyl)pyrrolidine-2-carboxylic acid hydrochloride A mixture of (S)-tert-butyl 1-(10-amino-13-oxo-6,7,8,13-tetrahydrodibenzo[b,f][1,4]dioxecine-4-carbonyl)pyrrolidine-2-carboxylate (236 mg), 4 M hydrogen chloride in cyclopentyl methyl ether (2 mL), and acetic acid (2 mL) was stirred at 40° C. for 3 hours. The reaction mixture was concentrated under reduced pressure to obtain the title compound (265 mg).

MS: [M+H]$^+$ 411.1.

C) (S)-Dibenzyl 2-((S)-1-(10-amino-13-oxo-6,7,8,13-tetrahydrodibenzo[b,f][1,4]dioxecine-4-carbonyl)pyrrolidine-2-carboxamide)succinate A mixture of (S)-1-(10-amino-13-oxo-6,7,8,13-tetrahydrodibenzo[b,f][1,4]dioxecine-4-carbonyl)pyrrolidine-2-carboxylic acid hydrochloride (263 mg), (S)-dibenzyl 2-aminosuccinate hydrochloride (309 mg), WSC hydrochloride (169 mg), HOBt.H$_2$O (135 mg), N,N-diisopropylethylamine (0.514 mL), and DMF (4 mL) was stirred at room temperature overnight. Water was added to the reaction mixture at 0° C., followed by extraction with ethyl acetate. The organic layer was washed with 1 N hydrochloric acid, water, and a saturated saline solution and was then dried over anhydrous magnesium sulfate, and the solvent was distilled under reduced pressure. The residue was purified by silica gel column chromatography (ethyl acetate/hexane) to obtain the title compound (218.9 mg).

MS: [M+H]$^+$ 706.3.

D) (S)-2-((S)-1-(10-Amino-13-oxo-6,7,8,13-tetrahydrodibenzo[b,f][1,4]dioxecine-4-carbonyl)pyrrolidine-2-carboxamide)succinic acid A mixture of (S)-dibenzyl 2-((S)-1-(10-amino-13-oxo-6,7,8,13-tetrahydrodibenzo[b,f][1,4]dioxecine-4-carbonyl)pyrrolidine-2-carboxamide)succinate (217 mg), 10% palladium on carbon (25 mg, water content: about 55%), and THF (4 mL) was stirred under a hydrogen atmosphere at room temperature for 6 hours. The catalyst was removed by filtration, and the filtrate was then concentrated under reduced pressure to obtain the title compound (190.6 mg).

MS: [M+H]$^+$ 526.2.

E) 1-((10-Carbamimidamido-13-oxo-6,7,8,13-tetrahydrodibenzo[b,f][1,4]dioxecin-4-yl)carbonyl)-L-prolyl-L-aspartic acid Four mole hydrogen chloride in cyclopentyl methyl ether (0.233 mL) and cyanamide (39.1 mg) were added to a mixture of (S)-2-((S)-1-(10-amino-13-oxo-6,7,8,13-tetrahydrodibenzo[b,f][1,4]dioxecine-4-carbonyl)pyrrolidine-2-carboxamide)succinic acid (163 mg) and tert-butyl alcohol (3 mL) at room temperature, followed by stirring at 60° C. for 4 hours. The reaction mixture was concentrated under reduced pressure, and the residue was purified by HPLC (C18, mobile phase: water/acetonitrile (system containing 0.1% TFA)). The obtained fraction was concentrated under reduced pressure. An aqueous solution (1 mL) of ammonium acetate (71.7 mg) was added to a mixture of the residue and water (1.5 mL) at room temperature, followed by stirring at 0° C. for 1 hour and further at room temperature for 1 hour. The precipitated solid was collected by filtration and was washed with water to obtain the title compound (89.1 mg).

$^1$H NMR (300 MHz, DMSO-d$_6$) δ 1.72-2.01 (6H, m), 3.13-3.22 (3H, m), 3.59 (1H, t, J=6.6 Hz), 3.84 (2H, d, J=10.3 Hz), 3.90-4.09 (2H, m), 4.23 (1H, brs), 4.52 (1H, dd, J=8.4, 4.4 Hz), 7.20-7.25 (3H, m), 7.29 (1H, s), 7.54 (1H, dd, J=6.0, 3.6 Hz), 7.67 (4H, brs), 7.79-7.89 (2H, m).

Example 104

N-((10-Carbamimidamido-13-oxo-6,7,8,13-tetrahydrodibenzo[b,f][1,4]dioxecin-4-yl)carbonyl)-N-(carboxymethyl)-L-aspartic acid A) (S)-Dibenzyl 2-((2-(benzyloxy)-2-oxoethyl)amino)succinate Benzyl 2-bromoacetate (0.377 mL) was added to a mixture of (S)-dibenzyl 2-aminosuccinate hydrochloride (555.7 mg), N,N-diisopropylethylamine (0.832 mL), and acetonitrile (10 mL) at 0° C., followed by stirring at room temperature overnight. N,N-Diisopropylethylamine (0.832 mL) was added to the reaction mixture at room temperature, followed by stirring at the same temperature for 72 hours. Water and ethyl acetate were added to the reaction mixture at 0° C., followed by extraction with ethyl acetate. The organic layer was washed with a saturated saline solution and was then dried over anhydrous sodium sulfate, and the solvent was distilled under reduced pressure. The residue was purified by silica gel column chromatography (ethyl acetate/hexane) to obtain the title compound (587 mg).

MS: [M+H]$^+$ 462.1.

B) N-((10-Carbamimidamido-13-oxo-6,7,8,13-tetrahydrodibenzo[b,f][1,4]dioxecin-4-yl)carbonyl)-N-(carboxymethyl)-L-aspartic acid N,N'-Dicyclohexylcarbodiimide (160 mg) was added to a mixture of 10-guanidino-13-oxo-6,7,8,13-tetrahydrodibenzo[b,f][1,4]dioxecine-4-carboxylic acid hydrochloride (152.1 mg), (S)-dibenzyl 2-((2-(benzyloxy)-2-oxoethyl)amino)succinate (202.0 mg), pyridine (1.5 mL), and DMF (1.5 mL) at room temperature, followed by stirring at 50° C. for 4 hours. Acetonitrile (2 mL) was added to the reaction mixture at room temperature, followed by stirring at the same temperature for 30 minutes. The insoluble matter was removed by filtration, and the filtrate was then concentrated under reduced pressure. A mixture of the residue, 10% palladium on carbon (56.8 mg, water content: about 55%), 6 N hydrochloric acid (0.323 mL), and THF (6 mL) was stirred under a hydrogen atmosphere at room temperature overnight. The catalyst was removed by filtration, and the filtrate was then concentrated under reduced pressure. The residue was purified by HPLC (C18, mobile phase: water/acetonitrile (system containing 0.1% TFA)), and the obtained fraction was concentrated under reduced pressure. Water and a 1 M ammonium acetate aqueous solution were added to the residue at room temperature to adjust the pH of the mixture to 4, followed by stirring at room temperature for 1 hour. The precipitated solid was collected by filtration and was washed with water to obtain the title compound (22.40 mg).

$^1$H NMR (300 MHz, DMSO-$d_6$) δ 1.58-2.18 (2H, m), 2.68-3.47 (4H, m), 3.49-4.37 (5H, m), 6.98 (1H, dd, J=7.6, 1.5 Hz), 7.15-7.38 (3H, m), 7.43-8.02 (6H, m), 9.99 (1H, brs), 12.46 (1H, s).

Example 106

3-(((10-Carbamimidamido-13-oxo-6,7,8,13-tetrahydrodibenzo[b,f][1,4]dioxecin-4-yl)carbonyl) (carboxymethyl)amino)pentanedioic acid

A) Dibenzyl 3-((2-(benzyloxy)-2-oxoethyl)amino) pentanedioate

Benzyl 2-bromoacetate (0.174 mL) was added to a mixture of dibenzyl 3-aminopentanedioate hydrochloride (199.7 mg), N,N-diisopropylethylamine (0.479 mL), and acetonitrile (4 mL) at 0° C., followed by stirring at room temperature overnight. Water was added to the reaction mixture, followed by extraction with ethyl acetate. The organic layer was washed with a saturated saline solution and was then dried over anhydrous sodium sulfate, and the solvent was distilled under reduced pressure. The residue was purified by silica gel column chromatography (ethyl acetate/hexane) to obtain the title compound (225 mg).

MS: [M+H]$^+$ 476.1.

B) 3-(((10-Carbamimidamido-13-oxo-6,7,8,13-tetrahydrodibenzo[b,f][1,4]dioxecin-4-yl)carbonyl) (carboxymethyl)amino)pentanedioic acid N,N'-Dicyclohexylcarbodiimide (174 mg) was added to a mixture of 10-guanidino-13-oxo-6,7,8,13-tetrahydrodibenzo[b,f][1,4]dioxecine-4-carboxylic acid hydrochloride (165.2 mg), dibenzyl 3-((2-(benzyloxy)-2-oxoethyl)amino)pentanedioate (220.1 mg), pyridine (1.5 mL), and DMF (1.5 mL) at room temperature, followed by stirring at 50° C. overnight. Acetonitrile (3 mL) was added to the reaction mixture at room temperature, followed by stirring at the same temperature for 30 minutes. The insoluble matter was removed by filtration, and the filtrate was then concentrated under reduced pressure. A mixture of the residue, 10% palladium on carbon (56.8 mg, water content: about 55%), 6 N hydrochloric acid (0.351 mL), and THF (9 mL) was stirred under a hydrogen atmosphere at room temperature overnight. The catalyst was removed by filtration, and the filtrate was then concentrated under reduced pressure. The residue was distributed between ethyl acetate and water, and the aqueous layer was purified by HPLC (C18, mobile phase: water/acetonitrile (system containing 0.1% TFA)). The obtained fraction was concentrated under reduced pressure. To the residue, water (3 mL) and a 1 M ammonium acetate aqueous solution were added at room temperature to adjust the pH of the mixture to 4, followed by stirring at room temperature for 2 hours. The precipitated solid was collected by filtration and was washed with water to obtain the title compound (75.3 mg).

$^1$H NMR (300 MHz, DMSO-$d_6$) δ 1.55-2.15 (2H, m), 2.20-3.00 (4H, m), 3.03-5.03 (7H, m), 6.92-7.30 (4H, m), 7.37-7.58 (1H, m), 7.66-8.33 (5H, m).

Example 108

O-(2-(Bis(carboxymethyl)amino)ethyl)-N-((10-carbamimidamido-13-oxo-6,7,8,13-tetrahydrodibenzo [b,f][1,4]dioxecin-4-yl)carbonyl)-N-(carboxymethyl)-L-tyrosine

A) (S)-tert-Butyl 3-(4-(2-(((benzyloxy)carbonyl)amino)ethoxy)phenyl)-2-((2-(tert-butoxy)-2-oxoethyl)amino)propanoate 1,1'-(Azodicarbonyl)dipiperidine (862 mg), tributylphosphine (0.842 mL), and toluene (40 mL) were added to a mixture of (S)-tert-butyl 2-((2-(tert-butoxy)-2-oxoethyl)amino)-3-(4-hydroxyphenyl)propanoate (600 mg), benzyl N-(2-hydroxyethyl)carbamate (500 mg), and toluene (12 mL) at room temperature, followed by stirring at the same temperature overnight. Benzyl N-(2-hydroxyethyl)carbamate (250 mg), 1,1'-(azodicarbonyl)dipiperidine (431 mg), and tributylphosphine (0.421 mL) were added to the mixture at room temperature, followed by stirring at the same temperature for 4 hours. Benzyl N-(2-hydroxyethyl)carbamate (125 mg), 1,1'-(azodicarbonyl)dipiperidine (215 mg), and tributylphosphine (0.210 mL) were further added to the mixture at room temperature, followed by stirring at the same temperature overnight. Hexane (52 mL) was added to the reaction mixture at room temperature, followed by stirring at the same temperature for 30 minutes. The insoluble matter was removed by filtration, and the filtrate was then concentrated under reduced pressure. The residue was purified by silica gel column chromatography (ethyl acetate/hexane) to obtain the title compound (752.1 mg).

MS: [M+H]$^+$ 529.3.

B) (S)-tert-Butyl 3-(4-(2-aminoethoxy)phenyl)-2-((2-(tert-butoxy)-2-oxoethyl)amino)propanoate A mixture of (S)-tert-butyl 3-(4-(2-(((benzyloxy)carbonyl)amino)ethoxy)phenyl)-2-((2-(tert-butoxy)-2-oxoethyl)amino)propanoate (751 mg), 10% palladium on carbon (75 mg, water content: about 55%), and ethanol (15 mL) was stirred under a hydrogen atmosphere at room temperature for 3 hours. The catalyst was removed by filtration, and the filtrate was then concentrated under reduced pressure to obtain the title compound (556.7 mg).

MS: [M+H]$^+$ 395.2.

C) (S)-Di-tert-butyl 2,2'-((2-(4-(3-(tert-butoxy)-2-((2-(tert-butoxy)-2-oxoethyl)amino)-3-oxopropyl)phenoxy)ethyl)azanediyl)diacetate tert-Butyl bromoacetate (0.169 mL) was added to a mixture of (S)-tert-butyl 3-(4-(2-aminoethoxy)phenyl)-2-((2-(tert-butoxy)-2-oxoethyl)amino)propanoate (179 mg), potassium carbonate (144 mg), and DMF (3 mL) at room temperature, followed by stirring at the same temperature overnight. Water was added to the reaction mixture at room temperature, followed by extraction with ethyl acetate. The organic layer was washed with water and a saturated saline solution and was then dried over anhydrous magnesium sulfate, and the solvent was distilled under reduced pressure. The residue was purified by silica gel column chromatography (ethyl acetate/hexane) to obtain the title compound (71.3 mg).

MS: [M+H]$^+$ 623.4.

D) (S)-Di-tert-butyl 2,2'-((2-(4-(3-(tert-butoxy)-2-(N-(2-(tert-butoxy)-2-oxoethyl)-10-guanidino-13-oxo-6,7,8,13-tetrahydrodibenzo[b,f][1,4]dioxecine-4-carboxamide)-3-oxopropyl)phenoxy)ethyl)azanediyl)diacetate ditrifluoroacetate N,N'-Dicyclohexylcarbodiimide (47.2 mg) was added to a mixture of 10-guanidino-13-oxo-6,7,8,13-tetrahydrodibenzo[b,f][1,4]dioxecine-4-carboxylic acid hydrochloride (44.9 mg), (S)-di-tert-butyl 2,2'-((2-(4-(3-(tert-butoxy)-2-((2-(tert-butoxy)-2-oxoethyl)amino)-3-oxopropyl)phenoxy)ethyl)azanediyl)diacetate (71.3 mg), pyridine (1 mL), and DMF (1 mL) at room temperature, followed by stirring at 50° C. overnight. The reaction mixture was concentrated under reduced pressure, acetonitrile was then added to the residue, and the insoluble matter was removed by filtration. The filtrate was purified by HPLC (C18, mobile phase: water/acetonitrile (system containing 0.1% TFA)) to obtain the title compound (68.2 mg).

MS: [M+H]$^+$ 960.5.

E) O-(2-(Bis(carboxymethyl)amino)ethyl)-N-((10-carbamimidamido-13-oxo-6,7,8,13-tetrahydrodibenzo[b,f][1,4]dioxecin-4-yl)carbonyl)-N-(carboxymethyl)-L-tyrosine (S)-Di-tert-butyl 2,2'-((2-(4-(3-(tert-butoxy)-2-(N-(2-(tert-butoxy)-2-oxoethyl)-10-guanidino-13-oxo-6,7,8,13-tetrahydrodibenzo[b,f][1,4]dioxecine-4-carboxamide)-3-oxopropyl)phenoxy)ethyl)azanediyl)diacetate ditrifluoroacetate (68 mg), 4 N hydrogen chloride in cyclopentyl methyl ether (0.5 mL), and acetic acid (0.5 mL) were added at room temperature, followed by stirring at the same temperature overnight. The reaction mixture was concentrated under reduced pressure, and an aqueous solution (0.5 mL) of ammonium acetate (32.8 mg) was added to a mixture of the residue (37 mg) and water (0.5 mL) at room temperature, followed by stirring at 0° C. for 1 hour. The precipitated solid was collected by filtration and was washed with water to obtain the title compound (24.1 mg).

$^1$H NMR (300 MHz, DMSO-d$_6$) δ 2.32-2.49 (2H, m), 2.87-3.20 (6H, m), 3.39-3.66 (10H, m), 3.92-4.07 (1H, m), 6.60-7.31 (9H, m), 7.30-7.40 (1H, m), 7.41-7.60 (1H, m), 7.60-8.18 (3H, m).

Example 110

N-((10-Carbamimidamido-3-(2-carboxyethyl)-13-oxo-6,7,8,13-tetrahydrodibenzo[b,f][1,4]dioxecin-4-yl)carbonyl)-L-aspartic acid A) Benzyl 2-(3-(6-(benzyloxy)-3-bromo-2-formylphenoxy)propyl)-4-((tert-butoxycarbonyl)amino)benzoate Methanesulfonyl chloride (1.56 mL) and triethylamine (6.39 mL) were added to a mixture of benzyl 4-((tert-butoxycarbonyl)amino)-2-(3-((methylsulfonyl)oxy)propyl)benzoate (7.07 g) and THF (140 mL) at 0° C., followed by stirring at room temperature for 1 hour. A saturated ammonium chloride aqueous solution was added to the reaction mixture at 0° C., followed by extraction with ethyl acetate. The organic layer was washed with a saturated saline solution and was then dried over anhydrous sodium sulfate, and the solvent was distilled under reduced pressure.

Potassium carbonate (5.29 g) was added to a mixture of a crude product (9.44 g) of benzyl 4-((tert-butoxycarbonyl)amino)-2-(3-((methylsulfonyl)oxy)propyl)benzoate, 3-(benzyloxy)-6-bromo-2-hydroxybenzaldehyde (4.7030 g), and DMF (90 mL) at room temperature, followed by stirring at 80° C. overnight. Ethyl acetate and 1 N hydrochloric acid were added to the reaction mixture at 0° C., followed by extraction with ethyl acetate. The organic layer was washed with water and a saturated saline solution and was then dried over anhydrous sodium sulfate, and the solvent was distilled under reduced pressure. The residue was purified by silica gel column chromatography (ethyl acetate/hexane) to obtain the title compound (9.33 g).

MS: [M+Na]$^+$696.2.

B) (E)-Benzyl 2-(3-(6-(benzyloxy)-3-(3-(tert-butoxy)-3-oxoprop-1-en-1-yl)-2-formylphenoxy)propyl)-4-((tert-butoxycarbonyl)amino)benzoate Tripotassium phosphate (77 mg) and palladium acetate (3.41 mg) were added to a mixture of benzyl 2-(3-(6-(benzyloxy)-3-bromo-2-formylphenoxy)propyl)-4-((tert-butoxycarbonyl)amino)benzoate (205.0 mg), tert-butyl acrylate (0.089 mL), and DMF (2 mL) at room temperature, followed by stirring under a nitrogen atmosphere at 100° C. for 150 minutes. Water was added to the reaction mixture at 0° C., followed by extraction with ethyl acetate. The organic layer was washed with water and a saturated saline solution and was then dried over anhydrous sodium sulfate, and the solvent was distilled under reduced pressure. The residue was purified by silica gel column chromatography (ethyl acetate/hexane) to obtain the title compound (176 mg).

MS: [M+Na]$^+$744.3.

C) (E)-3-(Benzyloxy)-2-(3-(2-((benzyloxy)carbonyl)-5-((tert-butoxycarbonyl)amino)phenyl)propoxy)-6-(3-(tert-butoxy)-3-oxoprop-1-en-1-yl)benzoic acid 2-Methyl-2-butene (0.200 mL), sodium dihydrogen phosphate dihydrate (112 mg), and sodium chlorite (82 mg) were added to a mixture of (E)-benzyl 2-(3-(6-(benzyloxy)-3-(3-(tert-butoxy)-3-oxoprop-1-en-1-yl)-2-formylphenoxy)propyl)-4-((tert-butoxycarbonyl)amino)benzoate (172.1 mg), acetonitrile (1.0 mL), and tert-butanol/water (4:1, 4 mL) at 0° C., followed by stirring at room temperature for 1 hour. Water was added to the reaction mixture at 0° C., followed by extraction with ethyl acetate. The organic layer was washed with a saturated saline solution and was then dried over anhydrous sodium sulfate, and the solvent was distilled under reduced pressure. The residue was purified by silica gel column chromatography (ethyl acetate/hexane) to obtain the title compound (127 mg).

MS: [M+Na]+760.3.

D) (S,E)-Di-tert-butyl 2-(3-(benzyloxy)-2-(3-(2-((benzyloxy)carbonyl)-5-((tert-butoxycarbonyl)amino)phenyl)propoxy)-6-(3-(tert-butoxy)-3-oxoprop-1-en-1-yl)benzamide)succinate N,N-Diisopropylethylamine (0.086 mL), HOBt.H$_2$O (76 mg), and WSC hydrochloride (95 mg) were added to a mixture of (E)-3-(benzyloxy)-2-(3-(2-((benzyloxy)carbonyl)-5-((tert-butoxycarbonyl)amino)phenyl)propoxy)-6-(3-(tert-butoxy)-3-oxoprop-1-en-1-yl)benzoic acid (121.7 mg), (S)-di-tert-butyl 2-aminosuccinate hydrochloride (69.7 mg), and DMF (2 mL) at room temperature, followed by stirring at the same temperature overnight. Water was added to the reaction mixture at 0° C., followed by extraction with ethyl acetate. The organic layer was washed with 1 N hydrochloric acid, water, a saturated sodium hydrogen carbonate aqueous solution, and a saturated saline solution and was then dried over anhydrous sodium sulfate, and the solvent was distilled under reduced pressure. The residue was purified by silica gel column chromatography (ethyl acetate/hexane) to obtain the title compound (146 mg).

MS: [M+H]+ 965.5.

E) (S)-2-(3-(3-(3-(tert-Butoxy)-3-oxopropyl)-2-((1,4-di-tert-butoxy-1,4-dioxobutan-2-yl)carbamoyl)-6-hydroxyphenoxy)propyl)-4-((tert-butoxycarbonyl)amino)benzoic acid A mixture of (S,E)-di-tert-butyl 2-(3-(benzyloxy)-2-(3-(2-((benzyloxy)carbonyl)-5-((tert-butoxycarbonyl)amino)phenyl)propoxy)-6-(3-(tert-butoxy)-3-oxoprop-1-en-1-yl)benzamide)succinate (138.0 mg), 10% palladium on carbon (15.3 mg, water content: about 55%), and THF (2 mL) was stirred under a hydrogen atmosphere at room temperature for 2 hours. The catalyst was removed by filtration, and the filtrate was then concentrated under reduced pressure to obtain the title compound (131 mg).

MS: [M+H]+ 787.4.

F) (S)-Di-tert-butyl 2-(3-(3-(tert-butoxy)-3-oxopropyl)-10-((tert-butoxycarbonyl)amino)-13-oxo-6,7,8,13-tetrahydrodibenzo[b,f][1,4]dioxecine-4-carboxamide)succinate WSC hydrochloride (41.1 mg) and N,N-dimethyl-4-aminopyridine (2.0 mg) were added to a mixture of (S)-2-(3-(3-(3-(tert-butoxy)-3-oxopropyl)-2-((1,4-di-tert-butoxy-1,4-dioxobutan-2-yl)carbamoyl)-6-hydroxyphenoxy)propyl)-4-((tert-butoxycarbonyl)amino)benzoic acid (113 mg) and pyridine (5 mL) at 0° C., followed by stirring at room temperature overnight. To the reaction mixture, 4 N hydrogen chloride in cyclopentyl methyl ether (0.071 mL) was added at 0° C., and the solvent was distilled under reduced pressure. Ethyl acetate was added to the residue. The mixture was washed with 1 N hydrochloric acid, water, a saturated sodium hydrogen carbonate aqueous solution, and a saturated saline solution and was then dried over anhydrous sodium sulfate, and the solvent was distilled under reduced pressure. The residue was purified by silica gel column chromatography (ethyl acetate/hexane) to obtain the title compound (89 mg).

MS: [M+H]+ 769.4.

G) (S)-2-(10-Amino-3-(2-carboxyethyl)-13-oxo-6,7,8,13-tetrahydrodibenzo[b,f][1,4]dioxecine-4-carboxamide)succinic acid hydrochloride A mixture of (S)-di-tert-butyl 2-(3-(3-(tert-butoxy)-3-oxopropyl)-10-((tert-butoxycarbonyl)amino)-13-oxo-6,7,8,13-tetrahydrodibenzo[b,f][1,4]dioxecine-4-carboxamide)succinate (87.1 mg), 4 N hydrogen chloride in cyclopentyl methyl ether (1.5 mL), and acetic acid (1.5 mL) was stirred at room temperature overnight. Ethyl acetate (3 mL) was added to the reaction mixture at room temperature, followed by stirring at the same temperature for 30 minutes. The precipitated solid was collected by filtration and was washed with ethyl acetate to obtain the title compound (52.5 mg).

MS: [M+H]+ 501.2.

H) N-((10-Carbamimidamido-3-(2-carboxyethyl)-13-oxo-6,7,8,13-tetrahydrodibenzo[b,f][1,4]dioxecin-4-yl)carbonyl)-L-aspartic acid A mixture of (S)-2-(10-amino-3-(2-carboxyethyl)-13-oxo-6,7,8,13-tetrahydrodibenzo[b,f][1,4]dioxecine-4-carboxamide)succinic acid hydrochloride (49.0 mg), 4 N hydrogen chloride in cyclopentyl methyl ether (0.068 mL), cyanamide (12.0 mg), and tert-butyl alcohol (1.5 mL) was stirred at 60° C. for 18 hours. Ethyl acetate was added to the reaction mixture, followed by extraction with water. The aqueous layer was purified by HPLC (C18, mobile phase: water/acetonitrile (system containing 0.1% TFA)), and the obtained fraction was concentrated under reduced pressure. Four normal hydrogen chloride in cyclopentyl methyl ether (2 mL) was added to the residue, followed by ultrasonication and then concentration under reduced pressure. Four normal hydrogen chloride in cyclopentyl methyl ether (2 mL) was further added to the residue, followed by ultrasonication and then concentration under reduced pressure. A 1 M ammonium acetate aqueous solution was added to a mixture of the residue and water (1 mL) at room temperature to adjust the pH of the mixture to 3 to 4, followed by stirring at room temperature for 2 hours. The precipitated solid was collected by filtration and was washed with water to obtain the title compound (13.8 mg).

$^1$H NMR (300 MHz, DMSO-d$_6$) δ 1.74-1.98 (1H, m), 2.39-2.57 (2H, m), 2.63 (1H, dd, J=15.7, 10.2 Hz), 2.80 (3H, d, J=6.8 Hz), 3.32 (2H, brs), 3.78-4.08 (3H, m), 4.38-4.55 (1H, m), 7.08 (1H, d, J=8.4 Hz), 7.15-7.32 (2H, m), 7.38 (1H, d, J=8.3 Hz), 7.49-8.05 (5H, m), 8.21 (1H, d, J=7.3 Hz).

Example 114

N-((10-Carbamimidamido-2-cyano-13-oxo-6,7,8,13-tetrahydrodibenzo[b,f][1,4]dioxecin-4-yl)carbonyl)-L-aspartic acid A) Benzyl 2-(3-(2-(benzyloxy)-4-bromo-6-formylphenoxy)propyl)-4-((tert-butoxycarbonyl)amino)benzoate A mixture of benzyl 4-((tert-butoxycarbonyl)amino)-2-(3-((methylsulfonyl)oxy)propyl)benzoate (5.40 g), 3-(benzyloxy)-5-bromo-2-hydroxybenzaldehyde (2.91 g), potassium carbonate (2.88 g), and DMF (100 mL) was stirred at 80° C. overnight. Water was added to the reaction mixture, followed by extraction with ethyl acetate. The organic layer was washed with a saturated saline solution and was dried over anhydrous magnesium sulfate, and the solvent was then distilled under reduced pressure. The residue was purified by silica gel column chromatography (ethyl acetate/hexane) to obtain the title compound (5.59 g).

$^1$H NMR (400 MHz, DMSO-d$_6$) δ 1.47 (9H, s), 1.86-1.97 (2H, m), 2.83-3.04 (2H, m), 4.10 (2H, t, J=6.5 Hz), 5.22 (2H, s), 5.25 (2H, s), 7.27-7.50 (13H, m), 7.64 (1H, d, J=2.3 Hz), 7.81 (1H, d, J=8.7 Hz), 9.65 (1H, s), 10.25 (1H, s).

B) Benzyl 2-(3-(2-(benzyloxy)-4-cyano-6-formylphenoxy)propyl)-4-((tert-butoxycarbonyl)amino)benzoate Tetrakis(triphenylphosphine)palladium (51.4 mg) was added to a mixture of benzyl 2-(3-(2-(benzyloxy)-4-bromo-6-formylphenoxy)propyl)-4-((tert-butoxycarbonyl)amino)benzoate (300 mg), zinc cyanide (78 mg), and DMF (3 mL) at room temperature, followed by stirring under an argon atmosphere at 100° C. for 3 hours. Water was added to the reaction mixture, followed by extraction with ethyl acetate. The organic layer was washed with a saturated saline solution and was dried over anhydrous sodium sulfate, and the solvent was then distilled under reduced pressure. The residue was purified by silica gel column chromatography (ethyl acetate/hexane) to obtain the title compound (241 mg).

MS: [M+Na]$^+$ 643.2.

C) 3-(Benzyloxy)-2-(3-(2-((benzyloxy)carbonyl)-5-((tert-butoxycarbonyl)amino)phenyl)propoxy)-5-cyanobenzoic acid Sodium chlorite (52.7 mg) was added to a mixture of benzyl 2-(3-(2-(benzyloxy)-4-cyano-6-formylphenoxy)propyl)-4-((tert-butoxycarbonyl)amino)benzoate (241 mg), sodium dihydrogen phosphate (140 mg), 2-methyl-2-butene (0.206 mL), tert-butyl alcohol (5 mL), and water (1 mL) at room temperature, followed by stirring at the same temperature overnight. Water was added to the reaction mixture, followed by extraction with ethyl acetate. The organic layer was washed with a saturated saline solution and was dried over anhydrous magnesium sulfate, and the solvent was then distilled under reduced pressure to obtain the title compound (246 mg).

MS: [M+Na]$^+$ 659.2.

D) (S)-Di-tert-butyl 2-(3-(benzyloxy)-2-(3-(2-((benzyloxy)carbonyl)-5-((tert-butoxycarbonyl)amino)phenyl)propoxy)-5-cyanobenzamide)succinate A mixture of 3-(benzyloxy)-2-(3-(2-((benzyloxy)carbonyl)-5-((tert-butoxycarbonyl)amino)phenyl)propoxy)-5-cyanobenzoic acid (246 mg), (S)-di-tert-butyl 2-aminosuccinate hydrochloride (120 mg), WSC hydrochloride (89 mg), HOBt.H$_2$O (71.0 mg), N,N-diisopropylethylamine (0.162 mL), and DMF (3 mL) was stirred at room temperature overnight. Water was added to the reaction mixture, followed by extraction with ethyl acetate. The organic layer was washed with a saturated saline solution and was dried over anhydrous magnesium sulfate, and the solvent was then distilled under reduced pressure. The residue was purified by silica gel column chromatography (ethyl acetate/hexane) to obtain the title compound (260 mg).

MS: [M+H]$^+$ 864.4.

E) (S)-4-((tert-Butoxycarbonyl)amino)-2-(3-(4-cyano-2-((1,4-di-tert-butoxy-1,4-dioxobutan-2-yl)carbamoyl)-6-hydroxyphenoxy)propyl)benzoic acid A mixture of (S)-di-tert-butyl 2-(3-(benzyloxy)-2-(3-(2-((benzyloxy)carbonyl)-5-((tert-butoxycarbonyl)amino)phenyl)propoxy)-5-cyanobenzamide)succinate (260 mg), 10% palladium on carbon (26 mg, water content: about 55%), and THF (4 mL) stirred under a hydrogen atmosphere at room temperature for 6 hours. The catalyst was removed by filtration, and the filtrate was then concentrated under reduced pressure to obtain the title compound (232 mg).

MS: [M+Na]$^+$ 706.3.

F) (S)-Di-tert-butyl 2-(10-((tert-butoxycarbonyl)amino)-2-cyano-13-oxo-6,7,8,13-tetrahydrodibenzo[b,f][1,4]dioxecine-4-carboxamide)succinate WSC hydrochloride (98 mg) and N,N-dimethyl-4-aminopyridine (2.073 mg) were added to a mixture of (S)-4-((tert-butoxycarbonyl)amino)-2-(3-(4-cyano-2-((1,4-di-tert-butoxy-1,4-dioxobutan-2-yl)carbamoyl)-6-hydroxyphenoxy)propyl)benzoic acid (232 mg) and pyridine (6 mL) at 0° C., followed by stirring at room temperature overnight. One mole hydrochloric acid was added to the reaction mixture, followed by extraction with ethyl acetate. The organic layer was washed with a saturated saline solution and was dried over anhydrous magnesium sulfate, and the solvent was then distilled under reduced pressure. The residue was purified by silica gel column chromatography (ethyl acetate/hexane) to obtain the title compound (121 mg).

MS: [M+H]$^+$ 666.3.

G) N-((10-Carbamimidamido-2-cyano-13-oxo-6,7,8,13-tetrahydrodibenzo[b,f][1,4]dioxecin-4-yl)carbonyl)-L-aspartic acid A mixture of (S)-di-tert-butyl 2-(10-((tert-butoxycarbonyl)amino)-2-cyano-13-oxo-6,7,8,13-tetrahydrodibenzo[b,f][1,4]dioxecine-4-carboxamide)succinate (121 mg), a solution of 4 M hydrogen chloride in cyclopropyl methyl ether (2 mL), and acetic acid (2 mL) was stirred at room temperature overnight and was concentrated under reduced pressure. A solution of 4 M hydrogen chloride in cyclopropyl methyl ether (0.135 mL) was added to a mixture of the residue, cyanamide (22.70 mg), and tert-butyl alcohol (2 mL) at room temperature, followed by stirring at 60° C. for 7 hours. The reaction mixture was concentrated under reduced pressure, and an aqueous solution prepared from ammonium acetate (55.5 mg) and water (5 mL) was added to a mixture of the residue and water (10 mL), followed by stirring at room temperature for 2 hours. The precipitated solid was collected by filtration and was washed with water and acetone to obtain the title compound (82.7 mg).

$^1$H NMR (400 MHz, DMSO-d$_6$) δ 1.93-2.24 (2H, m), 2.60-2.84 (2H, m), 3.08-3.53 (2H, m), 4.00-4.27 (2H, m), 4.38-4.58 (1H, m), 7.25-7.37 (2H, m), 7.84-8.08 (5H, m), 8.15 (1H, d, J=2.2 Hz), 8.21 (1H, d, J=2.1 Hz), 9.06 (1H, d, J=6.5 Hz).

Example 115

((2-(Bis(carboxymethyl)amino)-2-oxoethyl) ((10-carbamimidamido-13-oxo-6,7,8,13-tetrahydrodibenzo[b,f][1,4]dioxecin-4-yl)carbonyl)amino)acetic acid A) Di-tert-butyl 2,2'-((2-(N-(2-(tert-butoxy)-2-oxoethyl)-10-guanidino-13-oxo-6,7,8,13-tetrahydrodibenzo[b,f][1,4]dioxecine-4-carboxamide)acetyl)azanediyl)diacetate trifluoroacetate N,N'-Dicyclohexylcarbodiimide (105 mg) was added to a mixture of 10-guanidino-13-oxo-6,7,8,13-tetrahydrodibenzo[b,f][1,4]dioxecine-4-carboxylic acid hydrochloride (100 mg), di-tert-butyl 2,2'-((2-((2-(tert-butoxy)-2-oxoethyl)amino)acetyl)azanediyl)diacetate (106 mg), pyridine (1 mL), and DMF (1 mL) at room temperature, followed by stirring at 50° C. for 1 day. The reaction mixture was concentrated under reduced pressure, acetonitrile was then added to the residue, and the insoluble matter was removed by filtration. The filtrate was purified by HPLC (C18, mobile phase: water/acetonitrile (system containing 0.1% TFA)) to obtain the title compound (68.5 mg).
MS: [M+H]$^+$ 754.3.

B) ((2-(Bis(carboxymethyl)amino)-2-oxoethyl) ((10-carbamimidamido-13-oxo-6,7,8,13-tetrahydrodibenzo[b,f][1,4]dioxecin-4-yl)carbonyl)amino)acetic acid A mixture of di-tert-butyl 2,2'-((2-(N-(2-(tert-butoxy)-2-oxoethyl)-10-guanidino-13-oxo-6,7,8,13-tetrahydrodibenzo[b,f][1,4]dioxecine-4-carboxamide)acetyl)azanediyl)diacetate trifluoroacetate (68.4 mg) and TFA (1 mL) was stirred at room temperature for 30 minutes. The reaction mixture was concentrated under reduced pressure, and an ammonium acetate aqueous solution (0.5 mL) was added to a mixture of the residue and water (0.5 mL) to adjust the pH to about 4, followed by stirring at room temperature for 1 hour. The precipitated solid was collected by filtration and was washed with water to obtain the title compound (35.2 mg).
$^1$H NMR (300 MHz, DMSO-d$_6$) δ 1.84-2.00 (2H, m), 3.06-3.27 (4H, m), 3.74-3.96 (6H, m), 4.09 (2H, brs), 6.98-7.33 (4H, m), 7.33-7.59 (1H, m), 7.59-7.87 (5H, m).

Example 116

N-(3-((Bis(carboxymethyl)amino)methyl)benzyl)-N-((10-carbamimidamido-13-oxo-6,7,8,13-tetrahydrodibenzo[b,f][1,4]dioxecin-4-yl)carbonyl)glycine A) Di-tert-butyl 2,2'-((2-(N-(2-(tert-butoxy)-2-oxoethyl)-10-guanidino-13-oxo-6,7,8,13-tetrahydrodibenzo[b,f][1,4]dioxecine-4-carboxamide)acetyl)azanediyl)diacetate ditrifluoroacetate N,N'-Dicyclohexylcarbodiimide (126 mg) was added to a mixture of 10-guanidino-13-oxo-6,7,8,13-tetrahydrodibenzo[b,f][1,4]dioxecine-4-carboxylic acid hydrochloride (120 mg), di-tert-butyl 2,2'-((3-(((2-(tert-butoxy)-2-oxoethyl)amino)methyl)benzyl)azanediyl)diacetate (147 mg), pyridine (1 mL), and DMF (1 mL) at room temperature, followed by stirring at 50° C. for 8 hours. The reaction mixture was concentrated under reduced pressure, acetonitrile was then added to the residue, and the insoluble matter was removed by filtration. The filtrate was purified by HPLC (C18, mobile phase: water/acetonitrile (system containing 0.1% TFA)) to obtain the title compound (245.5 mg).
MS: [M+H]$^+$ 816.4.

B) N-(3-((Bis(carboxymethyl)amino)methyl)benzyl)-N-((10-carbamimidamido-13-oxo-6,7,8,13-tetrahydrodibenzo[b,f][1,4]dioxecin-4-yl)carbonyl)glycine A mixture of di-tert-butyl 2,2'-((2-(N-(2-(tert-butoxy)-2-oxoethyl)-10-guanidino-13-oxo-6,7,8,13-tetrahydrodibenzo[b,f][1,4]dioxecine-4-carboxamide)acetyl)azanediyl)diacetate ditrifluoroacetate (245 mg) and TFA (2 mL) was stirred at room temperature for 2 hours. The reaction mixture was concentrated under reduced pressure, and the residue was purified by HPLC (C18, mobile phase: water/acetonitrile (system containing 0.1% TFA)). The obtained fraction was concentrated under reduced pressure. An ammonium acetate aqueous solution was added to a mixture of the residue and water (1.0 mL) to adjust the pH to about 4, followed by stirring at room temperature for 1 hour. The precipitated solid was collected by filtration and was washed with water to obtain the title compound (62.2 mg).
$^1$H NMR (300 MHz, DMSO-d$_6$) δ 1.81-2.06 (2H, m), 3.30-3.41 (6H, m), 3.63 (2H, brs), 3.83 (4H, d, J=9.4 Hz), 4.29 (2H, brs), 7.03-7.40 (8H, m), 7.44-7.74 (2H, m), 7.75-7.89 (4H, m).

Example 118

N-((10-Carbamimidamido-3-(2-carboxyethyl)-13-oxo-6,7,8,13-tetrahydrodibenzo[b,f][1,4]dioxecin-4-yl)carbonyl)-N-methyl-L-aspartic acid A) 2-(3-(3-(3-(tert-Butoxy)-3-oxopropyl)-2-formyl-6-hydroxyphenoxy)propyl)-4-((tert-butoxycarbonyl)amino)benzoic acid A mixture of benzyl 2-(3-(6-(benzyloxy)-3-(3-(tert-butoxy)-3-oxoprop-1-en-1-yl)-2-formylphenoxy)propyl)-4-((tert-butoxycarbonyl)amino)benzoate (3.42 g), 10% palladium on carbon (345.4 mg, water content: about 55%), and THF (90 mL) was stirred under a hydrogen atmosphere at room temperature overnight. The catalyst was removed by filtration, and the filtrate was then concentrated under reduced pressure to obtain the title compound (2.86 g).
MS: [M+Na]$^+$ 566.2.

B) tert-Butyl 3-(10-((tert-butoxycarbonyl)amino)-4-formyl-13-oxo-6,7,8,13-tetrahydrodibenzo[b,f][1,4]dioxecin-3-yl)propanoate WSC hydrochloride (1.362 g) and N,N-dimethyl-4-aminopyridine (29.4 mg) were added to a mixture of 2-(3-(3-(3-(tert-butoxy)-3-oxopropyl)-2-formyl-6-hydroxyphenoxy)propyl)-4-((tert-butoxycarbonyl)amino)benzoic acid (2.86 g) and pyridine (65 mL) at 0° C., followed by stirring at room temperature overnight. The reaction mixture was concentrated under reduced pressure, and ethyl acetate was then added to the residue. The mixture was washed with 1 N hydrochloric acid, water, a saturated sodium hydrogen carbonate aqueous solution, and a saturated saline solution and was then dried over anhydrous sodium sulfate, and the solvent was distilled under reduced pressure. The residue was purified by silica gel column chromatography (ethyl acetate/hexane) to obtain the title compound (1.49 g).
MS: [M+Na]$^+$548.2.

C) 3-(3-(tert-Butoxy)-3-oxopropyl)-10-((tert-butoxycarbonyl)amino)-13-oxo-6,7,8,13-tetrahydrodibenzo[b,f][1,4]dioxecine-4-carboxylic acid 2-Methyl-2-butene (2.4 mL), sodium dihydrogen phosphate dihydrate (1.32 g), and sodium chlorite (0.967 g) were added to a mixture of tert-butyl 3-(10-((tert-butoxycarbonyl)amino)-4-formyl-13-oxo-6,7,8,13-tetrahydrodibenzo[b,f][1,4]dioxecin-3-yl)propanoate (1.48 g), acetonitrile (15 mL), and tert-butanol/water (4:1, 30 mL) at 0° C., followed by stirring at room temperature for 1 hour. Water was added to the reaction mixture at 0° C., followed by extraction with ethyl acetate. The organic layer was washed with a saturated saline solution and was then dried over anhydrous sodium sulfate, and the solvent was distilled under reduced pressure. The residue was purified by silica gel column chromatography (ethyl acetate/hexane) to obtain the title compound (1.280 g).
MS: [M+Na]$^+$564.2.

D) (S)-Dibenzyl 2-(3-(3-(tert-butoxy)-3-oxopropyl)-10-((tert-butoxycarbonyl)amino)-N-methyl-13-oxo-6,7,8,13-tetrahydrodibenzo[b,f][1,4]dioxecine-4-carboxamide)succinate HOBt.H$_2$O (35.1 mg) and WSC hydrochloride (44.0 mg) were added to a mixture of 3-(3-(tert-butoxy)-3-oxopropyl)-10-((tert-butoxycarbonyl)amino)-13-oxo-6,7,8,13-tetrahydrodibenzo[b,f][1,4]dioxecine-4-carboxylic acid (82.8 mg), (S)-dibenzyl 2-(methylamino)succinate (76.2 mg), N,N-diisopropylethylamine (0.080 mL), and DMF (2 mL) at room temperature, followed by stirring at the same temperature overnight. Water was added to the reaction mixture at 0° C., followed by extraction with ethyl acetate. The organic layer was washed with a saturated sodium hydrogen carbonate aqueous solution and a saturated saline solution and was then dried over anhydrous sodium sulfate, and the solvent was distilled under reduced pressure. The residue was purified by silica gel column chromatography (ethyl acetate/hexane) to obtain the title compound (65.1 mg).
MS: [M+H]$^+$ 851.4.

E) (S)-2-(3-(3-(tert-Butoxy)-3-oxopropyl)-10-((tert-butoxycarbonyl)amino)-N-methyl-13-oxo-6,7,8,13-tetrahydrodibenzo[b,f][1,4]dioxecine-4-carboxamide)succinic acid A mixture of (S)-dibenzyl 2-(3-(3-(tert-butoxy)-3-oxopropyl)-10-((tert-butoxycarbonyl)amino)-N-methyl-13-oxo-6,7,8,13-tetrahydrodibenzo[b,f][1,4]dioxecine-4-carboxamide)succinate (65.1 mg), 10% palladium on carbon (6.3 mg, water content: about 55%), and THF (3.0 mL) was stirred under a hydrogen atmosphere at room temperature overnight. The catalyst was removed by filtration, and the filtrate was then concentrated under reduced pressure to obtain the title compound (71.1 mg).
MS: [M+H]$^+$ 671.3.

F) (S)-2-(10-Amino-3-(2-carboxyethyl)-N-methyl-13-oxo-6,7,8,13-tetrahydrodibenzo[b,f][1,4]dioxecine-4-carboxamide)succinic acid hydrochloride A mixture of (S)-2-(3-(3-(tert-butoxy)-3-oxopropyl)-10-((tert-butoxycarbonyl)amino)-N-methyl-13-oxo-6,7,8,13-tetrahydrodibenzo[b,f][1,4]dioxecine-4-carboxamide)succinic acid (71.1 mg), 4 N hydrogen chloride in cyclopentyl methyl ether (1.0 mL), and acetic acid (1.0 mL) was stirred at room temperature overnight. The reaction mixture was concentrated to obtain the title compound (61.5 mg).
MS: [M+H]$^+$ 515.2

G) N-((10-Carbamimidamido-3-(2-carboxyethyl)-13-oxo-6,7,8,13-tetrahydrodibenzo[b,f][1,4]dioxecin-4-yl)carbonyl)-N-methyl-L-aspartic acid A mixture of (S)-2-(10-amino-3-(2-carboxyethyl)-N-methyl-13-oxo-6,7,8,13-tetrahydrodibenzo[b,f][1,4]dioxecine-4-carboxamide)succinic acid hydrochloride (61.5 mg), 4 N hydrogen chloride in cyclopentyl methyl ether (0.095 mL), cyanamide (15.9 mg), and tert-butyl alcohol (1.5 mL) was stirred at 60° C. overnight. Ethyl acetate was added to the reaction mixture at room temperature, followed by extraction with water. The aqueous layer was purified by HPLC (C18, mobile phase: water/acetonitrile (system containing 0.1% TFA)), and the obtained fraction was concentrated under reduced pressure. A 1 M ammonium acetate aqueous solution was added to a mixture of the residue and water (1 mL) at room temperature to adjust the pH of the mixture to 4, followed by stirring at room temperature for 1 hour. The precipitated solid was collected by filtration and was washed with water to obtain the title compound (17.4 mg).
$^1$H NMR (300 MHz, DMSO-d$_6$) δ 1.91 (2H, brs), 2.20-2.59 (2H, m), 2.60-2.90 (5H, m), 2.92-3.09 (1H, m), 3.32 (3H, d, J=2.9 Hz), 3.75-4.20 (2H, m), 5.00-5.33 (1H, m), 7.11 (1H, dd, J=8.5, 4.2 Hz), 7.25 (2H, dd, J=13.5, 3.7 Hz), 7.42 (1H, dd, J=8.3, 2.1 Hz), 7.56-8.28 (5H, m).

Example 119

3-(4-(Bis(carboxymethyl)carbamoyl)-10-carbamimidamido-13-oxo-6,7,8,13-tetrahydrodibenzo[b,f][1,4]dioxecin-3-yl)propanoic acid

A) Di-tert-butyl 2,2'-((3-(3-(tert-butoxy)-3-oxopropyl)-10-((tert-butoxycarbonyl)amino)-13-oxo-6,7,8,13-tetrahydrodibenzo[b,f][1,4]dioxecine-4-carbonyl)azanediyl)diacetate HOBt.H$_2$O (34.1 mg) and WSC hydrochloride (42.7 mg) were added to a mixture of 3-(3-(tert-butoxy)-3-oxopropyl)-10-((tert-butoxycarbonyl)amino)-13-oxo-6,7,8,13-tetrahydrodibenzo[b,f][1,4]dioxecine-4-carboxylic acid (80.5 mg), di-tert-butyl iminodiacetate (54.7 mg), N,N-diisopropylethylamine (0.078 mL), and DMF (2 mL) at room temperature, followed by stirring at the same temperature for 65 hours. Water was added to the reaction mixture at 0° C., followed by extraction with ethyl acetate. The organic layer was washed with a saturated sodium hydrogen carbonate aqueous solution and a saturated saline solution and was then dried over anhydrous sodium sulfate, and the solvent was distilled under reduced pressure. The residue was purified by silica gel column chromatography (ethyl acetate/hexane) to obtain the title compound (99.4 mg).
MS: [M+H]$^+$ 769.4.

B) 2,2'-((10-Amino-3-(2-carboxyethyl)-13-oxo-6,7,8,13-tetrahydrodibenzo[b,f][1,4]dioxecine-4-carbonyl)azanediyl)diacetic acid hydrochloride A mixture of di-tert-butyl 2,2'-((3-(3-(tert-butoxy)-3-oxopropyl)-10-((tert-butoxycarbonyl)amino)-13-oxo-6,7,8,13-tetrahydrodibenzo[b,f][1,4]dioxecine-4-carbonyl)azanediyl)diacetate (94.4 mg), 4 N hydrogen chloride in cyclopentyl methyl ether (1.0 mL), and acetic acid (1.0 mL) was stirred at room temperature overnight. Ethyl acetate (2 mL) was added to the reaction mixture at room temperature, followed by stirring at the same temperature for 30 minutes. The precipitated solid was collected by filtration and was washed with ethyl acetate to obtain the title compound (49.1 mg).
MS: [M+H]$^+$ 501.2.

C) 3-(4-(Bis(carboxymethyl)carbamoyl)-10-carbamimidamido-13-oxo-6,7,8,13-tetrahydrodibenzo[b,f][1,4]dioxecin-3-yl)propanoic acid A mixture of 2,2'-((10-amino-3-(2-carboxyethyl)-13-oxo-6,7,8,13-tetrahydrodibenzo[b,f][1,4]dioxecine-4-carbonyl)azanediyl)diacetic acid hydrochloride (45.5 mg), 4 N hydrogen chloride in cyclopentyl methyl ether (0.085 mL), cyanamide (14.25 mg), and tert-butyl alcohol (2 mL) was stirred at 60° C. overnight. Ethyl acetate was added to the reaction mixture, followed by extraction with water. A 1 M ammonium acetate aqueous solution was added to the aqueous layer at room temperature to adjust the pH of the mixture to 4, followed by stirring at room temperature for 2 hours. The precipitated solid was collected by filtration and was washed with water to obtain the title compound (34.9 mg).
$^1$H NMR (300 MHz, DMSO-d$_6$) δ 1.71-2.03 (2H, m), 2.36-2.61 (2H, m), 2.64-2.80 (2H, m), 3.11 (1H, d, J=6.5 Hz), 3.31 (1H, brs), 3.71 (2H, s), 3.77-4.02 (3H, m), 4.04-4.16 (1H, m), 7.10 (1H, d, J=8.5 Hz), 7.18-7.30 (2H, m), 7.44 (1H, d, J=8.4 Hz), 7.77 (4H, brs), 7.87 (1H, d, J=8.2 Hz).

Example 120

N-(2-(Bis(carboxymethyl)amino)ethyl)-N-((10-carbamimidamido-13-oxo-6,7,8,13-tetrahydrodibenzo[b,f][1,4]dioxecin-4-yl)carbonyl)glycine A) Di-tert-butyl 2,2'-((2-(benzyl(2-(tert-butoxy)-2-oxoethyl)amino)ethyl)azanediyl)diacetate A mixture of tert-butyl 2-(benzylamino)acetate (304 mg), di-tert-butyl 2,2'-((2-bromoethyl)azanediyl)diacetate (581 mg), potassium carbonate (475 mg), and DMF (5 mL) was stirred at room temperature for 1 day. Water was added to the reaction mixture at room temperature, followed by extraction with ethyl acetate. The organic layer was washed with water and a saturated saline solution and was then dried over anhydrous magnesium sulfate, and the solvent was distilled under reduced pressure. The residue was purified by silica gel column chromatography (ethyl acetate/hexane) to obtain the title compound (281 mg).
MS: [M+H]$^+$ 493.3.

B) Di-tert-butyl 2,2'-((2-((2-(tert-butoxy)-2-oxoethyl)amino)ethyl)azanediyl)diacetate A mixture of di-tert-butyl 2,2'-((2-(benzyl(2-(tert-butoxy)-2-oxoethyl)amino)ethyl)azanediyl)diacetate (278 mg), 10% palladium on carbon (30 mg, water content: about 55%), and methanol (6 mL) was stirred under a hydrogen atmosphere at room temperature for 5 hours. The catalyst was removed by filtration, and the filtrate was then concentrated under reduced pressure to obtain the title compound (226.4 mg).
MS: [M+H]$^+$ 403.2.

C) Di-tert-butyl 2,2'-((2-(N-(2-(tert-butoxy)-2-oxoethyl)-10-guanidino-13-oxo-6,7,8,13-tetrahydrodibenzo[b,f][1,4]dioxecine-4-carboxamide)ethyl)azanediyl)diacetate ditrifluoroacetate N,N'-Dicyclohexylcarbodiimide (134 mg) was added to a mixture of 10-guanidino-13-oxo-6,7,8,13-tetrahydrodibenzo[b,f][1,4]dioxecine-4-carboxylic acid hydrochloride (127 mg), di-tert-butyl 2,2'-((2-((2-(tert-butoxy)-2-oxoethyl)amino)ethyl)azanediyl)diacetate (130 mg), pyridine (1 mL), and DMF (1 mL) at room temperature, followed by stirring at 50° C. overnight. The reaction mixture was concentrated under reduced pressure, acetonitrile was then added to the residue, and the insoluble matter was removed by filtration. The filtrate was purified by HPLC (C18, mobile phase: water/acetonitrile (system containing 0.1% TFA)) to obtain the title compound (277 mg).
MS: [M+H]$^+$ 740.4.

D) N-(2-(Bis(carboxymethyl)amino)ethyl)-N-((10-carbamimidamido-13-oxo-6,7,8,13-tetrahydrodibenzo[b,f][1,4]dioxecin-4-yl)carbonyl)glycine A mixture of di-tert-butyl 2,2'-((2-(N-(2-(tert-butoxy)-2-oxoethyl)-10-guanidino-13-oxo-6,7,8,13-tetrahydrodibenzo[b,f][1,4]dioxecine-4-carboxamide)ethyl)azanediyl)diacetate ditrifluoroacetate (275 mg) and TFA (1.5 mL) was stirred at room temperature for 2 hours. The reaction mixture was concentrated under reduced pressure, and the residue was purified by HPLC (C18, mobile phase: water/acetonitrile (system containing 0.1% TFA)). The obtained fraction was concentrated under reduced pressure. An ammonium acetate aqueous solution was added to a mixture of the residue and water (1.0 mL) to adjust the pH to about 4, followed by stirring at room temperature for 1 hour. The precipitated solid was collected by filtration and was washed with water to obtain the title compound (61.5 mg).
$^1$H NMR (300 MHz, DMSO-d$_6$) δ 1.91 (2H, s), 2.65-3.57 (10H, m), 3.86 (2H, brs), 4.09 (2H, d, J=11.2 Hz), 6.99-7.28 (4H, m), 7.46-7.55 (1H, m), 7.63-7.96 (5H, m).

Example 121

N-((10-Carbamimidamido-13-oxo-6,7,8,13-tetrahydrodibenzo[b,f][1,4]dioxecin-4-yl)carbonyl)-N-(carboxymethyl)-O-(2-((carboxymethyl)amino)ethyl)-L-tyrosine A) ((S)-tert-Butyl 3-(4-(2-(benzyl(2-(tert-butoxy)-2-oxoethyl)amino)ethoxy)phenyl)-2-((2-(tert-butoxy)-2-oxoethyl)amino)propanoate 1,1'-(Azodicarbonyl)dipiperidine (431 mg), tributylphosphine (0.421 mL), and toluene (20 mL) were added to a mixture of (S)-tert-butyl 2-((2-(tert-butoxy)-2-oxoethyl)amino)-3-(4-hydroxyphenyl)propanoate (300 mg), tert-butyl 2-(benzyl(2-hydroxyethyl)amino)acetate (249 mg), and toluene (6 mL) at room temperature, followed by stirring at the same temperature overnight. 1,1'-(Azodicarbonyl)dipiperidine (215 mg) and tributylphosphine (0.211 mL) were added to the reaction mixture at room temperature, followed by stirring at the same temperature for 3 hours. Hexane (26 mL) was added to the reaction mixture at room temperature, followed by stirring at the same temperature for 30 minutes. The insoluble matter was removed by filtration, and the filtrate was then concentrated under reduced pressure. The residue was purified by silica gel column chromatography (ethyl acetate/hexane) to obtain the title compound (328.2 mg).

MS: [M+H]$^+$ 599.3.

B) (S)-tert-Butyl 3-(4-(2-(benzyl(2-(tert-butoxy)-2-oxoethyl)amino)ethoxy)phenyl)-2-(N-(2-(tert-butoxy)-2-oxoethyl)-10-guanidino-13-oxo-6,7,8,13-tetrahydrodibenzo[b,f][1,4]dioxecine-4-carboxamide)propanoate ditrifluoroacetate N,N'-Dicyclohexylcarbodiimide (108 mg) was added to a mixture of 10-guanidino-13-oxo-6,7,8,13-tetrahydrodibenzo[b,f][1,4]dioxecine-4-carboxylic acid hydrochloride (103 mg), (S)-tert-butyl 3-(4-(2-(benzyl(2-(tert-butoxy)-2-oxoethyl)amino)ethoxy)phenyl)-2-((2-(tert-butoxy)-2-oxoethyl)amino)propanoate (157 mg), pyridine (1 mL), and DMF (1 mL) at room temperature, followed by stirring at 50° C. for 7 hours. The reaction mixture was concentrated under reduced pressure, acetonitrile was then added to the residue, and the insoluble matter was removed by filtration. The filtrate was purified by HPLC (C18, mobile phase: water/acetonitrile (system containing 0.1% TFA)) to obtain the title compound (190 mg).

MS: [M+H]$^+$ 936.5.

C) 0-(2-(Benzyl(carboxymethyl)amino)ethyl)-N-((10-carbamimidamido-13-oxo-6,7,8,13-tetrahydrodibenzo[b,f][1,4]dioxecin-4-yl)carbonyl)-N-(carboxymethyl)-L-tyrosine ditrifluoroacetate A mixture of (S)-tert-butyl 3-(4-(2-(benzyl(2-(tert-butoxy)-2-oxoethyl)amino)ethoxy)phenyl)-2-(N-(2-(tert-butoxy)-2-oxoethyl)-10-guanidino-13-oxo-6,7,8,13-tetrahydrodibenzo[b,f][1,4]dioxecine-4-carboxamide)propanoate ditrifluoroacetate (190 mg) and TFA (2 mL) was stirred at room temperature for 1.5 hours. The reaction mixture was concentrated under reduced pressure, and the residue was purified by HPLC (C18, mobile phase: water/acetonitrile (system containing 0.1% TFA)) to obtain the title compound (220 mg).

MS: [M+H]$^+$ 768.3.

D) N-((10-Carbamimidamido-13-oxo-6,7,8,13-tetrahydrodibenzo[b,f][1,4]dioxecin-4-yl)carbonyl)-N-(carboxymethyl)-O-(2-((carboxymethyl)amino)ethyl)-L-tyrosine A mixture of 0-(2-(benzyl(carboxymethyl)amino)ethyl)-N-((10-carbamimidamido-13-oxo-6,7,8,13-tetrahydrodibenzo[b,f][1,4]dioxecin-4-yl)carbonyl)-N-(carboxymethyl)-L-tyrosine ditrifluoroacetate (180 mg), 10% palladium on carbon (20 mg, water content: about 55%), and THF (5 mL) was stirred under a hydrogen atmosphere at room temperature for 30 hours. The catalyst was removed by filtration, and the filtrate was then concentrated under reduced pressure. The residue was purified by HPLC (C18, mobile phase: water/acetonitrile (system containing 0.1% TFA)), and a desired fraction was concentrated under reduced pressure. An ammonium acetate aqueous solution was added to a mixture of the residue and water (1.0 mL) to adjust the pH to about 4, followed by stirring at room temperature for 1 hour. The precipitated solid was collected by filtration and was washed with water to obtain the title compound (45.8 mg).

$^1$H NMR (300 MHz, DMSO-d$_6$) δ 1.67-1.86 (1H, m), 1.98 (1H, brs), 2.97-3.52 (10H, m), 3.72 (3H, brs), 4.04-4.29 (3H, m), 6.83-7.34 (8H, m), 7.42-7.56 (1H, m), 7.72 (1H, brs), 7.76-7.98 (4H, m).

Example 122

O-(2-(Benzyl(carboxymethyl)amino)ethyl)-N-((10-carbamimidamido-13-oxo-6,7,8,13-tetrahydrodibenzo[b,f][1,4]dioxecin-4-yl)carbonyl)-N-(carboxymethyl)-L-tyrosine A mixture of (S)-tert-butyl 3-(4-(2-(benzyl(2-(tert-butoxy)-2-oxoethyl)amino)ethoxy)phenyl)-2-(N-(2-(tert-butoxy)-2-oxoethyl)-10-guanidino-13-oxo-6,7,8,13-tetrahydrodibenzo[b,f][1,4]dioxecine-4-carboxamide)propanoate ditrifluoroacetate (184.2 mg) and trifluoroacetic acid (2 mL) was stirred at room temperature for 1.5 hours. The reaction mixture was concentrated under reduced pressure, and the residue was purified by HPLC (C18, mobile phase: water/acetonitrile (system containing 0.1% TFA)). The obtained fraction was concentrated under reduced pressure. An ammonium acetate aqueous solution was added to a mixture of the residue and water (1.0 mL) to adjust the pH to about 4, followed by stirring at room temperature for 1 hour. The precipitated solid was collected by filtration and was washed with water to obtain the title compound (80.0 mg).

$^1$H NMR (300 MHz, DMSO-d$_6$) δ 1.79 (1H, brs), 1.95 (1H, brs), 3.01 (3H, brs), 3.25-3.45 (6H, m), 3.74 (1H, brs), 3.83-3.90 (2H, m), 3.91-4.09 (3H, m), 4.09-4.27 (2H, m), 6.69-7.03 (4H, m), 7.11-7.37 (9H, m), 7.44-7.58 (1H, m), 7.64 (4H, d, J=3.7 Hz), 7.86 (1H, dd, J=13.9, 8.6 Hz), 9.89-10.02 (1H, m).

Example 135

3-((((10-Carbamimidamido-13-oxo-6,7,8,13-tetrahydrodibenzo[b,f][1,4]dioxecin-4-yl)carbonyl) ((1S)-1-carboxyethyl)amino)methyl)benzoic acid A) (S)-tert-Butyl 3-((N-(1-(tert-butoxy)-1-oxopropan-2-yl)-10-guanidino-13-oxo-6,7,8,13-tetrahydrodibenzo[b,f][1,4]dioxecine-4-carboxamide) methyl)benzoate trifluoroacetate N,N'-Dicyclohexylcarbodiimide (158 mg) was added to a mixture of 10-guanidino-13-oxo-6,7,8,13-tetrahydrodibenzo[b,f][1,4]dioxecine-4-carboxylic acid hydrochloride (150 mg), (S)-tert-butyl 3-(((1-(tert-butoxy)-1-oxopropan-2-yl)amino)methyl)benzoate (128 mg), pyridine (1 mL), and DMF (1 mL) at room temperature, followed by stirring at 50° C. overnight. The reaction mixture was concentrated under reduced pressure, acetonitrile was then added to the residue, and the insoluble matter was removed by filtration. The filtrate was purified by HPLC (C18, mobile phase: water/acetonitrile (system containing 0.1% TFA)) to obtain the title compound (174 mg).

MS: [M+H]$^+$ 673.3.

B) 3-((((10-Carbamimidamido-13-oxo-6,7,8,13-tetrahydrodibenzo[b,f][1,4]dioxecin-4-yl)carbonyl) ((1S)-1-carboxyethyl)amino)methyl)benzoic acid A mixture of (S)-tert-butyl 3-((N-(1-(tert-butoxy)-1-oxopropan-2-yl)-10-guanidino-13-oxo-6,7,8,13-tetrahydrodibenzo[b,f][1,4]dioxecine-4-carboxamide)methyl)benzoate trifluoroacetate (153 mg) and TFA (2 mL) was stirred at room temperature for 30 minutes. The reaction mixture was concentrated under reduced pressure, and the residue was purified by HPLC (C18, mobile phase: water/acetonitrile (system containing 0.1% TFA)). The obtained fraction was concentrated under reduced pressure. An ammonium acetate aqueous solution was added to a mixture of the residue and water (1.0 mL) to adjust the pH to about 4, followed by stirring at room temperature for 1 hour. The precipitated solid was collected by filtration and was washed with water to obtain the title compound (61.6 mg).

$^1$H NMR (300 MHz, DMSO-$d_6$) δ 1.10-1.36 (3H, m), 1.63-2.13 (2H, m), 3.09 (1H, brs), 3.35-3.48 (1H, m), 3.86 (1H, brs), 3.98-4.25 (2H, m), 4.45-4.61 (1H, m), 4.93-5.33 (1H, m), 7.06-7.31 (4H, m), 7.32-7.64 (3H, m), 7.73-8.15 (6H, m), 8.30 (1H, brs).

Example 136

N-((10-Carbamimidamido-13-oxo-6,7,8,13-tetrahydrodibenzo[b,f][1,4]dioxecin-4-yl)carbonyl)-N-(3-carboxybenzyl)-L-aspartic acid A) (S)-Di-tert-butyl 2-((3-(tert-butoxycarbonyl)benzyl)amino) succinate Acetic acid (0.535 mL) was added to a mixture of L-aspartic acid di-t-butyl ester hydrochloride (1053 mg), tert-butyl 3-formylbenzoate (771 mg), and THF (20 mL) at room temperature, followed by stirring at the same temperature for 1 hour. Sodium triacetoxyborohydride (1981 mg) was added to the reaction mixture at room temperature, followed by stirring at the same temperature overnight. A saturated sodium hydrogen carbonate aqueous solution was added to the reaction mixture at 0° C., followed by extraction with ethyl acetate. The organic layer was washed with a saturated saline solution and was then dried over anhydrous magnesium sulfate, and the solvent was distilled under reduced pressure. The residue was purified by silica gel column chromatography (NH, ethyl acetate/hexane) to obtain the title compound (856.4 mg).

MS: [M+H]$^+$ 436.2.

B) (S)-Di-tert-butyl 2-(N-(3-(tert-butoxycarbonyl)benzyl)-10-guanidino-13-oxo-6,7,8,13-tetrahydrodibenzo[b,f][1,4]dioxecine-4-carboxamide)succinate trifluoroacetate N,N'-Dicyclohexylcarbodiimide (158 mg) was added to a mixture of 10-guanidino-13-oxo-6,7,8,13-tetrahydrodibenzo[b,f][1,4]dioxecine-4-carboxylic acid hydrochloride (150 mg), (S)-di-tert-butyl 2-((3-(tert-butoxycarbonyl)benzyl)amino) succinate (167 mg), pyridine (1 mL), and DMF (1 mL) at room temperature, followed by stirring at 50° C. overnight. The reaction mixture was concentrated under reduced pressure, acetonitrile was then added to the residue, and the insoluble matter was removed by filtration. The filtrate was purified by HPLC (C18, mobile phase: water/acetonitrile (system containing 0.1% TFA)) to obtain the title compound (90.1 mg).

MS: [M+H]$^+$ 773.4.

C) N-((10-Carbamimidamido-13-oxo-6,7,8,13-tetrahydrodibenzo[b,f][1,4]dioxecin-4-yl)carbonyl)-N-(3-carboxybenzyl)-L-aspartic acid A mixture of (S)-di-tert-butyl 2-(N-(3-(tert-butoxycarbonyl)benzyl)-10-guanidino-13-oxo-6,7,8,13-tetrahydrodibenzo[b,f][1,4]dioxecine-4-carboxamide)succinate trifluoroacetate (90.0 mg) and TFA (1 mL) was stirred at room temperature for 40 minutes. The reaction mixture was concentrated under reduced pressure, and the residue was purified by HPLC (C18, mobile phase: water/acetonitrile (system containing 0.1% TFA)). The obtained fraction was concentrated. An ammonium acetate aqueous solution was added to a mixture of the residue and water (1.0 mL) to adjust the pH to about 4, followed by stirring at room temperature for 1 hour. The precipitated solid was collected by filtration and was washed with water to obtain the title compound (39.8 mg).

$^1$H NMR (300 MHz, DMSO-$d_6$) δ 1.95-2.14 (2H, m), 2.69-2.92 (1H, m), 2.98-3.26 (2H, m), 3.33-3.53 (1H, m), 3.80-4.18 (3H, m), 4.51 (1H, s), 5.22 (1H, d, J=16.1 Hz), 7.08-7.33 (4H, m), 7.33-7.69 (7H, m), 7.77-8.02 (3H, m).

Example 140

N-((10-Carbamimidamido-13-oxo-6,7,8,13-tetrahydrodibenzo[b,f][1,4]dioxecin-4-yl)carbonyl)-N-(carboxymethyl)glycyl-N-benzylglycine A) Benzyl 2-((2-(tert-butoxy)-2-oxoethyl)amino) acetate tert-Butyl bromoacetate (1.321 mL) was added to a mixture of benzyl glycinate hydrochloride (1.5 g), N,N-diisopropylethylamine (3.25 mL), and DMF (10 mL) at 0° C., followed by stirring at room temperature for 5 days. Water was added to the reaction mixture, followed by extraction with ethyl acetate. The organic layer was washed with water and a saturated saline solution and was then dried over anhydrous magnesium sulfate, and the solvent was distilled under reduced pressure. The residue was purified by silica gel column chromatography (ethyl acetate/hexane) to obtain the title compound (1.5561 g).

MS: [M+H]$^+$ 280.1.

B) Benzyl 2-(10-amino-N-(2-(tert-butoxy)-2-oxoethyl)-13-oxo-6,7,8,13-tetrahydrodibenzo[b,f][1,4]dioxecine-4-carboxamide)acetate A mixture of 10-amino-13-oxo-6,7,8,13-tetrahydrodibenzo[b,f][1,4]dioxecine-4-carboxylic acid hydrochloride (200 mg), benzyl 2-((2-(tert-butoxy)-2-oxoethyl)amino)acetate (240 mg), WSC hydrochloride (164 mg), HOBt.H$_2$O (131 mg), N,N-diisopropylethylamine (0.300 mL), and DMF (3 mL) was stirred at room temperature overnight. Water was added to the reaction mixture at 0° C., followed by extraction with ethyl acetate. The organic layer was washed with 1 N hydrochloric acid, water, and a saturated saline solution and was then dried over anhydrous magnesium sulfate, and the solvent was distilled under reduced pressure. The residue was purified by silica gel column chromatography (ethyl acetate/hexane) to obtain the title compound (257 mg).

MS: [M+Na]$^+$597.2.

C) 2-(10-Amino-N-(2-(tert-butoxy)-2-oxoethyl)-13-oxo-6,7,8,13-tetrahydrodibenzo[b,f][1,4]dioxecine-4-carboxamide)acetic acid A mixture of (benzyl 2-(10-amino-N-(2-(tert-butoxy)-2-oxoethyl)-13-oxo-6,7,8,13-tetrahydrodibenzo[b,f][1,4]dioxecine-4-carboxamide)acetate (257.2 mg), 10% palladium on carbon (26 mg, water content: about 55%), and THF (7.5 mL) was stirred under a hydrogen atmosphere at room temperature for 3 hours. The catalyst was removed by filtration, and the filtrate was then concentrated under reduced pressure to obtain the title compound (244.1 mg).

MS: [M+Na]$^+$507.2.

D) tert-Butyl 2-(2-(10-amino-N-(2-(tert-butoxy)-2-oxoethyl)-13-oxo-6,7,8,13-tetrahydrodibenzo[b,f][1,4]dioxecine-4-carboxamide)-N-benzylacetamide)acetate A mixture of 2-(10-amino-N-(2-(tert-butoxy)-2-oxoethyl)-13-oxo-6,7,8,13-tetrahydrodibenzo[b,f][1,4]dioxecine-4-carboxamide)acetic acid (115 mg), tert-butyl 2-(benzylamino)acetate (79 mg), WSC hydrochloride (68.3 mg), HOBt.H$_2$O (54.5 mg), N,N-diisopropylethylamine (0.200 mL), and DMF (2 mL) was stirred at room temperature for 2 days. Water was added to the reaction mixture at 0° C., followed by extraction with ethyl acetate. The organic layer was washed with 1 N hydrochloric acid, water, and a saturated saline solution and was then dried over anhydrous magnesium sulfate, and the solvent was distilled under reduced pressure. The residue was purified by silica gel column chromatography (ethyl acetate/hexane) to obtain the title compound (122.4 mg).

MS: [M+Na]$^+$710.3.

E) 2-(10-Amino-N-(2-(benzyl(carboxymethyl)amino)-2-oxoethyl)-13-oxo-6,7,8,13-tetrahydrodibenzo[b,f][1,4]dioxecine-4-carboxamide)acetic acid hydrochloride A mixture of tert-butyl 2-(2-(10-amino-N-(2-(tert-butoxy)-2-oxoethyl)-13-oxo-6,7,8,13-tetrahydrodibenzo[b,f][1,4]dioxecine-4-carboxamide)-N-benzylacetamide)acetate (121 mg), 4 N hydrogen chloride in cyclopentyl methyl ether (1 mL), and acetic acid (1 mL) was stirred at room temperature overnight. The reaction mixture was concentrated under reduced pressure to obtain the title compound (143 mg).

MS: [M+H]$^+$ 576.2.

F) N-((10-Carbamimidamido-13-oxo-6,7,8,13-tetrahydrodibenzo[b,f][1,4]dioxecin-4-yl)carbonyl)-N-(carboxymethyl)glycyl-N-benzylglycine Four normal hydrogen chloride in cyclopentyl methyl ether (0.135 mL) and cyanamide (22.70 mg) were added to a mixture of 2-(10-amino-N-(2-(benzyl(carboxymethyl)amino)-2-oxoethyl)-13-oxo-6,7,8,13-tetrahydrodibenzo[b,f][1,4]dioxecine-4-carboxamide)acetic acid hydrochloride (110 mg) and tert-butyl alcohol (3 mL) at room temperature, followed by stirring at 60° C. overnight. The reaction mixture was concentrated under reduced pressure, and an aqueous solution (1 mL) of ammonium acetate (41.6 mg) was added to a mixture of the residue and water (1.0 mL) at room temperature, followed by stirring at the same temperature for 30 minutes. The precipitated solid was collected by filtration and was purified by HPLC (C18, mobile phase: water/acetonitrile (system containing 0.1% TFA)), and the obtained fraction was concentrated under reduced pressure. An ammonium acetate aqueous solution was added to a mixture of the residue and water (1.0 mL) to adjust the pH to about 4, followed by stirring at room temperature for 1 hour. The precipitated solid was collected by filtration and was washed with water to obtain the title compound (60.2 mg), $^1$H NMR (300 MHz, DMSO-d$_6$) δ 1.73-2.06 (2H, m), 3.08 (2H, brs), 3.34-3.45 (2H, m), 3.66-3.96 (4H, m), 4.17-4.74 (4H, m), 6.86-7.11 (2H, m), 7.13-7.42 (8H, m), 7.47-7.63 (1H, m), 7.65-7.99 (4H, m).

Example 141

N-((10-Carbamimidamido-13-oxo-6,7,8,13-tetrahydrodibenzo[b,f][1,4]dioxecin-4-yl)carbonyl)-N-(carboxymethyl)glycyl-N-(3-carboxybenzyl)glycine A) tert-Butyl 3-((2-(10-amino-N-(2-(tert-butoxy)-2-oxoethyl)-13-oxo-6,7,8,13-tetrahydrodibenzo[b,f][1,4]dioxecine-4-carboxamide)-N-(2-(tert-butoxy)-2-oxoethyl)acetamide)methyl)benzoate A mixture of 2-(10-amino-N-(2-(tert-butoxy)-2-oxoethyl)-13-oxo-6,7,8,13-tetrahydrodibenzo[b,f][1,4]dioxecine-4-carboxamide)acetic acid (112 mg), tert-butyl 3-(((2-(tert-butoxy)-2-oxoethyl)amino)methyl)benzoate (111 mg), WSC hydrochloride (66.5 mg), HOBt.H$_2$O (53.1 mg), N,N-diisopropylethylamine (0.200 mL), and DMF (2 mL) was stirred at room temperature overnight. Water was added to the reaction mixture at 0° C., followed by extraction with ethyl acetate. The organic layer was washed with 1 N hydrochloric acid, water, and a saturated saline solution and was then dried over anhydrous magnesium sulfate, and the solvent was distilled under reduced pressure. The residue was purified by silica gel column chromatography (ethyl acetate/hexane) to obtain the title compound (134.1 mg).

MS: [M+H]$^+$ 788.4.

B) 3-((2-(10-Amino-N-(carboxymethyl)-13-oxo-6,7,8,13-tetrahydrodibenzo[b,f][1,4]dioxecine-4-carboxamide)-N-(carboxymethyl)acetamide)methyl)benzoic acid hydrochloride A mixture of tert-butyl 3-((2-(10-amino-N-(2-(tert-butoxy)-2-oxoethyl)-13-oxo-6,7,8,13-tetrahydrodibenzo[b,f][1,4]dioxecine-4-carboxamide)-N-(2-(tert-butoxy)-2-oxoethyl)acetamide)methyl)benzoate (134 mg), 4 N hydrogen chloride in cyclopentyl methyl ether (1 mL), and acetic acid (1 mL) was stirred at room temperature overnight. The reaction mixture was concentrated under reduced pressure to obtain the title compound (139.1 mg).

MS: [M+H]$^+$ 620.2.

C) N-((10-Carbamimidamido-13-oxo-6,7,8,13-tetrahydrodibenzo[b,f][1,4]dioxecin-4-yl)carbonyl)-N-(carboxymethyl)glycyl-N-(3-carboxybenzyl)glycine Four normal hydrogen chloride in cyclopentyl methyl ether (0.128 mL) and cyanamide (21.44 mg) were added to a mixture of 3-((2-(10-amino-N-(carboxymethyl)-13-oxo-6,7,8,13-tetrahydrodibenzo[b,f][1,4]dioxecine-4-carboxamide)-N-(carboxymethyl)acetamide)methyl)benzoic acid hydrochloride (112 mg) and tert-butyl alcohol (3 mL) at room temperature, followed by stirring at 60° C. overnight. The reaction mixture was concentrated under reduced pressure, and an ammonium acetate aqueous solution was added to a mixture of the residue and water (1.0 mL) to adjust the pH to about 4, followed by stirring at room temperature for 1 hour. The precipitated solid was collected by filtration and was washed with water to obtain the title compound (60.5 mg).

¹H NMR (300 MHz, DMSO-d₆) δ 1.69-2.14 (2H, m), 3.01-3.11 (2H, m, J=7.7 Hz), 3.66-4.05 (6H, m), 4.17-4.39 (2H, m), 4.48-4.81 (2H, m), 6.61-7.29 (4H, m), 7.29-7.79 (5H, m), 7.79-8.15 (5H, m).

Example 143

N-((10-Carbamimidamido-13-oxo-6,7,8,13-tetrahydrodibenzo[b,f][1,4]dioxecin-4-yl)carbonyl)-N-(4-carboxybenzyl)-L-aspartic acid A) (S)-Di-tert-butyl 2-((4-(tert-butoxycarbonyl)benzyl)amino) succinate Acetic acid (0.212 mL) was added to a mixture of L-aspartic acid di-tert-butyl ester hydrochloride (418 mg), tert-butyl 4-formylbenzoate (306 mg), and THF (8 mL) at room temperature, followed by stirring at the same temperature for 1 hour. Sodium triacetoxyborohydride (786 mg) was added to the reaction mixture at room temperature, followed by stirring at the same temperature overnight. A saturated sodium hydrogen carbonate aqueous solution was added to the reaction mixture at 0° C., followed by extraction with ethyl acetate. The organic layer was washed with a saturated saline solution and was then dried over anhydrous magnesium sulfate, and the solvent was distilled under reduced pressure. The residue was purified by silica gel column chromatography (ethyl acetate/hexane) to obtain the title compound (346.1 mg).
MS: [M+H]⁺ 436.2.

B) (S)-Di-tert-butyl 2-(N-(4-(tert-butoxycarbonyl)benzyl)-10-guanidino-13-oxo-6,7,8,13-tetrahydrodibenzo[b,f][1,4]dioxecine-4-carboxamide)succinate trifluoroacetate N,N'-Dicyclohexylcarbodiimide (158 mg) was added to a mixture of 10-guanidino-13-oxo-6,7,8,13-tetrahydrodibenzo[b,f][1,4]dioxecine-4-carboxylic acid hydrochloride (150 mg), (S)-di-tert-butyl 2-((4-(tert-butoxycarbonyl)benzyl)amino) succinate (167 mg), pyridine (1 mL), and DMF (1 mL) at room temperature, followed by stirring at 50° C. overnight. The reaction mixture was concentrated under reduced pressure, acetonitrile was then added to the residue, and the insoluble matter was removed by filtration. The filtrate was purified by HPLC (C18, mobile phase: water/acetonitrile (system containing 0.1% TFA)) to obtain the title compound (118.1 mg).
MS: [M+H]⁺ 773.4.

C) N-((10-Carbamimidamido-13-oxo-6,7,8,13-tetrahydrodibenzo[b,f][1,4]dioxecin-4-yl)carbonyl)-N-(4-carboxybenzyl)-L-aspartic acid A mixture of (S)-di-tert-butyl 2-(N-(4-(tert-butoxycarbonyl)benzyl)-10-guanidino-13-oxo-6,7,8,13-tetrahydrodibenzo[b,f][1,4]dioxecine-4-carboxamide)succinate trifluoroacetate (118.1 mg) and TFA (2 mL) was stirred at room temperature for 30 minutes. The reaction mixture was concentrated under reduced pressure, and an ammonium acetate aqueous solution was added to a mixture of the residue and water (1.0 mL) to adjust the pH to about 4, followed by stirring at room temperature for 1 hour. The precipitated solid was collected by filtration and was washed with water to obtain the title compound (66.5 mg).
¹H NMR (300 MHz, DMSO-d₆) δ 2.06 (2H, d, J=14.4 Hz), 2.68-2.91 (1H, m), 3.13-3.27 (2H, m), 3.39-3.49 (1H, m), 3.87-4.17 (3H, m), 4.27-4.55 (1H, m), 5.23 (1H, d, J=16.5 Hz), 7.06-7.18 (1H, m), 7.18-7.35 (3H, m), 7.35-7.59 (3H, m), 7.59-7.88 (5H, m), 7.92 (2H, dd, J=8.3, 3.5 Hz).

Example 144

3-(((10-Carbamimidamido-13-oxo-6,7,8,13-tetrahydrodibenzo[b,f][1,4]dioxecin-4-yl)carbonyl) (3-carboxybenzyl)amino)pentanedioic acid A) Dibenzyl 3-((3-(tert-butoxycarbonyl)benzyl)amino)pentanedioate Acetic acid (0.100 mL) was added to a mixture of dibenzyl 3-aminopentanedioate hydrochloride (255 mg), tert-butyl 3-formylbenzoate (144 mg), and THF (3 mL) at room temperature, followed by stirring at the same temperature for 1 hour. Sodium triacetoxyborohydride (371 mg) was added to the reaction mixture at room temperature, followed by stirring at the same temperature overnight. A saturated sodium hydrogen carbonate aqueous solution was added to the reaction mixture at 0° C., followed by extraction with ethyl acetate. The organic layer was washed with a saturated saline solution and was then dried over anhydrous magnesium sulfate, and the solvent was distilled under reduced pressure. The residue was purified by silica gel column chromatography (NH, ethyl acetate/hexane) to obtain the title compound (191.5 mg).
MS: [M+H]⁺ 518.2.

B) Dibenzyl 3-(N-(3-(tert-butoxycarbonyl)benzyl)-10-guanidino-13-oxo-6,7,8,13-tetrahydrodibenzo[b,f][1,4]dioxecine-4-carboxamide)pentanedioate trifluoroacetate N,N'-Dicyclohexylcarbodiimide (151 mg) was added to a mixture of 10-guanidino-13-oxo-6,7,8,13-tetrahydrodibenzo[b,f][1,4]dioxecine-4-carboxylic acid hydrochloride (144 mg), dibenzyl 3-((3-(tert-butoxycarbonyl)benzyl)amino)pentanedioate (190 mg), pyridine (1 mL), and DMF (1 mL) at room temperature, followed by stirring at 50° C. overnight. The reaction mixture was concentrated under reduced pressure, acetonitrile was then added to the residue, and the insoluble matter was removed by filtration. The filtrate was purified by HPLC (C18, mobile phase: water/acetonitrile (system containing 0.1% TFA)) to obtain the title compound (86.9 mg).
MS: [M+H]⁺ 855.4.

C) 3-(N-(3-(tert-Butoxycarbonyl)benzyl)-10-guanidino-13-oxo-6,7,8,13-tetrahydrodibenzo[b,f][1,4]dioxecine-4-carboxamide)pentanedioic acid trifluoroacetate A mixture of dibenzyl 3-(N-(3-(tert-butoxycarbonyl)benzyl)-10-guanidino-13-oxo-6,7,8,13-tetrahydrodibenzo[b,f][1,4]dioxecine-4-carboxamide)pentanedioate trifluoroacetate (86.9 mg), 10% palladium on carbon (10 mg, water content: about 55%), and THF (2 mL) was stirred under a hydrogen atmosphere at room temperature for 3 hours. The catalyst was removed by filtration, and the filtrate was then concentrated under reduced pressure to obtain the title compound (68.7 mg).
MS: [M+H]⁺ 675.2.

D) 3-(((10-Carbamimidamido-13-oxo-6,7,8,13-tetra-
hydrodibenzo[b,f][1,4]dioxecin-4-yl)carbonyl)
(3-carboxybenzyl)amino)pentanedioic acid A mixture of 3-(N-(3-(tert-butoxycarbonyl)benzyl)-10-guanidino-13-oxo-6,7,8,13-tetrahydrodibenzo[b,f][1,4]dioxecine-4-carboxamide)pentanedioic acid trifluoroacetate (71.0 mg) and TFA (1 mL) was stirred at room temperature for 30 minutes. The reaction mixture was concentrated under reduced pressure, and the residue was purified by HPLC (C18, mobile phase: water/acetonitrile (system containing 0.1% TFA)). The obtained fraction was concentrated under reduced pressure. An ammonium acetate aqueous solution was added to a mixture of the residue and water (0.5 mL) to adjust the pH to about 4, followed by stirring at room temperature for 1 hour. The precipitated solid was collected by filtration and was washed with water to obtain the title compound (31.0 mg).

$^1$H NMR (300 MHz, DMSO-$d_6$) δ 1.27-2.19 (2H, m), 2.52-2.71 (4H, m, J=18.7 Hz), 2.74-3.10 (2H, m), 3.94-4.59 (4H, m), 4.89-5.07 (1H, m), 7.15-7.34 (4H, m), 7.39-7.59 (2H, m), 7.59-7.78 (4H, m), 7.78-7.97 (3H, m), 8.00 (1H, s).

Example 145

3-((((10-Carbamimidamido-3-(2-carboxyethyl)-13-oxo-6,7,8,13-tetrahydrodibenzo[b,f][1,4]dioxecin-4-yl)carbonyl) (carboxymethyl)amino)methyl)benzoic acid A) tert-Butyl 3-((N-(2-(tert-butoxy)-2-oxoethyl)-3-(3-(tert-butoxy)-3-oxopropyl)-10-((tert-butoxycarbonyl)amino)-13-oxo-6,7,8,13-tetrahydrodibenzo[b,f][1,4]dioxecine-4-carboxamide)methyl)benzoate HOBt.H$_2$O (63.6 mg) and WSC hydrochloride (80 mg) were added to a mixture of 3-(3-(tert-butoxy)-3-oxopropyl)-10-((tert-butoxycarbonyl)amino)-13-oxo-6,7,8,13-tetrahydrodibenzo[b,f][1,4]dioxecine-4-carboxylic acid (150.0 mg), tert-butyl 3-(((2-(tert-butoxy)-2-oxoethyl)amino) methyl)benzoate (135.1 mg), N,N-diisopropylethylamine (0.145 mL), and DMF (3 mL) at room temperature, followed by stirring at room temperature overnight. Water was added to the reaction mixture at 0° C., followed by extraction with ethyl acetate. The organic layer was washed with a saturated sodium hydrogen carbonate aqueous solution and a saturated saline solution and was then dried over anhydrous sodium sulfate, and the solvent was distilled under reduced pressure. The residue was purified by silica gel column chromatography (ethyl acetate/hexane) to obtain the title compound (194 mg).

MS: [M+H]$^+$ 845.4.

B) 3-((((10-Carbamimidamido-3-(2-carboxyethyl)-13-oxo-6,7,8,13-tetrahydrodibenzo[b,f][1,4]dioxecin-4-yl)carbonyl) (carboxymethyl)amino)methyl) benzoic acid A mixture of tert-butyl 3-((N-(2-(tert-butoxy)-2-oxoethyl)-3-(3-(tert-butoxy)-3-oxopropyl)-10-((tert-butoxycarbonyl)amino)-13-oxo-6,7,8,13-tetrahydrodibenzo[b,f][1,4]dioxecine-4-carboxamide)methyl)benzoate (190.2 mg), 4 N hydrogen chloride in cyclopentyl methyl ether (2.0 mL), and acetic acid (2.0 mL) was stirred at room temperature overnight, and the reaction mixture was then concentrated. A mixture of the residue, 4 N hydrogen chloride in cyclopentyl methyl ether (0.277 mL), cyanamide (46.4 mg), and tert-butyl alcohol (4 mL) was stirred at 60° C. for 6 hours. Ethyl acetate and toluene were added to the reaction mixture, followed by extraction with water. The aqueous layer was purified by HPLC (C18, mobile phase: water/acetonitrile (system containing 0.1% TFA)), and the obtained fraction was concentrated under reduced pressure. A 1 M ammonium acetate aqueous solution was added to a mixture of the residue and water (1 mL) at room temperature to adjust the pH of the mixture to 4, followed by stirring at room temperature for 2 hours. The precipitated solid was collected by filtration and was washed with water to obtain the title compound (60.8 mg).

$^1$H NMR (300 MHz, DMSO-$d_6$) δ 1.51-2.30 (2H, m), 2.32-2.66 (2H, m), 2.68-3.03 (3H, m), 3.06-4.13 (5H, m), 4.17-4.64 (2H, m), 7.02-7.17 (1H, m), 7.18-7.62 (5H, m), 7.69-8.53 (7H, m).

In Examples 4, 5, 7 to 10, 12, 14 to 17, 20, 21, 25, 27 to 29, 31 to 36, 38, 39, 41, 45, 46, 49, 51, 53 to 56, 60, 63, 64, 66, 70, 72 to 75, 78, 80 to 90, 92, 93, 95 to 98, 100 to 103, 105, 107, 109, 111 to 113, 117, 123 to 134, 137 to 139, 142, and 146 to 166, compounds were produced by the methods described above or in accordance with the methods. The example compounds are shown in the following table. The column "MS" in the table shows measured values.

TABLE A

| EXAMPLE | IUPACNAME | STRUCTURE | SALT | MS |
| --- | --- | --- | --- | --- |
| 1 | N-((10-carbamimidamido-13-oxo-6,7,8,13-tetrahydrodibenzo[b,f][1,4]dioxecin-4-yl)carbonyl)-L-aspartic acid | 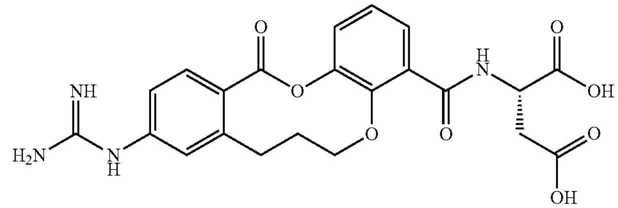 [SMILES: N=C(N)Nc1ccc2c(c1)CCCOc1c(cccc1C(=O)N[C@@H](CC(=O)O)C(=O)O)OC2=O] | | 471.2 |

TABLE A-continued

| EX-AMPLE | IUPACNAME | STRUCTURE | SALT | MS |
|---|---|---|---|---|
| 2 | N-((10-carbamimidamido-13-oxo-6,7,8,13-tetrahydro-dibenzo[b,f][1,4]dioxecin-4-yl)carbonyl)-D-aspartic acid | 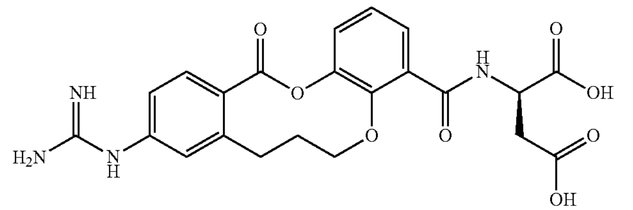 [SMILES: N=C(N)Nc1ccc2c(c1)CCCOc1c(cccc1C(=O)N[C@H](CC(=O)O)C(=O)O)OC2=O] | | 471.2 |
| 3 | N-((10-carbamimidamido-13-oxo-6,7,8,13-tetrahydro-dibenzo[b,f][1,4]dioxecin-4-yl)carbonyl)aspartic acid | 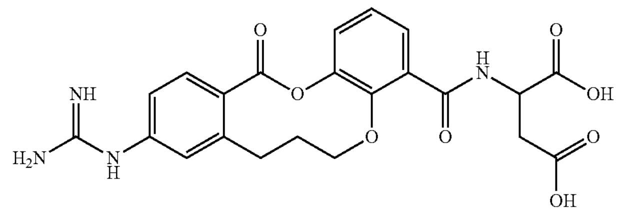 [SMILES: N=C(N)Nc1ccc2c(c1)CCCOc1c(cccc1C(=O)NC(CC(=O)O)C(=O)O)OC2=O] | | 471.2 |
| 4 | diethyl (4-(((10-carbamimidamido-13-oxo-6,7,8,13-tetrahydro-dibenzo[b,f][1,4]dioxecin-4-yl)carbonyl)amino)benzyl)phosphorate | 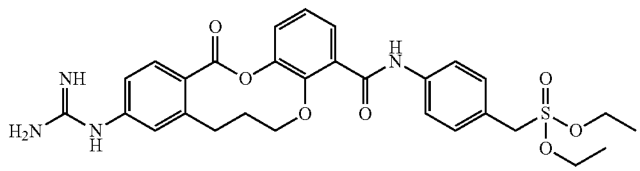 | HCl | 561.2 |
| 5 | N-(((10-carbamimidamido-13-oxo-6,7,8,13-tetrahydro-dibenzo[b,f][1,4]dioxecin-4-yl)carbonyl)amino)benzenesulfonic acid | 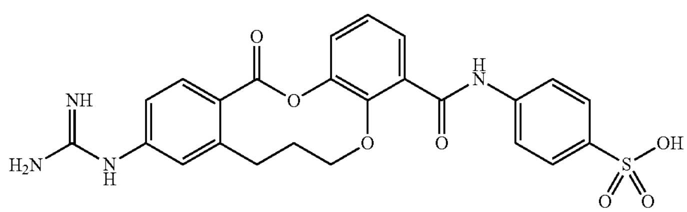 [SMILES: N=C(N)Nc1ccc2c(c1)CCCOc1c(cccc1C(=O)Nc1ccc(S(=O)(=O)O)cc1)OC2=O] | | 511.1 |
| 6 | N-((10-carbamimidamido-13-oxo-6,7,8,13-tetrahydro-dibenzo[b,f][1,4]dioxecin-4-yl)carbonyl)-3-sulfo-L-alanine | 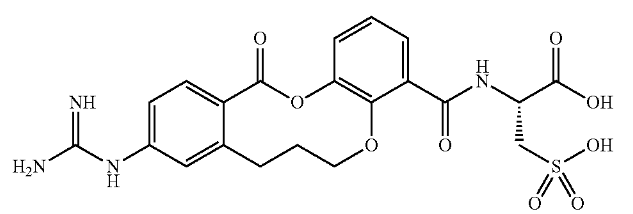 [SMILES: N=C(N)Nc1ccc2c(c1)CCCOc1c(cccc1C(=O)N[C@@H](CS(=O)(=O)O)C(=O)O)OC2=O] | | 507.1 |
| 7 | 10-carbamimidamido-4-(((2R)-1-methoxy-1-oxo-3-sulfopropan-2-yl)carbamoyl)-13-oxo-6,7,8,13-tetrahydro-dibenzo[b,f][1,4]dioxecine | 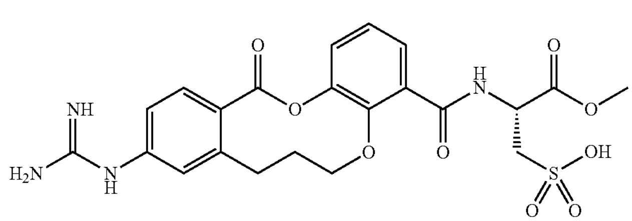 [SMILES: COC(=O)[C@H](CS(=O)(=O)O)NC(=O)c1cccc2c1OCCCc1cc(NC(=N)N)ccc1C(=O)O2] | | 521.1 |

TABLE A-continued

| EX-AMPLE | IUPACNAME | STRUCTURE | SALT | MS |
|---|---|---|---|---|
| 8 | N-2-((10-carbamimidamido-13-oxo-6,7,8,13-tetrahydro-dibenzo[b,f][1,4]dioxecin-4-yl)carbonyl)-L-arginine | 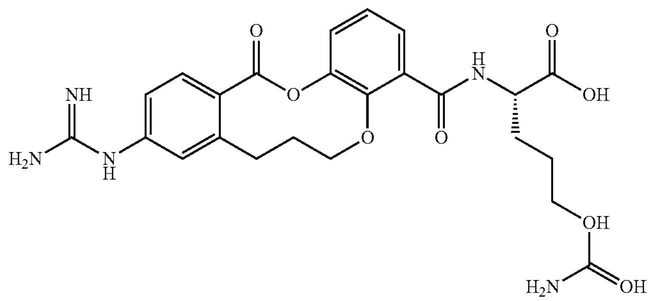 [SMILES: N=C(N)Nc1ccc2c(c1)CCCOc1c(cccc1C(=O)N[C@@H](CCCOC(N)=O)C(=O)O)OC2=O] | 2HCl | 512.2 |
| 9 | 3,3'-(((10-carbamimidamido-13-oxo-6,7,8,13-tetrahydro-dibenzo[b,f][1,4]dioxecin-4-yl)carbonyl)imino)dipropanoic acid (non-preferred name) | 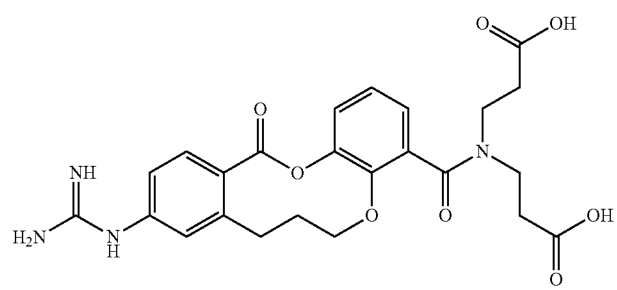 [SMILES: N=C(N)Nc1ccc2c(c1)CCCOc1c(cccc1C(=O)N(CCC(=O)O)CCC(=O)O)OC2=O] | | 499.1 |
| 10 | N-((10-carbamimidamido-13-oxo-6,7,8,13-tetrahydro-dibenzo[b,f][1,4]dioxecin-4-yl)carbonyl)-L-tyrosine | 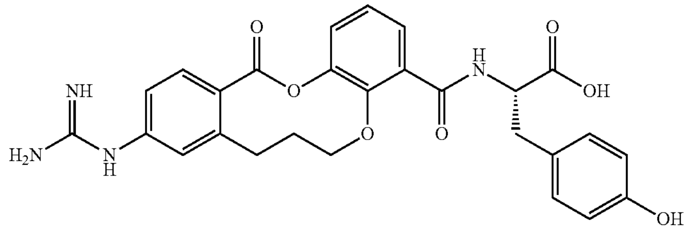 [SMILES: N=C(N)Nc1ccc2c(c1)CCCOc1c(cccc1C(=O)N[C@@H](Cc1ccc(O)cc1)C(=O)O)OC2=O] | | 519.1 |
| 11 | 3-(((10-carbamimidamido-13-oxo-6,7,8,13-tetrahydro-dibenzo[b,f][1,4]dioxecin-4-yl)carbonyl)amino)pantanedioic acid | 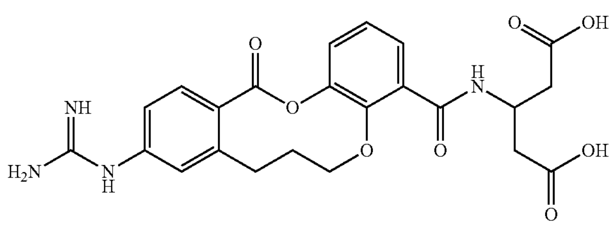 [SMILES: N=C(N)Nc1ccc2c(c1)CCCOc1c(cccc1C(=O)NC(CC(=O)O)CC(=O)O)OC2=O] | | 485.1 |
| 12 | 1-((10-carbamimidamido-13-oxo-6,7,8,13-tetrahydro-dibenzo[b,f][1,4]dioxecin-4-yl)carbonyl)-L-proline | 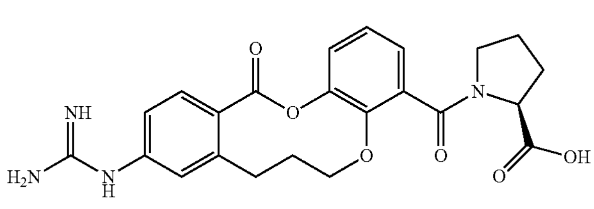 [SMILES: N=C(N)Nc1ccc2c(c1)CCCOc1c(cccc1C(=O)N1CCC[C@H]1C(=O)O)OC2=O] | | 453.2 |
| 13 | N-((9-carbamimidamido-6-oxo-11,12-dihydro-6Hdibenzo-[b,f][1,4]dioxonin-1-yl)carbonyl)-L-aspartic acid | 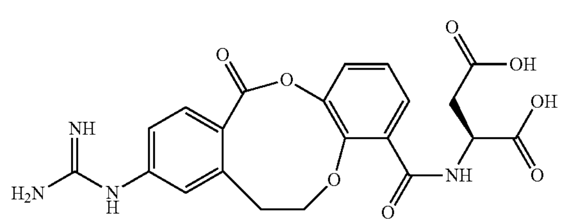 [SMILES: N=C(N)Nc1ccc2c(c1)CCOc1c(cccc1C(=O)N[C@@H](CC(=O)O)C(=O)O)OC2=O] | CF3COOH | 457.2 |

TABLE A-continued

| EXAMPLE | IUPACNAME | STRUCTURE | SALT | MS |
|---|---|---|---|---|
| 14 | 2,2'-(((10-carbamimidamido-13-oxo-6,7,8,13-tetrahydro-dibenzo[b,f][1,4]dioxecin-4-yl)carbonyl)imino)diacetic acid | 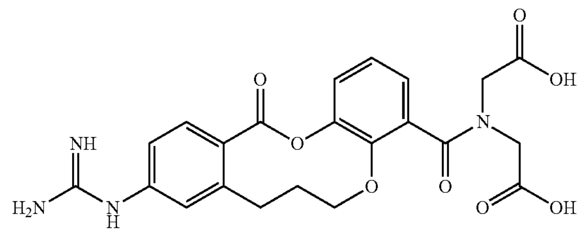 [SMILES: N=C(N)Nc1ccc2c(c1)CCCOc1c(cccc1C(=O)N(CC(=O)O)CC(=O)O)OC2=O] | | 471.1 |
| 15 | 2-(((9-carbamimidamido-6-oxo-11,12-dihydro-6H-dibenzo[b,f][1,4]dioxonin-1-yl)carbonyl)amino)ethanesulfonic acid | 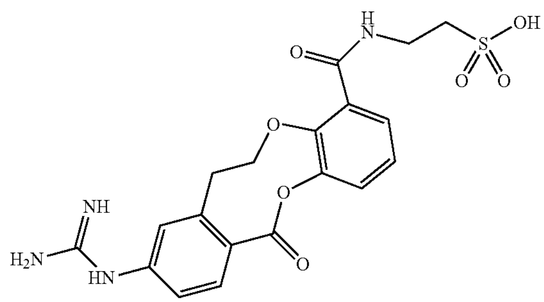 [SMILES: N=C(N)Nc1ccc2c(c1)CCOc1c(cccc1C(=O)NCCS(=O)(=O)O)OC2=O] | CF3COOH | 449.0 |
| 16 | N-2-((10-carbamimidamido-13-oxo-6,7,8,13-tetrahydro-dibenzo[b,f][1,4]dioxecin-4-yl)carbonyl)-L-glutamine | 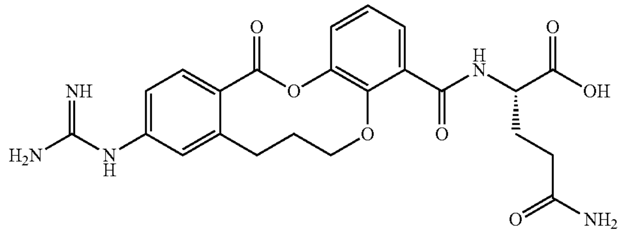 [SMILES: N=C(N)Nc1ccc2c(c1)CCCOc1c(cccc1C(=O)N[C@@H](CCC(N)=O)C(=O)O)OC2=O] | | 484.2 |
| 17 | N-2-((10-carbamimidamido-13-oxo-6,7,8,13-tetrahydro-dibenzo[b,f][1,4]dioxecin-4-yl)carbonyl)-L-asparagine | 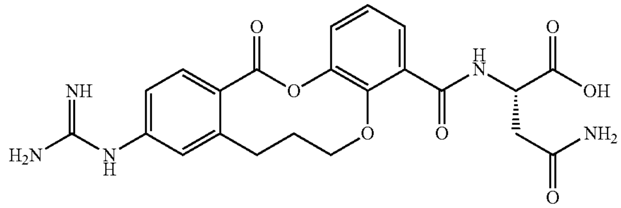 [SMILES: N=C(N)Nc1ccc2c(c1)CCCOc1c(cccc1C(=O)N[C@@H](CC(N)=O)C(=O)O)OC2=O] | | 470.2 |
| 18 | N-((10-carbamimidamido-13-oxo-6,7,8,13-tetrahydro-dibenzo[b,f][1,4]dioxecin-4-yl)carbonyl)-L-glutamic acid | 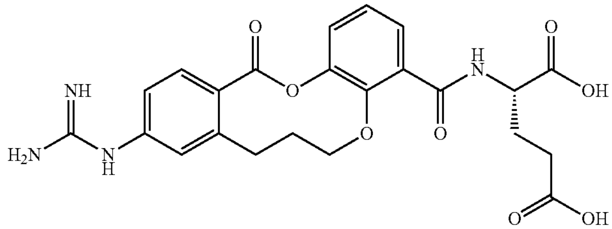 [SMILES: N=C(N)Nc1ccc2c(c1)CCCOc1c(cccc1C(=O)N[C@@H](CCC(=O)O)C(=O)O)OC2=O] | | 485.2 |
| 19 | N-((9-carbamimidamido-6-oxo-6,11-dihydro-dibenzo[b,f][1,4]dioxecin-1-yl)carbonyl)-L-aspartic acid | 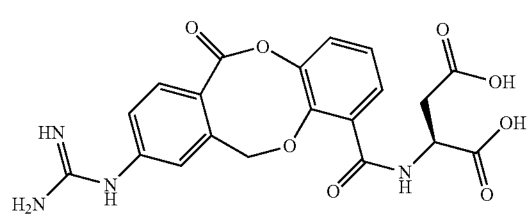 [SMILES: N=C(N)Nc1ccc2c(c1)COc1c(cccc1C(=O)N[C@@H](CC(=O)O)C(=O)O)OC2=O] | CF3COOH | 443.2 |

TABLE A-continued

| EXAMPLE | IUPACNAME | STRUCTURE | SALT | MS |
|---|---|---|---|---|
| 20 | N-((3-carbamimidamido-7-methyl-14-oxo-6,7,8,14-tetrahydro-6H-dibenzo[b,h]oxecin-9-yl)carbonyl)-L-aspartic acid | 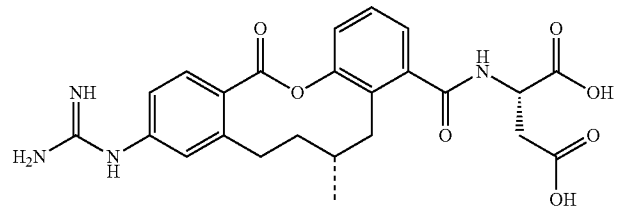 | | 483.0 |
| 21 | N-((3-carbamimidamido-8-methyl-14-oxo-5,7,8,14-tetrahydro-6H-dibenzo[b,h]oxecin-9-yl)carbonyl)-L-aspartic acid | 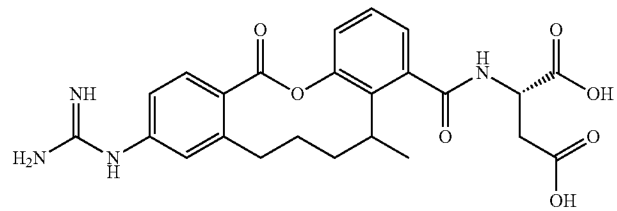 [SMILES: CC1CCCc2cc(NC(=N)N)ccc2C(=O)Oc2cccc(C(=O)N[C@@H](CC(=O)O)C(=O)O)c21] | | 483.1 |
| 22 | 3-(10-carbamimidamido-13-oxo-6,7,8,13-tetrahydro-dibenzo[b,f][1,4]dioxecin-4-yl)-5-(carboxymethyl)-4,5-dihydro-1,2-oxazole-5-carboxylic acid | 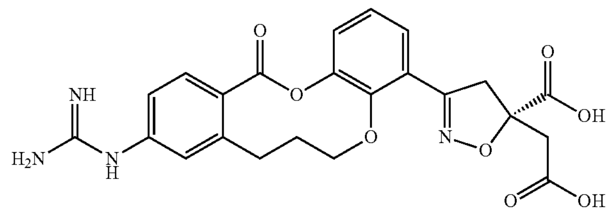 [SMILES: N=C(N)Nc1ccc2c(c1)CCCOc1c(cccc1C1=NO[C@@](CC(=O)O)(C(=O)O)C1)OC2=O] | | 483.1 |
| 23 | 3-(10-carbamimidamido-13-oxo-6,7,8,13-tetrahydro-dibenzo[b,f][1,4]dioxecin-4-yl)-5-(carboxymethyl)-4,5-dihydro-1,2-oxazole-5-carboxylic acid | 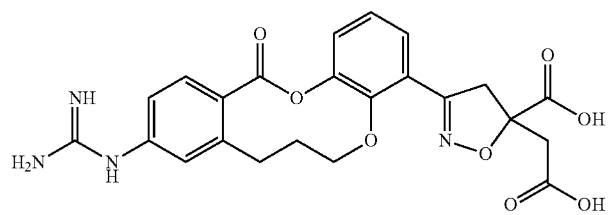 [SMILES: N=C(N)Nc1ccc2c(c1)CCCOc1c(cccc1C1=NOC(CC(=O)O)(C(=O)O)C1)OC2=O] | | 483.0 |
| 24 | 3-(10-carbamimidamido-13-oxo-6,7,8,13-tetrahydro-dibenzo[b,f][1,4]dioxecin-4-yl)-5-(carboxymethyl)-4,5-dihydro-1,2-oxazole-5-carboxylic acid | 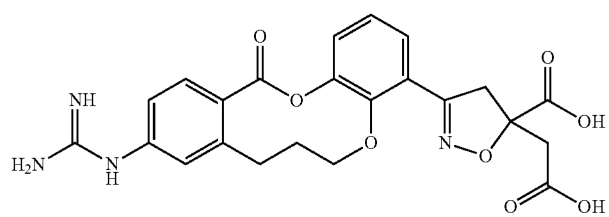 [SMILES: N=C(N)Nc1ccc2c(c1)CCCOc1c(cccc1C1=NOC(CC(=O)O)(C(=O)O)C1)OC2=O] | | 483.0 |
| 25 | ((((10-carbamimidamido-13-oxo-6,7,8,13-tetrahydro-dibenzo[b,f][1,4]dioxecin-4-yl)carbonyl)amino)methyl)phosphonic acid | 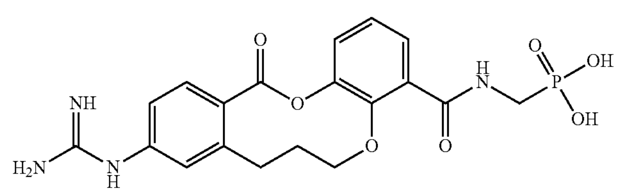 [SMILES: N=C(N)Nc1ccc2c(c1)CCCOc1c(cccc1C(=O)NCP(=O)(O)O)OC2=O] | | 446.9 |

TABLE A-continued

| EXAMPLE | IUPACNAME | STRUCTURE | SALT | MS |
|---|---|---|---|---|
| 26 | N-((9-carbamimidamido-12-oxo-5,6,7,12-tetrahydro-4H-thiano[3,2-c][2]benzoxecin-2-yl)carbonyl)-L-aspartic acid | 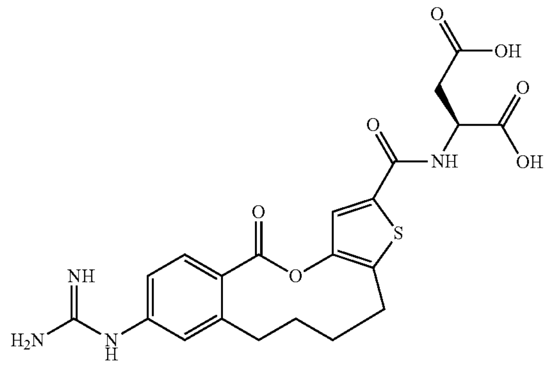 [SMILES: N=C(N)Nc1ccc2c(c1)CCCCc1sc(C(=O)N[C@@H](CC(=O)O)C(=O)O)cc1OC2=O] | | 474.9 |
| 27 | (((10-carbamimidamido-13-oxo-6,7,8,13-tetrahydro-dibenzo[b,f][1,4]dioxecin-4-yl)carbonyl)amino)methanesulfonic acid | 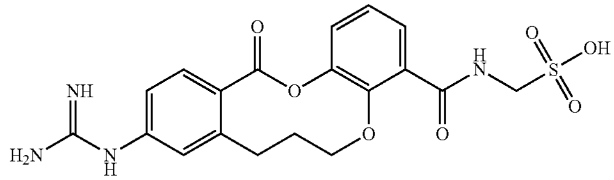 [SMILES: N=C(N)Nc1ccc2c(c1)CCCOc1c(cccc1C(=O)NCS(=O)(=O)O)OC2=O] | | 447.0 |
| 28 | 2-(((10-carbamimidamido-13-oxo-6,7,8,13-tetrahydro-dibenzo[b,f][1,4]dioxecin-4-yl)carbonyl)amino)ethanesulfonic acid | 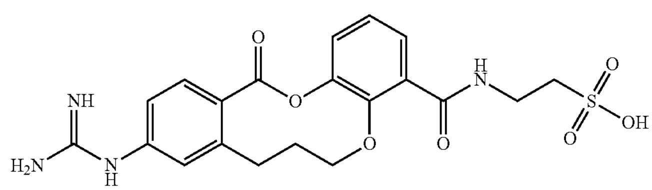 [SMILES: N=C(N)Nc1ccc2c(c1)CCCOc1c(cccc1C(=O)NCCS(=O)(=O)O)OC2=O] | | 463.1 |
| 29 | 10-carbamimidamido-13-oxo-6,7,8,13-tetrahydro-dibenzo[b,f][1,4]dioxecine-4-carboxylic acid | 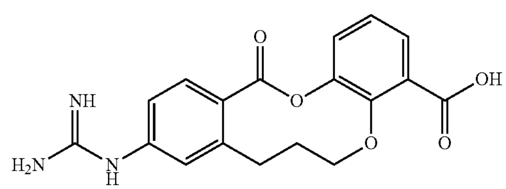 [SMILES: N=C(N)Nc1ccc2c(c1)CCCOc1c(cccc1C(=O)O)OC2=O] | CF3COOH | 356.0 |
| 30 | N-((9-carbamimidamido-6-oxo-6,11,12,13-tetrahydro-dibenzo[b,g]oxocin-1-yl)carbonyl)-L-aspartic acid | 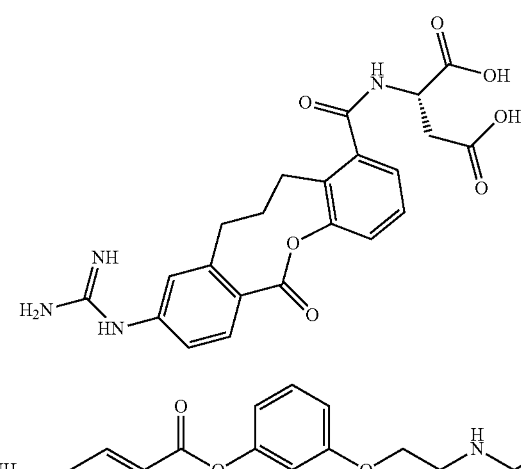 | CF3COOH | 455.2 |
| 31 | N-(((3-carbamimidamido-14-oxo-5,7,8,14-tetrahydro-6H-dibenzo[b,h]oxecin-9-yl)oxy)acetyl)-L-aspartic acid | 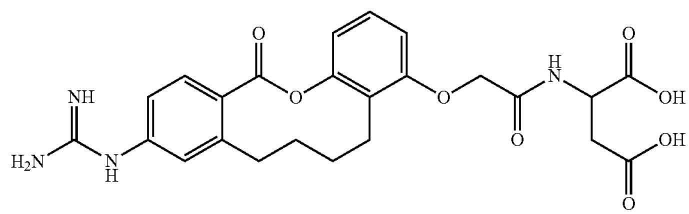 [SMILES: N=C(N)Nc1ccc2c(c1)CCCCc1c(OCC(=O)NC(CC(=O)O)C(=O)O)cccc1OC2=O] | | 497.1 |

TABLE A-continued

| EXAMPLE | IUPACNAME | STRUCTURE | SALT | MS |
|---|---|---|---|---|
| 32 | N-((3-carbamimidamido-14-oxo-5,7,8,14-tetrahydro-6H-dibenzo[b,h]oxecin-9-yl)acetyl)-L-aspartic acid | 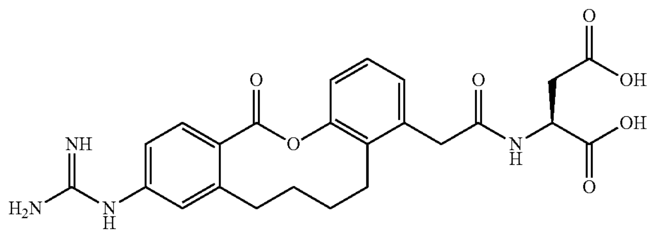 [SMILES: N=C(N)Nc1ccc2c(c1)CCCCc1c(CC(=O)N[C@@H](CC(=O)O)C(=O)O)cccc1OC2=O] | | 481.0 |
| 33 | 2-(((3-carbamimidamido-14-oxo-5,7,8,14-tetrahydro-6H-dibenzo[b,h]oxecin-9-yl)carbonyl)amino)ethanesulfonic acid | 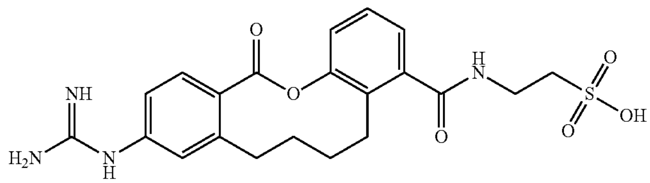 [SMILES: N=C(N)Nc1ccc2c(c1)CCCCc1c(cccc1C(=O)NCCS(=O)(=O)O)OC2=O] | | 461.0 |
| 34 | 3-carbamimidamido-14-oxo-6,7,8,14-tetrahydro-6H-dibenzo[b,h]oxecine-9-carboxylic acid | 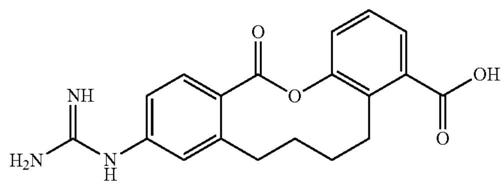 [SMILES: N=C(N)Nc1ccc2c(c1)CCCCc1c(cccc1C(=O)O)OC2=O] | | 354.0 |
| 35 | 2-((((10S)-3-carbamimidamido-15-oxo-5,7,8,10,11,15-hexahydro-6H-12,14-dioxabenzo[5,6]cyclodeca[1,2-f]inden-10-yl)acetyl)amino)ethanesulfonic acid | 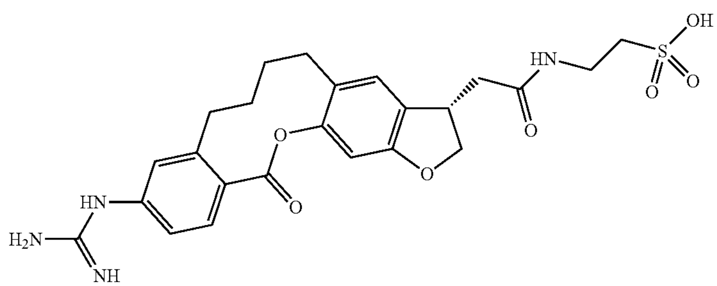 [SMILES: N=C(N)Nc1ccc2c(c1)CCCCc1cc3c(cc1OC2=O)OC[C@H]3CC(=O)NCCS(=O)(=O)O] | | 517.1 |
| 36 | 2-(((3-carbamimidamido-15-oxo-5,7,8,10,11,15-hexahydro-6H-12,14-dioxabenzo[5,6]cyclodeca[1,2-f]inden-9-yl)carbonyl)amino)ethanesulfonic acid | 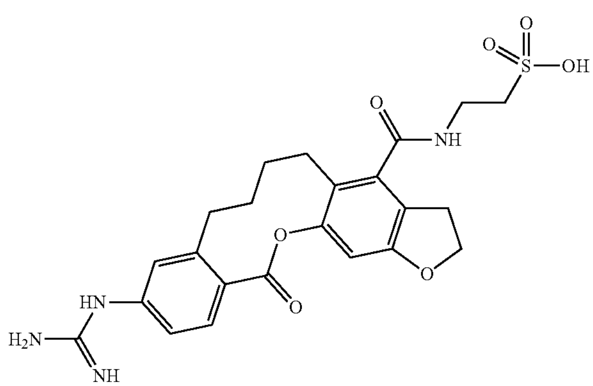 [SMILES: N=C(N)Nc1ccc2c(c1)CCCCc1c(cc3c(c1C(=O)NCCS(=O)(=O)O)CCO3)OC2=O] | | 503.0 |
| 37 | N-((3-carbamimidamido-14-oxo-5,7,8,14-tetrahydro-6H-dibenzo[b,h]oxecin-9-yl)carbonyl)-L-aspartic acid | 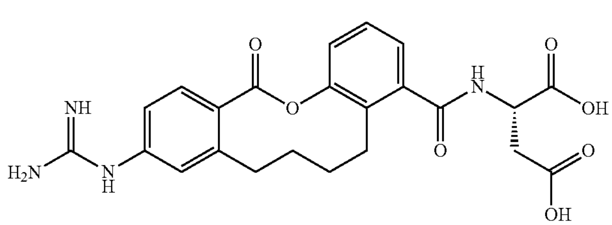 | | 469.2 |

TABLE A-continued

| EX-AMPLE | IUPACNAME | STRUCTURE | SALT | MS |
|---|---|---|---|---|
| 38 | N-(((9S)-2-carbamimidamido-5-oxo-9,10,12,13,14,15-hexahydro-5H-6,11-dioxabenzo[5,6]cyclodeca[1,2-a]inden-9-yl)acetyl)-L-aspartic acid | 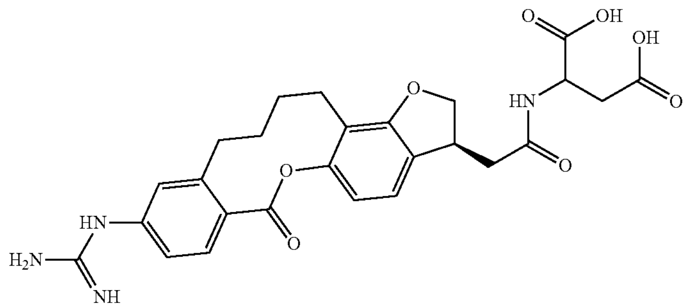 [SMILES: N=C(N)Nc1ccc2c(c1)CCCCc1c(ccc3c1OC[C@H]3CC(=O)NC(CC(=O)O)C(=O)O)OC2=O] | | 525.2 |
| 39 | N-(((10S)-3-carbamimidamido-15-oxo-5,7,8,10,11,15-hexahydro-6H-12,14-dioxabenzo[5,6]cyclodeca[1,2-f]inden-10-yl)acetyl)-L-aspartic acid | 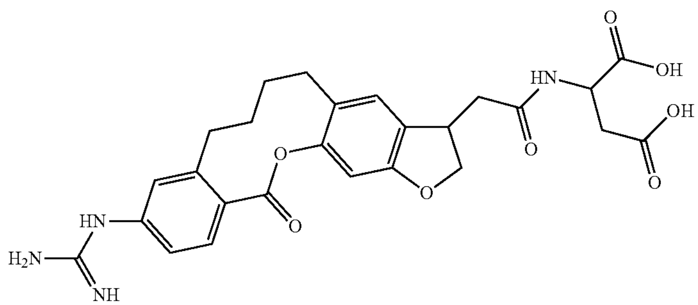 [SMILES: N=C(N)Nc1ccc2c(c1)CCCCc1cc3c(cc1OC2=O)OCC3CC(=O)NC(CC(=O)O)C(=O)O] | | 525.1 |
| 40 | N-((3-carbamimidamido-15-oxo-5,7,8,10,11,15-hexahydro-6H-12,14-dioxabenzo[5,6]cyclodeca[1,2-f]inden-9-yl)carbonyl)-L-aspartic acid | 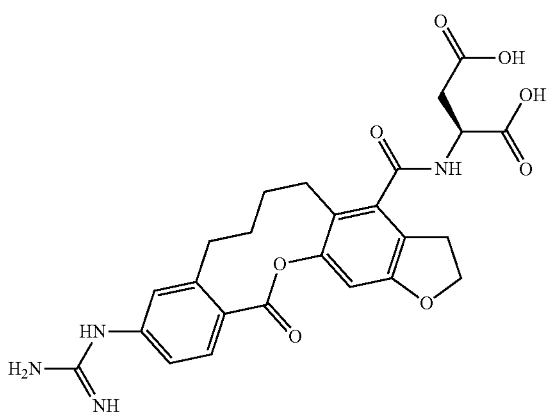 [SMILES: N=C(N)Nc1ccc2c(c1)CCCCc1c(cc3c(c1C(=O)N[C@@H](CC(=O)O)C(=O)O)CCO3)OC2=O] | | 511.1 |
| 41 | N-(3-(3-carbamimidamido-12-fluoro-14-oxo-5,7,8,14-tetrahydro-6H-dibenzo[b,h]oxacin-9-yl)propanoyl)-L-aspartic acid | 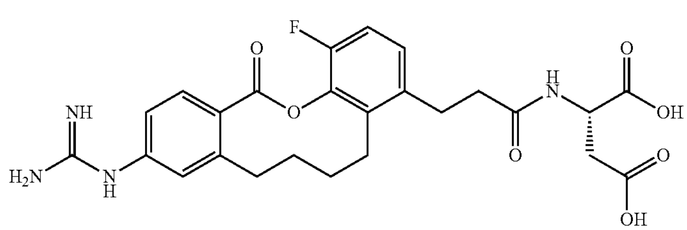 [SMILES: N=C(N)Nc1ccc2c(c1)CCCCc1c(CCC(=O)N[C@@H](CC(=O)O)C(=O)O)ccc(F)c1OC2=O] | | 515.1 |
| 42 | N-(3-(3-carbamimidamido-16-oxo-6,7,8,9-tetrahydro-16H-dibenzo[b,f][1,4,8]trioxacyclododecin-11-yl)propanoyl)aspartic acid | 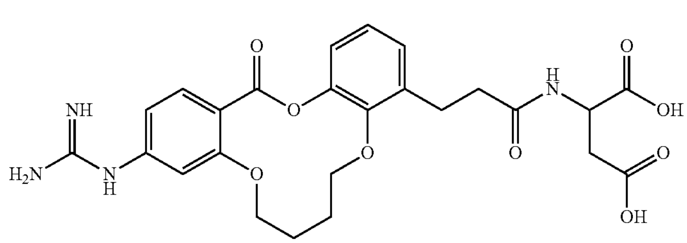 [SMILES: N=C(N)Nc1ccc2c(c1)OCCCCOc1c(CCC(=O)NC(CC(=O)O)C(=O)O)cccc1OC2=O] | CF3COOH | 529.1 |

TABLE A-continued

| EXAMPLE | IUPACNAME | STRUCTURE | SALT | MS |
|---|---|---|---|---|
| 43 | N-(3-(3-carbamimidamido-15-oxo-7,8-dihydro-6H,15H-dibenzo[b,f][1,4,8]trioxacycloundecin-10-yl)propanoyl)aspartic acid | 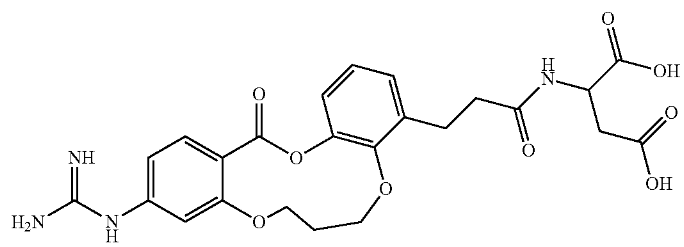 [SMILES: N=C(N)Nc1ccc2c(c1)OCCCOc1c(CCC(=O)NC(CC(=O)O)C(=O)O)cccc1OC2=O] | CF3COOH | 515.1 |
| 44 | N-(3-(11-carbamimidamido-14-oxo-7,8,9,14-tetrahydro-6H-dibenzo[b,f][1,4]dioxacycloundecin-4-yl)propanoyl)-L-aspartic acid | 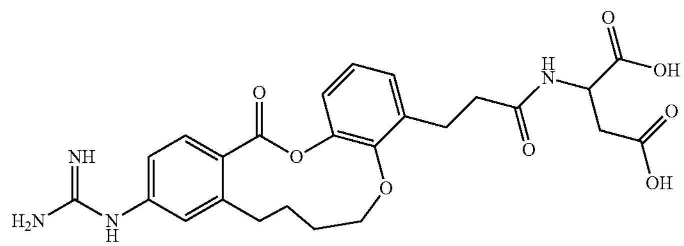 [SMILES: N=C(N)Nc1ccc2c(c1)CCCCOc1c(CCC(=O)NC(CC(=O)O)C(=O)O)cccc1OC2=O] | CF3COOH | 513.0 |
| 45 | N-((10-carbamimidamido-13-oxo-6,7,8,13-tetrahydro-dibenzo[b,f][1,4]dioxecin-3-yl)carbonyl)aspartic acid | 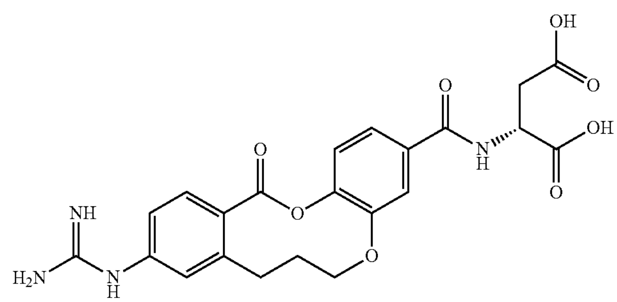 [SMILES: N=C(N)Nc1ccc2c(c1)CCCOc1cc(C(=O)N[C@H](CC(=O)O)C(=O)O)ccc1OC2=O] | | 471.0 |
| 46 | N-(3-(3-carbamimidamido-16-oxo-6,7,8,9-tetrahydro-16H-dibenzo[b,f][1,4,8]trioxacyclo-dodecin-12-yl)propanoyl)aspartic acid | 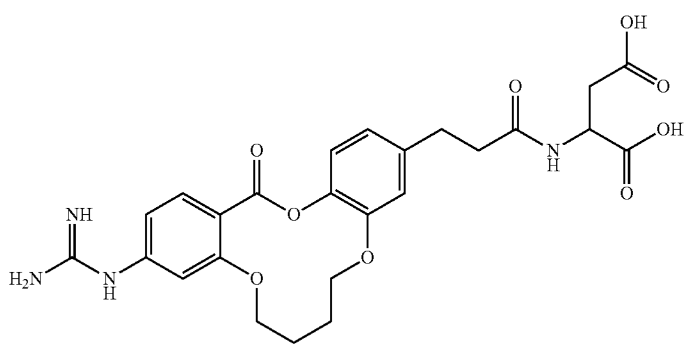 [SMILES: N=C(N)Nc1ccc2c(c1)OCCCCOc1cc(CCC(=O)NC(CC(=O)O)C(=O)O)ccc1OC2=O] | CF3COOH | 529.0 |
| 47 | N-(3-(10-carbamimidamido-13-oxo-6,7,8,13-tetrahydro-dibenzo[b,f][1,4]dioxecin-4-yl)propanoyl)aspartic acid | 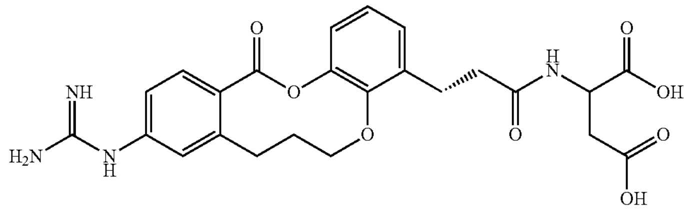 | | 499.1 |

TABLE A-continued

| EXAMPLE | IUPACNAME | STRUCTURE | SALT | MS |
|---|---|---|---|---|
| 48 | N-(3-(9-carbamimidamido-6-oxo-11,12-dihydro-6H-[2]benzoxocine[4,3-b]pyridin-2-yl)propanoyl)-L-aspartic acid | 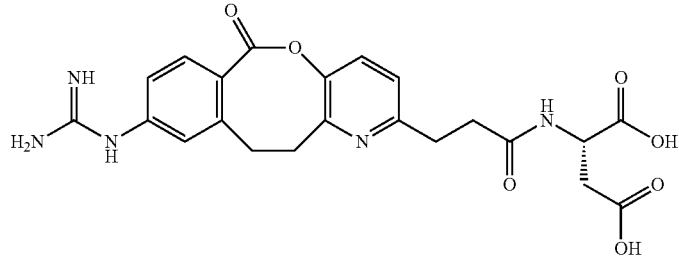 [SMILES: N=C(N)Nc1ccc2c(c1)CCc1nc(CCC(=O)N[C@@H](CC(=O)O)C(=O)O)ccc1OC2=O] | CF3COOH | 470.0 |
| 49 | N-(3-(10-carbamimidamido-13-oxo-6,7,8,13-tetrahydro-dibenzo[b,f][1,4]dioxecin-3-yl)propanoyl)-aspartic acid | 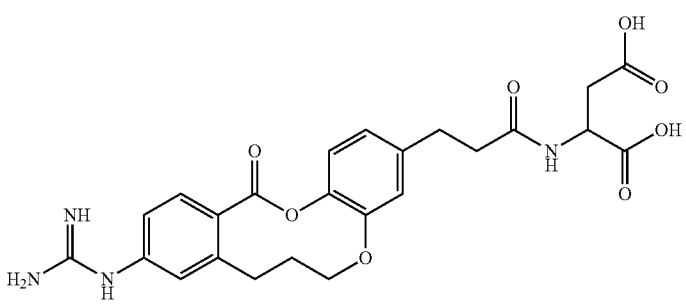 [SMILES: N=C(N)Nc1ccc2c(c1)CCCOc1cc(CCC(=O)NC(CC(=O)O)C(=O)O)ccc1OC2=O] | CF3COOH | 497.1 |
| 50 | N-(3-(9-carbamimidamido-6-oxo-12,13-dihydro-6H-dibenzo[b,f][1,5]dioxecin-2-yl)propanoyl)-L-aspartic acid | 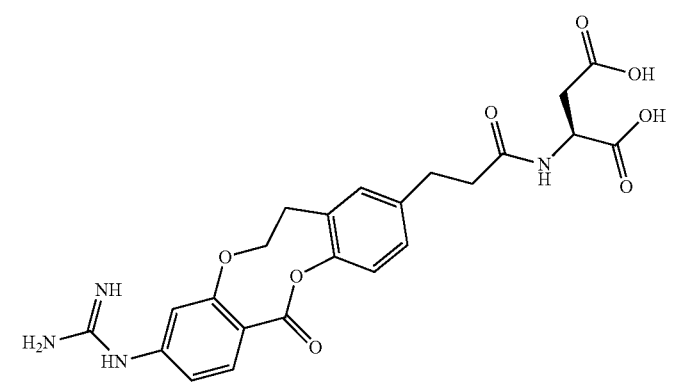 [SMILES: N=C(N)Nc1ccc2c(c1)OCCc1cc(CCC(=O)N[C@@H](CC(=O)O)C(=O)O)ccc1OC2=O] | CF3COOH | 485.0 |
| 51 | N-(3-(3-carbamimidamido-15-oxo-7,8-dihydro-6H,15H-dibenzo[b,f][1,4,8]trioxacycloundecin-11-yl)propanoyl)aspartic acid | 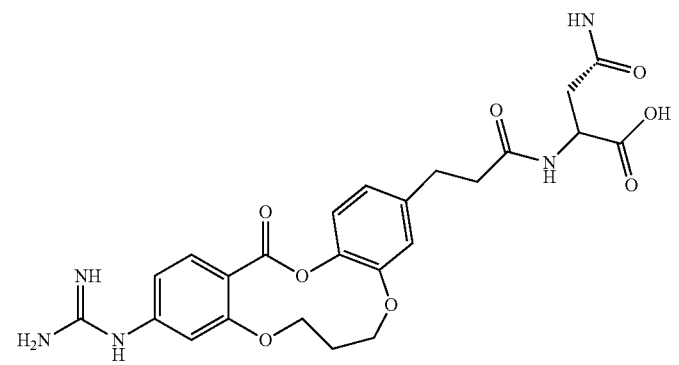 | CF3COOH | 515.0 |
| 52 | N-(3-(3-carbamimidamido-14-oxo-6,7-dihydro-14H-dibenzo[b,h][1,4,7]trioxecin-9-yl)propanoyl)aspartic acid | 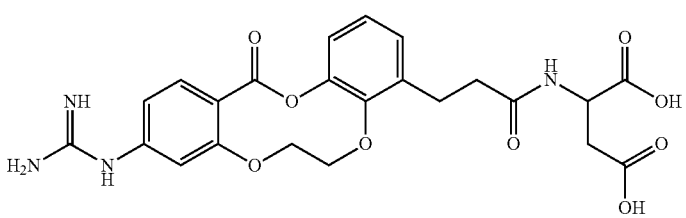 [SMILES: N=C(N)Nc1ccc2c(c1)OCCOc1c(CCC(=O)NC(CC(=O)O)C(=O)O)cccc1OC2=O] | CF3COOH | 501.1 |

TABLE A-continued

| EXAMPLE | IUPACNAME | STRUCTURE | SALT | MS |
|---|---|---|---|---|
| 53 | N-(3-(3-carbamimidamido-14-oxo-6,7-dihydro-14H-dibenzo[b,h][1,4,7]trioxecin-10-yl)propanoyl)aspartic acid | 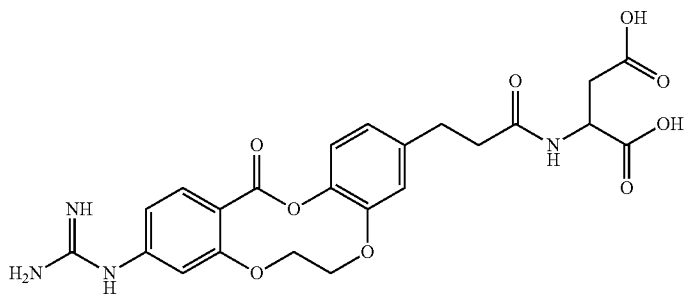 [SMILES: N=C(N)Nc1ccc2c(c1)OCCOc1cc(CCC(=O)NC(CC(=O)O)C(=O)O)ccc1OC2=O] | CF3COOH | 501.2 |
| 54 | N-(3-(9-carbamimidamido-6-oxo-11,12-dihydro-6H-dibenzo[b,f]oxocin-4-yl)propanoyl)-L-aspartic acid | 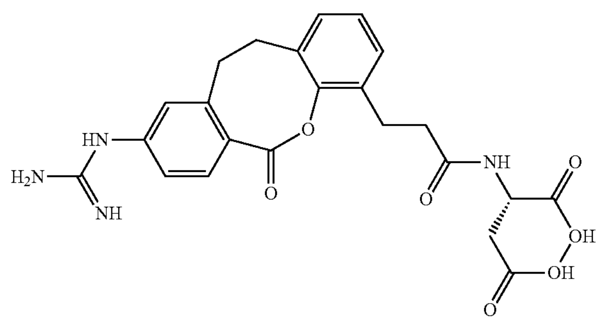 [SMILES: N=C(N)Nc1ccc2c(c1)CCc1cccc(CCC(=O)N[C@H]3CC(=O)OOC3=O)c1OC2=O] | CF3COOH | 469.0 |
| 55 | N-(3-(9-carbamimidamido-6-oxo-11,12-dihydro-6H-dibenzo[b,f]oxocin-3-yl)propanoyl)-L-aspartic acid | 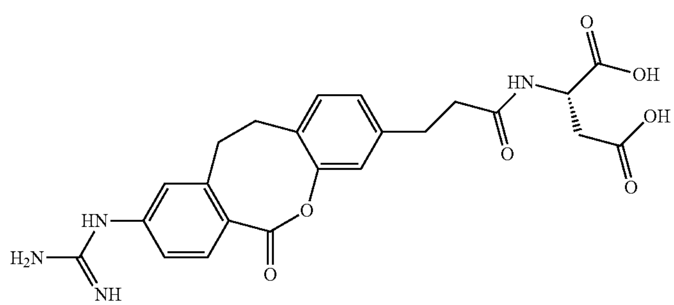 [SMILES: N=C(N)Nc1ccc2c(c1)CCc1ccc(CCC(=O)N[C@@H](CC(=O)O)C(=O)O)cc1OC2=O] | CF3COOH | 469.0 |
| 56 | N-(3-(9-carbamimidamido-6-oxo-11,12-dihydro-6H-dibenzo[b,f]oxocin-2-yl)propanoyl)-L-aspartic acid | 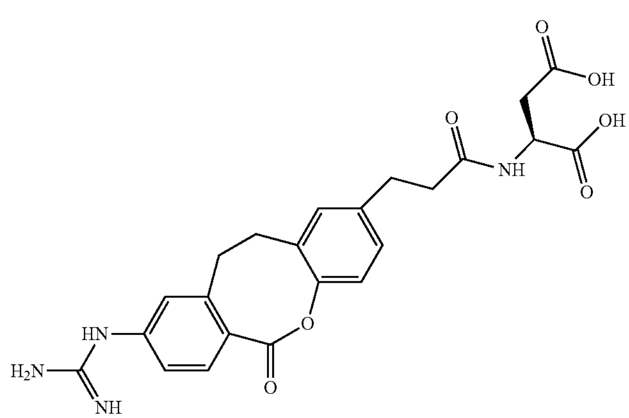 [SMILES: N=C(N)Nc1ccc2c(c1)CCc1cc(CCC(=O)N[C@@H](CC(=O)O)C(=O)O)ccc1OC2=O] | CF3COOH | 469.1 |

TABLE A-continued

| EXAMPLE | IUPACNAME | STRUCTURE | SALT | MS |
|---|---|---|---|---|
| 57 | N-(3-(9-carbamimidamido-6-oxo-11,12-dihydro-6H-dibenzo[b,f]oxocin-1-yl)propanoyl)-L-aspartic acid | 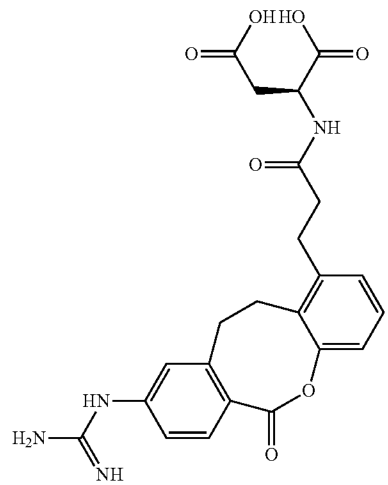 [SMILES: N=C(N)Nc1ccc2c(c1)CCc1c(CCC(=O)N[C@@H](CC(=O)O)C(=O)O)cccc1OC2=O] | CF3COOH | 469.0 |
| 58 | 1-(6-oxo-11,12-dihydro-6H-dibenzo[b,f]oxocin-9-yl)guanidine | 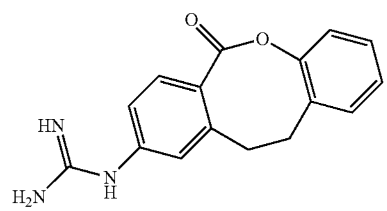 [SMILES: N=C(N)Nc1ccc2c(c1)CCc1ccccc1OC2=O] | CF3COOH | 282.1 |
| 59 | 6-oxo-11,12-dihydro-6H-dibenzo[b,f]oxocine-2-carboximidamide | 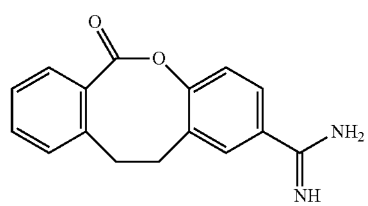 [SMILES: N=C(N)c1ccc2c(c1)CCc1ccccc1C(=O)O2] | CF3COOH | 267.2 |
| 60 | N-(3-(2-carbamimidoyl-6-oxo-11,12-dihydro-6H-dibenzo[b,f]oxocin-9-yl)propanoyl)-L-aspartic acid | 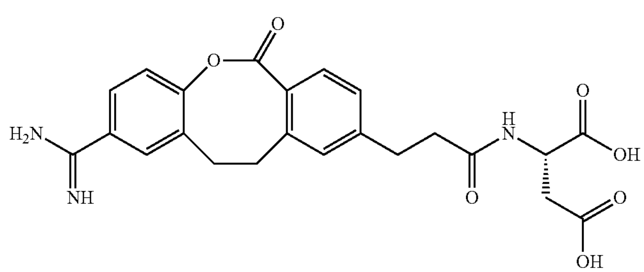 [SMILES: N=C(N)c1ccc2c(c1)CCc1cc(CCC(=O)N[C@@H](CC(=O)O)C(=O)O)ccc1C(=O)O2] | CF3COOH | 454.1 |
| 61 | N-(3-(2-carbamimidoyl-6-oxo-11,12-dihydro-6H-dibenzo[b,f]oxocin-10-yl)propanoyl)-L-aspartic acid | 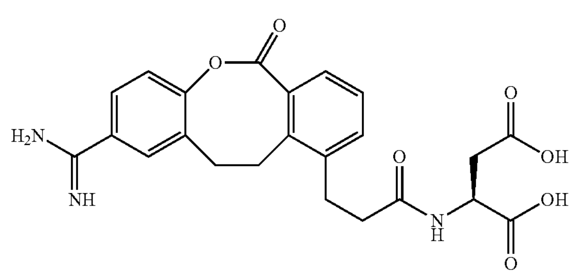 [SMILES: N=C(N)c1ccc2c(c1)CCc1c(CCC(=O)N[C@@H](CC(=O)O)C(=O)O)cccc1C(=O)O2] | CF3COOH | 454.1 |

TABLE A-continued

| EXAMPLE | IUPACNAME | STRUCTURE | SALT | MS |
|---|---|---|---|---|
| 62 | N-((2-carbamimidoyl-6-oxo-11,12-dihydro-6H-dibenzo[b,f]oxocin-10-yl)carbonyl)-L-aspartic acid | 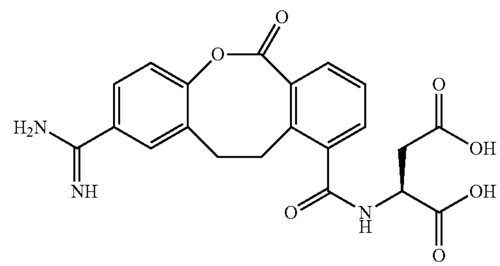 [SMILES: N=C(N)c1ccc2c(c1)CCc1c(C(=O)N[C@@H](CC(=O)O)C(=O)O)cccc1C(=O)O2] | CF3COOH | 426.1 |
| 63 | N-((2-carbamimidoyl-6-oxo-11,12-dihydro-6H-dibenzo[b,f]oxocin-9-yl)carbonyl)-L-aspartic acid | 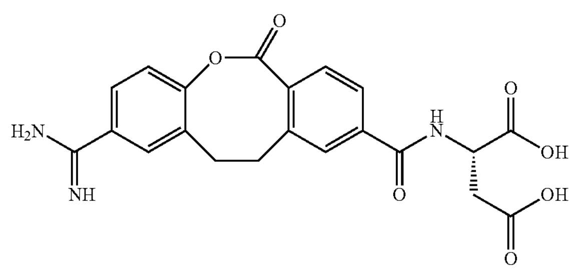 [SMILES: N=C(N)c1ccc2c(c1)CCc1cc(C(=O)N[C@@H](CC(=O)O)C(=O)O)ccc1C(=O)O2] | CF3COOH | 426.1 |
| 64 | N-((10-carbamimidamido-13-oxo-6,7,8,13-tetrahydrodibenzo[b,f][1,4]dioxecin-4-yl)carbonyl)-N-(carboxymethyl)-beta-alanine | 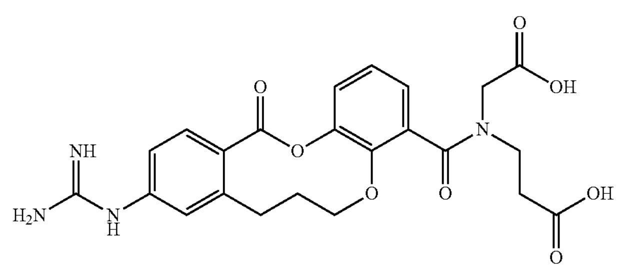 [SMILES: N=C(N)Nc1ccc2c(c1)CCCOc1c(cccc1C(=O)N(CCC(=O)O)CC(=O)O)OC2=O] | | 465.1 |
| 65 | N^2-((10-carbamimidamido-13-oxo-6,7,8,13-tetrahydrodibenzo[b,f][1,4]dioxecin-4-yl)carbonyl)-N^2-(carboxymethyl)-L-asparagine | 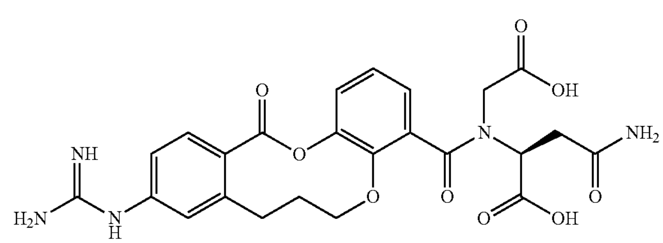 [SMILES: N=C(N)Nc1ccc2c(c1)CCCOc1c(cccc1C(=O)N(CC(=O)O)[C@@H](CC(N)=O)C(=O)O)OC2=O] | | 528.1 |
| 66 | N-((10-carbamimidamido-2-chloro-13-oxo-6,7,8,13-tetrahydrodibenzo[b,f][1,4]dioxecin-4-yl)carbonyl)-L-aspartic acid | 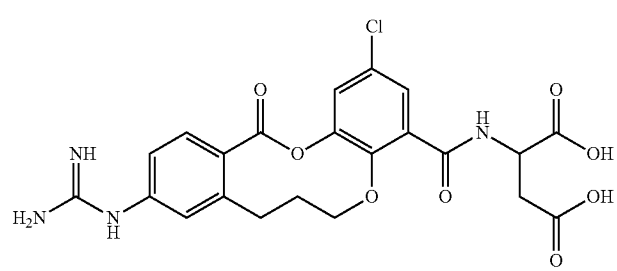 [SMILES: N=C(N)Nc1ccc2c(c1)CCCOc1c(cc(Cl)cc1C(=O)NC(CC(=O)O)C(=O)O)OC2=O] | CF3COOH | 505.1 |

TABLE A-continued

| EXAMPLE | IUPACNAME | STRUCTURE | SALT | MS |
|---|---|---|---|---|
| 67 | N-((3-carbamimidamido-11-methoxy-14-oxo-5,7,8,14-tetrahydro-6H-dibenzo[b,h]oxecin-9-yl)carbonyl)-L-aspartic acid | 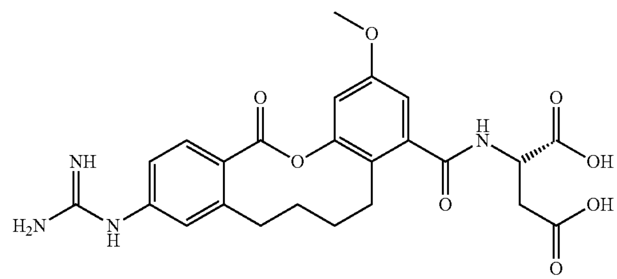 | | 499.1 |
| 68 | 1-(13-oxo-6,7,8,13-tetrahydro-dibenzo[b,f][1,4]dioxecin-10-yl)guaridine | 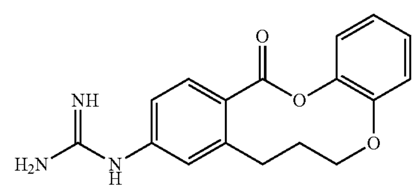 [SMILES: N=C(N)Nc1ccc2c(c1)CCCOc1ccccc1OC2=O] | CF3COOH | 312.2 |
| 69 | N-((10-carbamimidoyl-14-oxo-5,7,8,14-tetrahydro-6H-dibenzo[b,h]oxecin-3-yl)carbonyl)-L-aspartic acid | 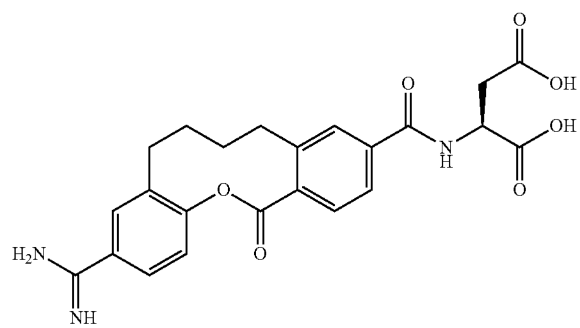 [SMILES: N=C(N)c1ccc2c(c1)CCCCc1cc(C(=O)N[C@@H](CC(=O)O)C(=O)O)ccc1C(=O)O2] | CF3COOH | 454.1 |
| 70 | N-((10-carbamimidamido-2-methyl-13-oxo-6,7,8,13-tetrahydro-dibenzo[b,f][1,4]dioxecin-4-yl)carbonyl)-L-aspartic acid | 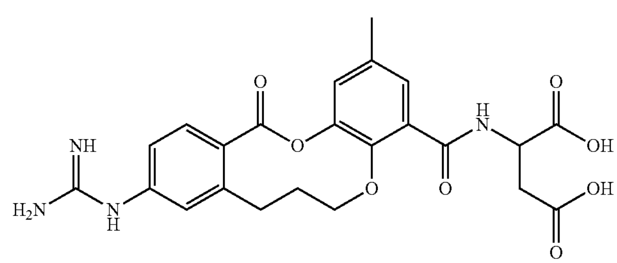 [SMILES: Cc1cc2c(c(C(=O)NC(CC(=O)O)C(=O)O)c1)OCCCc1cc(NC(=N)N)ccc1C(=O)O2] | CF3COOH | 485.2 |
| 71 | 3-((((10-carbamimidamido-13-oxo-6,7,8,13-tetrahydro-dibenzo[b,f][1,4]dioxecin-4-yl)carbonyl)(carboxymethyl)amino)methyl)benzoic acid | 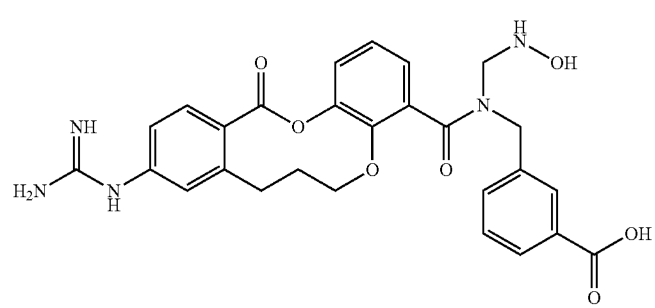 [SMILES: N=C(N)Nc1ccc2c(c1)CCCOc1c(cccc1C(=O)N(CNO)Cc1cccc(C(=O)O)c1)OC2=O] | | 547.2 |

TABLE A-continued

| EXAMPLE | IUPACNAME | STRUCTURE | SALT | MS |
|---|---|---|---|---|
| 72 | N-((3-carbamimidamido-11-methyl-14-oxo-5,7,8,14-tetrahydro-6H-dibenzo[b,h]oxecin-9-yl)carbonyl)-L-aspartic acid | 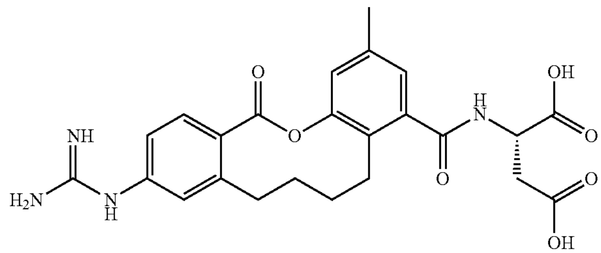 [SMILES: Cc1cc2c(c(C(=O)N[C@@H](CC(=O)O)C(=O)O)c1)CCCCc1cc(NC(=N)N)ccc1C(=O)O2] | | 483.1 |
| 73 | N-((9-carbamimidamido-6-oxo-6,11,12,13-tetrahydro-dibenzo[b,g]oxonin-2-yl)carbonyl)-L-aspartic acid | 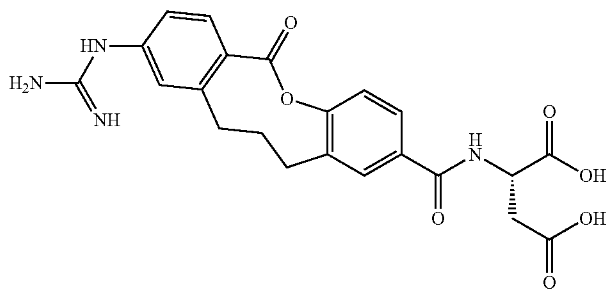 [SMILES: N=C(N)Nc1ccc2c(c1)CCCc1cc(C(=O)N[C@@H](CC(=O)O)C(=O)O)ccc1OC2=O] | CF3COOH | 455.1 |
| 74 | 3-(((3-carbamimidamido-14-oxo-5,7,8,14-tetrahydro-6H-dibenzo[b,h]oxecin-9-yl)carbony)amino)pentanedioic acid | 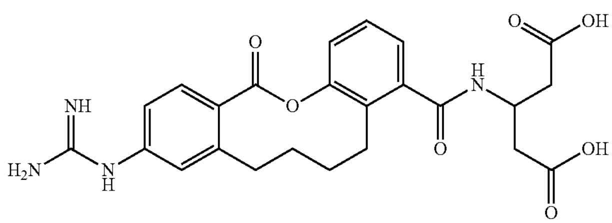 [SMILES: N=C(N)Nc1ccc2c(c1)CCCCc1c(cccc1C(=O)NC(CC(=O)O)CC(=O)O)OC2=O] | | 483.1 |
| 75 | N-(3-(10-carbamimidamido-13-oxo-6,7,8,13-tetrahydro-dibenzo[b,f][1,4]dioxecin-4-yl)propanoyl)-L-aspartic acid | 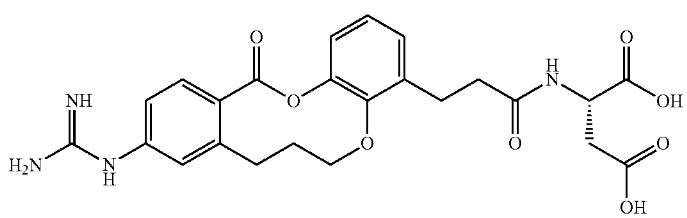 | | 499.1 |
| 76 | N-((3-carbamimidamido-15-oxo-5,6,7,8,9,15-hexahydro-dibenzo[b,i]oxacyclo-undecin-10-yl)carbonyl)-L-aspartic acid | 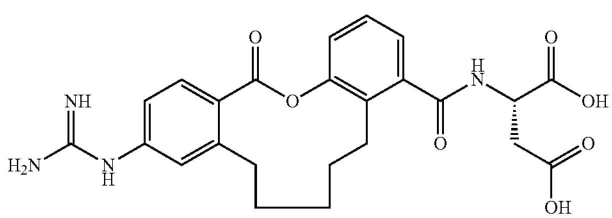 [SMILES: N=C(N)Nc1ccc2c(c1)CCCCCc1c(cccc1C(=O)N[C@@H](CC(=O)O)C(=O)O)OC2=O] | | 483.1 |
| 77 | N-((3-carbamimidamido-16-oxo-5,7,8,9,10,16-hexahydro-6H-dibenzo[b,j]oxacyclododecin-11-yl)carbonyl)-L-aspartic acid | 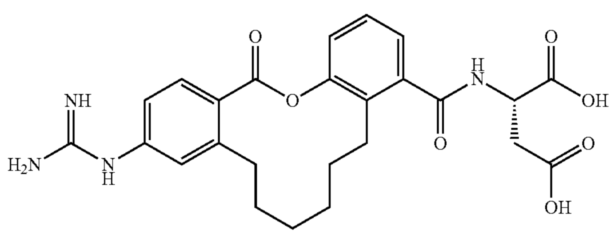 [SMILES: N=C(N)Nc1ccc2c(c1)CCCCCCc1c(cccc1C(=O)N[C@@H](CC(=O)O)C(=O)O)OC2=O] | | 497.2 |

TABLE A-continued

| EXAMPLE | IUPACNAME | STRUCTURE | SALT | MS |
|---|---|---|---|---|
| 78 | N-(3-(10-carbamimidamido-13-oxo-6,7,8,13-tetrahydro-dibenzo[b,f][1,4]dioxecin-2-yl)propanoyl) aspartic acid | 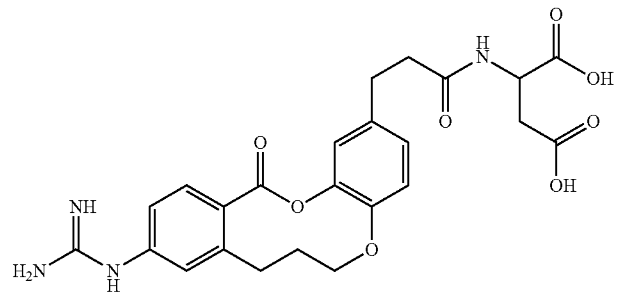 [SMILES: N=C(N)Nc1ccc2c(c1)CCCOc1ccc(CCC(=O)NC(CC(=O)O)C(=O)O)cc1OC2=O] | | 499.1 |
| 79 | N-(3-(3-carbamimidamido-14-oxo-7,8-dihydro-6H,14H-dibenzo[b,f][1,5] dioxecin-9-yl)propanoyl)-L-aspartic acid | 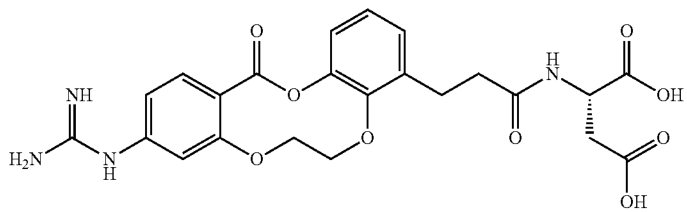 | | 499.1 |
| 80 | N-((9-carbamimidamido-6-oxo-6,11,12,13-tetrahydro-dibenzo[b,g]oxonin-1-yl)carbonyl)-L-aspartic acid | 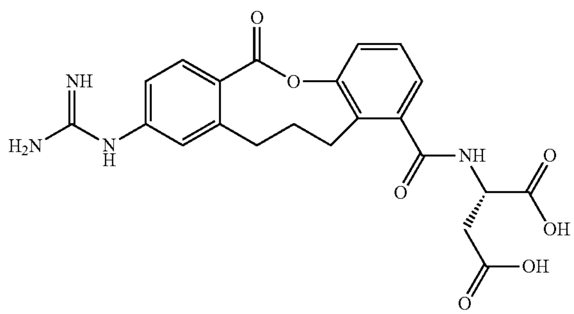 [SMILES: N=C(N)Nc1ccc2c(c1)CCCc1c(cccc1C(=O)N[C@@H](CC(=O)O)C(=O)O)OC2=O] | | 455.1 |
| 81 | N-((10-carbamimidamido-13-oxo-6,7,8,13-tetrahydro-dibenzo[b,f][1,4]dioxecin-3-yl)carbonyl)-L-aspartic acid | 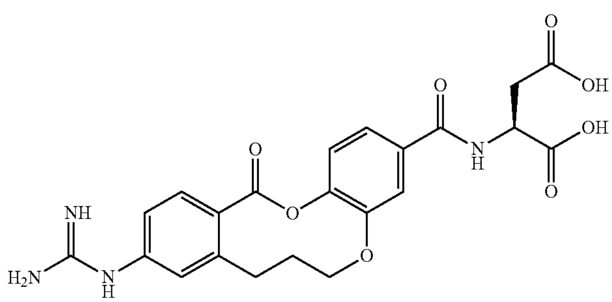 [SMILES: N=C(N)Nc1ccc2c(c1)CCCOc1cc(C(=O)N[C@@H](CC(=O)O)C(=O)O)ccc1OC2=O] | | 471.1 |
| 82 | N-((11-carbamimidamido-14-oxo-7,8,9,14-tetrahydro-6H-dibenzo[b,f][1,4] dioxacycloundecin-4-yl)carbonyl)-L-aspartic acid | 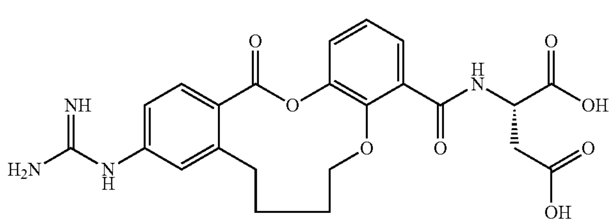 [SMILES: N=C(N)Nc1ccc2c(c1)CCCCOc1c(cccc1C(=O)N[C@@H](CC(=O)O)C(=O)O)OC2=O] | | 485.2 |
| 83 | N-(3-(3-carbamimidamido-14-oxo-5,7,8,14-tetrahydro-6H-dibenzo[b,h]oxecin-9-yl)propanoyl)-L-aspartic acid | 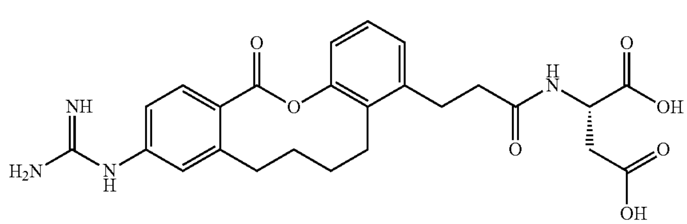 [SMILES: N=C(N)Nc1ccc2c(c1)CCCCc1c(CCC(=O)N[C@@H](CC(=O)O)C(=O)O)cccc1OC2=O] | | 497.2 |

TABLE A-continued

| EXAMPLE | IUPACNAME | STRUCTURE | SALT | MS |
|---|---|---|---|---|
| 84 | N-((3-carbamimidamido-14-oxo-7,8-dihydro-6H,14H-dibenzo[b,f][1,5]dioxecin-9-yl)carbonyl)-L-aspartic acid | 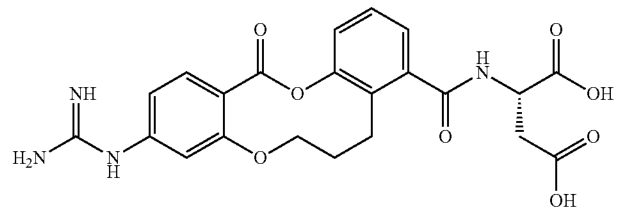 | | 471.1 |
| 85 | N-((10-carbamimidamido-13-oxo-6,7,8,13-tetrahydrodibenzo[b,f][1,4]dioxecin-4-yl)carbonyl)-N-methyl-L-aspartic acid | 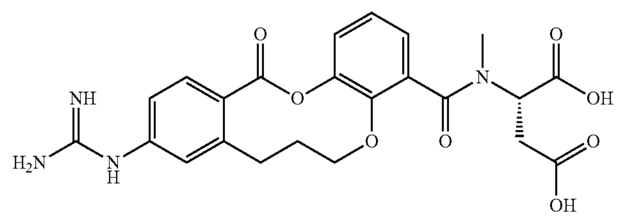 [SMILES: CN(C(=O)c1cccc2c1OCCCc1cc(NC(=N)N)ccc1C(=O)O2)[C@@H](CC(=O)O)C(=O)O] | | 485.2 |
| 86 | N-((10-carbamimidamido-13-oxo-6,7,8,13-tetrahydro-dibenzo[b,f][1,4]dioxecin-4-yl)carbonyl)-L-serine | 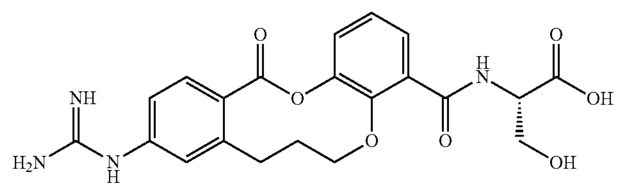 [SMILES: N=C(N)Nc1ccc2c(c1)CCCOc1c(cccc1C(=O)N[C@@H](CO)C(=O)O)OC2=O] | | 443.2 |
| 87 | N-((10-carbamimidamido-13-oxo-6,7,8,13-tetrahydro-dibenzo[b,f][1,4]dioxecin-4-yl)carbonyl)-L-phenylalanine | 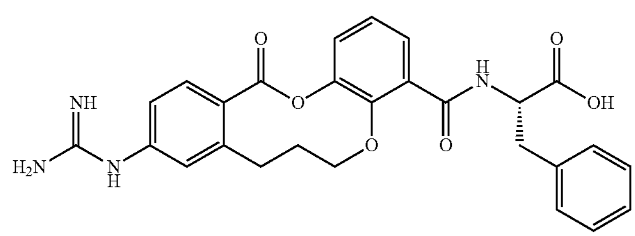 [SMILES: N=C(N)Nc1ccc2c(c1)CCCOc1c(cccc1C(=O)N[C@@H](Cc1ccccc1)C(=O)O)OC2=O] | | 503.2 |
| 88 | N-((10-carbamimidamido-13-oxo-6,7,8,13-tetrahydro-dibenzo[b,f][1,4]dioxecin-4-yl)carbonyl)-beta-alanine | 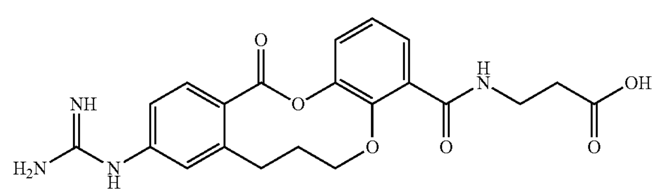 [SMILES: N=C(N)Nc1ccc2c(c1)CCCOc1c(cccc1C(=O)NCCC(=O)O)OC2=O] | | 427.2 |
| 89 | N-((10-carbamimidamido-13-oxo-6,7,8,13-tetrahydro-dibenzo[b,f][1,4]dioxecin-4-yl)carbonyl)glycine | 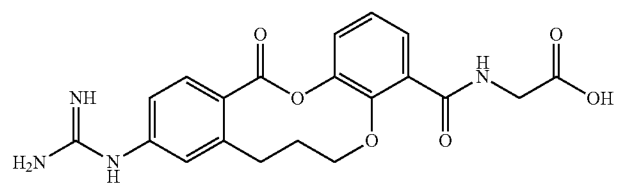 [SMILES: N=C(N)Nc1ccc2c(c1)CCCOc1c(cccc1C(=O)NCC(=O)O)OC2=O] | | 413.1 |
| 90 | N-((10-carbamimidamido-13-oxo-6,7,8,13-tetrahydro-dibenzo[b,f][1,4]dioxecin-4-yl)carbonyl)-L-threonine | 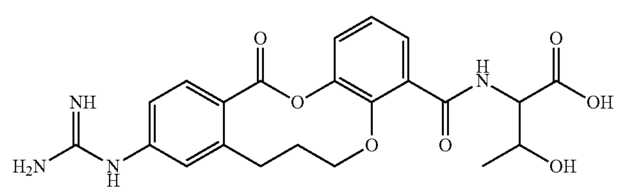 [SMILES: CC(O)C(NC(=O)c1cccc2c1OCCCc1cc(NC(=N)N)ccc1C(=O)O2)C(=O)O] | | 457.2 |

TABLE A-continued

| EXAMPLE | IUPACNAME | STRUCTURE | SALT | MS |
|---|---|---|---|---|
| 91 | N-(10-carbamimidamido-13-oxo-6,7,8,13-tetrahydro-dibenzo[b,f][1,4]dioxecin-4-yl)propanoic acid | 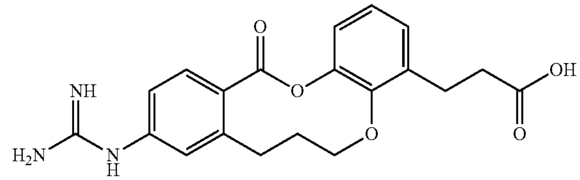 [SMILES: N=C(N)Nc1ccc2c(c1)CCCOc1c(CCC(=O)O)cccc1OC2=O] | CF3COOH | 364.1 |
| 92 | N-((10-carbamimidamido-13-oxo-6,7,8,13-tetrahydro-dibenzo[b,f][1,4]dioxecin-4-yl)carbonyl)-N-(carboxymethyl)-L-tyrosine | 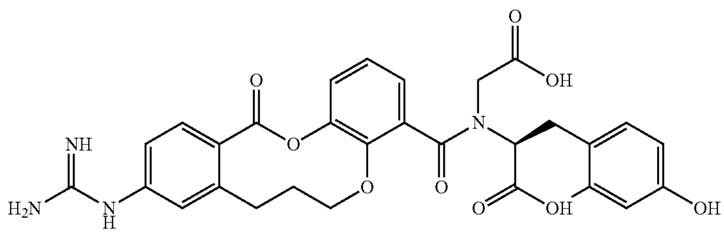 [SMILES: N=C(N)Nc1ccc2c(c1)CCCOc1c(cccc1C(=O)N(CC(=O)O)[C@H]1Cc3ccc(O)cc3OC1=O)OC2=O] | | 577.2 |
| 93 | N-(3-(10-carbamimidamido-13-oxo-6,7,8,13-tetrahydro-dibenzo[b,f][1,4]dioxecin-4-yl)propanoyl)-L-glutamic acid | 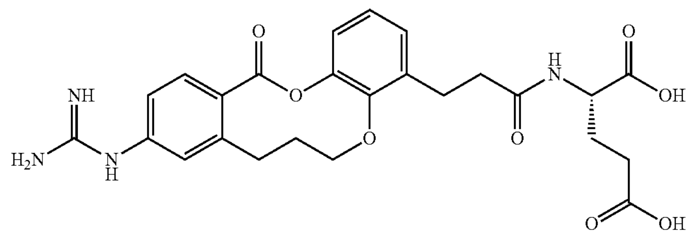 [SMILES: N=C(N)Nc1ccc2c(c1)CCCOc1c(CCC(=O)N[C@@H](CCC(=O)O)C(=O)O)cccc1OC2=O] | | 513.2 |
| 94 | N-((10-carbamimidamido-13-oxo-6,7,8,13-tetrahydro-dibenzo[b,f][1,4]dioxecin-4-yl)carbonyl)-N-(carboxymethyl)-O-methyl-L-tyrosine | 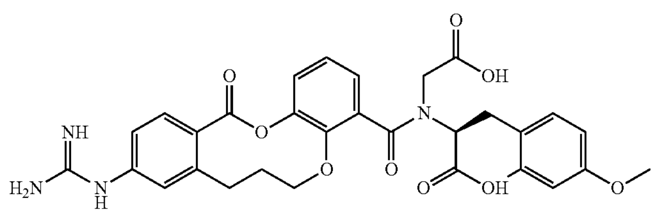 [SMILES: COc1ccc2c(c1)OC(=O)[C@@H](N(CC(=O)O)C(=O)c1cccc3c1OCCCc1cc(NC(=N)N)ccc1C(=O)O3)C2] | | 591.2 |
| 95 | N-(3-(10-carbamimidamido-13-oxo-6,7,8,13-tetrahydro-dibenzo[b,f][1,4]dioxecin-4-yl)propanoyl)-L-tyrosine | 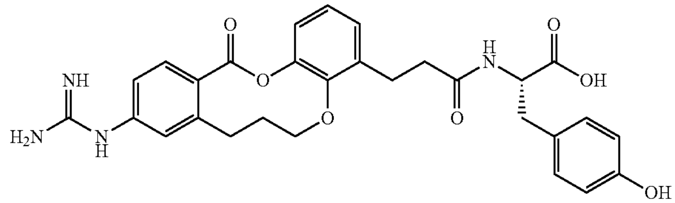 [SMILES: N=C(N)Nc1ccc2c(c1)CCCOc1c(CCC(=O)N[C@@H](Cc3ccc(O)cc3)C(=O)O)cccc1OC2=O] | | 547.2 |
| 96 | 3-((3-(10-carbamimidamido-13-oxo-6,7,8,13-tetrahydro-dibenzo[b,f][1,4]dioxecin-4-yl)propanoyl)amino)pentanedioic acid | 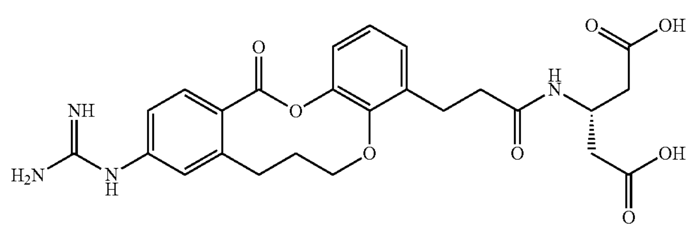 | | 513.2 |
| 97 | N-2-(3-(10-carbamimidamido-13-oxo-6,7,8,13-tetrahydro-dibenzo[b,f][1,4]dioxecin-4-yl)propanoyl)-L-asparagine | 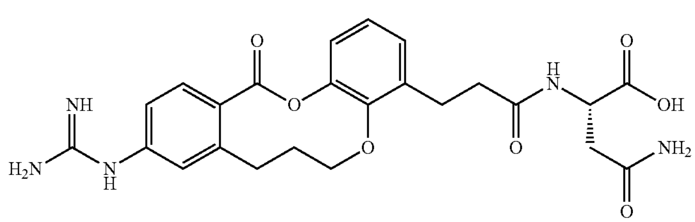 [SMILES: N=C(N)Nc1ccc2c(c1)CCCOc1c(CCC(=O)N[C@@H](CC(N)=O)C(=O)O)cccc1OC2=O] | | 498.1 |

TABLE A-continued

| EXAMPLE | IUPACNAME | STRUCTURE | SALT | MS |
|---|---|---|---|---|
| 98 | N-((10-carbamimidoyl-14-oxo-5,7,8,14-tetrahydro-6H-dibenzo[b,h]oxecin-4-yl)carbonyl)-L-aspartic acid | 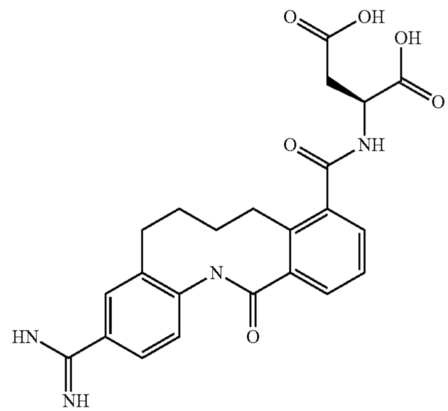 [SMILES: N=C(N)c1ccc2c(c1)CCCCc1c(cccc1C(=O)N[C@@H](CC(=O)O)C(=O)O)C(=O)N2] | CF3COOH | 454.2 |
| 99 | 1-((10-carbamimidamido-13-oxo-6,7,8,13-tetrahydro-dibenzo[b,f][1,4]dioxecin-4-yl)carbonyl)-L-prolyl-L-aspartic acid | 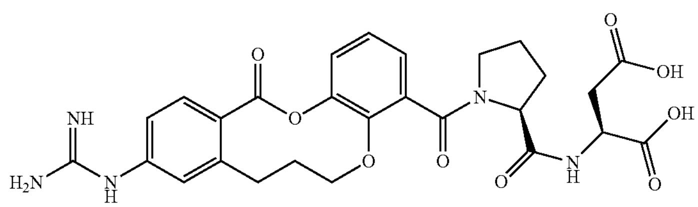 [SMILES: N=C(N)Nc1ccc2c(c1)CCCOc1c(cccc1C(=O)N1CCC[C@H]1C(=O)N[C@@H](CC(=O)O)C(=O)O)OC2=O] | | 568.2 |
| 100 | N-((10-carbamimidamido-13-oxo-6,7,8,13-tetrahydro-dibenzo[b,f][1,4]dioxecin-4-yl)carbonyl)glycyl-L-aspartic acid | 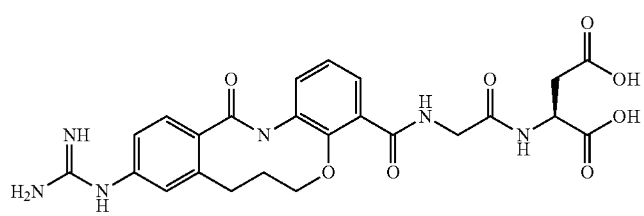 [SMILES: N=C(N)Nc1ccc2c(c1)CCCOc1c(cccc1C(=O)NCC(=O)N[C@@H](CC(=O)O)C(=O)O)NC2=O] | | 528.2 |
| 101 | N-((1-((10-carbamimidamido-13-oxo-6,7,8,13-tetrahydro-dibenzo[b,f][1,4]dioxecin-4-yl)carbonyl)-piperidin-4-yl)carbonyl)-L-aspartic acid | 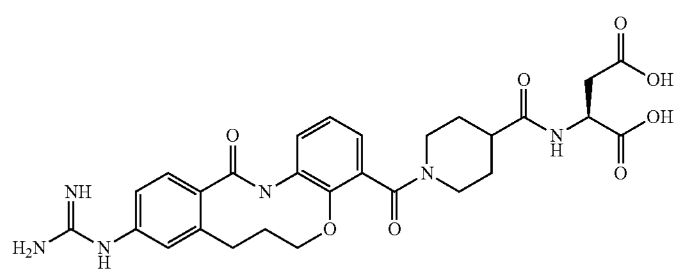 [SMILES: N=C(N)Nc1ccc2c(c1)CCCOc1c(cccc1C(=O)N1CCC(C(=O)N[C@@H](CC(=O)O)C(=O)O)CC1)NC2=O] | | 582.3 |
| 102 | N-(3-(10-carbamimidamido-13-oxo-6,7,8,13-tetrahydro-dibenzo[b,f][1,4]dioxecin-4-yl)propanoyl)-N-methyl-L-aspartic acid | 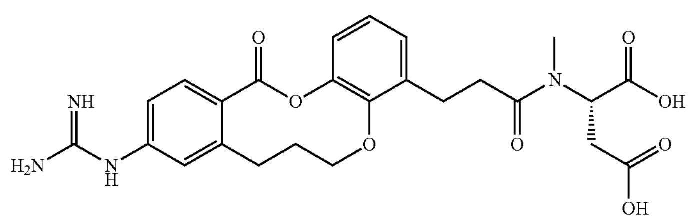 [SMILES: CN(C(=O)CCc1cccc2c1OCCCc1cc(NC(=N)N)ccc1C(=O)O2)[C@@H](CC(=O)O)C(=O)O] | | 513.2 |
| 103 | N-((10-carbamimidamido-13-oxo-6,7,8,13-tetrahydro-dibenzo[b,f][1,4]dioxecin-4-yl)carbonyl)-N-methylglycyl-L-aspartic acid | 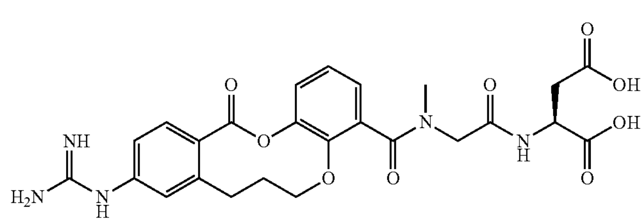 [SMILES: CN(CC(=O)N[C@@H](CC(=O)O)C(=O)O)C(=O)c1cccc2c1OCCCc1cc(NC(=N)N)ccc1C(=O)O2] | | 542.3 |

TABLE A-continued

| EXAMPLE | IUPACNAME | STRUCTURE | SALT | MS |
|---|---|---|---|---|
| 104 | N-((10-carbamimidamido-13-oxo-6,7,8,13-tetrahydro-dibenzo[b,f][1,4]dioxecin-4-yl)carbonyl)-N-(carboxymethyl)-L-aspartic acid | 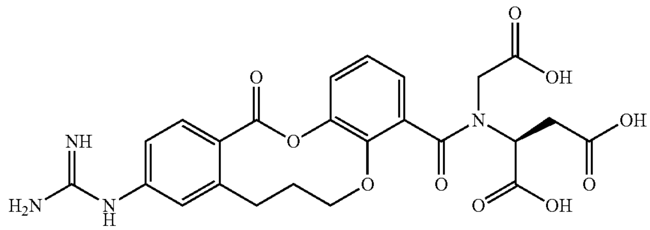 [SMILES: N=C(N)Nc1ccc2c(c1)CCCOc1c(cccc1C(=O)N(CC(=O)O)[C@@H](CC(=O)O)C(=O)O)OC2=O] | | 529.2 |
| 105 | N-((10-carbamimidamido-13-oxo-6,7,8,13-tetrahydro-dibenzo[b,f][1,4]dioxecin-4-yl)carbonyl)-N-methylglycyl-N-methyl-L-aspartic acid | 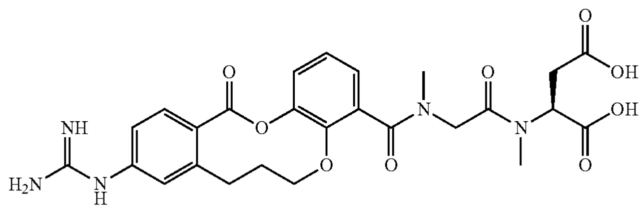 [SMILES: CN(CC(=O)N(C)[C@@H](CC(=O)O)C(=O)O)C(=O)c1cccc2c1OCCCc1cc(NC(=N)N)ccc1C(=O)O2] | | 556.3 |
| 106 | 3-(((10-carbamimidamido-13-oxo-6,7,8,13-tetrahydro-dibenzo[b,f][1,4]dioxecin-4-yl)carbonyl)-(carboxymethyl)amino)pentanedioic acid | 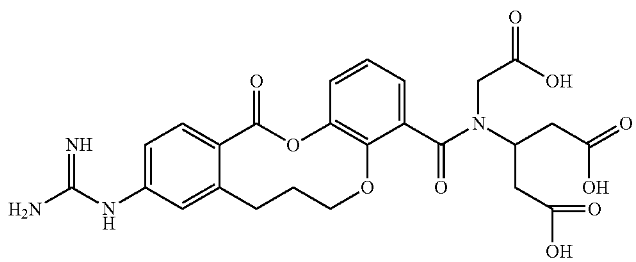 [SMILES: N=C(N)Nc1ccc2c(c1)CCCOc1c(cccc1C(=O)N(CC(=O)O)C(CC(=O)O)CC(=O)O)OC2=O] | | 543.2 |
| 107 | N-benzyl-N-((10-carbamimidamido-13-oxo-6,7,8,13-tetrahydro-dibenzo[b,f][1,4]dioxecin-4-yl)carbonyl)-L-aspartic acid | 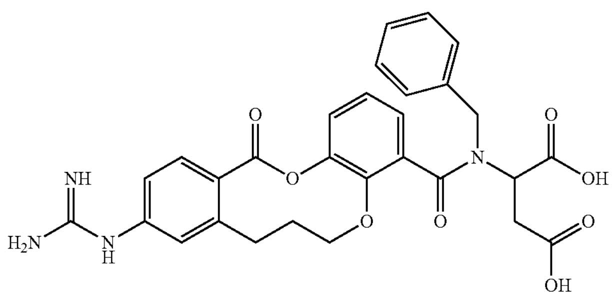 [SMILES: N=C(N)Nc1ccc2c(c1)CCCOc1c(cccc1C(=O)N(Cc1ccccc1)C(CC(=O)O)C(=O)O)OC2=O] | | 561.3 |
| 108 | O-(2-(bis(carboxymethyl)amino)ethyl)-N-((10-carbamimidamido-13-oxo-6,7,8,13-tetrahydro-dibenzo[b,f][1,4]dioxecin-4-yl)carbony)-N-(carboxymethyl)-L-tyrosine | 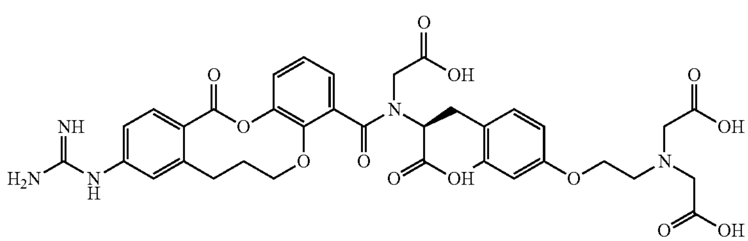 [SMILES: N=C(N)Nc1ccc2c(c1)CCCOc1c(cccc1C(=O)N(CC(=O)O)[C@H]1Cc3ccc(OCCN(CC(=O)O)CC(=O)O)cc3OC1=O)OC2=O] | | 736.3 |
| 109 | N-((10-carbamimidamido-13-oxo-6,7,8,13-tetrahydro-dibenzo[b,f][1,4]dioxecin-4-yl)carbonyl)-N-(2-methoxyethyl)-L-aspartic acid | 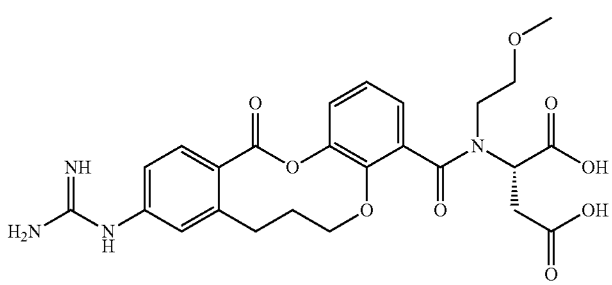 [SMILES: COCCN(C(=O)c1cccc2c1OCCCc1cc(NC(=N)N)ccc1C(=O)O2)[C@@H](CC(=O)O)C(=O)O] | | 529.3 |

TABLE A-continued

| EXAMPLE | IUPACNAME | STRUCTURE | SALT | MS |
|---|---|---|---|---|
| 110 | N-((10-carbamimidamido-3-(2-carboxyethyl)-13-oxo-6,7,8,13-tetrahydro-dibenzo[b,f][1,4]dioxecin-4-yl)carbonyl)-L-aspartic acid | 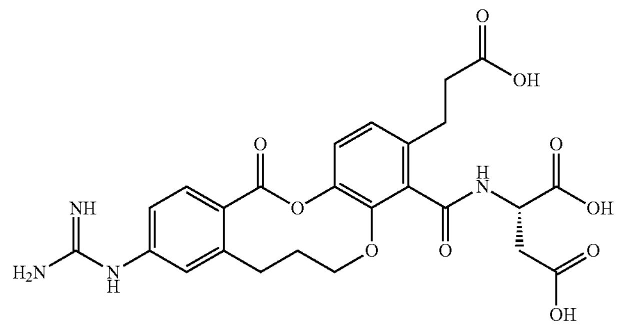 [SMILES: N=C(N)Nc1ccc2c(c1)CCCOc1c(ccc(CCC(=O)O)c1C(=O)N[C@@H](CC(=O)O)C(=O)O)OC2=O] | | 543.2 |
| 111 | 10-carbamimidamido-3-(2-carboxyethyl)-13-oxo-6,7,8,13-tetrahydro-dibenzo[b,f][1,4]dioxecine-4-carboxylic acid | 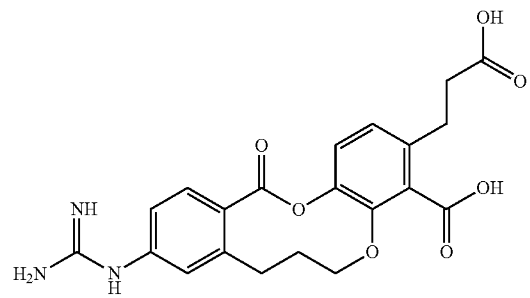 [SMILES: N=C(N)Nc1ccc2c(c1)CCCOc1c(ccc(CCC(=O)O)c1C(=O)O)OC2=O] | | 428.2 |
| 112 | N-((10-carbamimidamido-3-(2-carboxyethyl)-13-oxo-6,7,8,13-tetrahydro-dibenzo[b,f][1,4]dioxecin-4-yl)carbonyl)-O-methyl-L-tyrosine | 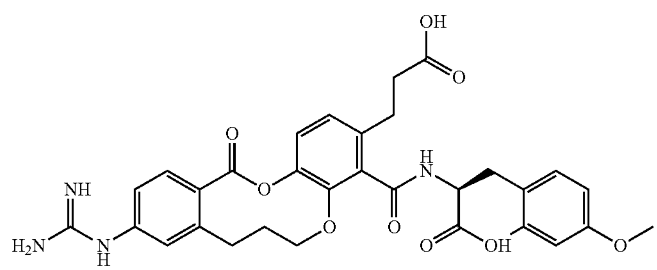 [SMILES: COc1ccc2c(c1)OC(=O)[C@@H](NC(=O)c1c(CCC(=O)O)ccc3c1OCCCc1cc(NC(=N)N)ccc1C(=O)O3)C2] | | 605.3 |
| 113 | N-((10-carbamimidamido-3-(2-carboxyethyl)-13-oxo-6,7,8,13-tetrahydro-dibenzo[b,f][1,4]dioxecin-4-yl)carbonyl)-L-tyrosine | 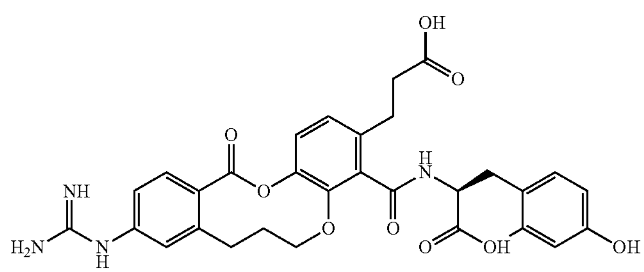 [SMILES: N=C(N)Nc1ccc2c(c1)CCCOc1c(ccc(CCC(=O)O)c1C(=O)N[C@H]1Cc3ccc(O)cc3OC1=O)OC2=O] | | 591.3 |
| 114 | N-((10-carbamimidamido-2-cyano-13-oxo-6,7,8,13-tetrahydro-dibenzo[b,f][1,4]dioxecin-4-yl)carbonyl)-L-aspartic acid | | | 496.2 | ns
TABLE A-continued

| EXAMPLE | IUPACNAME | STRUCTURE | SALT | MS |
|---|---|---|---|---|
| 115 | ((2-(bis(carboxymethyl)amino)-2-oxoethyl)((10-carbamimidamido-13-oxo-6,7,8,13-tetrahydrodibenzo[b,f][1,4]dioxecin-4-yl)carbonyl)amino)acetic acid | 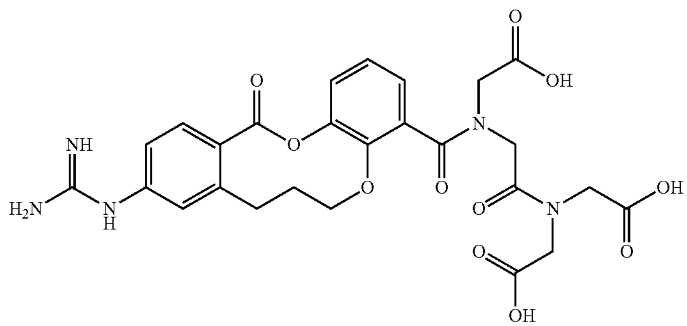 [SMILES: N=C(N)Nc1ccc2c(c1)CCCOc1c(cccc1C(=O)N(CC(=O)O)CC(=O)N(CC(=O)O)CC(=O)O)OC2=O] | | 586.3 |
| 116 | N-(3-((bis(carboxymethyl)amino)methyl)benzyl)-N-((10-carbamimidamido-13-oxo-6,7,8,13-tetrahydrodibenzo[b,f][1,4]dioxecin-4-yl)carbonyl)glycine | 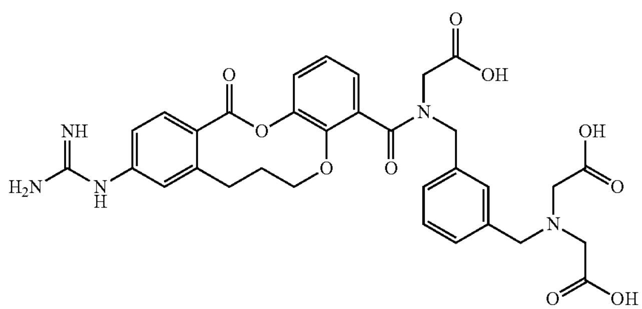 [SMILES: N=C(N)Nc1ccc2c(c1)CCCOc1c(cccc1C(=O)N(CC(=O)O)Cc1cccc(CN(CC(=O)O)CC(=O)O)c1)OC2=O] | | 648.3 |
| 117 | N-((10-carbamimidamido-2-(2-carboxyethyl)-13-oxo-6,7,8,13-tetrahydrodibenzo[b,f][1,4]dioxecin-4-yl)carbonyl)-L-aspartic acid | 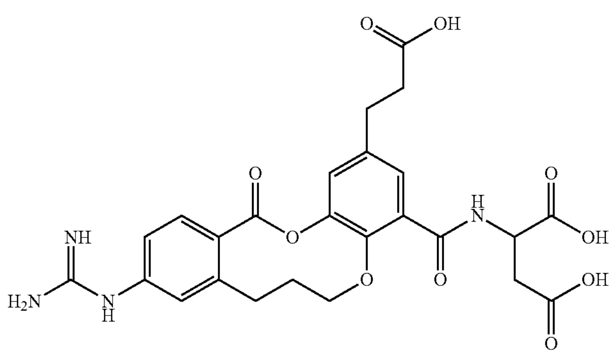 [SMILES: N=C(N)Nc1ccc2c(c1)CCCOc1c(cc(CCC(=O)O)cc1C(=O)NC(CC(=O)O)C(=O)O)OC2=O] | | 543.3 |
| 118 | N-((10-carbamimidamido-3-(2-carboxyethyl)-13-oxo-6,7,8,13-tetrahydrodibenzo[b,f][1,4]dioxecin-4-yl)carbonyl)-N-methyl-L-aspartic acid | 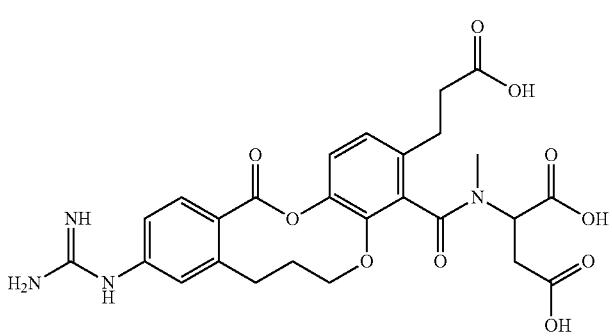 [SMILES: CN(C(=O)c1c(CCC(=O)O)ccc2c1OCCCc1cc(NC(=N)N)ccc1C(=O)O2)C(CC(=O)O)C(=O)O] | | 567.3 |

TABLE A-continued

| EXAMPLE | IUPACNAME | STRUCTURE | SALT | MS |
|---|---|---|---|---|
| 119 | 3-(4-(bis(carboxymethyl)carbamoyl)-10-carbamimidamido-13-oxo-6,7,8,13-tetrahydro-dibenzo[b,f][1,4]dioxecin-3-yl)propanoic acid | 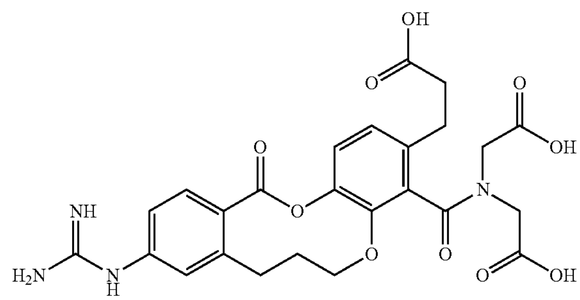 [SMILES: N=C(N)Nc1ccc2c(c1)CCCOc1c(ccc(CCC(=O)O)c1C(=O)N(CC(=O)O)CC(=O)O)OC2=O] | | 543.2 |
| 120 | N-(2-(bis(carboxymethyl)amine)ethyl)-N-((10-carbamimidamido-13-oxo-6,7,8,13-tetrahydro-dibenzo[b,f][1,4]dioxecin-4-yl)carbonyl)glycine | 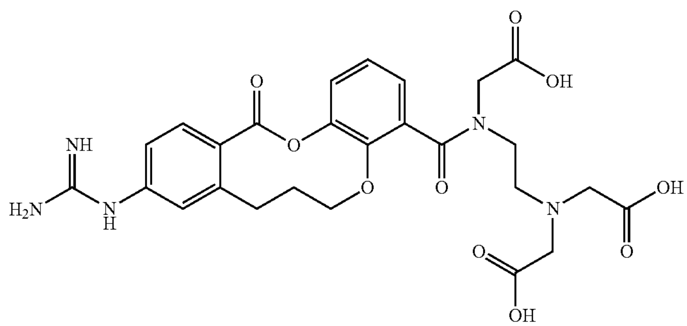 [SMILES: N=C(N)Nc1ccc2c(c1)CCCOc1c(cccc1C(=O)N(CCN(CC(=O)O)CC(=O)O)CC(=O)O)OC2=O] | | 572.3 |
| 121 | N-((10-carbamimidamido-13-oxo-6,7,8,13-tetrahydro-dibenzo[b,f][1,4]dioxecin-4-yl)carbonyl)-N-(carboxymethyl)-O-(2-((carboxymethyl)amino)ethyl)-L-tyrosine | 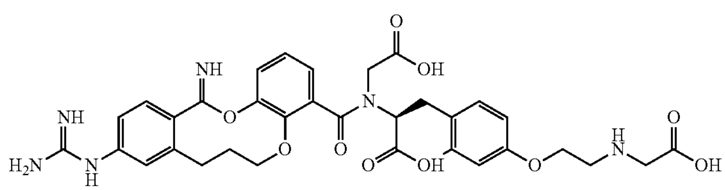 [SMILES: N=C(N)Nc1ccc2c(c1)CCCOc1c(cccc1C(=O)N(CC(=O)O)[C@H]1Cc3ccc(OCCNCC(=O)O)cc3OC1=O)OC2=N] | | 678.3 |
| 122 | O-(2-(benzyl(carboxymethyl)amino)ethyl)-N-((10-carbamimidamido-13-oxo-6,7,8,13-tetrahydro-dibenzo[b,f][1,4]dioxecin-4-yl)carbonyl)-N-(carboxy-methyl)-L-tyrosine | 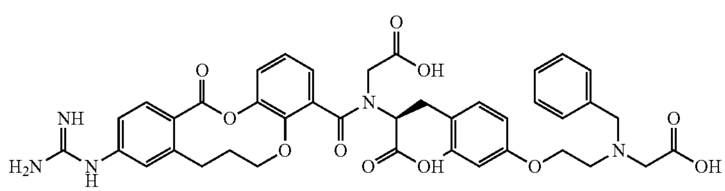 [SMILES: N=C(N)Nc1ccc2c(c1)CCCOc1c(cccc1C(=O)N(CC(=O)O)[C@H]1Cc3ccc(OCCN(CC(=O)O)Cc4ccccc4)cc3OC1=O)OC2=O] | | 768.3 |
| 123 | 3-((3-(10-carbamimidamido-4-(((1S)-1-carboxy-2-(4-hydroxyphenyl)ethyl)carbamoyl)-13-oxo-6,7,8,13-tetrahydro-dibenzo[b,f][1,4]dioxecin-3-yl)propanoyl)amino)pentanedioic acid | 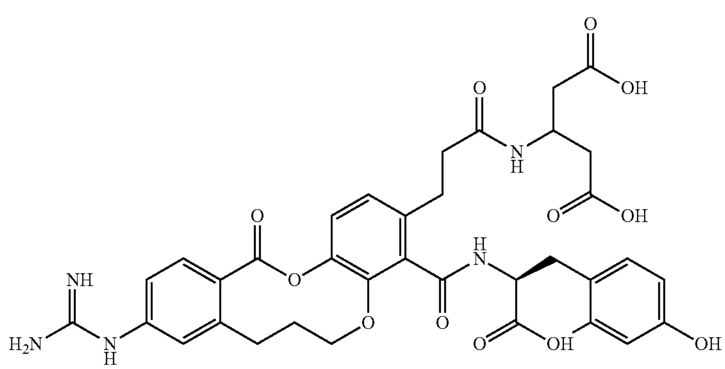 [SMILES: N=C(N)Nc1ccc2c(c1)CCCOc1c(ccc(CCC(=O)NC(CC(=O)O)CC(=O)O)c1C(=O)N[C@H]1Cc3ccc(O)cc3OC1=O)OC2=O] | | 720.4 |

TABLE A-continued

| EXAMPLE | IUPACNAME | STRUCTURE | SALT | MS |
|---|---|---|---|---|
| 124 | N-((3-(3-(bis(carboxymethyl)amino)-3-oxopropyl)-10-carbamimidamido-13-oxo-6,7,8,13-tetrahydro-dibenzo[b,f][1,4]dioxecin-4-yl)carbonyl)-L-tyrosine | 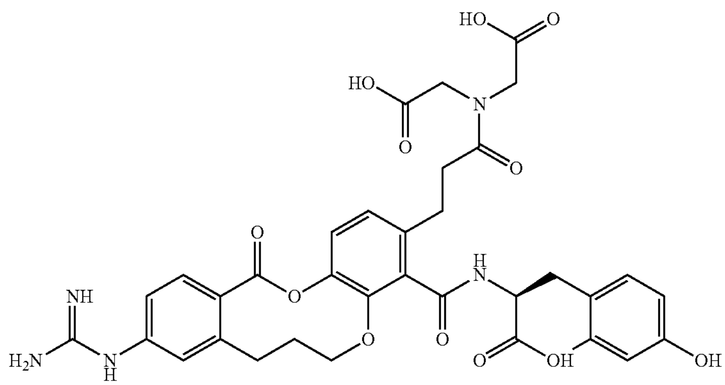 [SMILES: N=C(N)Nc1ccc2c(c1)CCCOc1c(ccc(CCC(=O)N(CC(=O)O)CC(=O)O)c1C(=O)N[C@H]1Cc3ccc(O)cc3OC1=O)OC2=O] | | 706.3 |
| 125 | 4-((((10-carbamimidamido-13-oxo-6,7,8,13-tetrahydro-dibenzo[b,f][1,4]dioxecin-4-yl)carbonyl)carboxymethyl)amino)methyl)thiophene-2-carboxylic acid | 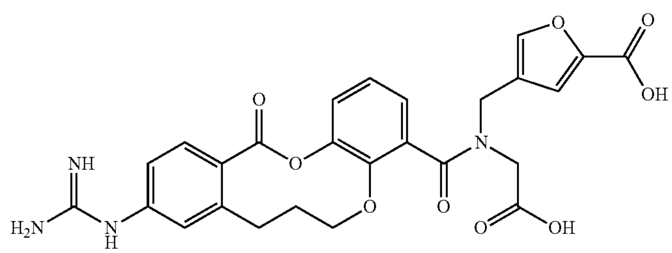 [SMILES: N=C(N)Nc1ccc2c(c1)CCCOc1c(cccc1C(=O)N(CC(=O)O)Cc1coc(C(=O)O)c1)OC2=O] | | 553.5 |
| 126 | N-((6-((bis(carboxymethyl)amino)methyl)pyridin-2-yl)methyl)-N-((10-carbamimidamido-13-oxo-6,7,8,13-tetrahydro-dibenzo[b,f][1,4]dioxecin-4-yl)carbonyl)glycine | 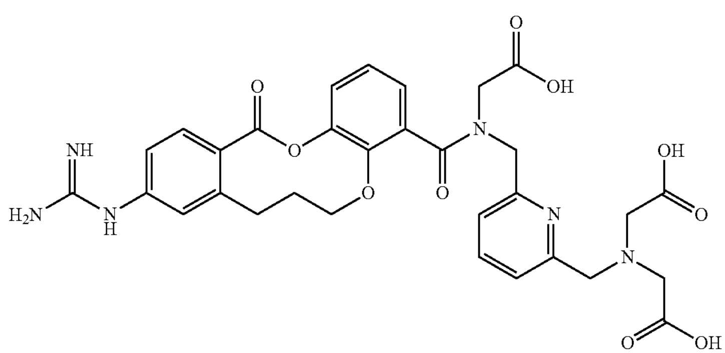 [SMILES: N=C(N)Nc1ccc2c(c1)CCCOc1c(cccc1C(=O)N(CC(=O)O)Cc1cccc(CN(CC(=O)O)CC(=O)O)n1)OC2=O] | | 649.2 |
| 127 | 2-((((10-carbamimidamido-13-oxo-6,7,8,13-tetrahydro-dibenzo[b,f][1,4]dioxecin-4-yl)carbonyl)carboxymethyl)amino)methyl)benzoic acid | 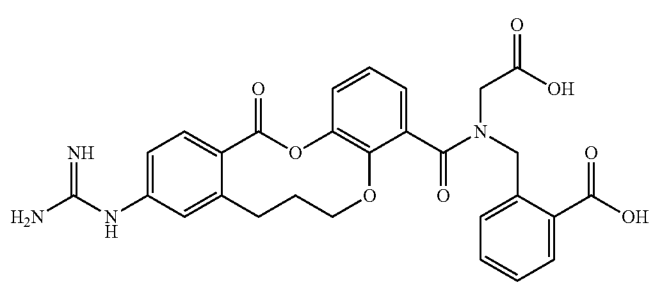 [SMILES: N=C(N)Nc1ccc2c(c1)CCCOc1c(cccc1C(=O)N(CC(=O)O)Cc1ccccc1C(=O)O)OC2=O] | | 547.2 |

TABLE A-continued

| EXAMPLE | IUPACNAME | STRUCTURE | SALT | MS |
|---|---|---|---|---|
| 128 | 3-((((3-carbamimidamido-14-oxo-5,7,8,14-tetrahydro-5H-dibenzo[b,h]oxecin-9-yl)carbonyl)carboxymethyl)amino)methyl)benzoic acid | 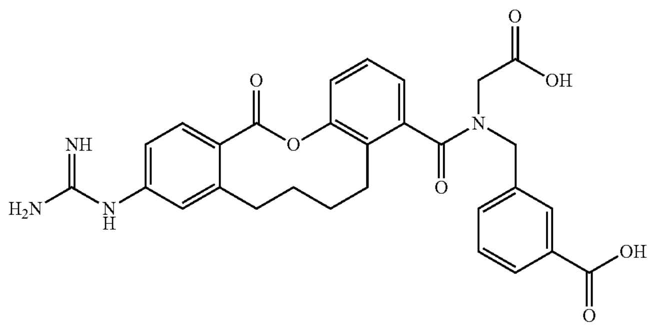 [SMILES: N=C(N)Nc1ccc2c(c1)CCCCc1c(cccc1C(=O)N(CC(=O)O)Cc1cccc(C(=O)O)c1)OC2=O] | | 545.1 |
| 129 | 3-(3-(bis(carboxymethyl)amino)-3-oxopropyl)-10-carbamimidamido-13-oxo-6,7,8,13-tetrahydrodibenzo[b,f][1,4]dioxecine-4-carboxylic acid | 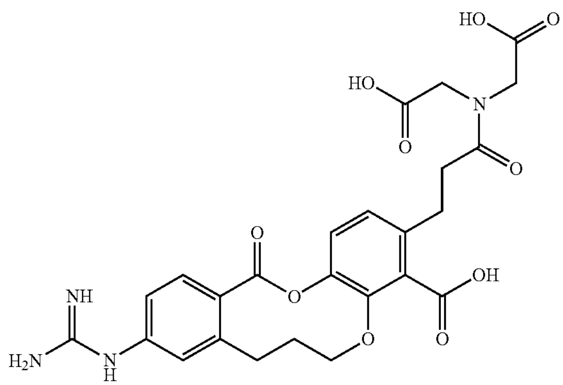 [SMILES: N=C(N)Nc1ccc2c(c1)CCCOc1c(ccc(CCC(=O)N(CC(=O)O)CC(=O)O)c1C(=O)O)OC2=O] | | 543.2 |
| 130 | N-((3-(3-(bis(carboxymethyl)amino)-3-oxopropyl)-10-carbamimidamido-13-oxo-6,7,8,13-tetrahydrodibenzo[b,f][1,4]dioxecin-4-yl)carbonyl)-O-methyl-L-tyrosine | 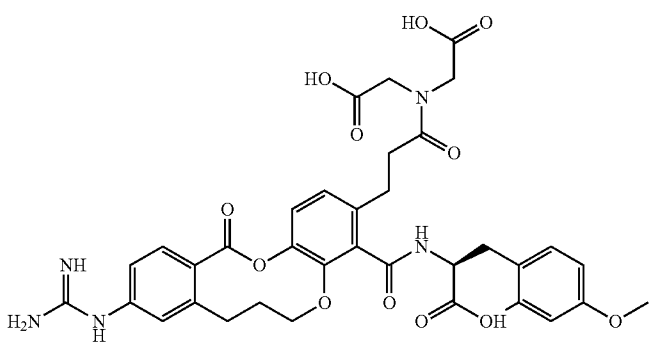 [SMILES: COc1ccc2c(c1)OC(=O)[C@@H](NC(=O)c1c(CCC(=O)N(CC(=O)O)CC(=O)O)ccc3c1OCCCc1cc(NC(=N)N)ccc1C(=O)O3)C2] | | 720.4 |
| 131 | 3-((3-(10-carbamimidamido-4-carboxy-13-oxo-6,7,8,13-tetrahydrodibenzo[b,f][1,4]dioxecin-3-yl)propanoyl)amino)pentanedioic acid | 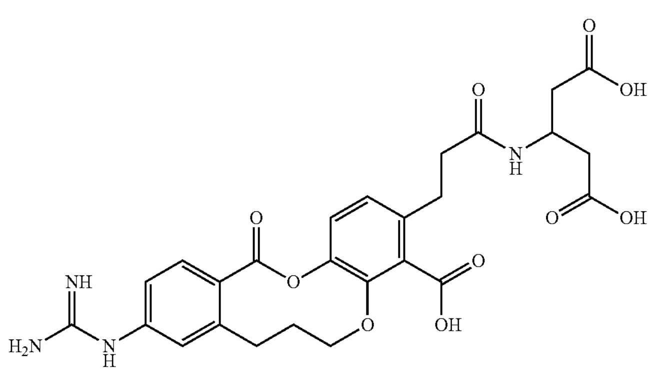 [SMILES: N=C(N)Nc1ccc2c(c1)CCCOc1c(ccc(CCC(=O)NC(CC(=O)O)CC(=O)O)c1C(=O)O)OC2=O] | | 557.0 |

TABLE A-continued

| EXAMPLE | IUPACNAME | STRUCTURE | SALT | MS |
|---|---|---|---|---|
| 132 | 3-((3-(10-carbamimidamido-4-(((1S)-1-carboxy-2-(4-methoxyphenyl)ethyl)carbamoyl)-13-oxo-6,7,8,13-tetrahydro-dibenzo[b,f][1,4]dioxecin-3-yl)propanoyl)amino)pentanedioic acid | 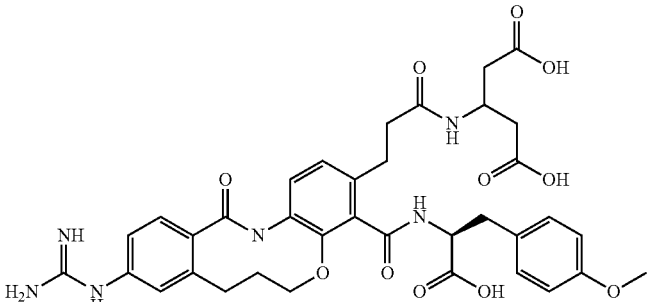 | | 734.4 |
| 133 | N-((10-carbamimidamido-13-oxo-6,7,8,13-tetrahydro-dibenzo[b,f][1,4]dioxecin-4-yl)carbonyl)-N-(carboxymethyl)-L-phenylalanine | 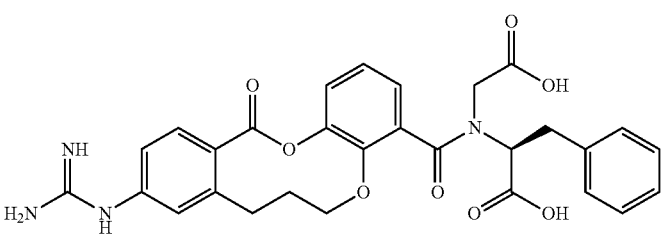 [SMILES: N=C(N)Nc1ccc2c(c1)CCCOc1c(cccc1C(=O)N(CC(=O)O)[C@@H](Cc1ccccc1)C(=O)O)OC2=O] | | 561.2 |
| 134 | 3-((((10-carbamimidamido-13-oxo-6,7,8,13-tetrahydro-dibenzo[b,f][1,4]dioxecin-4-yl)carbonyl)(2-carboxyethyl)amino)methyl)benzoic acid | 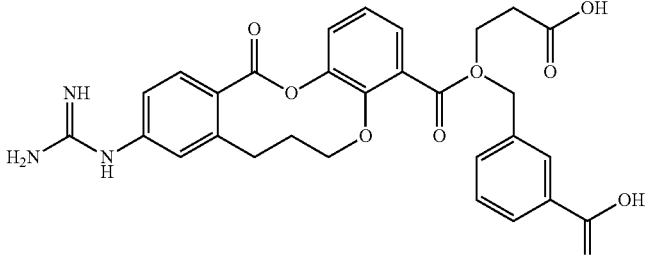 | | 561.2 |
| 135 | 3-((((10-carbamimidamido-13-oxo-6,7,8,13-tetrahydro-dibenzo[b,f][1,4]dioxecin-4-yl)carbonyl)((1S)-1-carboxyethyl)amino)methyl)benzoic acid | 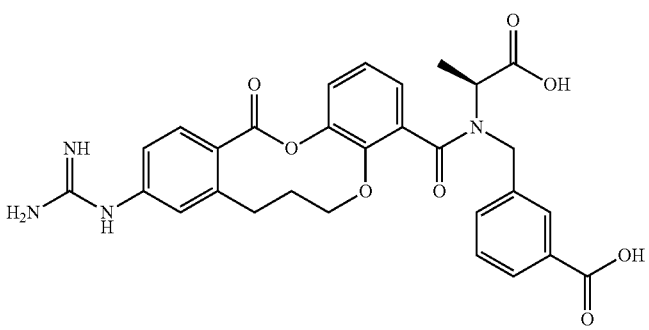 [SMILES: C[C@@H](C(=O)O)N(Cc1cccc(C(=O)O)c1)C(=O)c1cccc2c1OCCCc1cc(NC(=N)N)ccc1C(=O)O2] | | 561.2 |
| 136 | N-((10-carbamimidamido-13-oxo-6,7,8,13-tetrahydro-dibenzo[b,f][1,4]dioxecin-4-yl)carbonyl)-N-(3-carboxybenzyl)-L-aspartic acid | 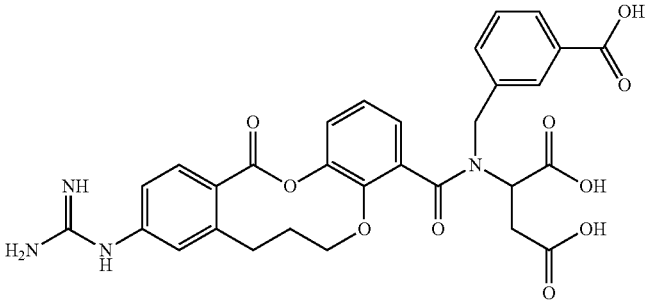 [SMILES: N=C(N)Nc1ccc2c(c1)CCCOc1c(cccc1C(=O)N(Cc1cccc(C(=O)O)c1)C(CC(=O)O)C(=O)O)OC2=O] | | 605.3 |

TABLE A-continued

| EXAMPLE | IUPACNAME | STRUCTURE | SALT | MS |
|---|---|---|---|---|
| 137 | N-(2-benzyloxy)ethyl)-N-((10-carbamimidamido-13-oxo-6,7,8,13-tetrahydro-dibanzo[b,f][1,4]dioxecin-4-yl)carbonyl)-L-aspartic acid | 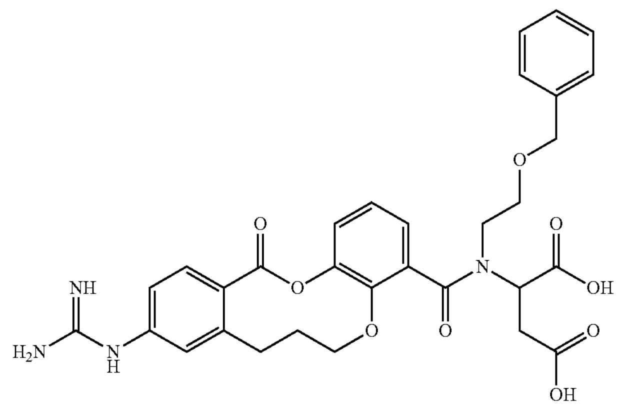 [SMILES: N=C(N)Nc1ccc2c(c1)CCCOc1c(cccc1C(=O)N(CCOCc1ccccc1)C(CC(=O)O)C(=O)O)OC2=O] | | 605.3 |
| 138 | N-((10-carbamimidamido-13-oxo-6,7,8,13-tetrahydro-dibenzo[b,f][1,4]dioxecin-4-yl)carbonyl)-N-(2-carboxyethyl)-L-aspartic acid | 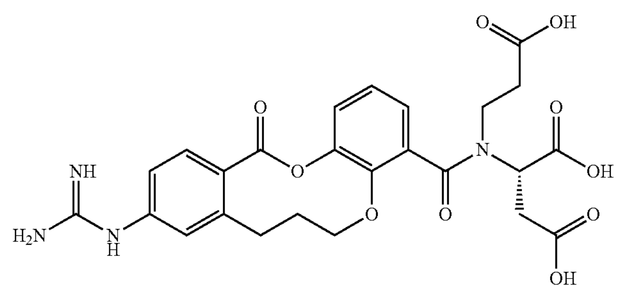 [SMILES: N=C(N)Nc1ccc2c(c1)CCCOc1c(cccc1C(=O)N(CCC(=O)O)[C@@H](CC(=O)O)C(=O)O)OC2=O] | | 543.2 |
| 139 | N-((10-carbamimidamido-13-oxo-6,7,8,13-tetrahydro-dibenzo[b,f][1,4]dioxecin-4-yl)carbonyl)-N-(2-methoxy-2-oxoethyl)-L-aspartic acid | 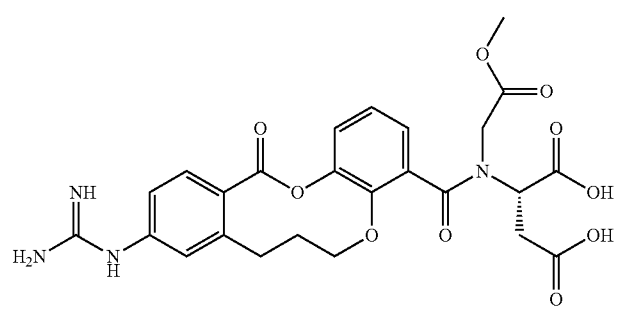 [SMILES: COC(=O)CN(C(=O)c1cccc2c1OCCCc1cc(NC(=N)N)ccc1C(=O)O2)[C@@H](CC(=O)O)C(=O)O] | | 543.2 |
| 140 | N-((10-carbamimidamido-13-oxo-6,7,8,13-tetrahydro-dibenzo[b,f][1,4]dioxecin-4-yl)carbonyl)-N-(carboxymethyl)glycyl-N-benzyl-glycine | 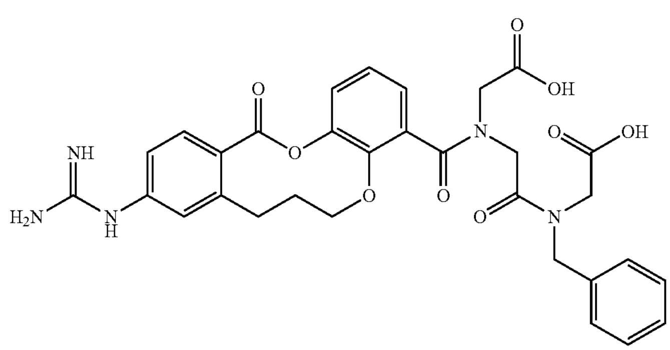 [SMILES: N=C(N)Nc1ccc2c(c1)CCCOc1c(cccc1C(=O)N(CC(=O)O)CC(=O)N(CC(=O)O)Cc1ccccc1)OC2=O] | | 618.3 |

TABLE A-continued

| EXAMPLE | IUPACNAME | STRUCTURE | SALT | MS |
|---|---|---|---|---|
| 141 | N-((10-carbamimidamido-13-oxo-6,7,8,13-tetrahydro-dibenzo[b,f][1,4]dioxecin-4-yl)carbonyl)-N-(carboxymethyl)glycyl-N-(3-carboxy-benzyl)glycine | 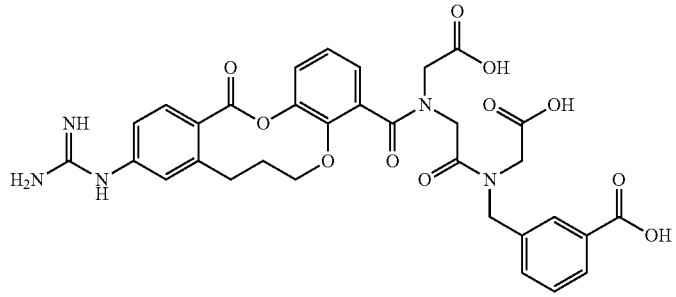 [SMILES: N=C(N)Nc1ccc2c(c1)CCCOc1c(cccc1C(=O)N(CC(=O)O)CC(=O)N(CC(=O)O)Cc1cccc(C(=O)O)c1)OC2=O] | | 662.2 |
| 142 | N-((10-carbamimidamido-13-oxo-6,7,8,13-tetrahydro-dibenzo[b,f][1,4]dioxecin-4-yl)carbonyl)-N-(4-(carboxymethyl)benzyl)glycine | 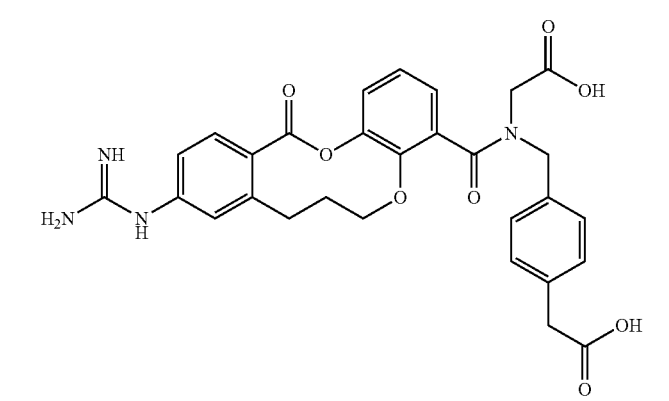 [SMILES: N=C(N)Nc1ccc2c(c1)CCCOc1c(cccc1C(=O)N(CC(=O)O)Cc1ccc(CC(=O)O)cc1)OC2=O] | | 561.2 |
| 143 | N-((10-carbamimidamido-13-oxo-6,7,8,13-tetrahydro-dibenzo[b,f][1,4]dioxecin-4-yl)carbonyl)-N-(4-carboxybenzyl)-L-aspartic acid | 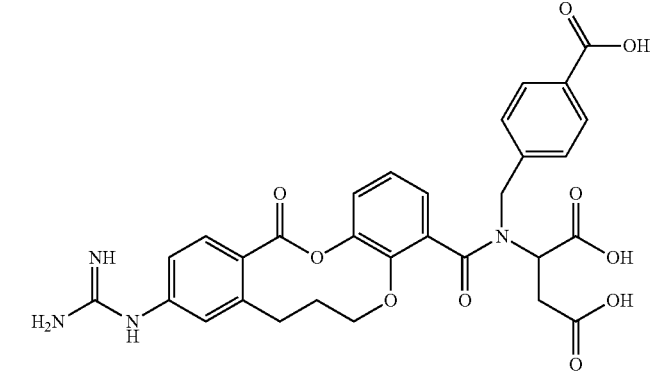 [SMILES: N=C(N)Nc1ccc2c(c1)CCCOc1c(cccc1C(=O)N(Cc1ccc(C(=O)O)cc1)C(CC(=O)O)C(=O)O)OC2=O] | | 605.3 |
| 144 | 3-(((10-carbamimidamido-13-oxo-6,7,8,13-tetrahydro-dibenzo[b,f][1,4]dioxecin-4-yl)carbonyl)(3-carboxybenzyl)amino)pentanedioic acid | 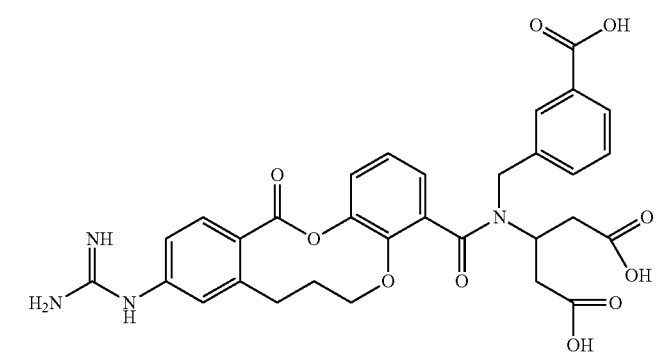 [SMILES: N=C(N)Nc1ccc2c(c1)CCCOc1c(cccc1C(=O)N(Cc1cccc(C(=O)O)c1)C(CC(=O)O)CC(=O)O)OC2=O] | | 619.2 |

TABLE A-continued

| EXAMPLE | IUPACNAME | STRUCTURE | SALT | MS |
|---|---|---|---|---|
| 145 | 3-((((10-carbamimidamido-3-(2-carboxyethyl)-13-oxo-6,7,8,13-tetrahydro-dibenzo[b,f][1,4]dioxecin-4-yl)carbonyl)-carboxy-methyl)-amino)methyl)benzoic acid | 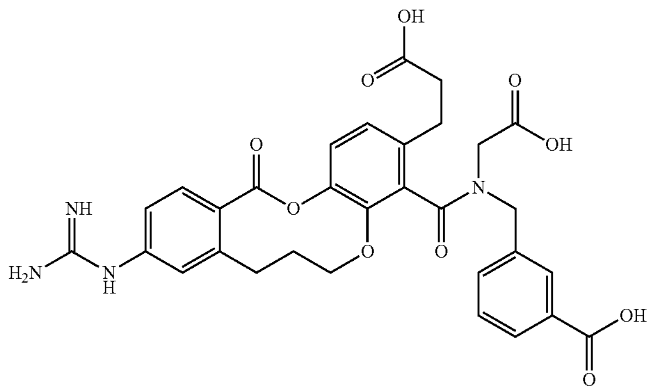 [SMILES: N=C(N)Nc1ccc2c(c1)CCCOc1c(ccc(CCC(=O)O)c1C(=O)N(CC(=O)O)Cc1cccc(C(=O)O)c1)OC2=O] | | 619.2 |
| 146 | 5-((((10-carbamimidamido-13-oxo-6,7,8,13-tetrahydro-dibenzo[b,f][1,4]dioxecin-4-yl)carbonyl)-(carboxy-methyl)-amino)methyl)isophthalic acid | 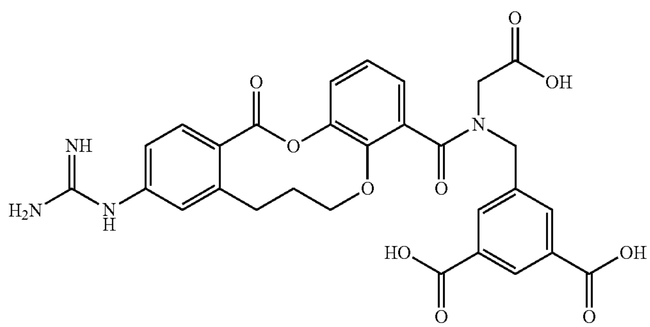 [SMILES: N=C(N)Nc1ccc2c(c1)CCCOc1c(cccc1C(=O)N(CC(=O)O)Cc1cc(C(=O)O)cc(C(=O)O)c1)OC2=O] | | 591.2 |
| 147 | 3-(((10-carbamimidamido-13-oxo-6,7,8,13-tetrahydro-dibenzo[b,f][1,4]dioxecin-4-yl)carbonyl)(4-carboxybenzyl)amino)pentanedioic acid | 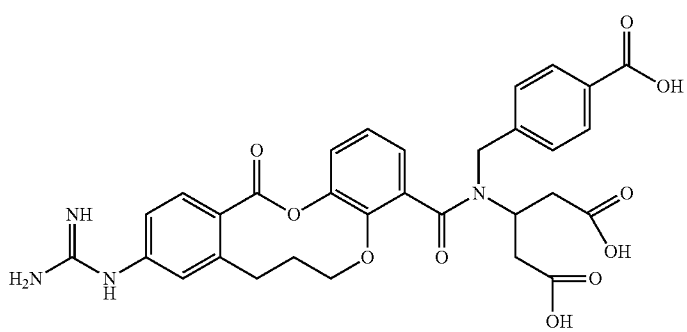 [SMILES: N=C(N)Nc1ccc2c(c1)CCCOc1c(cccc1C(=O)N(Cc1ccc(C(=O)O)cc1)C(CC(=O)O)CC(=O)O)OC2=O] | | 619.2 |
| 148 | 3-(4-((3-((bis(carboxymethyl)amino)methyl)-benzyl)(carboxymethyl)carbamoyl)-10-carbamimidamido-13-oxo-6,7,8,13-tetrahydro-dibenzo[b,f][1,4]dioxecin-3-yl)propanoic acid | 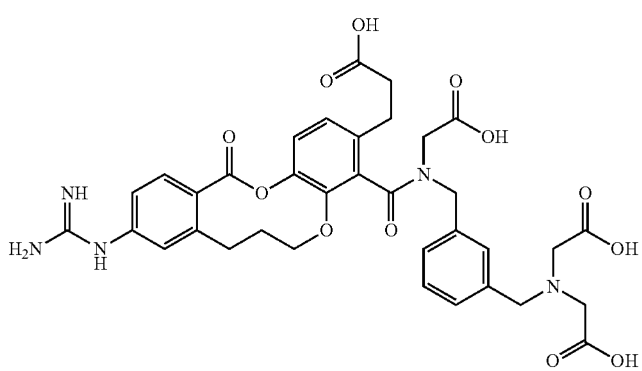 [SMILES: N=C(N)Nc1ccc2c(c1)CCCOc1c(ccc(CCC(=O)O)c1C(=O)N(CC(=O)O)Cc1cccc(CN(CC(=O)O)CC(=O)O)c1)OC2=O] | CF3COOH | 720.2 |

| EXAMPLE | IUPACNAME | STRUCTURE | SALT | MS |
|---|---|---|---|---|
| 149 | 3-(4-((2-((bis(carboxymethyl)amino)ethyl)(carboxymethyl)carbamoyl)-10-carbamimidamido-13-oxo-6,7,8,13-tetrahydrodibenzo[b,f][1,4]dioxecin-3-yl)propanoic acid | 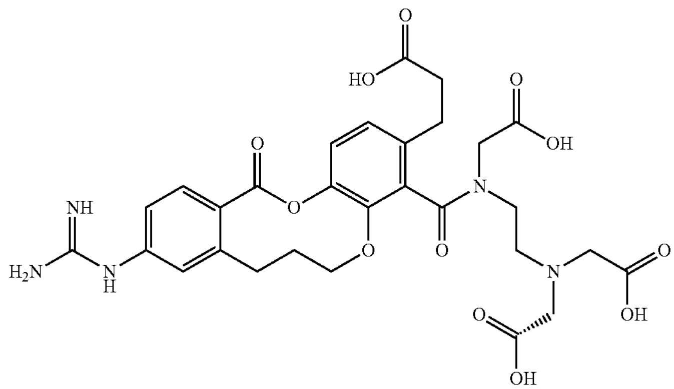 | CF3COOH | 644.2 |
| 150 | 3-((((10-carbamimidamido-3-cyclopropyl-13-oxo-6,7,8,13-tetrahydrodibenzo[b,f][1,4]dioxecin-4-yl)carbonyl)(carboxymethyl)amino)methyl)benzoic acid | 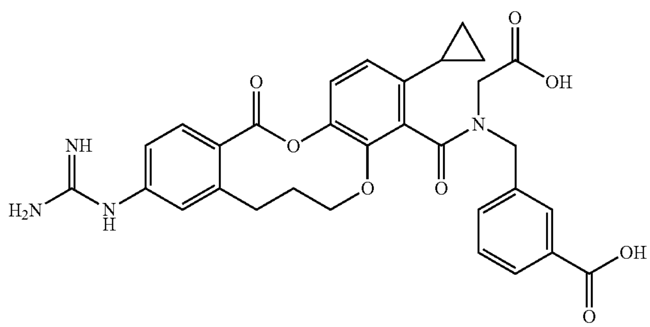 [SMILES: N=C(N)Nc1ccc2c(c1)CCCOc1c(ccc(C3CC3)c1C(=O)N(CC(=O)O)Cc1cccc(C(=O)O)c1)OC2=O] | | 587.2 |
| 151 | 2,2'-(((10-carbamimidamido-3-cyclopropyl-13-oxo-6,7,8,13-tetrahydrodibenzo[b,f][1,4]dioxecin-4-yl)carbonyl)imino)diacetic acid | 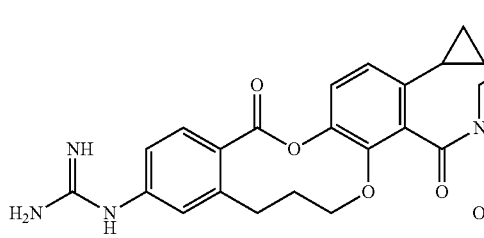 | | 511.2 |
| 152 | 3-((((10-carbamimidamido-3-methyl-13-oxo-6,7,8,13-tetrahydrodibenzo[b,f][1,4]dioxecin-4-yl)carbonyl)(carboxymethyl)amino)methyl)benzoic acid | 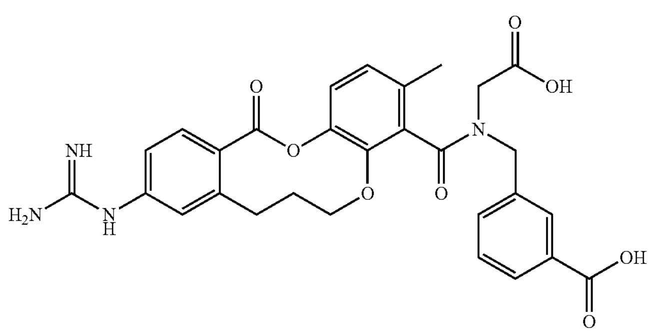 [SMILES: Cc1ccc2c(c1C(=O)N(CC(=O)O)Cc1cccc(C(=O)O)c1)OCCCc1cc(NC(=N)N)ccc1C(=O)O2] | | 561.2 |
| 153 | 2,2'-(((10-carbamimidamido-3-methyl-13-oxo-6,7,8,13-tetrahydrodibenzo[b,f][1,4]dioxecin-4-yl)carbonyl)imino)diacetic acid | 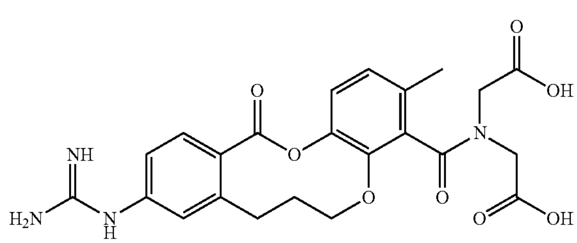 [SMILES: Cc1ccc2c(c1C(=O)N(CC(=O)O)CC(=O)O)OCCCc1cc(NC(=N)N)ccc1C(=O)O2] | | 485.2 |

TABLE A-continued

| EXAMPLE | IUPACNAME | STRUCTURE | SALT | MS |
|---|---|---|---|---|
| 154 | N-((10-carbamimidamido-3-methyl-13-oxo-6,7,8,13-tetrahydro-dibenzo[b,f][1,4]dioxacin-4-yl)carbonyl)-L-aspartic acid | 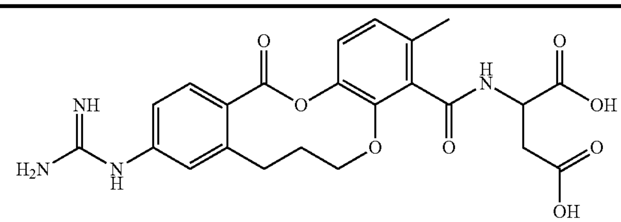 | | 465.1 |
| 155 | 3-(4-((2-(bis(carboxymethyl)amino)-2-oxoethyl)(carboxymethyl)carbamoyl)-10-carbamimidamido-13-oxo-6,7,8,13-tetrahydro-dibenzo[b,f][1,4]dioxacin-3-yl)propanoic acid | 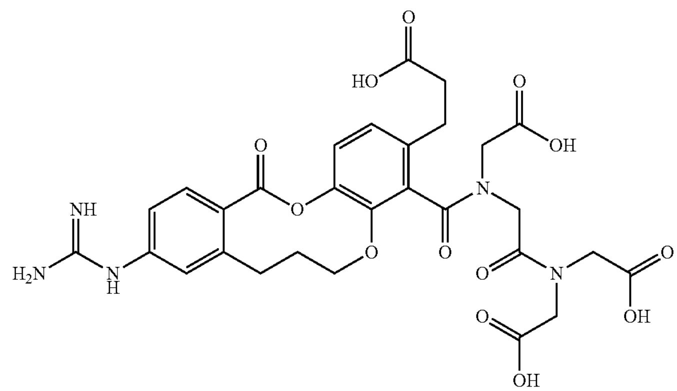 [SMILES: N=C(N)Nc1ccc2c(c1)CCCOc1c(ccc(CCC(=O)O)c1C(=O)N(CC(=O)O)CC(=O)N(CC(=O)O)CC(=O)O)OC2=O] | | 658.3 |
| 156 | N-((10-carbamimidamido-13-oxo-6,7,8,13-tetrahydro-dibenzo[b,f][1,4]dioxecin-4-yl)carbonyl)-N-(3-(carboxymethyl)benzyl)glycine | 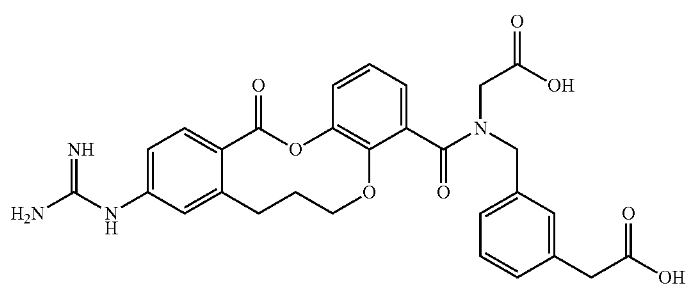 [SMILES: N=C(N)Nc1ccc2c(c1)CCCOc1c(cccc1C(=O)N(CC(=O)O)Cc1cccc(CC(=O)O)c1)OC2=O] | | 561.2 |
| 157 | N-((10-carbamimidamido-13-oxo-6,7,8,13-tetrahydro-dibenzo[b,f][1,4]dioxecin-4-yl)carbonyl)-N-(3-(carboxymethyl)benzyl)-L-aspartic acid | 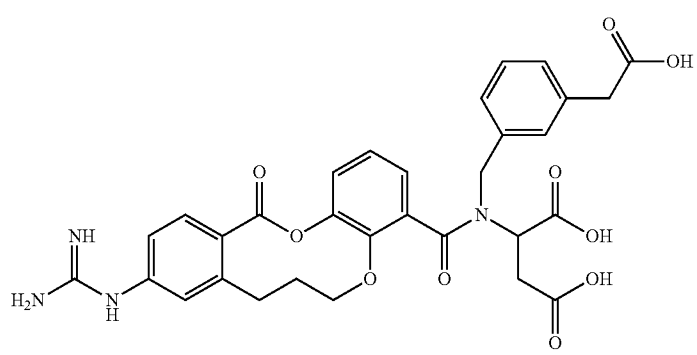 [SMILES: N=C(N)Nc1ccc2c(c1)CCCOc1c(cccc1C(=O)N(Cc1cccc(CC(=O)O)c1)C(CC(=O)O)C(=O)O)OC2=O] | | 619.2 |
| 158 | N-(3-(bis(carboxymethyl)carbamoyl)benzyl)-N-((10-carbamimidamido-13-oxo-6,7,8,13-tetrahydro-dibenzo[b,f][1,4]dioxecin-4-yl)carbonyl)glycine | 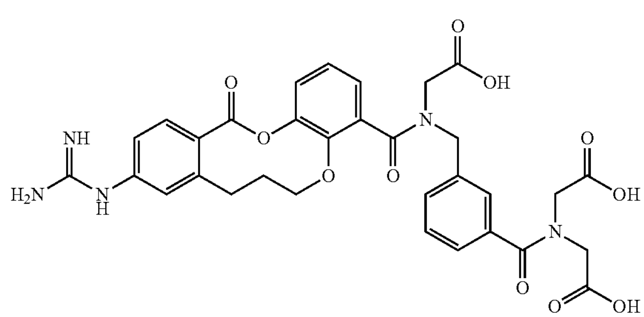 [SMILES: N=C(N)Nc1ccc2c(c1)CCCOc1c(cccc1C(=O)N(CC(=O)O)Cc1cccc(C(=O)N(CC(=O)O)CC(=O)O)c1)OC2=O] | | 662.2 |

TABLE A-continued

| EXAMPLE | IUPACNAME | STRUCTURE | SALT | MS |
|---|---|---|---|---|
| 159 | 2,2'-(((10-carbamimidamido-3-cyano-13-oxo-6,7,8,13-tetrahydro-dibenzo[b,f][1,4]dioxecin-4-yl)carbonyl)imino) diacetic acid | 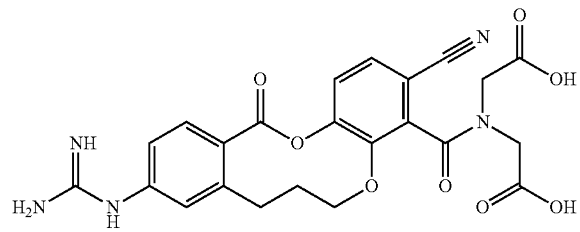 [SMILES: N#Cc1ccc2c(c1C(=O)N(CC(=O)O)CC(=O)O)OCCCc1cc(NC(=N)N)ccc1C(=O)O2] | | 496.1 |
| 160 | 3-((((10-carbamimidamido-3-cyano-13-oxo-6,7,8,13-tetrahydro-dibenzo[b,f][1,4]dioxecin-4-yl)carbonyl)(carboxymethyl)amino)methyl) benzoic acid | 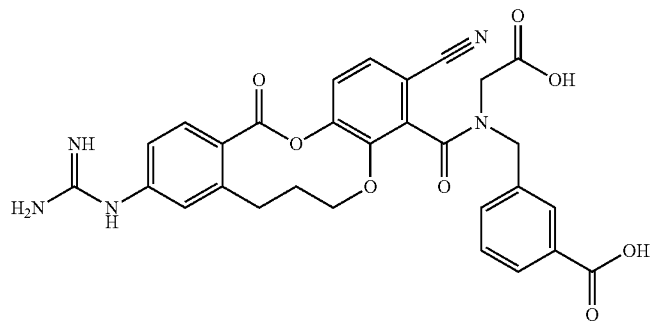 [SMILES: N#Cc1ccc2c(c1C(=O)N(CC(=O)O)Cc1cccc(C(=O)O)c1)OCCCc1cc(NC(=N)N)ccc1C(=O)O2] | | 572.1 |
| 161 | N-((10-carbamimidamido-3-cyano-13-oxo-6,7,8,13-tetrahydro-dibenzo[b,f][1,4]dioxecin-4-yl)carbonyl)-L-aspartic acid | 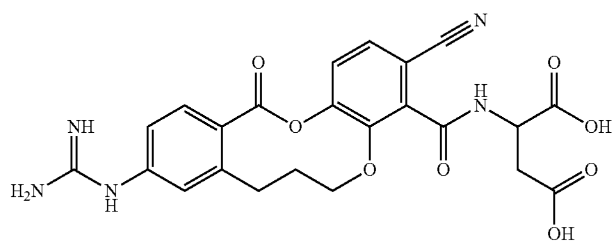 [SMILES: N#Cc1ccc2c(c1C(=O)NC(CC(=O)O)C(=O)O)OCCCc1cc(NC(=N)N)ccc1C(=O)O2] | | 496.1 |
| 162 | 5-((((3-carbamimidamido-14-oxo-5,7,8,14-tetrahydro-6H-dibenzo[b,h]oxecin-9-yl)carbonyl)-(carboxy-methyl)-amino)methyl) isophthalic acid | 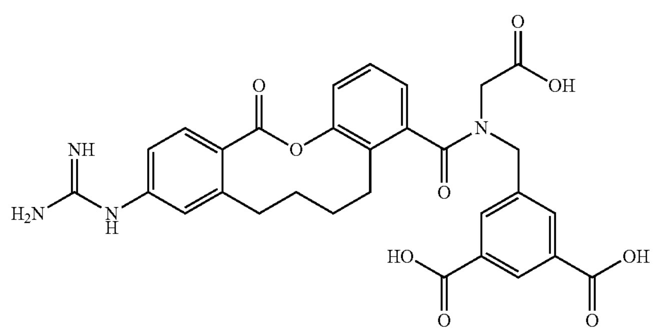 | | 589.2 |
| 163 | 5-((((10-carbamimidamido-3-(2-carboxyethyl)-13-oxo-6,7,8,13-tetrahydro-dibenzo[b,f][1,4]dioxecin-4-yl)carbonyl)-(carboxymethyl)amino)methyl) isophthalic acid | 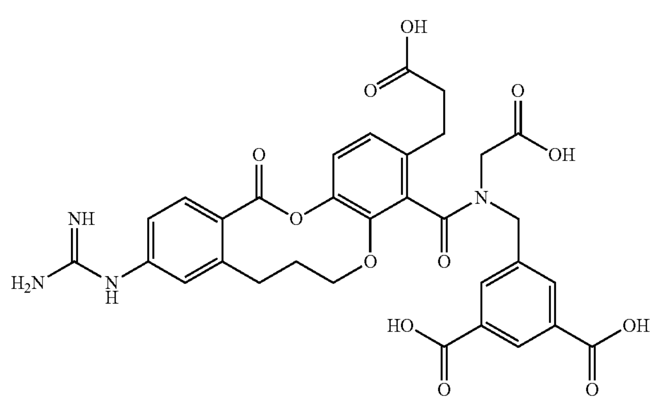 [SMILES: N=C(N)Nc1ccc2c(c1)CCCOc1c(ccc(CCC(=O)O)c1C(=O)N(CC(=O)O)Cc1cc(C(=O)O)cc(C(=O)O)c1)OC2=O] | | 663.1 |

TABLE A-continued

| EX-AMPLE | IUPACNAME | STRUCTURE | SALT | MS |
|---|---|---|---|---|
| 164 | 5-((((10-carbamimidamido-3-(3-ethoxy-3-oxopropyl)-13-oxo-6,7,8,13-tetrahydro-dibenzo[b,f][1,4]dioxecin-4-yl)carbonyl)-(carboxymethyl)-amino)methyl)isophthalic acid | 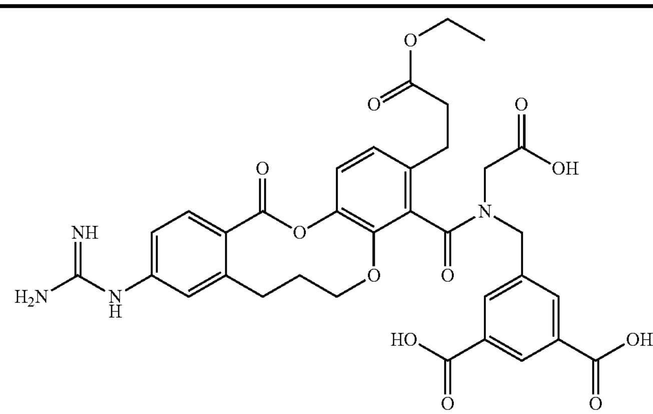 | | 691.2 |
| 165 | 3-((((10-carbamimidamido-3-(3-ethoxy-3-oxopropyl)-13-oxo-6,7,8,13-tetrahydro-dibenzo[b,f][1,4]dioxecin-4-yl)carbonyl)-(carboxymethyl)-amino)methyl)benzoic acid | 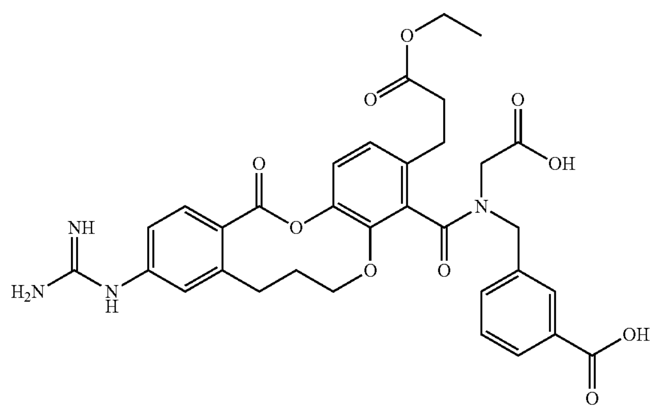 [SMILES: CCOC(=O)CCc1ccc2c(c1C(=O)N(CC(=O)O)Cc1cccc(C(=O)O)c1)OCCCc1cc(NC(=N)N)ccc1C(=O)O2] | | 647.2 |
| 166 | N-((10-carbamimidamido-3-(3-ethoxy-3-oxopropyl)-13-oxo-6,7,8,13-tetrahydro-dibenzo[b,f][1,4]dioxacin-4-yl)carbonyl)-L-aspartic acid | 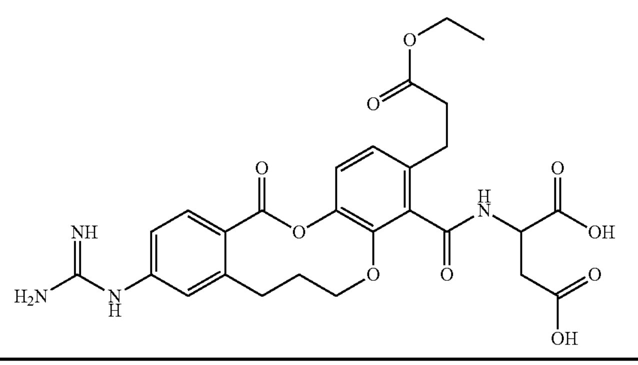 | | 571.2 |

Test Example 1: Human Enteropeptidase Inhibitory Activity

Human recombinant enteropeptidase (#REN-260, ITSI-Biosciences LLC) was diluted with an assay buffer (50 mM Tricine, pH 8.0, 0.01 (w/v) %, Tween 20, 10 mM $CaCl_2$) to prepare a 24 mU/mL enzyme solution. Subsequently, 5FAM-Abu-Gly-Asp-Asp-Asp-Lys-Ile-Val-Gly-Gly-Lys (CPQ2)-Lys-Lys-$NH_2$ (SEQ ID NO: 1, purity: 97.2%, CPC Scientific Inc.) was diluted with the assay buffer to prepare a 2.1 µM substrate solution. A test compound is dissolved in DMSO into a 1 mM solution, and the solution was diluted by 100-fold with the assay buffer to give a compound solution. To a 384-well black plate (#784076, Greiner Bio-One), 5 µL of the compound solution and 5 µL of the substrate solution were added and mixed, and 5 µL of the enzyme solution was then added to the mixture, followed by mixing to start the reaction. The fluorescence intensity was measured with a fluorescence plate reader EnVision (The Perkin-Elmer Corp.) at an excitation wavelength of 485 nm and a fluorescence wavelength of 535 nm. The same reaction as above except that the test compound was not contained was performed (test compound non-addition group). Furthermore, the same reaction as above except that the test compound and the enzyme were not contained was performed (control group). The inhibition rate was calculated using the fluorescence intensity at 2 hours after the start of the reaction by the following expression:

Inhibition rate (%)=(1−((fluorescence intensity of test compound addition group)−(fluorescence intensity of control group))/((fluorescence intensity of test compound non-addition group)−(fluorescence intensity of control group)))×100

The results are shown in Table 1.

TABLE 1

| Test Compound (Example No.) | 3.3 μM Inhibition |
|---|---|
| 1 | 101% |
| 2 | 101% |
| 3 | 101% |
| 4 | 98% |
| 5 | 101% |
| 6 | 101% |
| 7 | 102% |
| 8 | 100% |
| 9 | 101% |
| 10 | 101% |
| 11 | 101% |
| 12 | 101% |
| 13 | 101% |
| 14 | 101% |
| 15 | 101% |
| 16 | 101% |
| 17 | 100% |
| 18 | 101% |
| 19 | 99% |
| 20 | 102% |
| 21 | 102% |
| 22 | 101% |
| 23 | 102% |
| 24 | 102% |
| 25 | 102% |
| 26 | 45% |
| 27 | 102% |
| 28 | 102% |
| 29 | 101% |
| 30 | 101% |
| 31 | 101% |
| 32 | 71% |
| 33 | 98% |
| 34 | 75% |
| 35 | 90% |
| 36 | 94% |
| 37 | 101% |
| 38 | 99% |
| 39 | 98% |
| 40 | 100% |
| 41 | 71% |
| 42 | 100% |
| 43 | 101% |
| 44 | 96% |
| 45 | 100% |
| 46 | 100% |
| 47 | 101% |
| 48 | 42% |
| 49 | 100% |
| 50 | 101% |
| 51 | 101% |
| 52 | 101% |
| 53 | 101% |
| 54 | 89% |
| 55 | 98% |
| 56 | 100% |
| 57 | 100% |
| 58 | 55% |
| 59 | 57% |
| 60 | 59% |
| 61 | 72% |
| 62 | 84% |
| 63 | 93% |
| 64 | 101% |
| 65 | 100% |
| 66 | 101% |
| 67 | 100% |

TABLE 1-continued

| Test Compound (Example No.) | 3.3 μM Inhibition |
|---|---|
| 68 | 83% |
| 69 | 100% |
| 70 | 102% |
| 71 | 100% |
| 72 | 101% |
| 73 | 100% |
| 74 | 101% |
| 75 | 101% |
| 76 | 101% |
| 77 | 99% |
| 78 | 93% |
| 79 | 101% |
| 80 | 101% |
| 81 | 101% |
| 82 | 102% |
| 83 | 102% |
| 84 | 101% |
| 85 | 101% |
| 86 | 101% |
| 87 | 101% |
| 88 | 102% |
| 89 | 101% |
| 90 | 101% |
| 91 | 102% |
| 92 | 101% |
| 93 | 100% |
| 94 | 101% |
| 95 | 101% |
| 96 | 101% |
| 97 | 100% |
| 98 | 95% |
| 99 | 100% |
| 100 | 101% |
| 101 | 100% |
| 102 | 101% |
| 103 | 101% |
| 104 | 100% |
| 105 | 101% |
| 106 | 100% |
| 107 | 101% |
| 108 | 100% |
| 109 | 100% |
| 110 | 100% |
| 111 | 100% |
| 112 | 99% |
| 113 | 99% |
| 114 | 99% |
| 115 | 99% |
| 116 | 99% |
| 117 | 100% |
| 118 | 101% |
| 119 | 101% |
| 120 | 101% |
| 121 | 101% |
| 122 | 101% |
| 123 | 101% |
| 124 | 101% |
| 125 | 100% |
| 126 | 100% |
| 127 | 100% |
| 128 | 100% |
| 129 | 100% |
| 130 | 99% |
| 131 | 100% |
| 132 | 100% |
| 133 | 100% |
| 134 | 100% |
| 135 | 100% |
| 136 | 100% |
| 137 | 100% |
| 138 | 100% |
| 139 | 100% |
| 140 | 100% |
| 141 | 100% |
| 142 | 98% |
| 143 | 100% |
| 144 | 99% |
| 145 | 99% |

TABLE 1-continued

| Test Compound (Example No.) | 3.3 μM Inhibition |
| --- | --- |
| 146 | 102% |
| 147 | 100% |
| 148 | 101% |
| 149 | 101% |

As shown above, it was demonstrated that the invention compounds have excellent enteropeptidase inhibitory activities.

Test Example 2-1: Fecal Protein Concentration-Increasing Test Using HFD-Fed Mouse High fat diet-fed (HFD-fed) mice (D12079B diet, male, 19-week old) were orally administered with a 0.5% methyl cellulose suspension containing a test compound (10 mg/kg) (compound administration group, six mice per group) or a 0.5% methyl cellulose suspension (compound non-administration group (vehicle), five mice per group), and whole feces were collected on the first day of administration. Dried feces were dissolved in 0.5 N NaOH, followed by centrifugation at 12,000 rpm. The protein concentration in the supernatant was then quantitatively measured (Lowry method), and the amount of protein contained in 1 g of feces was calculated as the fecal protein concentration (mg/g feces). The average and the standard deviation of each group are shown below.

TABLE 2

| Test Compound | Dose of Compound (mg/kg) | Fecal protein concentration (mg/g feces) |
| --- | --- | --- |
| vehicle | 0 | 87.8 ± 7.2 |
| Example 3 | 10 | 233.3 ± 35.9 |

As shown above, it was demonstrated that the invention compounds have an effect of increasing the fecal protein concentration.

Test Example 2-2: Fecal Protein Concentration-Increasing Test Using HFD-Fed Mouse High fat diet-fed (HFD-fed) mice (D12079B diet, male, 47-week old) were orally administered with a 0.5% methyl cellulose suspension containing a test compound (10 mg/kg) (compound administration group, five mice per group) or a 0.5% methyl cellulose suspension (compound non-administration group (vehicle), five mice per group), and whole feces were collected on the first day of administration. Dried feces were dissolved in 0.5 N NaOH, followed by centrifugation at 12,000 rpm. The protein concentration in the supernatant was quantitatively measured (Lowry method), and the amount of protein contained in 1 g of feces was calculated as the fecal protein concentration (mg/g feces). The average and the standard deviation of each group are shown below.

TABLE 3

| Test Compound | Dose of Compound (mg/kg) | Fecal protein concentration (mg/g feces) |
| --- | --- | --- |
| vehicle | 0 | 104.3 ± 15.2 |
| Example 94 | 10 | 201.0 ± 21.8 |
| Example 120 | 10 | 194.6 ± 48.1 |
| Example 122 | 10 | 165.4 ± 16.2 |
| Example 136 | 10 | 274.3 ± 74.6 |
| Example 145 | 10 | 201.3 ± 45.3 |

As shown above, it was demonstrated that the invention compounds have an effect of increasing the fecal protein concentration.

Test Example 3: Anti-Obesity Effect Test Using DIO Mouse

Diet-induced obesity (DIO) mice (D12079B diet, male, 32-week old) were orally administered with a 0.5% methyl cellulose suspension containing a test compound (10 mg/kg) (compound administration group, six mice per group) or a 0.5% methyl cellulose suspension (compound non-administration group (vehicle), six mice per group) once a day for one week. The averages and the standard deviations of the body weights at the start of administration and after continuous administration for one week are shown below.

TABLE 4

| | | Body Weight (g) | |
| --- | --- | --- | --- |
| Test Compound | Dose of Compound (mg/kg) | Start of administration | After continuous administration for one week |
| vehicle | 0 | 42.9 ± 1.7 | 43.4 ± 1.9 |
| Example 3 | 10 | 44.5 ± 2.2 | 41.4 ± 2.2 |

As shown above, it was demonstrated that the invention compounds show an effect of decreasing body weight and have an anti-obesity effect.

| Pharmaceutical preparation example 1 (production of capsule) | | |
| --- | --- | --- |
| 1) | Compound of Example 1 | 30 mg |
| 2) | Fine powder cellulose | 10 mg |
| 3) | Lactose | 19 mg |
| 4) | Magnesium stearate | 1 mg |
| | | Total 60 mg |

| Pharmaceutical preparation example 2 (production of tablet) | | |
| --- | --- | --- |
| 1) | Compound of Example 1 | 30 g |
| 2) | Lactose | 50 g |
| 3) | Corn starch | 15 g |
| 4) | Carboxymethyl cellulose calcium | 44 g |
| 5) | Magnesium stearate | 1 g |
| 1000 tablets | | Total 140 g |

Total amount of the ingredients 1), 2), and 3) and 30 g of the ingredient 4) were kneaded with water. After vacuum drying, granulating was performed. The granulated grains were mixed with 14 g of the ingredient 4) and 1 g of the ingredient 5), and the mixture was made into tablets with a tableting machine. Thus, 1000 tablets each containing 30 mg of the compound of Example 1 were obtained.

INDUSTRIAL APPLICABILITY

The invention compounds have excellent enteropeptidase inhibitory activities and are useful in the treatment or prevention of, for example, obesity or diabetes mellitus.

All publications, patent publications, and patent application publications cited in this specification are herein incorporated by reference in their entirety.

Sequence Listing Free Text

SEQ ID NO: 1: artificial sequence (synthetic peptide)

The invention claimed is:

1. A compound represented by the formula (I) or a salt thereof:

[Formula I]

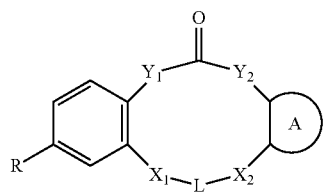

(I)

wherein
ring A represents an optionally substituted 5- or 6-membered aromatic ring, and the substituent of ring A optionally forms an optionally substituted ring together with constituent atoms of ring A;
L represents a bond or a $C_{1-6}$ alkylene group;
$X_1$ and $X_2$ are the same or different and each represent —O— or a bond;
R represents a guanidino group or an amidino group;
one of $Y_1$ and $Y_2$ is —O—, and the other moiety is a bond, provided that when R is a guanidino group, $Y_1$ represents a bond and $Y_2$ represents —O—, and when R is an amidino group, $Y_1$ represents —O— and $Y_2$ represents a bond.

2. The compound according to claim 1 or a salt thereof, wherein
ring A is
(1) a benzene ring optionally substituted by 1 to 3 substituents selected from
1) a halogen atom,
2) a carboxy group,
3) a cyano group,
4) a carbamoyl group optionally substituted by a $C_{6-14}$ aryl group optionally substituted by 1 to 3 substituents selected from a sulfo group; and a $C_{1-6}$ alkyl group optionally substituted by a mono- or di-$C_{1-6}$ alkylphosphono group,
5) 3- to 14-membered nonaromatic heterocyclylcarbonyl optionally substituted by 1 to 3 substituents selected from a carboxy group; and/or a mono- or di-$C_{1-6}$ alkyl-carbamoyl group substituted by 1 or 2 carboxy groups,
6) a 3- to 14-membered nonaromatic heterocyclic group optionally substituted by 1 to 3 substituents selected from a $C_{1-6}$ alkyl group substituted by 1 or 2 carboxy groups; and a carboxy group,
7) a $C_{1-6}$ alkyl group optionally substituted by 1 to 3 substituents selected from a mono- or di-$C_{1-6}$ alkyl-carbamoyl group substituted by 1 to 3 substituents selected from a carboxy group, a hydroxy-phenyl group, and a carbamoyl group; a $C_{1-6}$ alkoxy-carbonyl group; and a carboxy group,
8) a $C_{1-6}$ alkoxy group optionally substituted by a mono- or di-$C_{1-6}$ alkyl-carbamoyl group substituted by 1 or 2 carboxy groups,
9) a mono- or di-$C_{1-6}$ alkyl-carbamoyl group optionally substituted by 1 to 3 substituents selected from
(a) a carboxy group;
(b) a sulfo group;
(c) a hydroxy group;
(d) a $C_{1-6}$ alkoxy group optionally substituted by a phenyl group;

(e) a $C_{1-6}$ alkoxy-carbonyl group;
(f) a guanidino group;
(g) a $C_{6-14}$ aryl group optionally substituted by 1 to 3 substituents selected from
  (g-1) a hydroxy group,
  (g-2) a carboxy group,
  (g-3) a $C_{1-6}$ alkoxy group,
  (g-4) a $C_{1-6}$ alkyl group substituted by a carboxy group,
  (g-5) a $C_{1-6}$ alkyl group substituted by a mono- or di-$C_{1-6}$ alkyl-amino group substituted by 1 or 2 carboxy groups, and
  (g-6) a mono- or di-$C_{1-6}$ alkyl-amino-$C_{1-6}$ alkoxy group substituted by 1 or 2 substituents selected from a carboxy group and a phenyl group;
(h) a thienyl group optionally substituted by 1 or 2 carboxy groups;
(i) a pyridinyl group optionally substituted by a mono- or di-$C_{1-6}$ alkyl-amino-$C_{1-6}$ alkyl group substituted by 1 or 2 carboxy groups;
(j) a $C_{1-6}$ alkyl-amino group substituted by 1 or 2 carboxy groups;
(k) a carbamoyl group optionally substituted by 1 or 2 $C_{1-6}$ alkyl groups substituted by 1 or 2 substituents selected from a carboxy group and a carboxy-phenyl group; and
(l) a phosphono group; and
10) a $C_{3-10}$ cycloalkyl group,
(2) 2,3-dihydrobenzofuran optionally substituted by 1 to 3 substituents selected from
  1) a mono- or di-$C_{1-6}$ alkyl-carbamoyl group optionally substituted by 1 to 3 substituents selected from a carboxy group and a sulfo group, and
  2) a $C_{1-6}$ alkyl group optionally substituted by a mono- or di-$C_{1-6}$ alkyl-carbamoyl group substituted by 1 to 3 substituents selected from a carboxy group and a sulfo group,
(3) pyridine optionally substituted by $C_{1-6}$ alkyl optionally substituted by a mono- or di-$C_{1-6}$ alkyl-carbamoyl group substituted by 1 or 2 carboxy groups, or
(4) thiophene optionally substituted by a mono- or di-$C_{1-6}$ alkyl-carbamoyl group optionally substituted by 1 or 2 carboxy groups.

3. The compound according to claim 1 or a salt thereof, wherein L is propylene.

4. The compound according to claim 1 or a salt thereof, wherein $X_1$ is a bond, and $X_2$ is —O—.

5. The compound according to claim 1 or a salt thereof, wherein R is a guanidino group.

6. The compound according to claim 1 or a salt thereof, wherein $Y_1$ is a bond, and $Y_2$ is —O—.

7. The compound according to claim 1 or a salt thereof, wherein
ring A is
  (1) a benzene ring optionally substituted by 1 to 3 substituents selected from
    1) a halogen atom,
    2) a carboxy group,
    3) a cyano group,
    4) a carbamoyl group optionally substituted by a $C_{6-14}$ aryl group optionally substituted by 1 to 3 substituents selected from a sulfo group; and a $C_{1-6}$ alkyl group optionally substituted by a mono- or di-$C_{1-6}$ alkylphosphono group,
    5) 3- to 14-membered nonaromatic heterocyclylcarbonyl optionally substituted by 1 to 3 substituents selected from a carboxy group; and a mono- or di-$C_{1-6}$ alkyl-carbamoyl group substituted by 1 or 2 carboxy groups,
    6) a 3- to 14-membered nonaromatic heterocyclic group optionally substituted by 1 to 3 substituents selected from a $C_{1-6}$ alkyl group substituted by 1 or 2 carboxy groups; and a carboxy group,
    7) a $C_{1-6}$ alkyl group optionally substituted by 1 to 3 substituents selected from a mono- or di-$C_{1-6}$ alkyl-carbamoyl group substituted by 1 to 3 substituents selected from a carboxy group, a hydroxy-phenyl group, and a carbamoyl group; a $C_{1-6}$ alkoxy-carbonyl group; and a carboxy group,
    8) a $C_{1-6}$ alkoxy group optionally substituted by a mono- or di-$C_{1-6}$ alkyl-carbamoyl group substituted by 1 or 2 carboxy groups,
    9) a mono- or di-$C_{1-6}$ alkyl-carbamoyl group optionally substituted by 1 to 3 substituents selected from
      (a) a carboxy group;
      (b) a sulfo group;
      (c) a hydroxy group;
      (d) a $C_{1-6}$ alkoxy group optionally substituted by a phenyl group;
      (e) a $C_{1-6}$ alkoxy-carbonyl group;
      (f) a guanidino group;
      (g) a $C_{6-14}$ aryl group optionally substituted by 1 to 3 substituents selected from
        (g-1) a hydroxy group,
        (g-2) a carboxy group,
        (g-3) a $C_{1-6}$ alkoxy group,
        (g-4) a $C_{1-6}$ alkyl group substituted by a carboxy group,
        (g-5) a $C_{1-6}$ alkyl group substituted by a mono- or di-$C_{1-6}$ alkyl-amino group substituted by 1 or 2 carboxy groups, and
        (g-6) a mono- or di-$C_{1-6}$ alkyl-amino-$C_{1-6}$ alkoxy group substituted by 1 or 2 substituents selected from a carboxy group and a phenyl group;
      (h) a thienyl group optionally substituted by 1 or 2 carboxy group;
      (i) a pyridinyl group optionally substituted by a mono- or di-$C_{1-6}$ alkyl-amino-$C_{1-6}$ alkyl group substituted by 1 or 2 carboxy groups;
      (j) a $C_{1-6}$ alkyl-amino group substituted by 1 or 2 carboxy groups;
      (k) a carbamoyl group optionally substituted by 1 or 2 $C_{1-6}$ alkyl groups substituted by 1 or 2 substituents selected from a carboxy group and a carboxy-phenyl group; and
      (l) a phosphono group; and
    10) a $C_{3-10}$ cycloalkyl group,
  (2) 2,3-dihydrobenzofuran optionally substituted by 1 to 3 substituents selected from
    1) a mono- or di-$C_{1-6}$ alkyl-carbamoyl group optionally substituted by 1 to 3 substituents selected from a carboxy group and a sulfo group, and
    2) a $C_{1-6}$ alkyl group optionally substituted by a mono- or di-$C_{1-6}$ alkyl-carbamoyl group substituted by 1 to 3 substituents selected from a carboxy group and a sulfo group, (3) pyridine optionally substituted by $C_{1-6}$ alkyl optionally substituted by a mono- or di-$C_{1-6}$ alkyl-carbamoyl group substituted by 1 or 2 carboxy groups, or (4) thiophene optionally substituted by a mono- or di-$C_{1-6}$ alkyl-carbamoyl group optionally substituted by 1 or 2 carboxy group;

L is propylene;

$X_1$ is a bond, and $X_2$ is —O—;

R is a guanidino group; and $Y_1$ is a bond, and $Y_2$ is —O—.

8. N-((10-Carbamimidamido-13-oxo-6,7,8,13-tetrahydrodibenzo[b,f][1,4]dioxecin-4-yl)carbonyl)-N-(carboxymethyl)-O-methyl-L-tyrosine or a salt thereof.

9. N-(2-(Bis(carboxymethyl)amino)ethyl)-N-((10-carbamimidamido-13-oxo-6,7,8,13-tetrahydrodibenzo[b,f][1,4]dioxecin-4-yl)carbonyl)glycine or a salt thereof.

10. N-((10-Carbamimidamido-13-oxo-6,7,8,13-tetrahydrodibenzo[b,f][1,4]dioxecin-4-yl)carbonyl)-N-(3-carboxybenzyl)-L-aspartic acid or a salt thereof.

11. A method for preventing or treating obesity or diabetes mellitus in a mammal, comprising administering an effective amount of a compound according to claim 1 or a salt thereof to the mammal.

* * * * *

```
SEQUENCE LISTING

<160> NUMBER OF SEQ ID NOS: 1

<210> SEQ ID NO 1
<211> LENGTH: 13
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa stands for Abu (2-Aminobutyric acid)
<220> FEATURE:
<221> NAME/KEY: MOD_RES
<222> LOCATION: (1)..(1)
<223> OTHER INFORMATION: modified with 5FAM
<220> FEATURE:
<221> NAME/KEY: MOD_RES
<222> LOCATION: (11)..(11)
<223> OTHER INFORMATION: modified with CPQ2

<400> SEQUENCE: 1

Xaa Gly Asp Asp Asp Lys Ile Val Gly Gly Lys Lys Lys
1               5                   10
```